(12) United States Patent
Wittrup et al.

(10) Patent No.: US 10,888,603 B2
(45) Date of Patent: Jan. 12, 2021

(54) METHODS OF TREATING CANCER CELLS EXPRESSING TUMOR-ASSOCIATED INTEGRINS

(71) Applicants: Massachusetts Institute of Technology, Cambridge, MA (US); The Board of Trustees of the Leland Stanford Junior University, Stanford, CA (US)

(72) Inventors: Karl Dane Wittrup, Boston, MA (US); Darrell J. Irvine, Arlington, MA (US); Cary Francis Opel, Somerville, MA (US); Kelly Dare Moynihan, Allston, MA (US); Jennifer R. Cochran, Stanford, CA (US); Byron Hua Kwan, Seattle, WA (US)

(73) Assignees: The Board of Trustees of the Leland Stanford Junior University, Stanford, CA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/076,597

(22) PCT Filed: Feb. 10, 2017

(86) PCT No.: PCT/US2017/017365
§ 371 (c)(1),
(2) Date: Aug. 8, 2018

(87) PCT Pub. No.: WO2017/139570
PCT Pub. Date: Aug. 17, 2017

(65) Prior Publication Data
US 2019/0054145 A1 Feb. 21, 2019

Related U.S. Application Data

(60) Provisional application No. 62/294,755, filed on Feb. 12, 2016.

(51) Int. Cl.
| | | |
|---|---|---|
| *A61K 38/20* | (2006.01) | |
| *A61K 39/00* | (2006.01) | |
| *A61K 39/395* | (2006.01) | |
| *A61K 38/16* | (2006.01) | |
| *C07K 16/28* | (2006.01) | |
| *A61K 39/12* | (2006.01) | |
| *A61K 47/64* | (2017.01) | |
| *A61K 47/60* | (2017.01) | |
| *A61K 47/68* | (2017.01) | |
| *A61P 35/00* | (2006.01) | |
| *C07K 16/30* | (2006.01) | |

(52) U.S. Cl.
CPC ......... *A61K 38/2013* (2013.01); *A61K 38/16* (2013.01); *A61K 39/0011* (2013.01); *A61K 39/12* (2013.01); *A61K 39/3955* (2013.01); *A61K 39/39541* (2013.01); *A61K 39/39558* (2013.01); *A61K 47/60* (2017.08); *A61K 47/643* (2017.08); *A61K 47/6813* (2017.08); *A61P 35/00* (2018.01); *C07K 16/2818* (2013.01); *C07K 16/3053* (2013.01); *A61K 2039/505* (2013.01); *A61K 2039/507* (2013.01); *A61K 2039/55533* (2013.01); *A61K 2039/55561* (2013.01); *A61K 2039/585* (2013.01); *A61K 2039/6018* (2013.01); *A61K 2039/6025* (2013.01); *A61K 2039/6031* (2013.01); *A61K 2039/6056* (2013.01); *A61K 2039/6093* (2013.01); *C07K 2317/76* (2013.01); *C07K 2319/30* (2013.01); *C12N 2710/20034* (2013.01)

(58) Field of Classification Search
None
See application file for complete search history.

(56) References Cited

U.S. PATENT DOCUMENTS

| | | |
|---|---|---|
| 7,462,350 B2 | 12/2008 | Gillies et al. |
| 2017/0216403 A1 | 8/2017 | Wittrup et al. |
| 2017/0224777 A1 | 8/2017 | Wittrup et al. |

FOREIGN PATENT DOCUMENTS

| | | |
|---|---|---|
| WO | 2004002526 A1 | 1/2004 |
| WO | 2008/003473 A2 | 1/2008 |
| WO | 2008/045252 A2 | 4/2008 |
| WO | 2012/064658 A1 | 5/2012 |
| WO | 2013/151771 A1 | 10/2013 |
| WO | 2013/177187 A2 | 11/2013 |
| WO | 2014201378 A1 | 12/2014 |
| WO | 2016/025642 A1 | 2/2016 |
| WO | 2016/025645 A1 | 2/2016 |
| WO | 2016/025647 A1 | 2/2016 |

OTHER PUBLICATIONS

Antony et al. Interleukin 2 in Cancer Therapy, Current Medicinal Chemistry, 17, 3297-3302, 2010 (Year: 2010).*
Irvine DJ, Engineering amphiphiles that target lymphoid tissues and optimally engage immune cells for more effective vaccines. 249th ACS National Meeting & Exposition, Denver, CO, United States, Mar. 22-26, 2015 (2015), POLY-529. (Year: 2015).*
Becker, J. et al., "An antibody-interleukin 2 fusion protein overcomes tumor heterogeneity by induction of a cellular immune response,"Proc. Natl. Acad. Sci., vol. 93: 7829-7831(1996).

(Continued)

*Primary Examiner* — Elly-Gerald Stoica
(74) *Attorney, Agent, or Firm* — Nelson Mullins Riley & Scarborough LLP; Amy E. Mandragouras, Esq.; Ariana D. Harris

(57) ABSTRACT

The present invention provides a method of treating cancer with a combination of IL-2 (e.g., extended-PK IL-2), an integrin-binding-Fc fusion protein, and a cancer vaccine. The methods of the invention can be used to treat a broad range of cancer types.

35 Claims, 41 Drawing Sheets
Specification includes a Sequence Listing.

(56) References Cited

OTHER PUBLICATIONS

Broucek, J. et al., "Combination immunotherapy with Interleukin-2 and CTLA-4 blockade decreases tumor growth and improves overall survival," J. Immuno Ther. Cancer, 1, Abstract No. P70, Accession No. 0052009444 (2013).
Cho H. et al., "A potent vaccination strategy that circumvents lymphodepletion for effective antitumor adoptive T-cell therapy," Cancer Research, vol. 72: 1986-1995 (2012).
Zhu. E. et al., "Synergistic Innate and Adaptive Immune Response to Combination Immunotherapy with Anti-Tumor Antigen Antibodies and Extended Serum Half-Life IL-2,"Cancer Cell, vol. 27 (4):489-501 (2015).
Dela Cruz, J.S., et al. "Antibody-cytokine fusion proteins: innovative weapons in the war against cancer," Clin. Exp. Med., vol. 4: 57-64 (2004).
Ellis et al., VEGF-targeted therapy: mechanisms of anti-tumour activity, Nature Reviews Cancer, vol. 8(8):579-591 (2008).
Hornick, J. et al., "Chimeric CLL-1 antibody fusion proteins containing granulocyte-macrophage colony-stimulating factor or interleukin-2 with specificity for B-cell malignancies exhibit enhanced effector functions while retaining tumor targeting properties," Blood, vol. 89:4437-4447(1997).
International Preliminary Report on Patentability, PCT/US2015/044927, dated Feb. 14, 2017, 9 pages.
International Preliminary Report on Patentability, PCT/US2015/1044924, dated Feb. 14, 2017, 10 pages.
International Preliminary Report on Patentability, PCT/US2017/017365, dated Aug. 14, 2018, 9 pages.
International Search Report and Written Opinion, PCT/US2015/044924, dated Dec. 2, 2015, 15 pages.
International Search Report and Written Opinion, PCT/US2015/044927, dated Dec. 2, 2015, 14 pages.
International Search Report and Written Opinion, PCT/US2017/017365, dated May 8, 2017, 13 pages.
Jackaman, C. et al., "Intratumoral interleukin-2/agonist CD40 antibody drives CD4+-independent resolution of treated-tumors and CD4+-dependent systemic and memory responses," Cancer Immunol. Immunother., vol. 61:549-560 (2012).
Kohlhapp, F. et al., "NK cells and CD8+ T cells cooperate to improve therapeutic responses in melanoma treated with CTLA-4 blockade and IL-2 (TUM2P.1039)," J. Immunology, vol. 194(1):Supp. Abstract Number: 69.36, Accession No. 0051980006 , 2 pages. (2015).
Ly, L. V. et al., "Effective Cooperation of Monoclonal Antibody and Peptide Vaccine for the Treatment of Mouse Melanoma," The Journal of Immunology, vol. 190 (1):489-496 (2012).
Moynihan, K. et al., "Eradication of large established tumors in mice by combination immunotherapy that engages innate and adaptive immune responses," Nature Medicine, vol. 22(12):1402-1410 (2016).
Muller, D. "Antibody-cytokine fusion proteins for cancer immunotherapy: an update on recent developments," BioDrugs, vol. 28:123-131 (2014).
Pardoll, D. et al., "The blockade of immune checkpoints in cancer immunotherapy", Nature Reviews Cancer, vol. 12 (4): 252-264(2012).
West, E. et al., "PD-L1 blockade synergizes with IL-2 therapy in reinvigorating exhausted T cells," J. Clin. Investig., vol. 123(6):2604-2615 (2013).
U.S. Appl. No. 15/501,246, filed Feb. 2, 2017, Karl Dane Wittrup.
U.S. Appl. No. 15/501,535, filed Feb. 3, 2017, Karl Dane Wittrup.
U.S. Appl. No. 15/501,246, Jun. 27, 2018.
U.S. Appl. No. 15/501,246, Jan. 17, 2018.
U.S. Appl. No. 15/501,535, May 29, 2018.
U.S. Appl. No. 15/501,535, Jan. 29, 2018.

* cited by examiner

Vaccine alone

MSA-IL-2+TA99+Trp-2
Vaccine

METHODS OF TREATING CANCER CELLS EXPRESSING TUMOR-ASSOCIATED INTEGRINS

RELATED APPLICATIONS

This application is a 35 U.S.C. § 371 national stage filing of PCT Application No. PCT/US2017/017365, filed on Feb. 10, 2017, which claims the benefit of the priority date of U.S. Provisional Application No. 62/294,755, which was on filed Feb. 12, 2016. The entire content of each of the above-referenced patent applications is hereby incorporated by reference in its entirety.

GOVERNMENT FUNDING

This invention was made with government support under Grant No. CA174795 awarded by the National Institutes of Health. The government has certain rights in the invention.

REFERENCE TO SEQUENCE LISTING

The instant application contains a Sequence Listing which has been submitted electronically in ASCII format and is hereby incorporated by reference in its entirety. Said ASCII copy, created Jul. 25, 2018, is named "MITN-033US Sequence-Listing.txt" and is 164222 Kilobytes in size. The Sequence Listing is being submitted by EFS Web and is hereby incorporated by reference into the specification.

BACKGROUND

Interleukin-2 (IL-2) is a pleiotropic cytokine that activates and induces the proliferation of T cells and NK cells. Although IL-2 is an FDA approved therapy, systemic IL-2 treatment has significant toxicity and therefore the response rate of patients is less than 25%. Combining extended half-life IL-2 and an antibody against a tumor-specific antigen shows promising results for treatment. However, antibody-based therapies often suffer from the fact that many tumors lack known tumor-associated antigens.

Integrins are a family of extracellular matrix adhesion receptors that regulate a diverse array of cellular functions crucial to the initiation, progression and metastasis of solid tumors. The importance of integrins in tumor progression has made them an appealing target for cancer therapy and allows for the treatment of a variety of cancer types. The integrins present on cancerous cells include $\alpha_v\beta_3$, $\alpha_v\beta_5$, and $\alpha_5\beta_1$. A variety of therapeutics have been developed to target individual integrins associated with cancer, including antibodies, linear peptides, cyclic peptides, and peptidomimetics. However, none have utilized small, structured peptide scaffolds or targeted more than two integrins simultaneously. Additionally, current integrin targeting drugs are given as a monotherapy.

Cancer vaccines have also become therapeutics of interest. Cancer vaccines can be used to stimulate the immune system against a specific antigen. Individually, these various therapies show promising yet limited results. However, their effectiveness together remains unexplored. Novel combination therapies are needed to more effectively combat various cancers.

SUMMARY

The present invention is based, in part, on the discovery that administration of IL-2 attached to a pharmacokinetic modifying group (hereafter referred to as "extended-pharmacokinetic (PK) IL-2"), an integrin-binding-Fc fusion protein, and a cancer vaccine provides synergistic tumor control and prolongs survival relative to monotherapy of either agent alone or double combinations of these three agents. The integrin-binding-Fc fusion protein comprises (i) an integrin-binding polypeptide having an integrin-binding loop and a knottin polypeptide scaffold; and (ii) an immunoglobulin Fc domain, wherein the integrin-binding polypeptide is operably linked to the Fc domain. An improved cancer therapy is provided that involves the combined administration of an effective amount of IL-2, an integrin-binding-Fc fusion protein, and a cancer vaccine.

Accordingly, in one aspect, the invention provides methods of treating a hyperproliferative disorder in a subject comprising administering to the subject a therapeutically effective amount of interleukin (IL)-2; an integrin-binding-Fc fusion protein; and a cancer vaccine, wherein the integrin-binding-Fc fusion protein comprises (i) an integrin-binding polypeptide comprising an integrin-binding loop and a knottin polypeptide scaffold; and (ii) an immunoglobulin Fc domain, wherein the integrin-binding polypeptide is operably linked to the Fc domain.

In another aspect, the invention provides a method for inhibiting growth and/or proliferation of tumor cells in a subject comprising administering to the subject an effective amount of (i) IL-2 or extended-PK IL-2; (ii) an integrin-binding-Fc fusion protein; and (iii) a cancer vaccine, wherein the integrin-binding-Fc fusion protein comprises (i) an integrin-binding polypeptide comprising an integrin-binding loop and a knottin polypeptide scaffold; and (ii) an immunoglobulin Fc domain, wherein the integrin-binding polypeptide is operably linked to the Fc domain, thereby inhibiting growth and/or proliferation of tumor cells in the subject.

In certain embodiments of the foregoing aspects, the IL-2 is an extended-PK IL-2. In certain embodiments of the foregoing aspects the extended-PK IL-2 comprises a fusion protein. In certain embodiments of the foregoing aspects, the fusion protein comprises an IL-2 moiety and a moiety selected from the group consisting of an immunoglobulin fragment (e.g., an immunoglobulin Fc domain), serum albumin (e.g., human serum albumin), transferrin, and Fn3, or variants thereof. In certain embodiments of the foregoing aspects, the IL-2 or extended-PK IL-2 comprises an IL-2 moiety conjugated to a non-protein polymer, such as polyethylene glycol. In certain embodiments of the foregoing aspects, the IL-2 or extended-PK IL-2 comprises an IL-2 moiety operably linked to an immunoglobulin Fc domain. In certain embodiments of the foregoing aspects, the IL-2 or extended-PK IL-2 comprises an IL-2 moiety operably linked to human serum albumin.

In certain embodiments of the foregoing aspects, the integrin-binding-Fc fusion protein includes an integrin-binding polypeptide that binds to a tumor associated integrin selected from the group consisting of $\alpha_v\beta_3$, $\alpha_v\beta_5$, and $\alpha_5\beta_1$, or combination thereof. In one embodiment, the integrin-binding polypeptide binds to $\alpha_v\beta_3$, $\alpha_v\beta_5$, and $\alpha_5\beta_1$.

In one embodiment of the foregoing aspects, the integrin-binding polypeptide includes an integrin-binding loop within a knottin polypeptide scaffold. In some embodiments, the knottin polypeptide scaffold comprises at least three cysteine disulfide linkages or crosslinked cysteine residues, and the integrin-binding loop is adjacent to cysteine residues of the knottin polypeptide scaffold. In one embodiment, the integrin-binding loop comprises an RGD peptide sequence. In another embodiment, the knottin polypeptide scaffold is derived from a knottin protein selected from the group consisting of EETI-II, AgRP, and agatoxin. In one embodiment, the knottin protein is EETI-II.

In one embodiment of the foregoing aspects, the integrin-binding polypeptide includes an integrin-binding loop comprising an RGD peptide sequence and the knottin polypeptide scaffold is derived from EETI-II.

In one embodiment of the foregoing aspects, the knottin polypeptide scaffold is derived from EETI-II and the integrin-binding loop comprises the sequence, $X_1X_2X_3RGDX_7X_8X_9X_{10}X_{11}$, wherein each X represents any amino acid, wherein the loop is inserted between 2 cysteine residues in the EETI-II sequence and replaces the native EETI-II sequence. In another embodiment, the integrin-binding loop is inserted after the first cysteine in the native EETI-II sequence.

In one embodiment of the foregoing aspects, the integrin-binding polypeptide comprises the amino acid sequence set forth in SEQ ID NO: 42 or 43, wherein $X_1$ is selected from the group consisting of A, V, L, P, F, Y, S, H, D, and N; $X_2$ is selected from the group consisting of G, V, L, P, R, E, and Q; $X_3$ is selected from the group consisting of G, A, and P; $X_7$ is selected from the group consisting of W and N; $X_8$ is selected from the group consisting of A, P, and S; $X_9$ is selected from the group consisting of P and R; $X_{10}$ is selected from the group consisting of A, V, L, P, S, T, and E; and $X_{11}$ is selected from the group consisting of G, A, W, S, T, K, and E. In a further embodiment, the integrin-binding-Fc fusion comprises an integrin-binding polypeptide, as set forth in SEQ ID NOs: 42 or 43, operably linked to a human IgG Fc domain, as set forth in SEQ ID NOs: 2 or 3.

In one embodiment of the foregoing aspects, the integrin-binding polypeptide comprises an amino acid sequence selected from the amino acid sequences set forth in Table 1. In another embodiment, the integrin-binding polypeptide comprises an amino acid sequence from the group consisting of SEQ ID NOs: 67-133. In a further embodiment, an integrin-binding polypeptide, set forth in Table 1, is operably linked to a human IgG1 Fc domain, set forth in SEQ ID NOs: 2 or 3.

In one embodiment of the foregoing aspects, the integrin-binding polypeptide comprises the amino acid sequence of SEQ ID NO: 93, 94, 95 or 96. In certain embodiments of the foregoing aspects, the integrin-binding polypeptide comprises the amino acid sequence of SEQ ID NO: 94 or 96.

In one embodiment of the foregoing aspects, the Fc domain is a human IgG1 Fc domain.

In one embodiment of the foregoing aspects, the integrin-binding polypeptide is operably linked with or without a linker to the Fc domain. In some embodiments, the integrin-binding polypeptide is linked to the N-terminus or C-terminus of the Fc domain without a linker. In other embodiments, the integrin-binding polypeptide is linked to the N-terminus or C-terminus of the Fc donor with a linker such as a Gly-Ser linker.

In one embodiment of the foregoing aspects, the integrin-binding-Fc fusion protein comprises the amino acid sequence of SEQ ID NO: 48, 49, 50 or 51.

In some embodiments, the integrin-binding-Fc fusion protein is in the form of a dimer.

In certain embodiments of the foregoing aspects, the cancer vaccine is a population of cells immunized in vitro with a tumor antigen and administered to the subject. In certain embodiments of the foregoing aspects, the cancer vaccine is an amphiphilic peptide conjugate comprising a tumor-associated antigen, and a lipid component, and optionally a linker, wherein the amphiphilic peptide conjugate binds albumin under physiological conditions. In certain embodiments of the foregoing aspects, the tumor-associated antigen is conjugated to a lipid via a linker, wherein the linker is selected from hydrophilic polymers, a string of hydrophilic amino acids, polysaccharides or a combination thereof. In certain embodiments of the foregoing aspects, the linker comprises "N" consecutive polyethylene glycol units, wherein N is between 25-50. In certain embodiments of the foregoing aspects, the lipid is a diacyl lipid. In certain embodiments of the foregoing aspects, the cancer vaccine further comprises an adjuvant, such as an amphiphilic oligonucleotide conjugate comprising an immunostimulatory oligonucleotide conjugated to a lipid (e.g., a diacyl lipid) with or without a linker (e.g., an oligonucleotide linker which comprises, e.g., "N" consecutive guanines, wherein N is between 0-2), and optionally a polar compound, wherein the conjugate binds albumin under physiological conditions. In certain embodiments of the foregoing aspects, the molecular adjuvant is an immunostimulatory oligonucleotide (e.g., an oligonucleotide comprising CpG) that can bind a pattern recognition receptor. In certain embodiments of the foregoing aspects, the immunostimulatory oligonucleotide is a ligand for a toll-like receptor.

In any of the foregoing aspects, the methods further comprise administering an immune checkpoint blocker. In certain embodiments, the immune checkpoint blocker targets the interaction between PD-1 and PD-L1, CTLA-4 and CD80 or CD86, LAG3 and MHC class II molecules, or TIM3 and galectin 9. In certain embodiments, the immune checkpoint blocker is an antibody or antibody fragment targeting PD-1, PD-L1, CTLA-4, TIM3, LAG3, or a member of the B7 family. In certain embodiments, the immune checkpoint blocker activates an anti-tumor immune response. In certain embodiments, the immune checkpoint blocker induces an increase in T cell proliferation, enhances T cell activation, and/or increases cytokine production (e.g., IFN-γ, IL-2). In one embodiment, the immune checkpoint blocker is an antibody or antibody fragment thereof targeting PD-1. In another embodiment, the immune checkpoint blocker is an antibody or antibody fragment targeting CTLA4.

In certain embodiments, an antagonist of VEGF is administered in place of an immune checkpoint blocker. In a further embodiment, the antagonist of VEGF is an antibody or antibody fragment thereof that binds VEGF, an antibody or antibody fragment thereof that binds VEGF receptor, a small molecule inhibitor of the VEGF receptor tyrosine kinases, a dominant negative VEGF, or a VEGF receptor.

In certain embodiments of the foregoing aspects, the IL-2 or extended-PK IL-2, integrin-binding-Fc fusion protein, cancer vaccine, and optional immune checkpoint blocker are administered simultaneously or sequentially.

In certain embodiments of the foregoing aspects, the IL-2 or extended-PK IL-2, integrin-binding-Fc fusion protein, cancer vaccine, and optional antagonist of VEGF are administered simultaneously or sequentially.

In certain embodiments of the foregoing aspects, the subject has a tumor. In certain embodiments of the foregoing aspects, the invention provides a method for increasing the number of interferon gamma expressing CD8+ T cells in a tumor. In another aspect, the invention provides a method for increasing the ratio of CD8+ T cells to T regulatory cells in the tumor.

In certain embodiments of the foregoing aspects, the hyperproliferative disorder treated by the methods disclosed herein is cancer, such as melanoma, leukemia, lymphoma, lung cancer, breast cancer, prostate cancer, ovarian cancer, colon cancer, mesothelioma, renal cell carcinoma, and brain cancer.

In another aspect, the invention provides methods for inhibiting growth and/or proliferation of tumor cells in a subject comprising administering to the subject an effective amount of an integrin-binding-Fc fusion protein, wherein the integrin-binding-Fc fusion protein comprises (i) an integrin-binding polypeptide comprising an integrin-binding loop and a knottin polypeptide scaffold; and (ii) an immunoglobulin Fc domain, wherein the integrin-binding polypeptide is operably linked to the Fc domain, and a cancer vaccine.

In other aspects, the invention provides methods for inhibiting growth and/or proliferation of tumor cells in a subject comprising administering to the subject an effective amount of an integrin-binding-Fc fusion protein, wherein the integrin-binding-Fc fusion protein comprises (i) an integrin-binding polypeptide comprising an integrin-binding loop and a knottin polypeptide scaffold; and (ii) an immunoglobulin Fc domain, wherein the integrin-binding polypeptide is operably linked to the Fc domain, a cancer vaccine, and an immune checkpoint blocker.

In certain embodiments of the foregoing aspects, the immune checkpoint blocker is an antibody or antibody fragment targeting a protein selected from the group consisting of PD-1, PD-L1, CTLA4, TIM3, LAGS, and a member of the B7 family. In certain embodiments, the immune checkpoint blocker is an antibody or antibody fragment targeting PD-1. In certain embodiments, the immune checkpoint blocker is an antibody or antibody fragment targeting CTLA4.

In another aspect, the invention provides methods for inhibiting growth and/or proliferation of tumor cells in a subject comprising administering to the subject an effective amount of an integrin-binding-Fc fusion protein, wherein the integrin-binding-Fc fusion protein comprises (i) an integrin-binding polypeptide comprising an integrin-binding loop and a knottin polypeptide scaffold; and (ii) an immunoglobulin Fc domain, wherein the integrin-binding polypeptide is operably linked to the Fc domain, a cancer vaccine, and an antagonist of VEGF.

In certain embodiments of the foregoing aspects, the antagonist of VEGF is an antibody or antibody fragment thereof that binds VEGF, an antibody or antibody fragment thereof that binds VEGF receptor, a small molecule inhibitor of the VEGF receptor tyrosine kinase, a dominant negative VEGF, or a VEGF receptor.

BRIEF DESCRIPTION OF THE DRAWINGS

FIG. 2A shows tumor size trajectories. FIG. 2B shows a Kaplan-Meier survival plot.

FIG. 24A shows tumor size trajectories for each treatment. FIG. 24B shows a Kaplan-Meier survival plot.

FIG. 25A shows tumor size trajectories for each treatment. FIG. 25B shows a Kaplan-Meier survival plot.

FIG. 26A shows tumor size trajectories for each treatment.

FIG. 26B shows a Kaplan-Meier survival plot.

FIG. 27A shows tumor size trajectories for each treatment. FIG. 27B shows a Kaplan-Meier survival plot.

28A shows tumor size trajectories for each treatment. FIG. 28B shows Kaplan-Meier survival plots.

FIG. 29A shows tumor size trajectories for previously cured mice and age-matched naïve mice following secondary tumor challenge. FIG. 29B shows a Kaplan-Meier plot of mice subjected to secondary tumor challenge.

FIG. 30A shows tumor size trajectories for each treatment. FIG. 30B shows a Kaplan-Meier survival plot.

FIG. 32A shows tumor size trajectories for each treatment. FIG. 32B shows Kaplan-Meier survival plots.

FIG. 35A shows tumor size trajectories for each treatment. FIG. 35B shows a Kaplan-Meier survival plot. A=knottin-Fc; I=MSA-IL=2; P=anti-PD-1; V=HPV-E7 cancer vaccine.

DETAILED DESCRIPTION

Overview

Figure 1A:
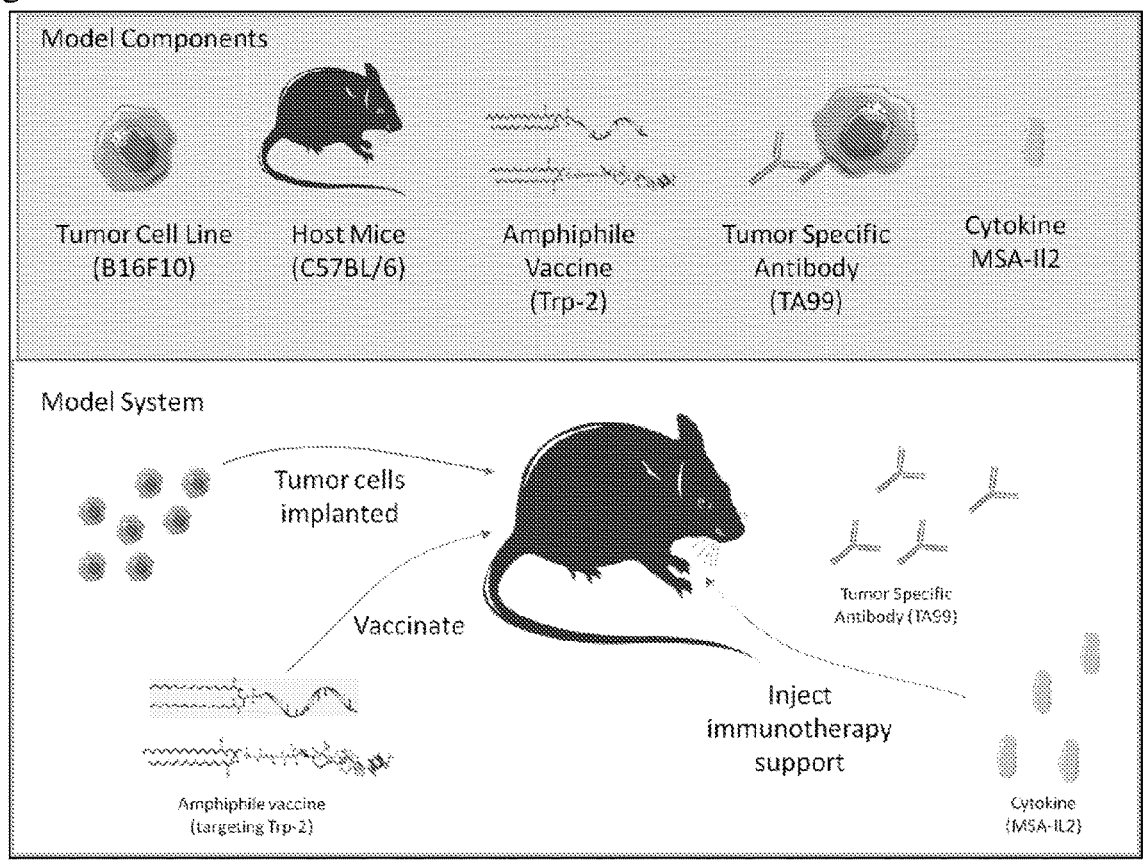
FIG. 1A is a schematic of the melanoma in vivo model depicting components for tumor establishment and treatment, as described in the Examples. B16F10 melanoma cells were injected into C57BL/6 mice. After tumor establishment, treatment was administered. Treatment included a combination of an amphiphile vaccine against Trp-2, a tumor specific antibody against Trp-1, an antigen overexpressed on melanoma cells (TA99), and MSA-IL-2.

Various diseases are characterized by the development of progressive immunosuppression in a patient. The presence of an impaired immune response in patients with malignancies has been particularly well documented. Cancer patients and tumor-bearing mice exhibit a variety of altered immune functions such as a decrease in delayed type hypersensitivity, a decrease in lytic function and proliferative response of lymphocytes. Augmenting immune functions in cancer patients could have beneficial effects for tumor control.

In one aspect, the present invention relates to a method of treating cancer comprising administering IL-2 (e.g., extended-PK IL-2), an integrin-binding-Fc fusion protein, a cancer vaccine, and optionally an immune checkpoint blocker. Each of these therapeutics individually target the immune system. In another aspect, the methods of the present invention prolong survival of subjects with cancer. In yet another aspect, the methods of the present invention inhibit metastases. In another aspect, the methods of the present invention reduce tumor size. In yet another aspect, the methods of the present invention inhibit the growth of tumor cells.

Definitions

Terms used in the claims and specification are defined as set forth below unless otherwise specified. In the case of direct conflict with a term used in a parent provisional patent application, the term used in the instant application shall control.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups {e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g. insertion of about three to about five or even up to about ten, fifteen, or twenty amino acid residues. The inserted residue (s) may be naturally occurring or non-naturally occurring as disclosed above. An "amino acid deletion" refers to the removal of at least one amino acid residue from a predetermined amino acid sequence.

"Polypeptide," "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene.

Polynucleotides used herein can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, "interleukin (IL)-2," refers to a pleiotropic cytokine that activates and induces proliferation of T cells and natural killer (NK) cells. IL-2 signals by binding its receptor, IL-2R, which is comprised of alpha, beta, and gamma subunits. IL-2 signaling stimulates proliferation of antigen-activated T cells.

As used herein, the term "PK" is an acronym for "pharmacokinetic" and encompasses properties of a compound including, by way of example, absorption, distribution, metabolism, and elimination by a subject. As used herein, an "extended-PK group" refers to a protein, peptide, or moiety that increases the circulation half-life of a biologically active molecule when fused to or administered together with the biologically active molecule. Examples of an extended-PK group include PEG, human serum albumin (HSA) binders (as disclosed in U.S. Publication Nos. 2005/0287153 and 2007/0003549, PCT Publication Nos. WO 2009/083804 and WO 2009/133208, and SABA molecules as described in US2012/094909), serum albumin (e.g., HSA), Fc or Fc fragments and variants thereof, transferrin and variants thereof, and sugars (e.g., sialic acid). Other exemplary extended-PK groups are disclosed in Kontermann et al., Current Opinion in Biotechnology 2011; 22:868-876, which is herein incorporated by reference in its entirety. As used herein, an "extended-PK IL-2" refers to an IL-2 moiety in combination with an extended-PK group. In one embodiment, the extended-PK IL-2 is a fusion protein in which an IL-2 moiety is linked or fused to an extended-PK group. An exemplary fusion protein is an HSA/IL-2 fusion in which one or more IL-2 moieties are linked to HSA.

The term "extended-PK IL-2" is also intended to encompass IL-2 mutants with mutations in one or more amino acid residues that enhance the affinity of IL-2 for one or more of its receptors, for example, CD25. In one embodiment, the IL-2 moiety of extended-PK IL-2 is wild-type IL-2. In another embodiment, the IL-2 moiety is a mutant IL-2 which exhibits greater affinity for CD25 than wild-type IL-2. When a particular type of extended-PK group is indicated, such as HSA-IL-2, it should be understood that this encompasses both HSA or MSA fused to a wild-type IL-2 moiety or HSA or MSA fused to a mutant IL-2 moiety.

In certain aspects, the extended-PK IL-2 or knottin-Fc described can employ one or more "linker domains," such as polypeptide linkers. As used herein, the term "linker" or "linker domain" refers to a sequence which connects two or more domains (e.g., the PK moiety and IL-2) in a linear sequence. As used herein, the term "polypeptide linker" refers to a peptide or polypeptide sequence (e.g., a synthetic peptide or polypeptide sequence) which connects two or more domains in a linear amino acid sequence of a polypeptide chain. For example, polypeptide linkers may be used to connect an IL-2 moiety to an Fc domain. Preferably, such polypeptide linkers can provide flexibility to the polypeptide molecule. In certain embodiments the polypeptide linker is used to connect (e.g., genetically fuse) one or more Fc domains and/or IL-2.

As used herein, the terms "linked," "fused", or "fusion", are used interchangeably. These terms refer to the joining together of two more elements or components or domains, by whatever means including chemical conjugation or recombinant means. Methods of chemical conjugation (e.g., using heterobifunctional crosslinking agents) are known in the art.

The term "integrin" means a transmembrane heterodimeric protein important for cell adhesion. Integrins comprise an α and β subunit. These proteins bind to extracellular matrix components (e.g., fibronectin, collagen, laminin, etc.) and respond by inducing signaling cascades. Integrins bind to extracellular matrix components by recognition of the RGD motif. Certain integrins are found on the surface of tumor cells and therefore make promising therapeutic targets. In certain embodiments, the integrins being targeted are $\alpha_v\beta_3$, $\alpha_v\beta_5$, and $\alpha_5\beta_1$, individually or in combination.

The term "integrin-binding polypeptide" refers to a polypeptide which includes an integrin-binding domain or loop within a knottin polypeptide scaffold. The integrin binding domain or loop includes at least one RGD peptide. In certain embodiments, the RGD peptide is recognized by $\alpha_v\beta_3$, $\alpha_v\beta_5$, or $\alpha_5\beta_1$. In certain embodiments the RGD peptide binds to a combination of $\alpha_v\beta_3$, $\alpha_v\beta_5$, and/or $\alpha_5\beta_1$. These specific integrins are found on tumor cells and their vasculature and are therefore the targets of interest.

The term "loop domain" refers to an amino acid subsequence within a peptide chain that has no ordered secondary structure, and resides generally on the surface of the peptide. The term "loop" is understood in the art as referring to secondary structures that are not ordered as in the form of an alpha helix, beta sheet, etc.

The term "integrin-binding loop" refers to a primary sequence of about 9-13 amino acids which is typically created ab initio through experimental methods such as directed molecular evolution to bind to integrins. In certain embodiments, the integrin-binding loop includes an RGD peptide sequence, or the like, placed between amino acids which are particular to the scaffold and the binding specificity desired. The RGD-containing peptide or like (RYD, etc) is generally not simply taken from a natural binding sequence of a known protein. The integrin-binding loop is preferably inserted within a knottin polypeptide scaffold between cysteine residues, and the length of the loop adjusted for optimal integrin-binding depending on the three-dimensional spacing between cysteine residues. For example, if the flanking cysteine residues in the knottin scaffold are linked to each other, the optimal loop may be shorter than if the flanking cysteine residues are linked to cysteine residues separated in primary sequence. Otherwise, particular amino acid substitutions can be introduced to constrain a longer RGD-containing loop into an optimal conformation for high affinity integrin binding. The knottin polypeptide scaffolds used herein may contain certain modifications made to truncate the native knottin, or to remove a loop or unnecessary cysteine residue or disulfide bond.

Incorporation of integrin-binding sequences into a molecular (e.g., knottin polypeptide) scaffold provides a framework for ligand presentation that is more rigid and stable than linear or cyclic peptide loops. In addition, the conformational flexibility of small peptides in solution is high, and results in large entropic penalties upon binding. Incorporation of an integrin-binding sequence into a knottin polypeptide scaffold provides conformational constraints that are required for high affinity integrin binding. Furthermore, the scaffold provides a platform to carry out protein engineering studies such as affinity or stability maturation.

As used herein, the term "knottin protein" refers to a structural family of small proteins, typically 25-40 amino acids, which bind to a range of molecular targets like proteins, sugars and lipids. Their three-dimensional structure is essentially defined by a peculiar arrangement of three to five disulfide bonds. A characteristic knotted topology with one disulfide bridge crossing the macro-cycle limited by the two other intra-chain disulfide bonds, which was found in several different microproteins with the same cystine network, lent its name to this class of biomolecules. Although their secondary structure content is generally low, the knottins share a small triple-stranded antiparallel β-sheet, which is stabilized by the disulfide bond framework. Biochemically well-defined members of the knottin family, also called cystine knot proteins, include the trypsin inhibitor EETI-II from Ecballium elaterium seeds, the neuronal N-type Ca2+ channel blocker ω-conotoxin from the venom of the predatory cone snail Conus geographus, agouti-related protein (AgRP, See Millhauser et al., "Loops and Links: Structural Insights into the Remarkable Function of the Agouti-Related Protein," Ann. N.Y. Acad. Sci., Jun. 1, 2003; 994(1): 27-35), the omega agatoxin family, etc. A suitable agatoxin sequence [SEQ ID NO: 41] is given in U.S. Pat. No. 8,536,301, having a common inventor with the present application. Other agatoxin sequences suitable for use in the methods disclosed herein include, Omega-agatoxin-Aa4b (GenBank Accession number P37045) and Omega-agatoxin-Aa3b (GenBank Accession number P81744). Other knottin sequences suitable for use in the methods disclosed herein include, knottin [Bemisia tabaci] (GenBank Accession number FJ601218.1), Omega-lycotoxin (Genbank Accession number P85079), mu-O conotoxin MrVIA=voltage-gated sodium channel blocker (Genbank Accession number AAB34917) and Momordica cochinchinensis Trypsin Inhibitor I (MCoTI-I) or II (McoTI-II) (Uniprot Accession numbers P82408 and P82409 respectively).

Knottin proteins have a characteristic disulfide linked structure. This structure is also illustrated in Gelly et al., "The KNOTTIN website and database: a new information system dedicated to the knottin scaffold," Nucleic Acids Research, 2004, Vol. 32, Database issue D156-D159. A triple-stranded β-sheet is present in many knottins. The spacing between cysteine residues is important, as is the molecular topology and conformation of the integrin-binding loop.

The term "molecular scaffold" means a polymer having a predefined three-dimensional structure, into which an integrin-binding loop is incorporated, such as an RGD peptide sequence as described herein. The term "molecular scaffold" has an art-recognized meaning (in other contexts), which is also intended here. For example, a review by Skerra, "Engineered protein scaffolds for molecular recognition," *J. Mol. Recognit.* 2000; 13:167-187 describes the following scaffolds: single domains of antibodies of the immunoglobulin superfamily, protease inhibitors, helix-bundle proteins, disulfide-knotted peptides and lipocalins. Guidance is given for the selection of an appropriate molecular scaffold.

The term "knottin polypeptide scaffold" refers to a knottin protein suitable for use as a molecular scaffold, as described herein. Characteristics of a desirable knottin polypeptide scaffold for engineering include 1) high stability in vitro and in vivo, 2) the ability to replace amino acid regions of the scaffold with other sequences without disrupting the overall fold, 3) the ability to create multifunctional or bispecific targeting by engineering separate regions of the molecule, and 4) a small size to allow for chemical synthesis and incorporation of non-natural amino acids if desired. Scaffolds derived from human proteins are favored for therapeutic applications to reduce toxicity or immunogenicity concerns, but are not always a strict requirement. Other scaffolds that have been used for protein design include fibronectin (Koide et al., 1998), lipocalin (Beste et al., 1999), cytotoxic T lymphocyte-associated antigen 4 (CTLA-4) (Hufton et al., 2000), and tendamistat (McConnell and Hoess, 1995; Li et al., 2003). While these scaffolds have proved to be useful frameworks for protein engineering, molecular scaffolds such as knottins have distinct advantages: their small size and high stability.

As used herein, the term "EETI" means Protein Data Bank Entry (PDB) 2ETI. Its entry in the Knottin database is EETI-II. It has the sequence:

(SEQ ID NO: 39)
GC PRILMRCKQDSDCLAGCVCGPNGFCG.

As used herein, the term "AgRP" means PDB entry 1HYK. Its entry in the Knottin database is SwissProt AGRP_HUMAN, where the full-length sequence of 129 amino acids may be found. It comprises the sequence beginning at amino acid 87. An additional G is added to this construct. It also includes a C105A mutation described in Jackson, et al. 2002 Biochemistry, 41, 7565.

(SEQ ID NO: 40)
GCVRLHESCLGQQVPCCDPCATCYC RFFNAF CYCR-KLGTAMNPCSRT

The bold and underlined portion, from loop 4, is replaced by the RGD sequences described herein. Loops 1 and 3 are shown between brackets below:

GC[VRLHES]CLGQQVPCC[DPCAT]CYCRFFNAFCYCR-

KLGTAMNPCSRT

As used herein, "integrin-binding-Fc fusion" is used interchangeably with "knottin-Fc" and refers to an integrin-binding polypeptide that includes an integrin-binding amino acid sequence within a knottin polypeptide scaffold and is operably linked to an Fc domain. In certain embodiments, the Fc domain is fused to the N-terminus of the integrin-binding polypeptide. In certain embodiments, the Fc domain is fused to the C-terminus of the integrin binding polypeptide. In some embodiments, the Fc domain is operably linked to the integrin-binding polypeptide via a linker.

As used herein, the term "Fc region" refers to the portion of a native immunoglobulin formed by the respective Fc domains (or Fc moieties) of its two heavy chains. As used herein, the term "Fc domain" refers to a portion of a single immunoglobulin (Ig) heavy chain wherein the Fc domain does not comprise an Fv domain. As such, an Fc domain can also be referred to as "Ig" or "IgG." In certain embodiments, an Fc domain begins in the hinge region just upstream of the papain cleavage site and ends at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In certain embodiments, an Fc domain comprises a complete Fc domain (i.e., a hinge domain, a CH2 domain, and a CH3 domain). In certain embodiments, an Fc domain comprises a hinge domain (or portion thereof) fused to a CH3 domain (or portion thereof). In certain embodiments, an Fc domain comprises a CH2 domain (or portion thereof) fused to a CH3 domain (or portion thereof). In certain embodiments, an Fc domain consists of a CH3 domain or portion thereof. In certain embodiments, an Fc domain consists of a hinge domain (or portion thereof) and a CH3 domain (or portion thereof). In certain embodiments, an Fc domain consists of a CH2 domain (or portion thereof) and a CH3 domain. In certain embodiments, an Fc domain consists of a hinge domain (or portion thereof) and a CH2 domain (or portion thereof). In certain embodiments, an Fc domain lacks at least a portion of a CH2 domain (e.g., all or part of a CH2 domain). An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. A human IgG1 constant region can be found at Uniprot P01857 and in Table 2 (i.e., SEQ ID NO: 1) The Fc domain of human IgG1 can be found in Table 2 (i.e., SEQ ID NO: 2). The Fc domain of human IgG1 with a deletion of the upper hinge region can be found in Table 2 (i.e., SEQ ID NO: 3). The Fc domain encompasses native Fc and Fc variant molecules. As with Fc variants and native Fc's, the term Fc domain includes molecules in monomeric or multimeric form, whether digested from whole antibody or produced by other means. The assignment of amino acid residue numbers to an Fc domain is in accordance with the definitions of Kabat. See, e.g., Sequences of Proteins of Immunological Interest (Table of Contents, Introduction and Constant Region Sequences sections), 5th edition, Bethesda, Md.:NIH vol. 1:647-723 (1991); Kabat et al., "Introduction" Sequences of Proteins of Immunological Interest, US Dept of Health and Human Services, NIH, 5th edition, Bethesda, Md. vol. 1:xiii-xcvi (1991); Chothia & Lesk, J. Mol. Biol. 196:901-917 (1987); Chothia et al., Nature 342:878-883 (1989), each of which is herein incorporated by reference for all purposes.

As set forth herein, it will be understood by one of ordinary skill in the art that any Fc domain may be modified such that it varies in amino acid sequence from the native Fc domain of a naturally occurring immunoglobulin molecule. In certain embodiments, the Fc domain has reduced effector function (e.g., FcγR binding).

The Fc domains of a polypeptide of the invention may be derived from different immunoglobulin molecules. For example, an Fc domain of a polypeptide may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide may have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants necessarily have less than 100% sequence identity or similarity with the starting molecule. In certain embodiments, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In certain embodiments, there is one amino acid difference between a starting polypeptide sequence and the sequence derived therefrom. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity.

In one embodiment, a polypeptide comprising IL-2 or a variant thereof, for use in extended-PK IL-2 consists of, consists essentially of, or comprises an amino acid sequence selected from SEQ ID Nos: 5, 7, 9, 11, 13, 15, 17, 19, 21, 23, 25, 27, 29, 31, 33, and 35. In an embodiment, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from SEQ ID Nos: 5, 7, 9, 11, 13, 15, 17, 19, 21, 23, 25, 27, 29, 31, 33, and 35. In an embodiment, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from SEQ ID Nos: 5, 7, 9, 11, 13, 15, 17, 19, 21, 23, 25, 27, 29, 31, 33, and 35. In an embodiment, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from SEQ ID Nos: 5, 7, 9, 11, 13, 15, 17, 19, 21, 23, 25, 27, 29, 31, 33, and 35.

In an embodiment, the peptides are encoded by a nucleotide sequence. Nucleotide sequences can be useful for a number of applications, including: cloning, gene therapy, protein expression and purification, mutation introduction, DNA vaccination of a host in need thereof, antibody generation for, e.g., passive immunization, PCR, primer and probe generation, and the like. In an embodiment, the nucleotide sequence of the invention comprises, consists of, or consists essentially of, a nucleotide sequence of IL-2, or a variant thereof, selected from SEQ ID Nos: 4, 6, 8, 10, 12, 14, 16, 18, 20, 22, 24, 26, 28, 30, 32, and 34. In an embodiment, a nucleotide sequence includes a nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence set forth in SEQ ID Nos: 4, 6, 8, 10, 12, 14, 16, 18, 20, 22, 24, 26, 28, 30, 32, and 34. In an embodiment, a nucleotide sequence includes a contiguous nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous nucleotide sequence set forth in SEQ ID Nos: 4, 6, 8, 10, 12, 14, 16, 18, 20, 22, 24, 26, 28, 30, 32, and 34. In an embodiment, a nucleotide sequence includes a nucleotide sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous nucleotides of a nucleotide sequence set forth in SEQ ID Nos: 4, 6, 8, 10, 12, 14, 16, 18, 20, 22, 24, 26, 28, 30, 32, and 34.

In one embodiment, a polypeptide comprising integrin-binding peptide or a variant thereof, consists of, consists essentially of, or comprises an amino acid sequence selected from SEQ ID Nos: 67-133. In an embodiment, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from SEQ ID Nos: 67-133. In an embodiment, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from SEQ ID Nos: 67-133. In an embodiment, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from SEQ ID Nos: 67-133.

It will also be understood by one of ordinary skill in the art that the IL-2 (e.g., extended-PK IL-2) or a knottin-Fc fusion suitable for use in the methods disclosed herein may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. Mutations may be introduced by standard techniques, such as site-directed mutagenesis and PCR-mediated mutagenesis.

The polypeptides described herein (e.g., IL-2, extended-PK IL-2, PK moieties, knottin, Fc, knottin-Fc, and the like) may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In certain embodiments, a string of amino acids can be replaced with a structurally similar string that differs in order and/or composition of side chain family members. Alternatively, in certain embodiments, mutations may be introduced randomly along all or part of a coding sequence, such as by saturation mutagenesis, and the resultant mutants can be incorporated into binding polypeptides of the invention and screened for their ability to bind to the desired target.

The term "ameliorating" refers to any therapeutically beneficial result in the treatment of a disease state, e.g., cancer, including prophylaxis, lessening in the severity or progression, remission, or cure thereof.

The term "in vivo" refers to processes that occur in a living organism.

The term "mammal" or "subject" or "patient" as used herein includes both humans and non-humans and includes, but is not limited to, humans, non-human primates, canines, felines, murines, bovines, equines, and porcines.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As used herein, the term "gly-ser polypeptide linker" refers to a peptide that consists of glycine and serine residues. An exemplary gly-ser polypeptide linker comprises the amino acid sequence Ser(Gly$_4$Ser)n (SEQ ID NO: 134). In certain embodiments, n=1. In certain embodiments, n=2. In certain embodiments, n=3, i.e., Ser(Gly$_4$Ser)3 (SEQ ID NO: 135). In certain embodiments, n=4, i.e., Ser(Gly$_4$Ser)4 (SEQ ID NO: 136). In certain embodiments, n=5. In certain embodiments, n=6. In certain embodiments, n=7. In certain embodiments, n=8. In certain embodiments, n=9. In certain embodiments, n=10. Another exemplary gly-ser polypeptide linker comprises the amino acid sequence (Gly$_4$Ser)n (SEQ ID NO: 137). In certain embodiments, n=1. In certain embodiments, n=2. In certain embodiments, n=3. In certain embodiments, n=4. In certain embodiments, n=5. In certain embodiments, n=6. Another exemplary gly-ser polypeptide linker comprises the amino acid sequence (Gly$_3$Ser)n (SEQ ID NO: 138). In certain embodiments, n=1. In certain embodiments, n=2. In certain embodiments, n=3. In certain embodiments, n=4. In certain embodiments, n=5. In certain embodiments, n=6.

As used herein, the terms "linked," "fused", or "fusion" are used interchangeably. These terms refer to the joining together of two or more elements or components or domains, by whatever means including chemical conjugation or recombinant means. Methods of chemical conjugation (e.g., using heterobifunctional crosslinking agents) are known in the art.

As used herein, "half-life" refers to the time taken for the serum or plasma concentration of a polypeptide to reduce by 50%, in vivo, for example due to degradation and/or clearance or sequestration by natural mechanisms. The extended-PK IL-2 suitable for use in the methods disclosed herein is stabilized in vivo and its half-life increased by, e.g., fusion to an Fc region, fusion to serum albumin (e.g., HSA or MSA), through PEGylation, or by binding to serum albumin molecules (e.g., human serum albumin) which resist degradation and/or clearance or sequestration. The half-life can be determined in any manner known per se, such as by pharmacokinetic analysis. Suitable techniques will be clear to the person skilled in the art, and may for example generally involve the steps of suitably administering a suitable dose of the amino acid sequence or compound to a subject; collecting blood samples or other samples from said subject at regular intervals; determining the level or concentration of the amino acid sequence or compound in said blood sample; and calculating, from (a plot of) the data thus obtained, the time until the level or concentration of the amino acid sequence or compound has been reduced by 50% compared to the initial level upon dosing. Further details are provided in, e.g., standard handbooks, such as Kenneth, A. et al., Chemical Stability of Pharmaceuticals: A Handbook for Pharmacists and in Peters et al., Pharmacokinetic Analysis: A Practical Approach (1996). Reference is also made to Gibaldi, M. et al., Pharmacokinetics, 2nd Rev. Edition, Marcel Dekker (1982).

A "therapeutic antibody" is an antibody, fragment of an antibody, or construct that is derived from an antibody, and can bind to a cell-surface antigen on a target cell to cause a therapeutic effect. Such antibodies can be chimeric, humanized or fully human antibodies. Methods are known in the art for producing such antibodies. Such antibodies include single chain Fc fragments of antibodies, minibodies and diabodies. Any of the therapeutic antibodies known in the art to be useful for cancer therapy can be used in the combination therapy suitable for use in the methods disclosed herein. Therapeutic antibodies may be monoclonal antibodies or polyclonal antibodies. In preferred embodiments, the therapeutic antibodies target cancer antigens.

As used herein, "cancer antigen" refers to (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

As used herein, a "small molecule" is a molecule with a molecular weight below about 500 Daltons.

As used herein, "therapeutic protein" refers to any polypeptide, protein, protein variant, fusion protein and/or fragment thereof which may be administered to a subject as a medicament. An exemplary therapeutic protein is an interleukin, e.g., IL-7.

As used herein, "synergy" or "synergistic effect" with regard to an effect produced by two or more individual components refers to a phenomenon in which the total effect produced by these components, when utilized in combination, is greater than the sum of the individual effects of each component acting alone.

The term "sufficient amount" or "amount sufficient to" means an amount sufficient to produce a desired effect, e.g., an amount sufficient to reduce the size of a tumor.

The term "therapeutically effective amount" is an amount that is effective to ameliorate a symptom of a disease. A therapeutically effective amount can be a "prophylactically effective amount" as prophylaxis can be considered therapy.

As used herein, "combination therapy" embraces administration of each agent or therapy in a sequential manner in a regimen that will provide beneficial effects of the combination, and co-administration of these agents or therapies in a substantially simultaneous manner, such as in a single capsule having a fixed ratio of these active agents or in multiple, separate capsules for each agent. Combination therapy also includes combinations where individual elements may be administered at different times and/or by different routes but which act in combination to provide a beneficial effect by co-action or pharmacokinetic and pharmacodynamics effect of each agent or tumor treatment approaches of the combination therapy.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein, "cancer vaccine" refers to a treatment that induces the immune system to attack cells with one or more tumor associated antigens. The vaccine can treat existing cancer (e.g., therapeutic cancer vaccine) or prevent the development of cancer in certain individuals (e.g., prophylactic cancer vaccine). The vaccine creates memory cells that will recognize tumor cells with the antigen and therefore prevent tumor growth. In certain embodiments, the cancer vaccine comprises an immunostimulatory oligonucleotide.

As used herein, an "immunostimulatory oligonucleotide" is an oligonucleotide that can stimulate (e.g., induce or enhance) an immune response.

As used herein, "CG oligodeoxynucleotides (CG ODNs)", also referred to as "CpG ODNs", are short single-stranded synthetic DNA molecules that contain a cytosine nucleotide (C) followed by a guanine nucleotide (G). In certain embodiments, the immunostimulatory oligonucleotide is a CG ODN.

As used herein, "immune cell" is a cell of hematopoietic origin and that plays a role in the immune response. Immune cells include lymphocytes (e.g., B cells and T cells), natural killer cells, and myeloid cells (e.g., monocytes, macrophages, eosinophils, mast cells, basophils, and granulocytes).

The term "T cell" refers to a CD4+ T cell or a CD8+ T cell. The term T cell encompasses TH1 cells, TH2 cells and TH17 cells.

The term "T cell cytoxicity" includes any immune response that is mediated by CD8+ T cell activation. Exemplary immune responses include cytokine production, CD8+ T cell proliferation, granzyme or perforin production, and clearance of an infectious agent.

The "Programmed Death-1 (PD-1)" receptor refers to an immuno-inhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. AAC51773 (SEQ ID NO: 52).

"Programmed Death Ligand-1 (PD-L1)" is one of two cell surface glycoprotein ligands for PD-1 (the other being PD-L2) that downregulates T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7 (SEQ ID NO: 53).

"Cytotoxic T Lymphocyte Associated Antigen-4 (CTLA-4)" is a T cell surface molecule and is a member of the immunoglobulin superfamily. This protein downregulates the immune system by binding to CD80 and CD86. The term "CTLA-4" as used herein includes human CTLA-4 (hCTLA-4), variants, isoforms, and species homologs of hCTLA-4, and analogs having at least one common epitope with hCTLA-4. The complete hCTLA-4 sequence can be found under GenBank Accession No. P16410 (SEQ ID NO: 54):

"Lymphocyte Activation Gene-3 (LAG3)" is an inhibitory receptor associated with inhibition of lymphocyte activity by binding to MHC class II molecules. This receptor enhances the function of Treg cells and inhibits CD8+ effector T cell function. The term "LAG3" as used herein includes human LAG3 (hLAG3), variants, isoforms, and species homologs of hLAG3, and analogs having at least one common epitope. The complete hLAG3 sequence can be found under GenBank Accession No. P18627 (SEQ ID NO: 55).

"T Cell Membrane Protein-3 (TIM3)" is an inhibitory receptor involved in the inhibition of lymphocyte activity by inhibition of $T_H1$ cells responses. Its ligand is galectin 9, which is upregulated in various types of cancers. The term "TIM3" as used herein includes human TIM3 (hTIM3), variants, isoforms, and species homologs of hTIM3, and analogs having at least one common epitope. The complete hTIM3 sequence can be found under GenBank Accession No. Q8TDQo (SEQ ID NO: 56).

The "B7 family" refers to inhibitory ligands with undefined receptors. The B7 family encompasses B7-H3 and B7-H4, both upregulated on tumor cells and tumor infiltrating cells. The complete hB7-H3 and hB7-H4 sequence can be found under GenBank Accession Nos. Q5ZPR3 and AAZ17406 (SEQ ID NOs: 57 and 58) respectively.

Vascular Endothelial Growth Factor (VEGF)" is a secreted disulfide-linked homodimer that selectively stimulates endothelial cells to proliferate, migrate, and produce matrix-degrading enzymes, all of which are processes required for the formation of new vessels. In addition to being the only known endothelial cell specific mitogen, VEGF is unique among angiogenic growth factors in its ability to induce a transient increase in blood vessel permeability to macromolecules. The term "VEGF" or "VEGF-A" is used to refer to the 165-amino acid human vascular endothelial cell growth factor and related 121-, 145-, 189-, and 206-amino acid human vascular endothelial cell growth factors, as described by, e.g., Leung et al. Science, 246: 1306 (1989), and Houck et al. Mol. Endocrin., 5: 1806 (1991), together with the naturally occurring allelic and processed forms thereof. VEGF-A is part of a gene family including VEGF-B, VEGF-C, VEGF-D, VEGF-E, VEGF-F, and P1GF. VEGF-A primarily binds to two high affinity receptor tyrosine kinases, VEGFR-1 (Flt-1) and VEGFR-2 (Flk-1/KDR), the latter being the major transmitter of vascular endothelial cell mitogenic signals of VEGF-A.

As used herein, "immune checkpoint" refers to co-stimulatory and inhibitory signals that regulate the amplitude and quality of T cell receptor recognition of an antigen. In certain embodiments, the immune checkpoint is an inhibitory signal. In certain embodiments, the inhibitory signal is the interaction between PD-1 and PD-L1. In certain embodiments, the inhibitory signal is the interaction between CTLA-4 and CD80 or CD86 to displace CD28 binding. In certain embodiments the inhibitory signal is the interaction between LAG3 and MHC class II molecules. In certain embodiments, the inhibitory signal is the interaction between TIM3 and galectin 9.

As used herein, "immune checkpoint blocker" refers to a molecule that totally or partially reduces, inhibits, interferes with or modulates one or more checkpoint proteins. In certain embodiments, the immune checkpoint blocker prevents inhibitory signals associated with the immune checkpoint. In certain embodiments, the immune checkpoint blocker is an antibody, or fragment thereof that disrupts inhibitory signaling associated with the immune checkpoint. In certain embodiments, the immune checkpoint blocker is a small molecule that disrupts inhibitory signaling. In certain embodiments, the immune checkpoint blocker is an antibody, fragment thereof, or antibody mimic, that prevents the interaction between checkpoint blocker proteins, e.g., an antibody, or fragment thereof, that prevents the interaction between PD-1 and PD-L1. In certain embodiments, the immune checkpoint blocker is an antibody, or fragment thereof, that prevents the interaction between CTLA-4 and CD80 or CD86. In certain embodiments, the immune checkpoint blocker is an antibody, or fragment thereof, that prevents the interaction between LAG3 and its ligands, or TIM-3 and its ligands. The checkpoint blocker may also be in the form of the soluble form of the molecules (or variants thereof) themselves, e.g., a soluble PD-L1 or PD-L1 fusion.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

It must be noted that, as used in the specification and the appended claims, the singular forms "a," "an" and "the" include plural referents unless the context clearly dictates otherwise.

IL-2 and Extended-PK IL-2

Interleukin-2 (IL-2) is a cytokine that induces proliferation of antigen-activated T cells and stimulates natural killer (NK) cells. The biological activity of IL-2 is mediated through a multi-subunit IL-2 receptor complex (IL-2R) of three polypeptide subunits that span the cell membrane: p55 (IL-2Rα, the alpha subunit, also known as CD25 in humans), p75 (IL-2Rβ, the beta subunit, also known as CD 122 in humans) and p64 (IL-2Rγ, the gamma subunit, also known as CD 132 in humans). T cell response to IL-2 depends on a variety of factors, including: (1) the concentration of IL-2; (2) the number of IL-2R molecules on the cell surface; and (3) the number of IL-2R occupied by IL-2 (i.e., the affinity of the binding interaction between IL-2 and IL-2R (Smith, "Cell Growth Signal Transduction is Quantal" In Receptor Activation by Antigens, Cytokines, Hormones, and Growth Factors 766:263-271, 1995)). The IL-2:IL-2R complex is internalized upon ligand binding and the different components undergo differential sorting. IL-2Rα is recycled to the cell surface, while IL-2 associated with the IL-2:IL-2Rβγ complex is routed to the lysosome and degraded. When administered as an intravenous (i.v.) bolus, IL-2 has a rapid systemic clearance (an initial clearance phase with a half-life of 12.9 minutes followed by a slower clearance phase with a half-life of 85 minutes) (Konrad et al., Cancer Res. 50:2009-2017, 1990).

However, in certain embodiments, IL-2 therapy, such as systemic IL-2 is administered to a subject in an effective amount in combination with an integrin-binding-Fc fusion protein, a cancer vaccine, and optionally an immune checkpoint blocker.

Outcomes of systemic IL-2 administration in cancer patients are far from ideal. While 15 to 20 percent of patients respond objectively to high-dose IL-2, the great majority do not, and many suffer severe, life-threatening side effects, including nausea, confusion, hypotension, and septic shock. The severe toxicity associated with high-dose IL-2 treatment is largely attributable to the activity of natural killer (NK) cells. NK cells express the intermediate-affinity receptor, IL-2Rβγ$_c$, and thus are stimulated at nanomolar concentrations of IL-2, which do in fact result in patient sera during high-dose IL-2 therapy. Attempts to reduce serum concentration, and hence selectively stimulate IL-2Rαβγ$_c$-bearing cells, by reducing dose and adjusting dosing regimen have been attempted, and while less toxic, such treatments were also less efficacious. Given the toxicity issues associated with high dose IL-2 cancer therapy, numerous groups have attempted to improve anti-cancer efficacy of IL-2 by simultaneously administering therapeutic antibodies. Yet, such efforts have been largely unsuccessful, yielding no additional or limited clinical benefit compared to IL-2 therapy alone. Accordingly, novel IL-2 therapies are needed to more effectively combat various cancers.

Applicants recently discovered that the ability of IL-2 to control tumors in various cancer models could be substantially increased by attaching IL-2 to a pharmacokinetic modifying group. The resulting molecule, hereafter referred to as "extended-pharmacokinetic (PK) IL-2," has a prolonged circulation half-life relative to free IL-2. The prolonged circulation half-life of extended-PK IL-2 permits in vivo serum IL-2 concentrations to be maintained within a therapeutic range, leading to the enhanced activation of many types of immune cells, including T cells. Because of its favorable pharmacokinetic profile, extended-PK IL-2 can be dosed less frequently and for longer periods of time when compared with unmodified IL-2. Extended-PK IL-2 is described in detail in International Patent Application NO. PCT/US2013/042057, filed May 21, 2013, and claiming the benefit of priority to U.S. Provisional Patent Application No. 61/650,277, filed May 22, 2012. The entire contents of the foregoing applications are incorporated by reference herein.

1. IL-2 and Mutants Thereof

In certain embodiments, an effective amount of human IL-2 is administered systemically. In some embodiments, an effective amount of an extended-PK IL-2 is administered systemically. In one embodiment, the IL-2 is a human recombinant IL-2 such as Proleukin® (aldesleukin). Proleukin® is a human recombinant interleukin-2 product produced in E. coli. Proleukin® differs from the native interleukin-2 in the following ways: a) it is not glycosylated; b) it has no N-terminal alanine; and c) it has serine substituted for cysteine at amino acid positions 125. Proleukin® exists as biologicially active, non-covalently bound microaggregates with an average size of 27 recombinant interleukin-2 molecules. Proleukin® (aldesleukin) is administered by intravenous infusion. In some aspects, the IL-2 portion of the extended-PK IL-2 is wild-type IL-2 (e.g., human IL-2 in its precursor form (SEQ ID NO: 33) or mature IL-2 (SEQ ID NO: 35)).

In certain embodiments, the extended-PK IL-2 is mutated such that it has an altered affinity (e.g., a higher affinity) for the IL-2R alpha receptor compared with unmodified IL-2.

Site-directed mutagenesis can be used to isolate IL-2 mutants that exhibit high affinity binding to CD25, i.e., IL-2Rα, as compared to wild-type IL-2. Increasing the affinity of IL-2 for IL-2Rα at the cell surface will increase receptor occupancy within a limited range of IL-2 concentration, as well as raise the local concentration of IL-2 at the cell surface.

In certain embodiments, the invention features IL-2 mutants, which may be, but are not necessarily, substantially purified and which can function as high affinity CD25 binders. IL-2 is a T cell growth factor that induces proliferation of antigen-activated T cells and stimulation of NK cells. Exemplary IL-2 mutants which are high affinity binders include those described in WO2013/177187A2 (herein incorporated by reference in its entirety), such as those with amino acid sequences set forth in SEQ ID NOs: 7, 23, 25, 27, 29, and 31. Further exemplary IL-2 mutants with increased affinity for CD25 are disclosed in U.S. Pat. No. 7,569,215, the contents of which are incorporated herein by reference. In one embodiment, the IL-2 mutant does not bind to CD25, e.g., those with amino acid sequences set forth in SEQ ID NOs: 9 and 11.

IL-2 mutants include an amino acid sequence that is at least 80% identical to SEQ ID NO: 33 that bind CD25. For example, an IL-2 mutant can have at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) that increases the affinity for the alpha subunit of the IL-2 receptor relative to wild-type IL-2. It should be understood that mutations identified in mouse IL-2 may be made at corresponding residues in full length human IL-2 (nucleic acid sequence (accession: NM000586) of SEQ ID NO: 32; amino acid sequence (accession: P60568) of SEQ ID NO: 33) or human IL-2 without the signal peptide (nucleic acid sequence of SEQ ID NO: 34; amino acid sequence of SEQ ID NO: 35). Accordingly, in certain embodiments, the IL-2 moiety of the extended-PK IL-2 is human IL-2. In other embodiments, the IL-2 moiety of the extended-PK IL-2 is a mutant human IL-2.

IL-2 mutants can be at least or about 50%, at least or about 65%, at least or about 70%, at least or about 80%, at least or about 85%, at least or about 87%, at least or about 90%, at least or about 95%, at least or about 97%, at least or about 98%, or at least or about 99% identical in amino acid sequence to wild-type IL-2 (in its precursor form or, preferably, the mature form). The mutation can consist of a change in the number or content of amino acid residues. For example, the IL-2 mutants can have a greater or a lesser number of amino acid residues than wild-type IL-2. Alternatively, or in addition, IL-2 mutants can contain a substitution of one or more amino acid residues that are present in the wild-type IL-2.

By way of illustration, a polypeptide that includes an amino acid sequence that is at least 95% identical to a reference amino acid sequence of SEQ ID NO: 33 is a polypeptide that includes a sequence that is identical to the reference sequence except for the inclusion of up to five alterations of the reference amino acid of SEQ ID NO: 33. For example, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino (N-) or carboxy (C-) terminal positions of the reference amino acid sequence or anywhere between those terminal positions, interspersed either individually among residues in the reference sequence or in one or more contiguous groups within the reference sequence.

The substituted amino acid residue(s) can be, but are not necessarily, conservative substitutions, which typically include substitutions within the following groups: glycine, alanine; valine, isoleucine, leucine; aspartic acid, glutamic acid; asparagine, glutamine; serine, threonine; lysine, arginine; and phenylalanine, tyrosine. These mutations can be at amino acid residues that contact IL-2Rα.

In general, the polypeptides suitable for use in the methods disclosed herein will be synthetic, or produced by expression of a recombinant nucleic acid molecule. In the event the polypeptide is an extended-PK IL-2 (e.g., a fusion protein containing at least IL-2 and a heterologous polypeptide, such as a hexa-histidine tag or hemagglutinin tag or an Fc region or human serum albumin), it can be encoded by a hybrid nucleic acid molecule containing one sequence that encodes IL-2 and a second sequence that encodes all or part of the heterologous polypeptide.

The techniques that are required to make IL-2 mutants are routine in the art, and can be performed without resort to undue experimentation by one of ordinary skill in the art. For example, a mutation that consists of a substitution of one or more of the amino acid residues in IL-2 can be created using a PCR-assisted mutagenesis technique (e.g., as known in the art and/or described herein for the creation of IL-2 mutants). Mutations that consist of deletions or additions of amino acid residues to an IL-2 polypeptide can also be made with standard recombinant techniques. In the event of a deletion or addition, the nucleic acid molecule encoding IL-2 is simply digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

In addition to generating IL-2 mutants via expression of nucleic acid molecules that have been altered by recombinant molecular biological techniques, IL-2 mutants can be chemically synthesized. Chemically synthesized polypeptides are routinely generated by those of skill in the art.

As noted above, IL-2 can also be prepared as fusion or chimeric polypeptides that include IL-2 and a heterologous polypeptide (i.e., a polypeptide that is not IL-2). The heterologous polypeptide can increase the circulating half-life of the chimeric polypeptide in vivo, and may, therefore, further enhance the properties of IL-2. As discussed in further detail infra, the polypeptide that increases the circulating half-life may be serum albumin, such as human or mouse serum albumin.

In certain embodiments, the chimeric polypeptide can include IL-2 and a polypeptide that functions as an antigenic tag, such as a FLAG sequence. FLAG sequences are recognized by biotinylated, highly specific, anti-FLAG antibodies, as described herein (see also Blanar et al., Science 256: 1014, 1992; LeClair et al., Proc. Natl. Acad. Sci. USA 89:8145, 1992). In certain embodiments, the chimeric polypeptide further comprises a C-terminal c-myc epitope tag.

Chimeric polypeptides can be constructed using no more than conventional molecular biological techniques, which are well within the ability of those of ordinary skill in the art to perform.

a. Nucleic Acid Molecules Encoding IL-2

IL-2, either alone or as a part of a chimeric polypeptide, such as those described herein, can be obtained by expression of a nucleic acid molecule. Thus, nucleic acid molecules encoding polypeptides containing IL-2 or an IL-2 mutant are considered within the scope of the invention, such as those with nucleic acid sequences set forth in SEQ ID Nos: 4, 6, 8, 10, 12, 14, 16, 18, 20, 22, 24, 26, 28, 30, 32, and 34. Just as IL-2 mutants can be described in terms of their identity with wild-type IL-2, the nucleic acid molecules encoding them will necessarily have a certain identity with those that encode wild-type IL-2. For example, the nucleic acid molecule encoding an IL-2 mutant can be at least 50%, at least 65%, preferably at least 75%, more preferably at least 85%, and most preferably at least 95% (e.g., 99%) identical to the nucleic acid encoding full length wild-type IL-2 (e.g., SEQ ID NO: 32 or wild-type IL-2 without the signal peptide (e.g., SEQ ID NO: 34).

The nucleic acid molecules suitable for use in the methods disclosed herein contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules are not limited to sequences that encode polypeptides; some or all of the non-coding sequences that lie upstream or downstream from a coding sequence (e.g., the coding sequence of IL-2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The isolated nucleic acid molecules can include fragments not found as such in the natural state. Thus, the invention encompasses use of recombinant molecules, such as those in which a nucleic acid sequence (for example, a sequence encoding an IL-2 mutant) is incorporated into a vector (e.g., a plasmid or viral vector) or into the genome of a heterologous cell (or the genome of a homologous cell, at a position other than the natural chromosomal location).

As described above, IL-2 mutants suitable for use in the methods disclosed herein may exist as a part of a chimeric polypeptide. In addition to, or in place of, the heterologous polypeptides described above, a nucleic acid molecule suitable for use in the methods disclosed herein can contain sequences encoding a "marker" or "reporter." Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-hosphotransferase (HPH), thymidine kinase (TK), lacz (encoding β-galactosidase), and xanthine guanine phosphoribosyl transferase (XGPRT). Skilled artisans will be aware of additional useful reagents, for example, of additional sequences that can serve the function of a marker or reporter.

The nucleic acid molecules suitable for use in the methods disclosed herein can be obtained by introducing a mutation into IL-2-encoding DNA obtained from any biological cell, such as the cell of a mammal. Thus, the nucleic acids (and the polypeptides they encode) can be those of a mouse, rat, guinea pig, cow, sheep, horse, pig, rabbit, monkey, baboon, dog, or cat. Typically, the nucleic acid molecules will be those of a human.

2. Extended-PK Groups

As described supra, IL-2 or mutant IL-2 is fused to an extended-PK group, which increases circulation half-life. Non-limiting examples of extended-PK groups are described infra. It should be understood that other PK groups that increase the circulation half-life of IL-2, or variants thereof, are also applicable to the present invention. In certain embodiments, the extended-PK group is a serum albumin domain (e.g., mouse serum albumin, human serum albumin).

In certain embodiments, the serum half-life of extended-PK IL-2 is increased relative to IL-2 alone (i.e., IL-2 not fused to an extended-PK group). In certain embodiments, the serum half-life of extended-PK IL-2 is at least 20, 40, 60, 80, 100, 120, 150, 180, 200, 400, 600, 800, or 1000% longer relative to the serum half-life of IL-2 alone. In certain embodiments, the serum half-life of the extended-PK IL-2 is at least 1.5-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of IL-2 alone. In certain embodiments, the serum half-life of the extended-PK IL-2 is at least 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours.

a. Serum Albumin and Serum Albumin Binding Proteins

In certain embodiments, the extended-PK group is a serum albumin, or fragments thereof. Methods of fusing serum albumin to proteins are disclosed in, e.g., US2010/0144599, US2007/0048282, and US2011/0020345, which are herein incorporated by reference in their entirety. In certain embodiments, the extended-PK group is HSA, or variants or fragments thereof, such as those disclosed in U.S. Pat. No. 5,876,969, WO 2011/124718, WO 2013/075066, and WO 2011/0514789.

In certain embodiments, the extended-PK group is a serum albumin binding protein such as those described in US2005/0287153, US2007/0003549, US2007/0178082, US2007/0269422, US2010/0113339, WO2009/083804, and WO2009/133208, which are herein incorporated by reference in their entirety.

b. PEGylation

In certain embodiments, an extended-PK IL-2 suitable for use in the methods disclosed herein includes a polyethylene glycol (PEG) domain. PEGylation is well known in the art to confer increased circulation half-life to proteins. Methods of PEGylation are well known and disclosed in, e.g., U.S. Pat. Nos. 7,610,156, 7,847,062, all of which are hereby incorporated by reference.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X-O(CH$_2$CH$_2$O)$_{n-1}$CH$_2$CH$_2$OH, where n is 20 to 2300 and X is H or a terminal modification, e.g., a C$_{1-4}$ alkyl. In certain embodiments, the PEG suitable for use in the methods disclosed herein terminates on one end with hydroxy or methoxy, i.e., X is H or CH$_3$ ("methoxy PEG"). PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462, both of which are hereby incorporated by reference. One form of PEGs includes two PEG side-chains (PEG2) linked via the primary amino groups of a lysine (Monfardini et al., Bioconjugate Chem 1995; 6:62-9).

In certain embodiments, pegylated IL-2 is produced by site-directed pegylation, particularly by conjugation of PEG to a cysteine moiety at the N- or C-terminus. A PEG moiety may also be attached by other chemistry, including by conjugation to amines.

PEG conjugation to peptides or proteins generally involves the activation of PEG and coupling of the activated PEG-intermediates directly to target proteins/peptides or to a linker, which is subsequently activated and coupled to target proteins/peptides (see Abuchowski et al., JBC 1977; 252:3571 and JBC 1977; 252:3582, and Harris et. al., in: Poly(ethylene glycol) Chemistry: Biotechnical and Biomedical Applications; (J. M. Harris ed.) Plenum Press: New York, 1992; Chap. 21 and 22).

A variety of molecular mass forms of PEG can be selected, e.g., from about 1,000 Daltons (Da) to 100,000 Da (n is 20 to 2300), for conjugating to IL-2. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

One skilled in the art can select a suitable molecular mass for PEG, e.g., based on how the pegylated IL-2 will be used therapeutically, the desired dosage, circulation time, resistance to proteolysis, immunogenicity, and other considerations. For a discussion of PEG and its use to enhance the properties of proteins, see N. V. Katre, Advanced Drug Delivery Reviews 1993; 10:91-114.

In certain embodiments, PEG molecules may be activated to react with amino groups on IL-2 such as with lysines (Bencham C. O. et al., Anal. Biochem., 131, 25 (1983); Veronese, F. M. et al., Appl. Biochem., 11, 141 (1985); Zalipsky, S. et al., Polymeric Drugs and Drug Delivery Systems, adrs 9-110 ACS Symposium Series 469 (1999); Zalipsky, S. et al., Europ. Polym. J., 19, 1177-1183 (1983); Delgado, C. et al., Biotechnology and Applied Biochemistry, 12, 119-128 (1990)).

In certain embodiments, carbonate esters of PEG are used to form the PEG-IL-2 conjugates. N,N'-disuccinimidylcarbonate (DSC) may be used in the reaction with PEG to form active mixed PEG-succinimidyl carbonate that may be subsequently reacted with a nucleophilic group of a linker or an amino group of IL-2 (see U.S. Pat. Nos. 5,281,698 and 5,932,462). In a similar type of reaction, 1,1'-(dibenzotriazolyl)carbonate and di-(2-pyridyl)carbonate may be reacted with PEG to form PEG-benzotriazolyl and PEG-pyridyl mixed carbonate (U.S. Pat. No. 5,382,657), respectively. Pegylation of IL-2 can be performed according to the methods of the state of the art, for example by reaction of IL-2 with electrophilically active PEGs (Shearwater Corp., USA, www.shearwatercorp.com). Preferred PEG reagents suitable for use in the methods disclosed herein are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini, C, et al., Bioconjugate Chem. 6 (1995) 62-69).

In certain embodiments, PEG molecules may be coupled to sulfhydryl groups on IL-2 (Sartore, L., et al., Appl. Biochem. Biotechnol., 27, 45 (1991); Morpurgo et al., Biocon. Chem., 7, 363-368 (1996); Goodson et al., Bio/Technology (1990) 8, 343; U.S. Pat. No. 5,766,897). U.S. Pat. Nos. 6,610,281 and 5,766,897 describe exemplary reactive PEG species that may be coupled to sulfhydryl groups.

In certain embodiments where PEG molecules are conjugated to cysteine residues on IL-2 the cysteine residues are native to IL-2 whereas in certain embodiments, one or more cysteine residues are engineered into IL-2. Mutations may be introduced into the coding sequence of IL-2 to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein.

In certain embodiments, pegylated IL-2 comprise one or more PEG molecules covalently attached to a linker.

In certain embodiments, IL-2 is pegylated at the C-terminus. In certain embodiments, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., C-Terminal Site-Specific PEGylation of a Truncated Thrombomodulin Mutant with Retention of Full Bioactivity, Bioconjug Chem. 2004; 15(5): 1005-1009.

Monopegylation of IL-2 can also be achieved according to the general methods described in WO 94/01451. WO 94/01451 describes a method for preparing a recombinant polypeptide with a modified terminal amino acid alpha-carbon reactive group. The steps of the method involve forming the recombinant polypeptide and protecting it with one or more biologically added protecting groups at the N-terminal alpha-amine and C-terminal alpha-carboxyl. The polypeptide can then be reacted with chemical protecting agents to selectively protect reactive side chain groups and thereby prevent side chain groups from being modified. The polypeptide is then cleaved with a cleavage reagent specific for the biological protecting group to form an unprotected terminal amino acid alpha-carbon reactive group. The unprotected terminal amino acid alpha-carbon reactive group is modified with a chemical modifying agent. The side chain protected terminally modified single copy polypeptide is then deprotected at the side chain groups to form a terminally modified recombinant single copy polypeptide. The number and sequence of steps in the method can be varied to achieve selective modification at the N- and/or C-terminal amino acid of the polypeptide.

The ratio of IL-2 to activated PEG in the conjugation reaction can be from about 1:0.5 to 1:50, between from about 1:1 to 1:30, or from about 1:5 to 1:15. Various aqueous buffers can be used to catalyze the covalent addition of PEG to IL-2, or variants thereof. In certain embodiments, the pH of a buffer used is from about 7.0 to 9.0. In certain embodiments, the pH is in a slightly basic range, e.g., from about 7.5 to 8.5. Buffers having a pKa close to neutral pH range may be used, e.g., phosphate buffer.

Conventional separation and purification techniques known in the art can be used to purify PEGylated IL-2, such as size exclusion (e.g. gel filtration) and ion exchange chromatography. Products may also be separated using SDS-PAGE. Products that may be separated include mono-, di-, tri-poly- and un-pegylated IL-2 as well as free PEG. The percentage of mono-PEG conjugates can be controlled by pooling broader fractions around the elution peak to increase the percentage of mono-PEG in the composition.

In certain embodiments, PEGylated IL-2 suitable for use in the methods disclosed herein contains one, two or more PEG moieties. In certain embodiments, the PEG moiety(ies) are bound to an amino acid residue which is on the surface of the protein and/or away from the surface that contacts CD25. In certain embodiments, the combined or total molecular mass of PEG in PEG-IL-2 is from about 3,000 Da to 60,000 Da, optionally from about 10,000 Da to 36,000 Da. In certain embodiments, PEG in pegylated IL-2 is a substantially linear, straight-chain PEG.

In certain embodiments, pegylated IL-2 suitable for use in the methods disclosed herein will preferably retain at least 25%, 50%, 60%, 70%, 80%, 85%, 90%, 95% or 100% of the biological activity associated with the unmodified protein. In certain embodiments, biological activity refers to the ability to bind CD25. The serum clearance rate of PEG-modified IL-2 may be decreased by about 10%, 20%, 30%, 40%, 50%, 60%, 70%, 80%, or even 90%, relative to the clearance rate of the unmodified IL-2. PEG-modified IL-2 may have a circulation half-life (t$\hat{}$) which is enhanced relative to the half-life of unmodified IL-2. The half-life of PEG-IL-2, or variants thereof, may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of unmodified IL-2. In certain embodiments, the protein half-life is determined in vitro, such as in a buffered saline solution or in serum. In certain embodiments, the protein half-life is an in vivo circulation half-life, such as the half-life of the protein in the serum or other bodily fluid of an animal.

c. Other Extended-PK Groups

In certain embodiments, the extended-PK group is transferrin, as disclosed in U.S. Pat. Nos. 7,176,278 and 8,158,579, which are herein incorporated by reference in their entirety.

In certain embodiments, the extended-PK group is a serum immunoglobulin binding protein such as those disclosed in US2007/0178082, which is herein incorporated by reference in its entirety.

In certain embodiments, the extended-PK group is a fibronectin (Fn)-based scaffold domain protein that binds to serum albumin, such as those disclosed in US2012/0094909, which is herein incorporated by reference in its entirety. Methods of making fibronectin-based scaffold domain proteins are also disclosed in US2012/0094909. A non-limiting example of a Fn3-based extended-PK group is Fn3(HSA), i.e., a Fn3 protein that binds to human serum albumin.

d. Fc Domains

In certain embodiments, an extended-PK IL-2 includes an Fc domain, as described in WO2013177187. The Fc domain does not contain a variable region that binds to antigen. Fc domains useful for producing the extended-PK IL-2 described herein may be obtained from a number of different sources. In certain embodiments, an Fc domain of the extended-PK IL-2 is derived from a human immunoglobulin. In a certain embodiment, the Fc domain is from a human IgG1 constant region (SEQ ID NO: 1). The Fc domain of human IgG1 is set forth in SEQ ID NO: 2. In certain embodiments, the Fc domain of human IgG1 does not have the upper hinge region (SEQ ID NO: 3). It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species. Moreover, the Fc domain or portion thereof may be derived from any immunoglobulin class, including IgM, IgG, IgD, IgA, and IgE, and any immunoglobulin isotype, including IgG1, IgG2, IgG3, and IgG4.

In some aspects, an extended-PK IL-2 includes a mutant Fc domain. In some aspects, an extended-PK IL-2 includes a mutant, IgG1 Fc domain. In some aspects, a mutant Fc domain comprises one or more mutations in the hinge, CH2, and/or CH3 domains. In some aspects, a mutant Fc domain includes a D265A mutation.

In one embodiment, the extended-PK IL-2 of the invention lacks one or more constant region domains of a complete Fc region, i.e., they are partially or entirely deleted. In certain embodiments, the extended-PK IL-2 of the invention will lack an entire CH2 domain. In certain embodiments, the extended-PK IL-2 of the invention comprise CH2 domain-deleted Fc regions derived from a vector (e.g., from IDEC Pharmaceuticals, San Diego) encoding an IgG1 human constant region domain (see, e.g., WO02/060955A2 and WO02/096948A2). This exemplary vector is engineered to delete the CH2 domain and provide a synthetic vector expressing a domain-deleted IgG1 constant region. It will be noted that these exemplary constructs are preferably engineered to fuse a binding CH3 domain directly to a hinge region of the respective Fc domain.

Integrin-Binding-Fc Fusion Proteins

Integrins are a family of extracellular matrix adhesion receptors that regulate a diverse array of cellular functions crucial to the initiation, progression and metastasis of solid tumors. The importance of integrins in tumor progression has made them an appealing target for cancer therapy and allows for the treatment of a variety of cancer types. The integrins present on cancerous cells include $\alpha_v\beta_3$, $\alpha_v\beta_5$, and $\alpha_5\beta_1$.

Knottin proteins are small compact peptides that have high thermal and proteolytic stability and are tolerant to mutagenesis, making them good molecular scaffolds. These peptides contain at least 3 disulfide bonds that form a "knot" core. They also contain several loops exposed to the surface, allowing these loops to bind targets. These loops can be engineered to bind specific targets with high affinity, making them a useful tool for therapy.

The present invention involves the use of a knottin polypeptide scaffold engineered with an RGD sequence capable of binding integrins, fused to an Fc donor, which confers a therapeutic benefit (also referred to as "knottin-Fc"). As described supra, Fc fragments have been added to proteins and/or therapeutics to extend half-life. In the context of knottin-Fc as used herein, the effector function of Fc contributes to the treatment of a variety of cancers when used in conjunction with systemic IL-2, such as extended-PK IL-2. In certain embodiments, a knottin-Fc that binds two integrins simultaneously is used (2.5D, SEQ ID NO: 93 or 95). In certain embodiments, a knottin-Fc that binds three integrins simultaneously, reflected in Table 1, is used (2.5F, SEQ ID NO: 94 or 96).

1. Methods of Engineering Knottin Polypeptide Scaffolds

Knottin polypeptide scaffolds are used to insert an integrin-binding sequence, preferably in the form of a loop, to confer specific integrin binding. Integrin-binding is preferably engineered into a knottin polypeptide scaffold by inserting an integrin-binding peptide sequence, such as an RGD peptide. In some embodiments, insertion of an integrin-binding peptide sequence results in replacement of portion of the native knottin protein. For example, in one embodiment an RGD peptide sequence is inserted into a native solvent exposed loop by replacing all or a portion of the loop with an RGD-containing peptide sequence (e.g., 5-12 amino acid sequence) that has been selected for binding to one or more integrins. The solvent-exposed loop (i.e., on the surface) will generally be anchored by disulfide-linked cysteine residues in the native knottin protein sequence. The integrin-binding replacement amino acid sequence can be obtained by randomizing codons in the loop portion, expressing the engineered peptide, and selecting the mutants with the highest binding to the predetermined ligand. This selection step may be repeated several times, taking the tightest binding proteins from the previous step and re-randomizing the loops.

Integrin-binding polypeptides may be modified in a number of ways. For example, the polypeptide may be further cross-linked internally, or may be cross-linked to each other, or the RGD loops may be grafted onto other cross linked molecular scaffolds. There are a number of commercially available crosslinking reagents for preparing protein or peptide bioconjugates. Many of these crosslinkers allow dimeric homo- or heteroconjugation of biological molecules through free amine or sulfhydryl groups in protein side chains. More recently, other crosslinking methods involving coupling through carbohydrate groups with hydrazide moieties have been developed. These reagents have offered convenient, facile, crosslinking strategies for researchers with little or no chemistry experience in preparing bioconjugates.

The EETI-II knottin protein (SEQ ID NO: 39) contains a disulfide knotted topology and possesses multiple solvent-exposed loops that are amenable to mutagenesis. Preferred embodiments use EETI-II as the molecular scaffold.

Another example of a knottin protein which can be used as a molecular scaffold is AgRP or agatoxin. The amino acid sequences of AgRP (SEQ ID NO: 40) and agatoxin (SEQ ID NO: 41) differ but their structure is identical. Exemplary AgRP knottins are found in Table 1.

Additional AgRP engineered knottins can be made as described in the above-referenced US 2009/0257952 to Cochran et al. (the contents of which are incorporated herein by reference). AgRP knottin fusions can be prepared using AgRP loops 1, 2 and 3, as well as loop 4 as exemplified above.

The present polypeptides may be produced by recombinant DNA or may be synthesized in solid phase using a peptide synthesizer, which has been done for the peptides of all three scaffolds described herein. They may further be capped at their N-termini by reaction with fluorescein isothiocyanate (FITC) or other labels, and, still further, may be synthesized with amino acid residues selected for additional crosslinking reactions. TentaGel S RAM Fmoc resin (Advanced ChemTech) may be used to give a C-terminal amide upon cleavage. B-alanine is used as the N-terminal amino acid to prevent thiazolidone formation and release of fluorescein during peptide deprotection (Hermanson, 1996). Peptides are cleaved from the resin and side-chains are deprotected with 8% trifluoroacetic acid, 2% triisopropylsilane, 5% dithiothreitol, and the final product is recovered by ether precipitation. Peptides are purified by reverse phase HPLC using an acetonitrile gradient in 0.1% trifluoroacetic acid and a C4 or C18 column (Vydac) and verified using matrix-assisted laser desorption/ionization time-of-flight mass spectrometry (MALDI-TOF) or electro spray ionization-mass spectrometry (ESI-MS).

When the present peptides are produced by recombinant DNA, expression vectors encoding the selected peptide are transformed into a suitable host. The host should be selected to ensure proper peptide folding and disulfide bond formation as described above. Certain peptides, such as EETI-II, can fold properly when expressed in prokaryotic hosts such as bacteria.

Dimeric, trimeric, and tetrameric complexes of the present peptides can be formed through genetic engineering of the above sequences or by reaction of the synthetic cross-linkers with engineered peptides carrying an introduced cysteine residue, for example on the C-terminus of the peptide. These oligomeric peptide complexes can be purified by gel filtration. Oligomers of the present peptides can be prepared by preparing vectors encoding multiple peptide sequences end-to-end. Also, multimers may be prepared by complexing the peptides, such as, e.g., described in U.S. Pat. No. 6,265,539. There, an active HIV peptide is prepared in multimer form by altering the amino-terminal residue of the peptide so that it is peptide-bonded to a spacer peptide that contains an amino-terminal lysyl residue and one to about five amino acid residues such as glycyl residues to form a composite polypeptide. Alternatively, each peptide is synthesized to contain a cysteine (Cys) residue at each of its amino- and carboxy-termini. The resulting di-cysteine-terminated (di-Cys) peptide is then oxidized to polymerize the di-Cys peptide monomers into a polymer or cyclic peptide multimer. Multimers may also be prepared by solid phase peptide synthesis utilizing a lysine core matrix. The present peptides may also be prepared as nanoparticles. See, "Multivalent Effects of RGD Peptides Obtained by Nanoparticle Display," Montet, et al., J. Med. Chem.; 2006; 49(20) pp 6087-6093. EETI dimerization may be carried out with the present EETI-II peptides according to the EETI-II dimerization paper: "Grafting of thrombopoietin-mimetic peptides into cystine knot miniproteins yields high-affinity thrombopoietin antagonist and agonists," Krause, et al., FEBS Journal; 2006; 274 pp 86-95. This is further described in PCT application No. PCT/US2013/065610, herein incorporated by reference.

Synergistic sites on fibronectin and other adhesion proteins have been identified for enhanced integrin binding (Ruoslahti, 1996; Koivunen et al., 1994; Aota et al., 1994; Healy et al., 1995). The ability to incorporate different integrin-specific motifs into one soluble molecule would have an important impact on therapeutic development. Crosslinkers with heterofunctional specificity may be used for creating integrin-binding proteins with synergistic binding effects. In addition, these same crosslinkers could easily be used to create bispecific targeting molecules, or as vehicles for delivery of radionuclides or toxic agents for therapeutic applications.

a. Integrin-Binding Peptides

The integrin-binding polypeptides for use in Fc fusions include an integrin-binding loop (e.g., RGD peptide sequence) and a knottin polypeptide scaffold. Such integrin-binding polypeptides are described in U.S. Pat. No. 8,536,301, the contents of which are incorporated herein by reference. As described in U.S. Pat. No. 8,536,301, integrin-binding polypeptides may be varied in the non-RGD residues to a certain degree without affecting binding specificity and potency. For example, if three of the eleven residues were varied, one would have about 70% identity to 2.5D. Table 1 shows exemplary integrin-binding polypeptides within the scope of the invention, and their specific knottin polypeptide scaffold (e.g., EETI-II or AgRP). Preferred integrin-binding polypeptides for use in Fc fusions are peptides 2.5D and 2.5F.

In certain embodiments, the integrin-binding polypeptide binds to $\alpha_v\beta_3$, $\alpha_v\beta_5$, or $\alpha_5\beta_1$ separately.

In certain embodiments, the integrin-binding polypeptide binds to $\alpha_v\beta_3$ and $\alpha_v\beta_5$ simultaneously.

In certain embodiments, the integrin-binding polypeptide binds to $\alpha_v\beta_3$, $\alpha_v\beta_5$, and $\alpha_5\beta_1$ simultaneously.

In certain embodiments, the integrin-binding loop is within an engineered EETI-II scaffold. In certain embodiments, the lysine in position 15 of the EETI-II scaffold is replaced with a serine. In certain embodiments, the integrin-binding polypeptide comprises the amino acid sequence set forth in SEQ ID NO: 42 or 43, wherein $X_1$ is selected from the group consisting of A, V, L, P, F, Y, S, H, D, and N; $X_2$ is selected from the group consisting of G, V, L, P, R, E, and Q; $X_3$ is selected from the group consisting of G, A, and P;

$X_7$ is selected from the group consisting of W and N; $X_8$ is selected from the group consisting of A, P, and S; $X_9$ is selected from the group consisting of P and R; $X_{10}$ is selected from the group consisting of A, V, L, P, S, T, and E; and $X_{11}$ is selected from the group consisting of G, A, W, S, T, K, and E. In a further embodiment, the integrin-binding-Fc fusion comprises an integrin-binding polypeptide, as set forth in SEQ ID Nos: 42 or 43, operably linked to a human IgG Fc domain, as set forth in SEQ ID Nos: 2 or 3.

In certain embodiments, the integrin-binding loop is within an engineered AgRP or agatoxin scaffold.

In certain embodiments, the integrin-binding polypeptide is 2.5D and 2.5F, disclosed in Table 1. Any of the integrin-binding polypeptides in Table 1 can be used in Fc fusion as described herein.

TABLE 1

Integrin Binding Knottin Sequences

| SEQ ID NO | Peptide Identifier | Scaffold | Sequence (RGD motif is underlined with flanking residues) |
|---|---|---|---|
| 67 | 3 | EETI-II | GCAEPRGDMPWTWCKQDSDCLAGCVCGPNGFCG |
| 68 | 1.4B | EETI-II | GCVGGRGDWSPKWCKQDSDCPAGCVCGPNGFCG |
| 69 | 1.4C | EETI-II | GCAELRGDRSYPECKQDSDCLAGCVCGPNGFCG |
| 70 | 1.4E | EETI-II | GCRLPRGDVPRPHCKQDSDCQAGCVCGPNGFCG |
| 71 | 1.4H | EETI-II | GC YPLRGDNPYAA CKQDSDCRAGCVCGPNGFCG |
| 72 | 1.5B | EETI-II | GCTIGRGDWAPSE CKQDSDCLAGCVCGPNGFCG |
| 73 | 1.5F | EETI-II | GCHPPRGDNPPVT CKQDSDCLAGCVCGPNGFCG |
| 74 | 2.3A | EETI-II | GCPEPRGDNPPPSCKQDSDCRAGCVCGPNGFCG |
| 75 | 2.3B | EETI-II | GCLPPRGDNPPPSCKQDSDCQAGCVCGPNGFCG |
| 76 | 2.3C | EETI-II | GCHLGRGDWAPVGCKQDSDCPAGCVCGPNGFCG |
| 77 | 2.3D | EETI-II | GCNVGRGDWAPSECKQDSDCPAGCVCGPNGFCG |
| 78 | 2.3E | EETI-II | GCFPGRGDWAPSSCKQDSDCRAGCVCGPNGFCG |
| 79 | 2.3F | EETI-II | GCPLPRGDNPPTECKQDSDCQAGCVCGPNGFCG |
| 80 | 2.3G | EETI-II | GCSEARGDNPRLSCKQDSDCRAGCVCGPNGFCG |
| 81 | 2.3H | EETI-II | GCLLGRGDWAPEACKQDSDCRAGCVCPNGFCG |
| 82 | 2.3I | EETI-II | GCHVGRGDWAPLKCKQDSDCQAGCVCGPNGFCG |
| 83 | 2.3J | EETI-II | GCVRGRGDWAPPSCKQDSDCPAGCVCGPNGFCG |
| 84 | 2.4A | EETI-II | GCLGGRGDWAPPACKQDSDCRAGCVCGPNGFCG |
| 85 | 2.4C | EETI-II | GCFVGRGDWAPLTCKQDSDCQAGCVCGPNGFCG |
| 86 | 2.4D | EETI-II | GCPVGRGDWSPASCKQDSDCRAGCVCGPNGFCG |
| 87 | 2.4E | EETI-II | GCPRPRGDNPPLTCKQDSDCLAGCVCGPNGFCG |
| 88 | 2.4F | EETI-II | GCYOGRGDWSPSSCKQDSDCPAGCVCGPNGFCG |
| 89 | 2.4G | EETI-II | GCAPGRGDWAPSECKQDSDCQAGCVCGPNGFCG |
| 90 | 2.4J | EETI-II | GCVQGRGDWSPPSCKQDSDCPAGCVCGPNGFCG |
| 91 | 2.5A | EETI-II | GCHVGRGDWAPEECKQDSDCQAGCVCGPNGFCG |
| 92 | 2.5C | EETI-II | GCDGGRGDWAPPACKQDSDCRAGCVCGPNGFCG |
| 93 | 2.5D | EETI-II | GCPQGRGDWAPTSCKQDSDCRAGCVCGPNGFCG |
| 94 | 2.5F | EETI-II | GCPRPRGDNPPLT CKQDSDCLAGCVCGPNGFCG |
| 95 | 2.5D K15S Mutant | EETI-II | GCPQGRGDWAPTSCSQDSDCLAGCVCGPNGFCG |

TABLE 1-continued

Integrin Binding Knottin Sequences

| SEQ ID NO | Peptide Identifier | Scaffold | Sequence (RGD motif is underlined with flanking residues) |
|---|---|---|---|
| 96 | 2.5F K15S Mutant | EETI-II | GCPRPRGDNPPLTCSQDSDCLAGCVCGPNGFCG |
| 97 | 2.5H | EETI-II | GCPQGRGDWAPEWCKQDSDCPAGCVCGPNGFCG |
| 98 | 2.5J | EETI-II | GCPRGRGDWSPPACKQDSDCQAGCVCGPNGFCG |
| 99 | 3A | AgRp | GCVRLHESCLGQQVPCCDPAATCYCVVRGDWRKRCYCR |
| 100 | 3B | AgRp | GCVRLHESCLGQQVPCCDPAATCYCEERGDMLEKCYCR |
| 101 | 3C | AgRp | GCVRLHESCLGQQVPCCDPAATCYCETRGDGKEKCYCR |
| 102 | 3D | AgRp | GCVRLHESCLGQQVPCCDPAATCYCQWRGDGDVKCYCR |
| 103 | 3E | AgRp | GCVRLHESCLGQQVPCCDPAATCYCSRRGDMRERCYCR |
| 104 | 3F | AgRp | GCVRLHESCLGQQVPCCDPAATCYCQYRGDGMKHCYCR |
| 105 | 3G | AgRp | GCVRLHESCLGQQVPCCDPAATCYCTGRGDTKVLCYCR |
| 106 | 3H | AgRp | GCVRLHESCLGQQVPCCDPAATCYCVERGDMKRRCYCR |
| 107 | 3I | AgRp | GCVRLHESCLGQQVPCCDPAATCYCTGRGDVRMNCYCR |
| 108 | 3J | AgRp | GCVRLHESCLGQQVPCCDPAATCYCVERGDGMSKCYCR |
| 109 | 4A | AgRp | GCVRLHESCLGQQVPCCDPAATCYCRGRGDMRRECYCR |
| 110 | 4B | AgRp | GCVRLHESCLGQQVPCCDPAATCYCEGRGDVKVNCYCR |
| 111 | 4C | AgRp | GCVRLHESCLGQQVPCCDPAATCYCVGRGDEKMSCYCR |
| 112 | 4D | AgRp | GCVRLHESCLGQQVPCCDPAATCYCVSRGDMRKRCYCR |
| 113 | 4E | AgRp | GCVRLHESCLGQQVPCCDPAATCYCERRGDSVKKCYCR |
| 114 | 4F | AgRp | GCVRLHESCLGQQVPCCDPAATCYCEGRGDTRRRCYCR |
| 115 | 4G | AgRp | GCVRLHESCLGQQVPCCDPAATCYCEGRGDVVRRCYCR |
| 116 | 4H | AgRp | GCVRLHESCLGQQVPCCDPAATCYCKGRGDNKRKCYCR |
| 117 | 4I | AgRp | GCVRLHESCLGQQVPCCDPAXTCYCKGRGDVRRVCYCR |
| 118 | 4J | AgRp | GCVRLHESCLGQQVPCCDPAATCYCVGRGDNKVKCYCR |
| 119 | 5A | AgRp | GCVRLHESCLGQQVPCCDPAATCYCVGRGDNRLKCYCR |
| 120 | 5B | AgRp | GCVRLHESCLGQQVPCCDPAATCYCVERGDGMKKCYCR |
| 121 | 5C | AgRp | GCVRLHESCLGQQVPCCDPAATCYCEGRGDMRRRCYCR |
| 122 | 5D | AgRp | GCVRLHESCLGQQVPCCDPAATCYCQGRGDGDVKCYCR |
| 123 | 5E | AgRp | GCVRLHESCLGQQVPCCDPAATCYCSGRGDNDLVCYCR |
| 124 | 5F | AgRp | GCVRLHESCLGQQVPCCDPAATCYCVERGDGMIRCYCR |
| 125 | 5G | AgRp | GCVRLHESCLGQQVPCCDPAATCYC SGRGDNDLVCYCR |
| 126 | 5H | AgRp | GCVRLHESCLGQQVPCCDPAATCYCEGRGDMKMKCYCR |
| 127 | 5I | AgRp | GCVRLHESCLGQQVPCCDPAATCYCIGRGDVRRRCYCR |
| 128 | 5J | AgRp | GCVRLHESCLGQQVPCCDPAATCYCEERGDGRKKCYCR |
| 129 | 6B | AgRp | GCVRLHESCLGQQVPCCDPAATCYCEGRGDRDMKCYCR |
| 130 | 6C | AgRp | GCVRLHESCLGQQVPCCDPAATCYCTGRGDEKLRCYCR |
| 131 | 6E | AgRp | GCVRLHESCLGQQVPCCDPAATCYCVERGDGNRRCYCR |

TABLE 1 -continued

Integrin Binding Knottin Sequences

| SEQ ID NO | Peptide Identifier | Scaffold | Sequence (RGD motif is underlined with flanking residues) |
|---|---|---|---|
| 132 | 6F | AgRp | GCVRLHESCLGQQVPCCDPAATCYCESRGDVVRKCYCR |
| 133 | 7C | AgRp | GCVRLHESCLGQQVPCCDPAATCYCYGRGDNDLRCYCR |

The present polypeptides target $\alpha_v\beta_3$, $\alpha_v\beta_5$, and in some cases $\alpha_5\beta_1$ integrin receptors. They do not bind to other integrins tested, such as $\alpha_{IIb}\beta_3$, where there was little to no affinity. Thus, these engineered integrin-binding polypeptides have broad diagnostic and therapeutic applications in a variety of human cancers that specifically overexpress the above named integrins. As described below, these polypeptides bind with high affinity to both detergent-solubilized and tumor cell surface integrin receptors.

The $\alpha_v\beta_3$ (and $\alpha_v\beta_5$) integrins are also highly expressed on many tumor cells including osteosarcomas, neuroblastomas, carcinomas of the lung, breast, prostate, and bladder, glioblastomas, and invasive melanomas The $\alpha_v\beta_3$ integrin has been shown to be expressed on tumor cells and/or the vasculature of breast, ovarian, prostate, and colon carcinomas, but not on normal adult tissues or blood vessels. Also, the $\alpha_5\beta_1$ integrin has been shown to be expressed on tumor cells and/or the vasculature of breast, ovarian, prostate, and colon carcinomas, but not on normal adult tissue or blood vessels. The present, small, conformationally-constrained polypeptides (about 33 amino acids) are so constrained by intramolecular bonds. For example, EETI-II has three disulfide linkages. This will make it more stable in vivo. These peptides target $\alpha_v$ integrins alone, or both $\alpha_v$ and $\alpha_5\beta_1$ integrins. Until now, it is believed that the development of a single agent that can bind $\alpha_v\beta_3$, $\alpha_v\beta_5$, and $\alpha_5\beta_1$ integrins with high affinity and specificity has not been achieved. Since all three of these integrins are expressed on tumors and are involved in mediating angiogenesis and metastasis, a broad spectrum targeting agent (i.e., $\alpha_v\beta_3$, $\alpha_v\beta_5$, and $\alpha_5\beta_1$) will likely be more effective for diagnostic and therapeutic applications.

The present engineered knottin-Fc fusions have several advantages over previously identified integrin-targeting compounds. They possess a compact, disulfide-bonded core that confers proteolytic resistance and exceptional in vivo stability.

Our studies indicate the half-life of integrin-binding-Fc fusion protein in mouse serum to be greater than 90 hours. Their larger size C3-4 kDa) and enhanced affinity compared to RGD-based cyclic peptides confer enhanced pharmacokinetics and biodistribution for molecular imaging and therapeutic applications. These knottin-Fc proteins are small enough to allow for chemical synthesis and site-specific conjugation of imaging probes, radioisotopes, or chemotherapeutic agents. Furthermore, they can easily be chemically modified to further improve in vivo properties if necessary.

2. Knottin-Fc Fusion

The knottin-Fc fusions described herein and in U.S. Patent Application No. 2014/0073518, herein incorporated by reference in its entirety, combine an engineered integrin-binding polypeptide (within a knottin scaffold) and an Fc domain or antibody like construct capable of binding FcγR and inducing ADCC.

The Fc portion of an antibody is formed by the two carboxy terminal domains of the two heavy chains that make up an immunoglobin molecule. The IgG molecule contains 2 heavy chains (~50 kDa each) and 2 light chains (~25 kDa each). The general structure of all antibodies is very similar, a small region at the tip of the protein is extremely variable, allowing millions of antibodies with slightly different tip structures to exist. This region is known as the hypervariable region (Fab). The other fragment contains no antigen-binding activity but was originally observed to crystallize readily, and for this reason was named the Fc fragment, for Fragment crystallizable. This fragment corresponds to the paired $CH_2$ and $CH_3$ domains and is the part of the antibody molecule that interacts with effector molecules and cells. The functional differences between heavy-chain isotypes lie mainly in the Fc fragment. The hinge region that links the Fc and Fab portions of the antibody molecule is in reality a flexible tether, allowing independent movement of the two Fab arms, rather than a rigid hinge. This has been demonstrated by electron microscopy of antibodies bound to haptens. Thus the present fusion proteins can be made to contain two knottin peptides, one on each arm of the antibody fragment.

The Fc portion varies between antibody classes (and subclasses) but is identical within that class. The C-terminal end of the heavy chain forms the Fc region. The Fc region plays an important role as a receptor binding portion. The Fc portion of antibodies will bind to Fc receptors in two different ways. For example, after IgG and IgM bind to a pathogen by their Fab portion their Fc portions can bind to receptors on phagocytic cells (like macrophages) inducing phagocytosis.

The present knottin-Fc fusions can be implemented such that the Fc portion is used to provide dual binding capability, and/or for half-life extension, for improving expression levels, etc. The Fc fragment in the knottin-Fc can be, for example, from murine IgG2a or human IgG1. Linkers can be optionally used to connect the knottin to the Fc portion. Preferably, the linkers do not affect the binding affinity of the knottin-Fc to integrins or Fc receptors. A variety of Fc domain gene sequences (e.g., mouse and human constant region gene sequences) are available in the form of publicly accessible deposits.

a. Fc-Domains

A variety of Fc domain gene sequences (e.g., mouse and human constant region gene sequences) are available in the form of publicly accessible deposits. Constant region domains comprising an Fc domain sequence can be selected lacking a particular effector function and/or with a particular modification to reduce immunogenicity. Many sequences of antibodies and antibody-encoding genes have been published and suitable Fc domain sequences (e.g., hinge, CH2, and/or CH3 sequences, or portions thereof) can be derived from these sequences using art recognized techniques. The genetic material obtained using any of the foregoing methods may then be altered or synthesized to obtain polypeptides used herein. It will further be appreciated that alleles, variants and mutations of constant region DNA sequences are suitable for use in the methods disclosed herein.

Knottin-Fc suitable for use in the methods disclosed herein may comprise one or more Fc domains (e.g., 2, 3, 4, 5, 6, 7, 8, 9, 10, or more Fc domains). In one embodiment, the Fc domains may be of different types. In one embodiment, at least one Fc domain present in a knottin-Fc comprises a hinge domain or portion thereof. In another embodiment, a knottin-Fc comprises at least one Fc domain which comprises at least one CH2 domain or portion thereof. In another embodiment, a knottin-Fc comprises at least one Fc domain which comprises at least one CH3 domain or portion thereof. In another embodiment, a knottin-Fc comprises at least one Fc domain which comprises at least one CH4 domain or portion thereof. In another embodiment, a knottin-Fc comprises at least one Fc domain which comprises at least one hinge domain or portion thereof and at least one CH2 domain or portion thereof (e.g, in the hinge-CH2 orientation). In another embodiment, a knottin-Fc comprises at least one Fc domain which comprises at least one CH2 domain or portion thereof and at least one CH3 domain or portion thereof (e.g, in the CH2-CH3 orientation). In another embodiment, a knottin-Fc comprises at least one Fc domain comprising at least one hinge domain or portion thereof, at least one CH2 domain or portion thereof, and least one CH3 domain or portion thereof, for example in the orientation hinge-CH2-CH3, hinge-CH3-CH2, or CH2-CH3-hinge.

In certain embodiments, a knottin-Fc comprises at least one complete Fc region derived from one or more immunoglobulin heavy chains (e.g., an Fc domain including hinge, CH2, and CH3 domains, although these need not be derived from the same antibody). In other embodiments a knottin-Fc comprises at least two complete Fc domains derived from one or more immunoglobulin heavy chains. In certain embodiments, the complete Fc domain is derived from a human IgG immunoglobulin heavy chain (e.g., human IgG1).

In another embodiment, a knottin-Fc comprises at least one Fc domain comprising a complete CH3 domain. In another embodiment, a knottin-Fc comprises at least one Fc domain comprising a complete CH2 domain. In another embodiment, a knottin-Fc comprises at least one Fc domain comprising at least a CH3 domain, and at least one of a hinge region, and a CH2 domain. In one embodiment, a knottin-Fc comprises at least one Fc domain comprising a hinge and a CH3 domain. In another embodiment, a knottin-Fc comprises at least one Fc domain comprising a hinge, a CH2, and a CH3 domain. In certain embodiments, the Fc domain is derived from a human IgG immunoglobulin heavy chain (e.g., human IgG1). In certain embodiments, a human IgG1 Fc domain is used with a hinge region mutation, substitution, or deletion to remove or substitute one or more hinge retion cysteine residues.

The constant region domains or portions thereof making up an Fc domain of a knottin-Fc may be derived from different immunoglobulin molecules. For example, a polypeptide used in the invention may comprise a CH2 domain or portion thereof derived from an IgG1 molecule and a CH3 region or portion thereof derived from an IgG3 molecule. In another example, a knottin-Fc can comprise an Fc domain comprising a hinge domain derived, in part, from an IgG1 molecule and, in part, from an IgG3 molecule. As set forth herein, it will be understood by one of ordinary skill in the art that an Fc domain may be altered such that it varies in amino acid sequence from a naturally occurring antibody molecule.

In other constructs it may be desirable to provide a peptide spacer between one or more constituent Fc domains. For example, a peptide spacer may be placed between a hinge region and a CH2 domain and/or between a CH2 and a CH3 domain. For example, compatible constructs could be expressed wherein the CH2 domain has been deleted and the remaining CH3 domain (synthetic or unsynthetic) is joined to the hinge region with a 1-20, 1-10, or 1-5 amino acid peptide spacer. Such a peptide spacer may be added, for instance, to ensure that the regulatory elements of the constant region domain remain free and accessible or that the hinge region remains flexible. Preferably, any linker peptide compatible with the instant invention will be relatively non-immunogenic and not prevent proper folding of the Fc.

b. Changes to Fc Amino Acids

In certain embodiments, an Fc domain is altered or modified, e.g., by amino acid mutation (e.g., addition, deletion, or substitution). As used herein, the term "Fc domain variant" refers to an Fc domain having at least one amino acid modification, such as an amino acid substitution, as compared to the wild-type Fc from which the Fc domain is derived. For example, wherein the Fc domain is derived from a human IgG1 antibody, a variant comprises at least one amino acid mutation (e.g., substitution) as compared to a wild type amino acid at the corresponding position of the human IgG1 Fc region.

In certain embodiments, the hinge region of human IgG1 Fc domain is altered by an amino acid substitution or deletion to mutate or remove one or more of three hinge region cysteine residues (located at residues 220, 226, and 229 by EU numbering). In some aspects, the upper hinge region is deleted to remove a cysteine that pairs with the light chain. For example, amino acids "EPKSC" (SEQ ID NO: 139) in the upper hinge region are deleted, as set forth in SEQ ID NO: 3. In other aspects, one or more of three hinge region cysteines is mutated (e.g., to serine). In certain embodiments, cysteine 220 is mutated to serine.

In certain embodiments, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

In certain embodiments, a knottin-Fc fusion comprises an Fc variant comprising more than one amino acid substitution. The knottin-Fc fusion used in the methods described herein may comprise, for example, 2, 3, 4, 5, 6, 7, 8, 9, 10 or more amino acid substitutions. Preferably, the amino acid substitutions are spatially positioned from each other by an interval of at least 1 amino acid position or more, for example, at least 2, 3, 4, 5, 6, 7, 8, 9, or 10 amino acid positions or more. More preferably, the engineered amino acids are spatially positioned apart from each other by an interval of at least 5, 10, 15, 20, or 25 amino acid positions or more.

In certain embodiments, a knottin-Fc fusion comprises an amino acid substitution to an Fc domain which alters the antigen-independent effector functions of the polypeptide, in particular the circulating half-life of the polypeptide.

In one embodiment, the knottin-Fc exhibits enhanced binding to an activating FcγR (e.g. Fcγ1, Fcγ1a, or FcγRIIIa). Exemplary amino acid substitutions which altered FcR or complement binding activity are disclosed in International PCT Publication No. WO 2005/063815 which is incorporated by reference herein. In certain embodiments the Fc region contains at least one of the following mutations: S239D, S239E, L261A, H268D, S298A, A330H, A330L, I332D, I332E, I332Q, K334V, A378F, A378K, A378W, A378Y, H435S, or H435G. In certain embodiments, the Fc region contains at least one of the following mutations: S239D, S239E, I332D or I332E or H268D. In certain embodiments, the Fc region contains at least one of the following mutations: I332D or I332E or H268D.

The knottin-Fc used herein may also comprise an amino acid substitution which alters the glycosylation of the knottin-Fc. For example, the Fc domain of the knottin-Fc may comprise an Fc domain having a mutation leading to reduced glycosylation (e.g., N- or O-linked glycosylation) or may comprise an altered glycoform of the wild-type Fc domain (e.g., a low fucose or fucose-free glycan). In another embodiment, the knottin-Fc has an amino acid substitution near or within a glycosylation motif, for example, an N-linked glycosylation motif that contains the amino acid sequence NXT or NXS. Exemplary amino acid substitutions which reduce or alter glycosylation are disclosed in WO05/018572 and US2007/0111281, which are incorporated by reference herein. In other embodiments, the knottin-Fc used herein comprises at least one Fc domain having engineered cysteine residue or analog thereof which is located at the solvent-exposed surface. In certain embodiments, the knottin-Fc used herein comprises an Fc domain comprising at least one engineered free cysteine residue or analog thereof that is substantially free of disulfide bonding with a second cysteine residue. Any of the above engineered cysteine residues or analogs thereof may subsequently be conjugated to a functional domain using art-recognized techniques (e.g., conjugated with a thiol-reactive heterobifunctional linker).

In one embodiment, the knottin-Fc used herein may comprise a genetically fused Fc domain having two or more of its constituent Fc domains independently selected from the Fc domains described herein. In one embodiment, the Fc domains are the same. In another embodiment, at least two of the Fc domains are different. For example, the Fc domains of the knottin-Fc used herein comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc domains of the knottin-Fc used herein may differ in sequence at one or more amino acid positions. For example, at least two of the Fc domains may differ at about 5 amino acid positions (e.g., 1, 2, 3, 4, or 5 amino acid positions), about 10 positions, about 15 positions, about 20 positions, about 30 positions, about 40 positions, or about 50 positions).

Cancer Vaccine

1. Overview

In certain embodiments, cancer vaccines are used in addition to the other therapeutic agents described herein (e.g., extended-PK IL-2, knottin-Fc, and optional immune checkpoint blocker). In certain embodiments, the cancer vaccine stimulates a specific immune response against a specific target, such as a tumor-associated antigen.

In certain embodiments, the cancer vaccine will include viral, bacterial or yeast vectors to deliver recombinant genes to antigen presenting cells (APCs). In certain embodiments the cancer vaccine uses autologous or allogeneic tumor cells. In certain embodiments, these tumor cells may be modified for expression of MHC, costimulatory molecules, or cytokines.

In certain embodiments, the tumor-associated antigen is determined by sequencing a patient's tumor cells and identifying mutated proteins only found in the tumor. These antigens are referred to as "neoantigens." Once a neoantigen has been identified, it can be used as the antigen for a vaccine or for developing monoclonal antibodies specifically reactive with the neoantigen.

In certain embodiments, the vaccine includes irradiated tumor cells transduced with cytokines such as GM-CSF or loaded with adjuvant compounds, such as the GM-CSF-secreting tumor cell vaccine GVAX (*Immunological Reviews*, 222(1): 287-298, 2008). In certain embodiments the vaccine includes one or more tumor-associated antigens in the form of an immunogenic composition, optionally in combination with an adjuvant. For example, vaccination against HPV-16 oncoproteins resulted in positive clinical outcomes for vulvar intraepithelial neoplasia (*The New England Journal of Medicine*, 361(19), 1838-1847. 2012). Also, multipeptide immune response to cancer vaccine IMA901 after single-dose cyclophosphamide associates with longer patient survival (*Nature Medicine.*, 18(8): 1254-61, 2012). Alternatively, a DNA based approach can be used to immunize a patient with one or more tumor-associated antigens. Improved tumor immunity is observed using a DNA vaccine in combination with an anti-tyrosinase related protein-1 monoclonal antibody in murine melanoma (*Cancer Research*, 68(23), 9884-9891, 2008).

Other vaccine approaches utilize patient immune cells, such as dendritic cells which can be cultured with a tumor-associated antigen to produce antigen presenting cells that will stimulate the immune system and target the antigen of interest. A current FDA approved cancer treatment vaccine using this approach is Provenge® (Dendreon), approved for use in some men with metastatic prostate cancer. This vaccine stimulates an immune response to prostatic acid phosphatase (PAP), an antigen found on most prostate cancer cells. The vaccine is created by isolating a specific patient's immune cells and culturing dendritic cells with PAP to produce antigen presenting cells that will stimulate the immune system and target PAP. These and other cancer vaccines can be used in combination with other treatments as described herein.

2. Amphiphile Vaccines

In certain embodiments, an amphiphile vaccine, as described in US 2013/0295129, herein incorporated by reference, is used in the methods disclosed herein. An amphiphile vaccine combines an albumin-binding lipid and a peptide antigen or molecular adjuvant to efficiently target the peptide or adjuvant to lymph nodes in vivo. Lipid conjugates bind to endogenous albumin, which targets them to lymphatics and draining lymph nodes where they accumulate due to the filtering of albumin by antigen presenting cells. When the lipid conjugate includes an antigenic peptide or molecular adjuvant, the conjugates induce or enhance a robust immune response.

Lymph node-targeting conjugates typically include three domains: a highly lipophilic, albumin-binding domain (e.g., an albumin-binding lipid), a cargo such as a molecular adjuvant or a peptide antigen, and a polar block linker, which promotes solubility of the conjugate and reduces the ability of the lipid to insert into cellular plasma membranes. Accordingly, in certain embodiments, the general structure of the conjugate is L-P-C, where "L" is an albumin-binding lipid, "P" is a polar block, and "C" is a cargo such as a molecular adjuvant or a polypeptide. In some embodiments, the cargo itself can also serve as the polar block domain, and a separate polar block domain is not required. Therefore, in certain embodiments the conjugate has only two domains: an albumin-binding lipid and a cargo.

The cargo of the conjugates suitable for use in the methods disclosed herein is typically a molecular adjuvant such as an immunostimulatory oligonucleotide, or a peptide antigen. However, the cargo can also be other oligonucleotides, peptides, Toll-like receptor agonists or other immunomodulatory compounds, dyes, MRI contrast agents, fluorophores or small molecule drugs that require efficient trafficking to the lymph nodes.

Figure 6:
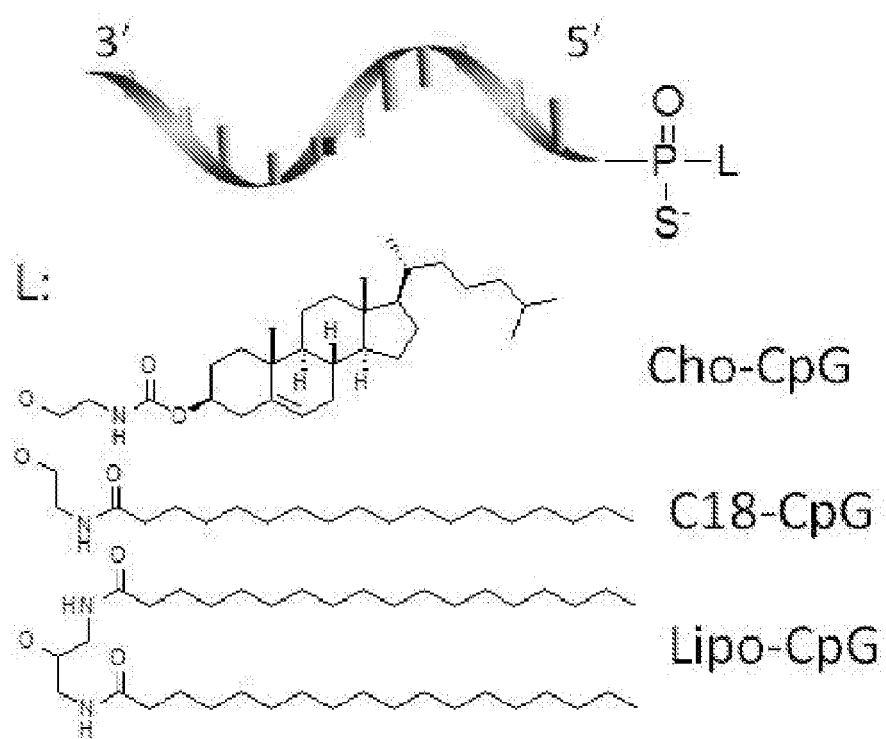
FIG. 6 is a schematic representation of lipid-oligonucleotide conjugates.
Figure 7:
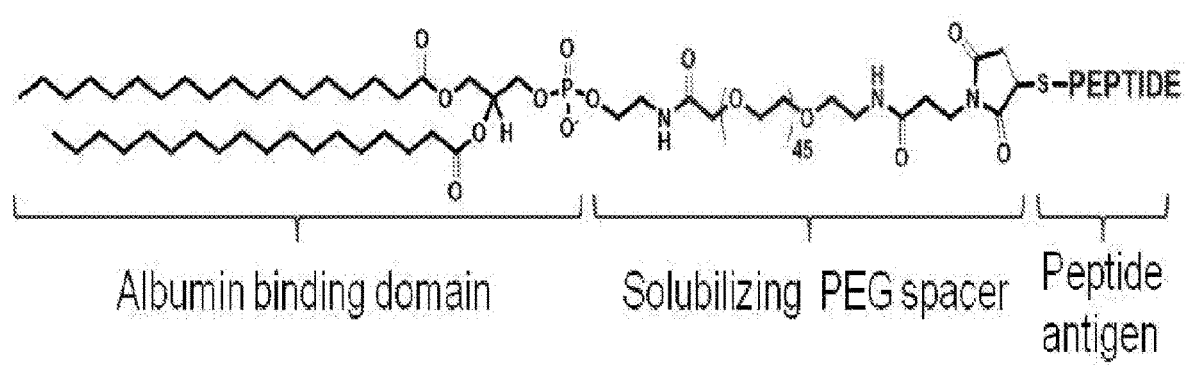
FIG. 7 is a schematic representation of a lipid-peptide conjugate, as described herein.

In certain embodiments, a lipid-oligonucleotide conjugates includes an immunostimulatory oligonucleotide which is conjugated directly to a lipid, or is linked to a linker which is conjugated to a lipid. A schematic representation of an exemplary lipid-oligonucleotide conjugate is shown in FIG. 6. Other embodiments are directed to lipid-peptide conjugates which include an antigenic peptide conjugated directly to a lipid, or is linked to a linker which is conjugated to a lipid. A schematic representation of an exemplary lipid-peptide conjugate is shown in FIG. 7.

a. Lipids

The lipid conjugates typically include a hydrophobic lipid. The lipid can be linear, branched, or cyclic. The lipid is preferably at least 17 to 18 carbons in length, but may be shorter if it shows good albumin binding and adequate targeting to the lymph nodes.

Lymph node-targeting conjugates include lipid-oligonucleotide conjugates and lipid-peptide conjugates that can be trafficked from the site of delivery through the lymph to the lymph node. In certain embodiments, the activity relies, in-part, on the ability of the conjugate to associate with albumin in the blood of the subject. Therefore, lymph node-targeted conjugates typically include a lipid that can bind to albumin under physiological conditions. Lipids suitable for targeting the lymph node can be selected based on the ability of the lipid or a lipid conjugate including the lipid to bind to albumin. Suitable methods for testing the ability of the lipid or lipid conjugate to bind to albumin are known in the art.

For example, in certain embodiments, a plurality of lipid conjugates is allowed to spontaneously form micelles in aqueous solution. The micelles are incubated with albumin, or a solution including albumin such as Fetal Bovine Serum (FBS). Samples can be analyzed, for example, by ELISA, size exclusion chromatography or other methods to determine if binding has occurred. Lipid conjugates can be selected as lymph node-targeting conjugates if in the presence of albumin, or a solution including albumin such as Fetal Bovine Serum (FBS), the micelles dissociate and the lipid conjugates bind to albumin as discussed above.

Examples of preferred lipids for use in lymph node targeting lipid conjugates include, but are not limited to fatty acids with aliphatic tails of 8-30 carbons including, but not limited to, linear unsaturated and saturated fatty acids, branched saturated and unsaturated fatty acids, and fatty acids derivatives, such as fatty acid esters, fatty acid amides, and fatty acid thioesters, diacyl lipids, cholesterol, cholesterol derivatives, and steroid acids such as bile acids; Lipid A or combinations thereof.

In certain embodiments, the lipid is a diacyl lipid or two-tailed lipid. In some embodiments, the tails in the diacyl lipid contain from about 8 to about 30 carbons and can be saturated, unsaturated, or combinations thereof. The tails can be coupled to the head group via ester bond linkages, amide bond linkages, thioester bond linkages, or combinations thereof. In a particular embodiment, the diacyl lipids are phosphate lipids, glycolipids, sphingolipids, or combinations thereof.

Preferably, lymph node-targeting conjugates include a lipid that is 8 or more carbon units in length. It is believed that increasing the number of lipid units can reduce insertion of the lipid into plasma membrane of cells, allowing the lipid conjugate to remain free to bind albumin and traffic to the lymph node.

For example, the lipid can be a diacyl lipid composed of two C18 hydrocarbon tails. In certain embodiments, the lipid for use in preparing lymph node targeting lipid conjugates is not a single chain hydrocarbon (e.g., C18), or cholesterol. Cholesterol conjugation has been explored to enhance the immunomodulation of molecular adjuvants such as CpG and immunogenicity of peptides, but cholesterol conjugates, which associate well with lipoproteins but poorly with albumin, show poor lymph node targeting and low immunogenicity in vaccines compared to optimal albumin-binding conjugates.

b. Molecular Adjuvants

In certain embodiments, lipid-oligonucleotide conjugates are used in the vaccine. The oligonucleotide conjugates typically contain an immunostimulatory oligonucleotide.

In certain embodiments, the immunostimulatory oligonucleotide can serve as a ligand for pattern recognition receptors (PRRs). Examples of PRRs include the Toll-like family of signaling molecules that play a role in the initiation of innate immune responses and also influence the later and more antigen specific adaptive immune responses. Therefore, the oligonucleotide can serve as a ligand for a Toll-like family signaling molecule, such as Toll-Like Receptor 9 (TLR9).

For example, unmethylated CpG sites can be detected by TLR9 on plasmacytoid dendritic cells and B cells in humans (Zaida, et al., *Infection and Immunity*, 76(5):2123-2129, (2008)). Therefore, the sequence of oligonucleotide can include one or more unmethylated cytosine-guanine (CG or CpG, used interchangeably) dinucleotide motifs. The 'p' refers to the phosphodiester backbone of DNA, as discussed in more detail below, some oligonucleotides including CG can have a modified backbone, for example a phosphorothioate (PS) backbone. In certain embodiments, an immunostimulatory oligonucleotide can contain more than one CG dinucleotide, arranged either contiguously or separated by intervening nucleotide(s). The CpG motif(s) can be in the interior of the oligonucleotide sequence. Numerous nucleotide sequences stimulate TLR9 with variations in the number and location of CG dinucleotide(s), as well as the precise base sequences flanking the CG dimers.

Typically, CG ODNs are classified based on their sequence, secondary structures, and effect on human peripheral blood mononuclear cells (PBMCs). The five classes are Class A (Type D), Class B (Type K), Class C, Class P, and Class S (Vollmer, J & Krieg, A M, *Advanced drug delivery reviews* 61(3): 195-204 (2009), incorporated herein by reference). CG ODNs can stimulate the production of Type I interferons (e.g., IFNα) and induce the maturation of dendritic cells (DCs). Some classes of ODNs are also strong activators of natural killer (NK) cells through indirect cytokine signaling. Some classes are strong stimulators of human B cell and monocyte maturation (Weiner, G L, PNAS USA 94(20): 10833-7 (1997); Dalpke, A H, Immunology 106(1): 102-12 (2002); Hartmann, G, J of Immun. 164(3): 1617-2 (2000), each of which is incorporated herein by reference).

According to some embodiments, a lipophilic-CpG oligonucleotide conjugate is used to enhance an immune response to a peptide antigen. The lipophilic-CpG oligonucleotide is represented by the following, wherein "L" is a lipophilic compound, such as diacyl lipid, "$G_n$" is a guanine repeat linker and "n" represents 1, 2, 3, 4, or 5.

(SEQ ID NO: 147)
5'-L-$G_n$TCCATGACGTTCCTGACGTT-3'

Other PRR Toll-like receptors include TLR3, and TLR7 which may recognize double-stranded RNA, single-stranded and short double-stranded RNAs, respectively, and retinoic acid-inducible gene I (RIG-I)-like receptors, namely RIG-I and melanoma differentiation-associated gene 5 (MDA5), which are best known as RNA-sensing receptors in the cytosol. Therefore, in certain embodiments, the oligonucleotide contains a functional ligand for TLR3, TLR7, or RIG-I-like receptors, or combinations thereof.

Examples of immunostimulatory oligonucleotides, and methods of making them are known in the art, see for example, Bodera, P. *Recent Pat Inflamm Allergy Drug Discov.* 5(1):87-93 (2011), incorporated herein by reference.

In certain embodiments, the oligonucleotide cargo includes two or more immunostimulatory sequences.

The oligonucleotide can be between 2-100 nucleotide bases in length, including for example, 5 nucleotide bases in length, 10 nucleotide bases in length, 15 nucleotide bases in length, 20 nucleotide bases in length, 25 nucleotide bases in length, 30 nucleotide bases in length, 35 nucleotide bases in length, 40 nucleotide bases in length, 45 nucleotide bases in length, 50 nucleotide bases in length, 60 nucleotide bases in length, 70 nucleotide bases in length, 80 nucleotide bases in length, 90 nucleotide bases in length, 95 nucleotide bases in length, 98 nucleotide bases in length, 100 nucleotide bases in length or more.

The 3' end or the 5' end of the oligonucleotides can be conjugated to the polar block or the lipid. In certain embodiments the 5' end of the oligonucleotide is linked to the polar block or the lipid.

The oligonucleotides can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose sugar linked by phosphodiester bonds. In certain embodiments, the oligonucleotides are composed of nucleotide analogs that have been chemically modified to improve stability, half-life, or specificity or affinity for a target receptor, relative to a DNA or RNA counterpart. The chemical modifications include chemical modification of nucleobases, sugar moieties, nucleotide linkages, or combinations thereof. As used herein 'modified nucleotide" or "chemically modified nucleotide" defines a nucleotide that has a chemical modification of one or more of the heterocyclic base, sugar moiety or phosphate moiety constituents. In certain embodiments, the charge of the modified nucleotide is reduced compared to DNA or RNA oligonucleotides of the same nucleobase sequence. For example, the oligonucleotide can have low negative charge, no charge, or positive charge.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). In certain embodiments, the analogs have a substantially uncharged, phosphorus containing backbone.

c. Peptide Antigens

The peptide conjugates suitable for use in the methods disclosed herein typically include an antigenic protein or polypeptide, such as a tumor-associated antigen or portion thereof.

The peptide can be 2-100 amino acids, including for example, 5 amino acids, 10 amino acids, 15 amino acids, 20 amino acids, 25 amino acids, 30 amino acids, 35 amino acids, 40 amino acids, 45 amino acids, or 50 amino acids. In some embodiments, a peptide can be greater than 50 amino acids. In some embodiments, the peptide can be >100 amino acids. A protein/peptide can be linear, branched or cyclic. The peptide can include D amino acids, L amino acids, or a combination thereof. The peptide or protein can be conjugated to the polar block or lipid at the N-terminus or the C-terminus of the peptide or protein.

The protein or polypeptide can be any protein or peptide that can induce or increase the ability of the immune system to develop antibodies and T-cell responses to the protein or peptide. A cancer antigen is an antigen that is typically expressed preferentially by cancer cells (i.e., it is expressed at higher levels in cancer cells than on non-cancer cells) and in some instances it is expressed solely by cancer cells. The cancer antigen may be expressed within a cancer cell or on the surface of the cancer cell. The cancer antigen can be, but is not limited to, TRP-1, TRP-2, MART-1/Melan-A, gp100, adenosine deaminase-binding protein (ADAbp), FAP, cyclophilin b, colorectal associated antigen (CRC)-C017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-1, GAGE-2, GAGE-3, GAGE-4, GAGE-5, GAGE-6, GAGE-7, GAGE-8, GAGE-9, BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pme1117, PRAME, NY-ESO-1, cdc27, adenomatous polyposis *coli* protein (APC), fodrin, Connexin 37, Ig-idiotype, p15, gp75, GM2 ganglioside, GD2 ganglioside, human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, or c-erbB-2. Additional cancer antigens include the tumor antigens described herein.

Suitable antigens are known in the art and are available from commercial government and scientific sources. In certain embodiments, the antigens are whole inactivated or irradiated tumor cells. The antigens may be purified or partially purified polypeptides derived from tumors. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

In certain embodiments, antigens may be provided as single antigens or may be provided in combination. Antigens may also be provided as complex mixtures of polypeptides or nucleic acids.

d. Polar Block/Linker

For the conjugate to be trafficked efficiently to the lymph node, the conjugate should remain soluble. Therefore, a polar block linker can be included between the cargo and the lipid to increase solubility of the conjugate. The polar block reduces or prevents the ability of the lipid to insert into the plasma membrane of cells, such as cells in the tissue adjacent to the injection site. The polar block can also reduce or prevent the ability of cargo, such as synthetic oligonucleotides containing a PS backbone, from non-specifically associating with extracellular matrix proteins at the site of administration. The polar block increases the solubility of the conjugate without preventing its ability to bind to albumin. It is believed that this combination of characteristics allows the conjugate to bind to albumin present in the serum or interstitial fluid, and remain in circulation until the albumin is trafficked to, and retained in a lymph node. The length and composition of the polar block can be adjusted based on the lipid and cargo selected. For example, for oligonucleotide conjugates, the oligonucleotide itself may be polar enough to insure solubility of the conjugate, for example, oligonucleotides that are 10, 15, 20 or more nucleotides in length. Therefore, in certain embodiments, no additional polar block linker is required. However, depending on the amino acid sequence, some lipidated peptides can be essentially insoluble. In these cases, it can be desirable to include a polar block that mimics the effect of a polar oligonucleotide.

A polar block can be used as part of any of lipid conjugates suitable for use in the methods disclosed herein, for example, lipid-oligonucleotide conjugates and lipid-peptide conjugates, which reduce cell membrane insertion/preferential portioning ont albumin. Suitable polar blocks include, but are not limited to, oligonucleotides such as those discussed above, a hydrophilic polymer including but not limited to poly(ethylene glycol) (MW: 500 Da to 20,000 Da), polyacrylamide (MW: 500 Da to 20,000 Da), polyacrylic acid; a string of hydrophilic amino acids such as serine, threonine, cysteine, tyrosine, asparagine, glutamine, aspartic acid, glutamic acid, lysine, arginine, histidine, or combinations thereof polysaccharides, including but not limited to, dextran (MW: 1,000 Da to 2,000,000 Da), or combinations thereof.

The hydrophobic lipid and the linker/cargo are covalently linked. The covalent bond may be a non-cleavable linkage or a cleavable linkage. The non-cleavable linkage can include an amide bond or phosphate bond, and the cleavable linkage can include a disulfide bond, acid-cleavable linkage, ester bond, anhydride bond, biodegradable bond, or enzyme-cleavable linkage.

i. Ethylene Glycol Linkers

In certain embodiments, the polar block is one or more ethylene glycol (EG) units, more preferably two or more EG units (i.e., polyethylene glycol (PEG)). For example, in certain embodiments, a peptide conjugate includes a protein or peptide (e.g., peptide antigen) and a hydrophobic lipid linked by a polyethylene glycol (PEG) molecule or a derivative or analog thereof.

In certain embodiments, protein conjugates suitable for use in the methods disclosed herein contain protein antigen linked to PEG which is in turn linked to a hydrophobic lipid, or lipid-Gn-ON conjugates, either covalently or via formation of protein-oligo conjugates that hybridize to oligo micelles. The precise number of EG units depends on the lipid and the cargo, however, typically, a polar block can have between about 1 and about 100, between about 20 and about 80, between about 30 and about 70, or between about 40 and about 60 EG units. In certain embodiments, the polar block has between about 45 and 55 EG, units. For example, in certain embodiments, the polar block has 48 EG units.

ii. Oligonucleotide Linkers

As discussed above, in certain embodiments, the polar block is an oligonucleotide. The polar block linker can have any sequence, for example, the sequence of the oligonucleotide can be a random sequence, or a sequence specifically chosen for its molecular or biochemical properties (e.g., highly polar). In certain embodiments, the polar block linker includes one or more series of consecutive adenine (A), cytosine (C), guanine (G), thymine (T), uracil (U), or analog thereof. In certain embodiments, the polar block linker consists of a series of consecutive adenine (A), cytosine (C), guanine (G), thymine (T), uracil (U), or analog thereof.

In certain embodiments, the linker is one or more guanines, for example between 1-10 guanines. It has been discovered that altering the number of guanines between a cargo such as a CpG oligonucleotide, and a lipid tail controls micelle stability in the presence of serum proteins. Therefore, the number of guanines in the linker can be selected based on the desired affinity of the conjugate for serum proteins such as albumin. When the cargo is a CpG immunostimulatory oligonucleotide and the lipid tail is a diacyl lipid, the number of guanines affects the ability of micelles formed in aqueous solution to dissociate in the presence of serum: 20% of the non-stabilized micelles (lipo-$G_0T_{10}$-CG) (SEQ ID NO: 140) were intact, while the remaining 80% were disrupted and bonded with FBS components. In the presence of guanines, the percentage of intact micelles increased from 36% (lipo-$G_2T_8$-CG) (SEQ ID NO: 141) to 73% (lipo-$G_4T_6$-CG) (SEQ ID NO: 142), and finally reached 90% (lipo-$G_6T_4$-CG) (SEQ ID NO: 143). Increasing the number of guanines to eight (lipo-$G_8T_2$-CG) (SEQ ID NO: 144) and ten (lipo-$G_{10}T_0$-CG) (SEQ ID NO: 145) did not further enhance micelle stability.

Therefore, in certain embodiments, the linker in a lymph node-targeting conjugate suitable for use in the methods disclosed herein can include 0, 1, or 2 guanines. As discussed in more detail below, linkers that include 3 or more consecutive guanines can be used to form micelle-stabilizing conjugates with properties that are suitable for use in the methods disclosed herein.

3. Immunogenic Compositions

The conjugates suitable for use in the methods disclosed herein can be used in immunogenic compositions or as components in vaccines. Typically, immunogenic compositions disclosed herein include an adjuvant, an antigen, or a combination thereof. The combination of an adjuvant and an antigen can be referred to as a vaccine. When administered to a subject in combination, the adjuvant and antigen can be administered in separate pharmaceutical compositions, or they can be administered together in the same pharmaceutical composition. When administered in combination, the adjuvant can be a lipid conjugate, the antigen can be a lipid conjugate, or the adjuvant and the antigen can both be lipid conjugates.

An immunogenic composition suitable for use in the methods disclosed herein can include a lipid conjugate that is an antigen such as an antigenic polypeptide-lipid conjugate, administered alone, or in combination with an adjuvant. The adjuvant may be without limitation alum (e.g., aluminum hydroxide, aluminum phosphate); saponins purified from the bark of the *Q. saponaria* tree such as QS21 (a glycolipid that elutes in the 21st peak with HPLC fractionation; Antigenics, Inc., Worcester, Mass.); poly[di(carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immunostimulant, Seppic).

Adjuvants may be TLR ligands, such as those discussed above. Adjuvants that act through TLR3 include, without limitation, double-stranded RNA. Adjuvants that act through TLR4 include, without limitation, derivatives of lipopolysaccharides such as monophosphoryl lipid A (MPLA; Ribi ImmunoChem Research, Inc., Hamilton, Mont.) and muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland). Adjuvants that act through TLR5 include, without limitation, flagellin. Adjuvants that act through TLR7 and/or TLR8 include single-stranded RNA, oligoribonucleotides (ORN), synthetic low molecular weight compounds such as imidazoquinolinamines (e.g., imiquimod (R-837), resiquimod (R-848)). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

The adjuvant can also be oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor.

Immune Checkpoint Blocker

In certain embodiments, immune checkpoint blockers are used in combination with other therapeutic agents described herein (e.g., extended-PK IL-2, integrin-binding-Fc fusion protein, and cancer vaccine). T cell activation and effector functions are balanced by co-stimulatory and inhibitory signals, referred to as "immune checkpoints." Inhibitory ligands and receptors that regulate T cell effector functions are overexpressed on tumor cells. Subsequently, agonists of co-stimulatory receptors or antagonists of inhibitory signals, result in the amplification of antigen-specific T cell responses. In contrast to therapeutic antibodies which target tumor cells directly, immune checkpoint blocker enhances endogenous anti-tumor activity. In certain embodiments, the immune checkpoint blocker suitable for use in the methods disclosed herein, is an antagonist of inhibitory signals, e.g., an antibody which targets, for example, PD-1, PD-L1, CTLA-4, LAGS, B7-H3, B7-H4, or TIM3. These ligands and receptors are reviewed in Pardoll, D., Nature. 12: 252-264, 2012.

Disclosed herein are methods for treating a subject afflicted with diseases such as cancer, which methods comprise administering to the subject a composition comprising a therapeutically effective amount of an immune checkpoint blocker, IL-2 (e.g., extended-PK IL-2), cancer vaccine and an integrin-binding-Fc fusion protein. In certain embodiments, the immune checkpoint blocker is an antibody or an antigen-binding portion thereof, that disrupts or inhibits signaling from an inhibitory immunoregulator. In certain embodiments, the immune checkpoint blocker is a small molecule that disrupts or inhibits signaling from an inhibitory immunoregulator.

In certain embodiments, the inhibitory immunoregulator (immune checkpoint blocker) is a component of the PD-1/PD-L1 signaling pathway. Accordingly, certain embodiments of the invention provide methods for immunotherapy of a subject afflicted with cancer, which methods comprise administering to the subject a therapeutically effective amount of an antibody or an antigen-binding portion thereof that disrupts the interaction between the PD-1 receptor and its ligand, PD-L1. Antibodies known in the art which bind to PD-1 and disrupt the interaction between the PD-1 and its ligand, PD-L1, and stimulates an anti-tumor immune response, are suitable for use in the methods disclosed herein. In certain embodiments, the antibody or antigen-binding portion thereof binds specifically to PD-1. For example, antibodies that target PD-1 and are in clinical trials include, e.g., nivolumab (BMS-936558, Bristol-Myers Squibb) and pembrolizumab (lambrolizumab, MK03475, Merck). Other suitable antibodies for use in the methods disclosed herein are anti-PD-1 antibodies disclosed in U.S. Pat. No. 8,008,449, herein incorporated by reference. In certain embodiments, the antibody or antigen-binding portion thereof binds specifically to PD-L1 and inhibits its interaction with PD-1, thereby increasing immune activity. Antibodies known in the art which bind to PD-L1 and disrupt the interaction between the PD-1 and PD-L1, and stimulates an anti-tumor immune response, are suitable for use in the methods disclosed herein. For example, antibodies that target PD-L1 and are in clinical trials, include BMS-936559 (Bristol-Myers Squibb) and MPDL3280A (Genetech). Other suitable antibodies that target PD-L1 are disclosed in U.S. Pat. No. 7,943,743. It will be understood by one of ordinary skill that any antibody which binds to PD-1 or PD-L1, disrupts the PD-1/PD-L1 interaction, and stimulates an anti-tumor immune response, is suitable for use in the methods disclosed herein.

In certain embodiments, the inhibitory immunoregulator is a component of the CTLA4 signaling pathway. Accordingly, certain embodiments of the invention provide methods for immunotherapy of a subject afflicted with cancer, which methods comprise administering to the subject a therapeutically effective amount of an antibody or an antigen-binding portion thereof that targets CTLA4 and disrupts its interaction with CD80 and CD86. Exemplary antibodies that target CTLA4 include ipilimumab (MDX-010, MDX-101, Bristol-Myers Squibb), which is FDA approved, and tremelimumab (ticilimumab, CP-675, 206, Pfizer), currently undergoing human trials. Other suitable antibodies that target CTLA4 are disclosed in WO 2012/120125, U.S. Pat. Nos. 6,984,720, 6,682,7368, and 2002/0039581, 2002/0086014, and 2005/0201994, herein incorporated by reference. It will be understood by one of ordinary skill that any antibody which binds to CTLA4, disrupts its interaction with CD80 and CD86, and stimulates an anti-tumor immune response, is suitable for use in the methods disclosed herein.

In certain embodiments, the inhibitory immunoregulator is a component of the LAG3 (lymphocyte activation gene 3) signaling pathway. Accordingly, certain embodiments of the invention provide methods for immunotherapy of a subject afflicted with cancer, which methods comprise administering to the subject a therapeutically effective amount of an antibody or an antigen-binding portion thereof that targets LAG3 and disrupts its interaction with MHC class II molecules. An exemplary antibody that targets LAG3 is IMP321 (Immutep), currently undergoing human trials. Other suitable antibodies that target LAG3 are disclosed in U.S. Patent Application 2011/0150892, herein incorporated by reference. It will be understood by one of ordinary skill that any antibody which binds to LAG3, disrupts its interaction with MHC class II molecules, and stimulates an anti-tumor immune response, is suitable for use in the methods disclosed herein.

In certain embodiments, the inhibitory immunoregulator is a component of the B7 family signaling pathway. In certain embodiments, the B7 family members are B7-H3 and B7-H4. Accordingly, certain embodiments of the invention provide methods for immunotherapy of a subject afflicted with cancer, which methods comprise administering to the subject a therapeutically effective amount of an antibody or an antigen-binding portion thereof that targets B7-H3 or H4. The B7 family does not have any defined receptors but these ligands are upregulated on tumor cells or tumor-infiltrating cells. Preclinical mouse models have shown that blockade of these ligands can enhance anti-tumor immunity. An exemplary antibody that targets B7-H3 is MGA271 (Macrogenics), currently undergoing human trials. Other suitable antibodies that target LAG3 are disclosed in U.S. Patent Application 2013/0149236, herein incorporated by reference. It will be understood by one of ordinary skill that any antibody which binds to B7-H3 or H4, and stimulates an anti-tumor immune response, is suitable for use in the methods disclosed herein.

In certain embodiments, the inhibitory immunoregulator is a component of the TIM3 (T cell membrane protein 3) signaling pathway. Accordingly, certain embodiments of the invention provide methods for immunotherapy of a subject afflicted with cancer, which methods comprise administering to the subject a therapeutically effective amount of an antibody or an antigen-binding portion thereof that targets LAG3 and disrupts its interaction with galectin 9. Suitable antibodies that target TIM3 are disclosed in U.S. Patent Application 2013/0022623, herein incorporated by reference. It will be understood by one of ordinary skill that any antibody which binds to TIM3, disrupts its interaction with galectin 9, and stimulates an anti-tumor immune response, is suitable for use in the methods disclosed herein.

It should be understood that antibodies targeting immune checkpoints suitable for use in the methods disclosed herein are not limited to those described supra. Moreover, it will be understood by one of ordinary skill in the art that other immune checkpoint targets can also be targeted by antagonists or antibodies in the methods described herein, provided that the targeting results in the stimulation of an anti-tumor immune response as reflected in, e.g., an increase in T cell proliferation, enhanced T cell activation, and/or increased cytokine production (e.g., IFN-γ, IL-2).

Alternatives to Immune Checkpoint Blockers

In certain embodiments, an antagonist of vascular endothelial growth factor (VEGF) is used in place of an immune checkpoint blocker. VEGF has recently been demonstrated to play a role in immune suppression (Liang, W.-C. et al. *J. Biol. Chem.* (2006) Vol 281: 951-961; Voron, T. et al. *Front Oncol* (2014) Vol. 4: Article 70; Terme, M. et al., *Clin Dev Immunol* (2012) Vol. 2012: Article ID 492920; Kandalaft, E. et al., *Curr Top Microbiol Immunol* (2011) Vol 344: 129-48), therefore blocking its activity enhances the immune response, similar to that of an immune checkpoint blocker. A "VEGF antagonist" refers to a molecule capable of neutralizing, blocking, inhibiting, abrogating, reducing or interfering with VEGF activities including its binding to one or more VEGF receptors. Non-limiting examples of VEGF antagonists include anti-VEGF antibodies and antigen-binding fragments thereof, receptor molecules and derivatives which bind specifically to VEGF thereby sequestering its binding to one or more receptors (e.g., a VEGF receptor), anti-VEGF receptor antibodies, VEGF receptor antagonists such as small molecule inhibitors of the VEGFR tyrosine kinases, or a dominant negative VEGF.

In certain embodiments, the VEGF antagonist is an antibody. An "anti-VEGF antibody" is an antibody that binds to VEGF with sufficient affinity and specificity. Non-limiting examples of anti-VEGF antibodies are described in U.S. Pat. Nos. 6,884,879, 7,060,269, 6,582,959, 6,703,030, 6,054,297, US Patent Application Nos. 2006009360, 20050186208, 20030206899, 20030190317, 20030203409, 20050112126, and PCT Publication Nos. WO 98/45332, 96/30046, 94/10202, 05/044853, 13/181452. The contents of these patents and patent applications are herein incorporated by reference. In certain embodiments the VEGF antibody is bevacizumab (Avastin® Genentech/Roche) or ranibizumab (Lucentis® Genentech/Roche).

In certain embodiments, the VEGF antagonist binds to the VEGF receptor. VEGF receptors, or fragments thereof, that specifically bind to VEGF can be used to bind to and sequester the VEGF protein, thereby preventing it from activating downstream signaling. In certain embodiments, the VEGF receptor, or VEGF binding fragment thereof, is a soluble VEGF receptor, such as sFlt-1. The soluble form of the receptor exerts an inhibitory effect on the biological activity of VEGF by binding to VEGF, thereby preventing it from binding to its natural receptors present on the surface of target cells. Non-limiting examples of VEGF antagonists which bind the VEGF receptor are disclosed in PCT Application Nos. 97/44453, 05/000895 and U.S. Patent Application No. 20140057851.

Other Therapeutic Agents

The integrin-binding-Fc fusion protein suitable for use in the methods disclosed herein, can be used in conjunction with one or more therapeutic agents. In one embodiment, the therapeutic agent is a therapeutic antibody. In another embodiment, the therapeutic agent is a therapeutic protein. In another embodiment, the therapeutic agent is a small molecule. In another embodiment, the therapeutic agent is an antigen. In another embodiment, the therapeutic agent is a population of cells.

Linkers

In certain embodiments, the extended-PK group is optionally fused to IL-2 via a linker. In certain embodiments, an integrin-binding polypeptide is fused to an Fc fragment via a linker. Suitable linkers are well known in the art, such as those disclosed in, e.g., US2010/0210511 US2010/0179094, and US2012/0094909, which are herein incorporated by reference in its entirety. Exemplary linkers include gly-ser polypeptide linkers, glycine-proline polypeptide linkers, and proline-alanine polypeptide linkers. In a certain embodiment, the linker is a gly-ser polypeptide linker, i.e., a peptide that consists of glycine and serine residues.

Exemplary gly-ser polypeptide linkers comprise the amino acid sequence Ser(Gly$_4$Ser)n. In one embodiment, n=1. In one embodiment, n=2. In another embodiment, n=3, i.e., Ser(Gly$_4$Ser)3. In another embodiment, n=4, i.e., Ser (Gly$_4$Ser)4. In another embodiment, n=5. In yet another embodiment, n=6. In another embodiment, n=7. In yet another embodiment, n=8. In another embodiment, n=9. In yet another embodiment, n=10. Another exemplary gly-ser polypeptide linker comprises (Gly$_4$Ser)n. In one embodiment, n=1. In one embodiment, n=2. In a certain embodiment, n=3. In another embodiment, n=4. In another embodiment, n=5. In yet another embodiment, n=6. Another exemplary gly-ser polypeptide linker comprises (Gly$_3$Ser)n. In one embodiment, n=1. In one embodiment, n=2. In a certain embodiment, n=3. In another embodiment, n=4. In another embodiment, n=5. In yet another embodiment, n=6.

Engineered Fusion Molecules

Also provided herein are engineered molecules that comprise two or more of IL-2, and an antibody (e.g., a therapeutic antibody, an immune checkpoint blocker, or an antibody that antagonizes VEGF) or antibody fragment described herein, a tumor antigen peptide (e.g., Trp1, Trp2) described herein, and a CpG oligonucleotide. Such engineered molecules can effectively reduce the number of components to be administered to a subject (e.g., a cancer patient) in the methods described herein. In some embodiments, the antibody or antibody fragment serves as the scaffold for conjugation with other components (e.g., IL-2, tumor antigen, and/or CpG oligonucleotide).

Accordingly, in certain embodiments, the engineered molecule comprises IL-2 and an antibody or antibody fragment. In some embodiments, the engineered molecule comprises a tumor antigen peptide and an antibody or antibody fragment. The tumor antigen component can be used to augment the natural delivery of antigenic material from tumor cells killed by innate immune effector mechanisms. In other embodiments, the engineered molecule comprises a CpG oligonucleotide and an antibody or antibody fragment. In yet other embodiments, the engineered molecule comprises IL-2, an antibody or antibody fragment, and a CpG oligonucleotide. In further embodiments, the engineered molecule comprises IL-2, an antibody or antibody fragment, a tumor antigen peptide, and a CpG oligonucleotide.

In certain embodiments, the antibody is an immune checkpoint blocker. In a particular embodiment, the antibody for use in the engineered protein is a bispecific antibody, wherein one component is a therapeutic antibody and the other component is an antibody that binds to an immune checkpoint blocker or an antibody that antagonizes VEGF activity. Methods for generating bispecific antibodies are known in the art.

Accordingly, in certain embodiments, the engineered molecule comprises IL-2 and a bispecific antibody which binds to a therapeutic target and an immune checkpoint blocker. In other embodiments, the engineered molecule comprises a tumor antigen and a bispecific antibody which binds to a therapeutic target and an immune checkpoint blocker. In yet other embodiments, the engineered molecule comprises a CpG oligonucleotide and a bispecific antibody which binds to a therapeutic target and an immune checkpoint blocker. In further embodiments, the engineered molecule comprises IL-2, a tumor antigen, and a bispecific antibody which binds to a therapeutic target and an immune checkpoint blocker. In further embodiments, the engineered molecule comprises IL-2, a CpG oligonucleotide, and a bispecific antibody which binds to a therapeutic target and an immune checkpoint blocker. In additional embodiments, the engineered molecule comprises IL-2, a tumor antigen, a CpG oligonucleotide, and a bispecific antibody which binds to a therapeutic target and an immune checkpoint blocker.

In certain embodiments, the IL-2 component for use in the engineered protein is an IL-2 lacking a pharmacokinetic moiety (i.e., a non-extended PK IL-2). In other embodiments, the IL-2 comprises a pharmacokinetic moiety (an extended-PK IL-2).

In certain embodiments, the components of the engineered molecule are conjugated to the antibody or bispecific antibody with or without a linker. Suitable linkers for conjugation are described herein and extensively described in the art.

Regions to which polypeptide-based components (e.g., tumor antigen and IL-2) of the engineered molecule can be fused, with or without a linker, to the antibody are generally known in the art, and include, for example, the C-terminus of the antibody heavy chain and the C-terminus of the antibody light chain. In certain embodiments, CpG oligonucleotides (as a cancer vaccine adjuvant) are site-specifically conjugated to artificially-induced single cysteine thiols in the antibody. In other embodiments, CpG oligonucleotides can be randomly conjugated to the antibody or antibody fragment, as described in Yang et al. (*Mol Ther* 2013; 21:91-100) and Schettini et al. (*Cancer Immunol Immunother* 2012; 61:2055-65).

In certain embodiments, components of the engineered molecule do not interfere with the function of the other components. By way of example, when the engineered protein comprises an antibody and IL-2, the IL-2 will be fused to the antibody in a manner such that the antibody retains its antigen-binding function, and IL-2 retains the ability to interact with its receptor. Similarly, when the engineered protein comprises an antibody and tumor antigen, the tumor antigen (e.g., a polypeptide from Trp1 or Trp2) retains the ability to stimulate a specific response against the antigen, and the antibody retains its antigen-binding function. The methods described herein, e.g., in the Examples, can be used to determine whether components of the engineered protein retain their respective functions.

Methods of Making Polypeptides

In some aspects, the polypeptides described herein (e.g., IL-2, such as extended-PK IL-2, and knottin-Fc) are made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The methods of making polypeptides also include a vector capable of expressing the peptides in an appropriate host. The vector comprises the DNA molecule that codes for the peptides operatively linked to appropriate expression control sequences. Methods of affecting this operative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be suitable for use in the methods disclosed herein. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides. Compounds that contain derivatized peptides or which contain non-peptide groups may be synthesized by well-known organic chemistry techniques.

Other methods are of molecule expression/synthesis are generally known in the art to one of ordinary skill.

Expression of Polypeptides

The nucleic acid molecules described above can be contained within a vector that is capable of directing their expression in, for example, a cell that has been transduced with the vector. Accordingly, in addition to extended-PK IL-2 and knottin-Fc mutants, expression vectors containing a nucleic acid molecule encoding an extended-PK IL-2 or knottin-Fc mutant and cells transfected with these vectors are among the certain embodiments.

Vectors suitable for use include T7-based vectors for use in bacteria (see, for example, Rosenberg et al., Gene 56: 125, 1987), the pMSXND expression vector for use in mammalian cells (Lee and Nathans, J. Biol. Chem. 263:3521, 1988), and baculovirus-derived vectors (for example the expression vector pBacPAKS from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (neo$^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that are suitable for use include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encodes an extended-PK IL-2 or knottin-Fc mutant are also features of the invention. A cell of the invention is a transfected cell, i.e., a cell into which a nucleic acid molecule, for example a nucleic acid molecule encoding an extended-PK IL-2 mutant or knottin-Fc, has been introduced by means of recombinant DNA techniques. The progeny of such a cell are also considered within the scope of the invention.

The precise components of the expression system are not critical. For example, an extended-PK IL-2 or knottin-Fc mutant can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed polypeptides can be purified from the expression system using routine biochemical procedures, and can be used, e.g., as therapeutic agents, as described herein.

Pharmaceutical Compositions and Modes of Administration

In certain embodiments, IL-2 (e.g., extended-PK IL-2) is administered together (simultaneously or sequentially) with a knottin-Fc. In certain embodiments, IL-2 (e.g., extended-PK IL-2) is administered prior to the administration of a knottin-Fc. In certain embodiments, IL-2 (e.g., extended-PK IL-2) is administered concurrently with the administration of a knottin-Fc. In certain embodiments, IL-2 (e.g., extended-PK IL-2) is administered subsequent to the administration of a knottin-Fc. In certain embodiments, the IL-2 (e.g., extended-PK IL-2) and a knottin-Fc are administered simultaneously. In other embodiments, the IL-2 (e.g., extended-PK IL-2) and a knottin-Fc are administered sequentially. In yet other embodiments, the IL-2 and a knottin-Fc are administered within one, two, or three days of each other.

In certain embodiments, IL-2 (e.g., extended-PK IL-2), a knottin-Fc, a cancer vaccine, and optionally an immune checkpoint blocker, are administered together (simultaneously or sequentially). In certain embodiments, IL-2 (e.g., extended-PK IL-2) and a knottin-Fc are administered together (simultaneously or sequentially). In certain embodiments, IL-2 (e.g., extended-PK IL-2) and a cancer vaccine are administered together (simultaneously or sequentially). In certain embodiments, IL-2 (e.g., extended-PK IL-2) and an immune checkpoint blocker are administered together (simultaneously or sequentially). In certain embodiments, IL-2 (e.g., extended-PK IL-2), a knottin-Fc, a cancer vaccine, and optionally an immune checkpoint blocker, are administered separately. In certain embodiments, an antagonist of VEGF is used in place of an immune checkpoint blocker.

In certain embodiments, the invention provides for a pharmaceutical composition comprising IL-2 (e.g., extended-PK IL-2) with a pharmaceutically acceptable diluent, carrier, solubilizer, emulsifier, preservative and/or adjuvant, a pharmaceutical composition comprising a cancer vaccine with a pharmaceutically acceptable diluent, carrier, solubilizer, emulsifier, preservative and/or adjuvant, a pharmaceutical composition comprising a knottin-Fc with a pharmaceutically acceptable diluent, carrier, solubilizer, emulsifier, preservative and/or adjuvant, or a pharmaceutical composition comprising an immune checkpoint blocker with a pharmaceutically acceptable diluent, carrier, solubilizer, emulsifier, preservative and/or adjuvant.

In certain embodiments, the invention provides for pharmaceutical compositions comprising IL-2 (e.g., extended-PK IL-2), a knottin-Fc, a cancer vaccine, and optionally an immune checkpoint blocker, with a pharmaceutically acceptable diluent, carrier, solubilizer, emulsifier, preservative and/or adjuvant. In certain embodiments, each of the agents, e.g., IL-2 (e.g., extended-PK IL-2), knottin-Fc, a cancer vaccine, and optionally an immune checkpoint blocker can be formulated as separate compositions. In certain embodiments, acceptable formulation materials preferably are nontoxic to recipients at the dosages and concentrations employed. In certain embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of IL-2 (e.g., extended-PK IL-2), the knottin-Fc, the cancer vaccine, and the optional immune checkpoint blocker.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising IL-2 (e.g., extended-PK IL-2), a knottin-Fc, a cancer vaccine, and optionally an immune checkpoint blocker (or an antagonist of VEGF), can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising IL-2 (e.g., extended-PK IL-2), a cancer vaccine, a knottin-Fc, and optionally an immune checkpoint blocker (or an antagonist of VEGF), can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising IL-2 (e.g., extended-PK IL-2), a knottin-Fc, a cancer vaccine, and optionally an immune checkpoint blocker (or an antagonist of VEGF), in a pharmaceutically acceptable vehicle. In certain embodiments, a vehicle for parenteral injection is sterile distilled water in which IL-2 (e.g., extended-PK IL-2), a knottin-Fc, a cancer vaccine, and optionally an immune checkpoint blocker (or an antagonist of VEGF), are formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, IL-2 (e.g., extended-PK IL-2), a knottin-Fc, a cancer vaccine, and optionally an immune checkpoint blocker (or an antagonist of VEGF) can be formulated as a dry powder for inhalation. In certain embodiments, an inhalation solution comprising IL-2 (e.g., extended-PK IL-2), a knottin-Fc, a cancer vaccine, and optionally an immune checkpoint blocker (or an antagonist of VEGF) can be formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations can be administered orally. In certain embodiments, IL-2 (e.g., extended-PK IL-2), a knottin-Fc, a cancer vaccine, and optionally an immune checkpoint blocker (or an antagonist of VEGF) that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of IL-2 (e.g., extended-PK IL-2), the knottin-Fc, the cancer vaccine, and the optional immune checkpoint blocker (or an antagonist of VEGF). In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of IL-2 (e.g., extended-PK IL-2), a knottin-Fc, a cancer vaccine, and optionally an immune checkpoint blocker (or an antagonist of VEGF) in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving IL-2 (e.g., extended-PK IL-2), a knottin-Fc, a cancer vaccine, and optionally an immune checkpoint blocker (or an antagonist of VEGF) in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising IL-2 (e.g., extended-PK IL-2) and/or one or more pharmaceutical compositions comprising a knottin-Fc and/or a cancer vaccine and/or an immune checkpoint blocker (or an antagonist of VEGF) to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which IL-2 (e.g., extended-PK IL-2), the knottin-Fc, the cancer vaccine, and optionally an immune checkpoint blocker (or an antagonist of VEGF), are being used, the route of administration, and the size (body weight, body surface or organ size) and/or condition (the age and general health) of the patient. In certain embodiments, the clinician can titer the dosage and modify the route of administration to obtain the optimal therapeutic effect. In certain embodiments, a typical dosage for IL-2 (e.g., extended-PK IL-2) can range from about 0.1 µg/kg to up to about 100 mg/kg or more, depending on the factors mentioned above. In certain embodiments, the dosage can range from 0.1 µg/kg up to about 100 mg/kg; or 1 µg/kg up to about 100 mg/kg; or 5 µg/kg up to about 100 mg/kg.

In certain embodiments, a typical dosage for an immune checkpoint blocker can range from about 0.1 mg/kg to up to about 300 mg/kg or more, depending on the factors mentioned above. In certain embodiments, the dosage can range from 1 mg/kg up to about 300 mg/kg; or 5 mg/kg up to about 300 mg/kg; or 10 mg/kg up to about 300 mg/kg.

In certain embodiments, the frequency of dosing will take into account the pharmacokinetic parameters of IL-2 (e.g., extended-PK IL-2), the knottin-Fc, the cancer vaccine, and optionally the immune checkpoint blocker in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition comprising IL-2 (e.g., extended-PK IL-2), a knottin-Fc, a cancer vaccine, and optionally an immune checkpoint blocker (or an antagonist of VEGF) in an ex vivo manner. In such instances, cells, tissues and/or organs that have been removed from the patient are exposed to a pharmaceutical composition comprising IL-2 (e.g., extended-PK IL-2), a knottin-Fc, a cancer vaccine, and optionally an immune checkpoint blocker (or an antagonist of VEGF) after which the cells, tissues and/or organs are subsequently implanted back into the patient.

In certain embodiments, IL-2 (e.g., extended-PK IL-2), a knottin-Fc, a cancer vaccine, and optionally an immune checkpoint blocker (or an antagonist of VEGF) can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Kits

A kit can include IL-2 (e.g., extended-PK IL-2), a cancer vaccine, a knottin-Fc, and optionally an immune checkpoint blocker (or an antagonist of VEGF) as disclosed herein, and instructions for use. The kits may comprise, in a suitable container, IL-2 (e.g., extended-PK IL-2), a cancer vaccine, a knottin-Fc, optionally an immune checkpoint blocker (or an antagonist of VEGF), one or more controls, and various buffers, reagents, enzymes and other standard ingredients well known in the art. Certain embodiments include a kit with IL-2 (e.g., extended-PK IL-2), a cancer vaccine, a knottin-Fc, and optionally an immune checkpoint blocker (or an antagonist of VEGF) in the same vial. In certain embodiments, a kit includes IL-2 (e.g., extended-PK IL-2), a cancer vaccine, a knottin-Fc, and optionally an immune checkpoint blocker (or an antagonist of VEGF) in separate vials.

The container can include at least one vial, well, test tube, flask, bottle, syringe, or other container means, into which IL-2 (e.g., extended-PK IL-2), a cancer vaccine, knottin-Fc, and optionally an immune checkpoint blocker (or an antagonist of VEGF) may be placed, and in some instances, suitably aliquoted. Where an additional component is provided, the kit can contain additional containers into which this component may be placed. The kits can also include a means for containing IL-2 (e.g., extended-PK IL-2), a cancer vaccine, a knottin-Fc, and optionally an immune checkpoint blocker (or an antagonist of VEGF), and any other reagent containers in close confinement for commercial sale. Such containers may include injection or blow-molded plastic containers into which the desired vials are retained. Containers and/or kits can include labeling with instructions for use and/or warnings.

Methods of Treatment

The IL-2 (e.g., extended-PK IL-2), cancer vaccine, knottin-Fc, and optional immune checkpoint blocker (or an antagonist of VEGF), and/or nucleic acids expressing them, described herein, are useful for treating a disorder associated with abnormal apoptosis or a differentiative process (e.g., cellular proliferative disorders (e.g., hyperproliferaetive disorders) or cellular differentiative disorders, such as cancer). Non-limiting examples of cancers that are amenable to treatment with the methods of the present invention are described below.

Examples of cellular proliferative and/or differentiative disorders include cancer (e.g., carcinoma, sarcoma, metastatic disorders or hematopoietic neoplastic disorders, e.g., leukemias). A metastatic tumor can arise from a multitude of primary tumor types, including but not limited to those of prostate, colon, lung, breast and liver. Accordingly, the compositions used herein, comprising, e.g., IL-2 (e.g., extended-PK IL-2), a cancer vaccine, a knottin-Fc, and optionally an immune checkpoint blocker (or an antagonist of VEGF), can be administered to a patient who has cancer.

As used herein, we may use the terms "cancer" (or "cancerous"), "hyperproliferative," and "neoplastic" to refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The term "cancer" or "neoplasm" are used to refer to malignancies of the various organ systems, including those affecting the lung, breast, thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The IL-2 (e.g., extended-PK IL-2), cancer vaccine, knottin-Fc, and optional immune checkpoint blocker (or an antagonist of VEGF) can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macro globulinemia (WM). Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Sternberg disease.

It will be appreciated by those skilled in the art that amounts for each of the IL-2 (e.g., extended-PK IL-2), cancer vaccine, knottin-Fc, and optional immune checkpoint blocker (or an antagonist of VEGF) that are sufficient to reduce tumor growth and size, or a therapeutically effective amount, will vary not only on the particular compounds or compositions selected, but also with the route of administration, the nature of the condition being treated, and the age and condition of the patient, and will ultimately be at the discretion of the patient's physician or pharmacist. The length of time during which the compounds used in the instant method will be given varies on an individual basis.

In certain embodiments, the IL-2 (e.g., extended-PK IL-2), cancer vaccine, knottin-Fc, and optional immune checkpoint blocker (or an antagonist of VEGF) disclosed herein are used to treat cancer.

In certain embodiments, the IL-2 (e.g., extended-PK IL-2), cancer vaccine, knottin-Fc, and optional immune checkpoint blocker (or an antagonist of VEGF) disclosed herein are used to treat melanoma, leukemia, lung cancer, breast cancer, prostate cancer, ovarian cancer, colon cancer, and brain cancer.

In certain embodiments, the IL-2 (e.g., extended-PK IL-2), cancer vaccine, knottin-Fc, and optional immune checkpoint blocker (or an antagonist of VEGF) disclosed herein inhibit the growth and/or proliferation of tumor cells.

In certain embodiments, the IL-2 (e.g., extended-PK IL-2), cancer vaccine, knottin-Fc, and optional immune checkpoint blocker (or an antagonist of VEGF) disclosed herein reduce tumor size.

In certain embodiments, the IL-2 (e.g., extended-PK IL-2), cancer vaccine, knottin-Fc, and optional immune checkpoint blocker (or an antagonist of VEGF) disclosed herein inhibit metastases of a primary tumor.

It will be appreciated by those skilled in the art that reference herein to treatment extends to prophylaxis as well as the treatment of the noted cancers and symptoms.

The present disclosure is further illustrated by the following examples, which should not be construed as further limiting. The contents of all figures and all references, Genbank sequences, patents and published patent applications cited throughout this application are expressly incorporated herein by reference. In particular, the disclosures of PCT publication WO 13/177187, U.S. Pat. No. 8,536,301, and U.S. Patent Publication No. 2014/0073518 are expressly incorporated herein by reference.

EXAMPLES

Below are examples of specific embodiments for carrying out the methods described herein. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for. The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sci-* ences, 18th Edition (Easton, Pa.: Mack Publishing Company, 1990); Carey and Sundberg *Advanced Organic Chemistry* 3rd Ed. (Plenum Press) Vols A and B(1992). Moreover, while the examples below employ extended-PK IL-2 of mouse origin (i.e., both the extended-PK group (mouse serum albumin) and IL-2 are of mouse origin), it should be understood that corresponding human extended-PK IL-2 (i.e., human serum albumin (HSA) and human IL-2, and variants thereof) can be readily generated by those of ordinary skill in the art using methods described supra, and used in the methods disclosed herein.

Example 1

Synergistic Tumor Control and Survival with Triple Combination Therapy

To assess the effectiveness of combination treatment in cancer, the B16F10 melanoma mouse model was utilized. 1×10$^6$B16F10 melanoma cells (ATCC), which are poorly immunogenic and aggressively form tumors, were subcutaneously injected into C57BL/6 mice. Immunotherapy was administered 8, 15, 22, 29, and 36 days after tumor inoculation. This consisted of 100 μg TA99 (an anti-Trp-1 antibody, produced by researcher) and 30 μg mouse serum albumin (MSA)-IL-2 (produced by researcher).

Figure 1B:
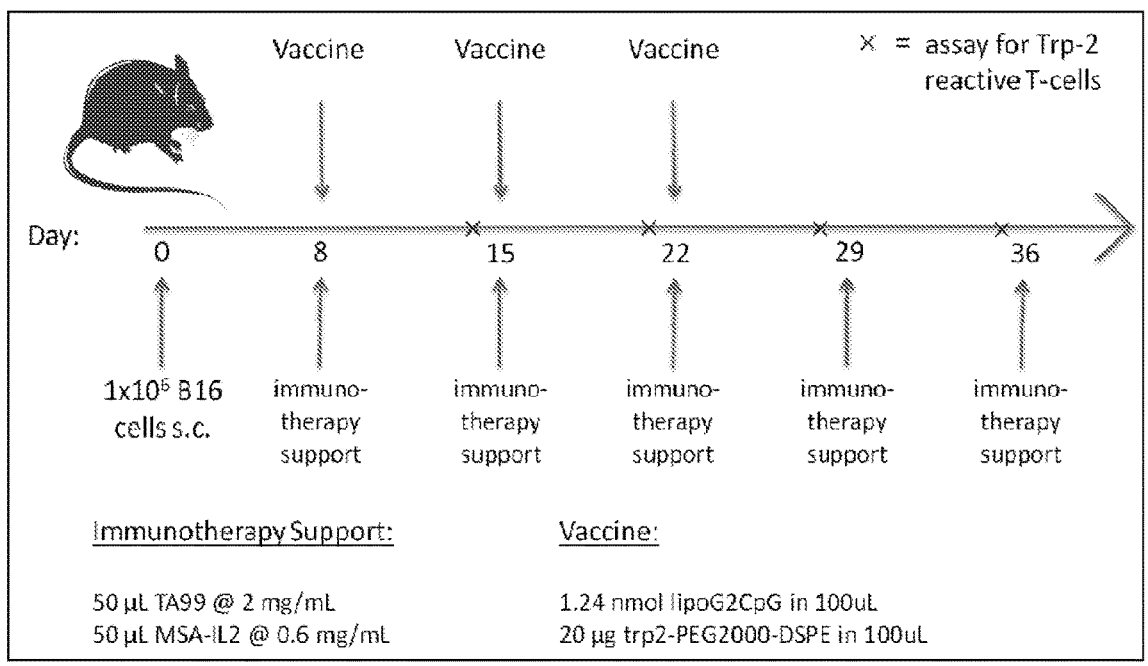
FIG. 1B is a schematic depicting the treatment regimen administered after tumor establishment, as described in the Examples. 1×10⁶ B16F10 melanoma cells were injected subcutaneously into C57BL/6 mice, and 8, 15, and 22 days after tumor injection, immunotherapy support and a vaccine was administered to the mice. Additional immunotherapy support was administered at days 29 and 35 after tumor injection. Blood was collected prior to immunotherapy support and an assay to measure Trp-2 reactive T-cells was performed (marked as "x" on the time line).

The amphiphile cancer vaccine targeting Trp-2 was administered on days 8, 15, and 22 after inoculation of B16F10 cells. Oligonucleotide amphiphiles were synthesized using an ABI 394 synthesizer on a 1.0 μmol scale. All lipophilic phosphoramidites were conjugated as a final 'base' on the 5'end of oligonucleotides. Lui, H. et al., *Angew. Chem. Int. Ed. Engl.* 50, 7052-7055 (2011). A lymph-node targeted molecular adjuvant was made in which a 20 base phosphorothioate (PS)-stabilized CpG oligonucleotide was linked at the 5' to diacyl lipid via a guanine linker (lipo-G$_2$-CpG) as described in Liu, H. et al., *Nature* 507: 519-522 (Mar. 27, 2014). The tumor-associated self-antigen Trp2 from melanoma was conjugated to 1,2-distearoyl-sn-glycero-3-phosphoethanolamine-N-PEG (DSPE-PEG 2 kDa) to generate amph-peptides for vaccination studies. Antigen amphiphiles were synthesized by reacting N-terminal cysteine-modified peptides with maleimide-PEG$_{2000}$-DSPE in dimethyl formamide. A schematic of the treatment regimen is shown in FIGS. 1A and 1B.

Figure 2A:
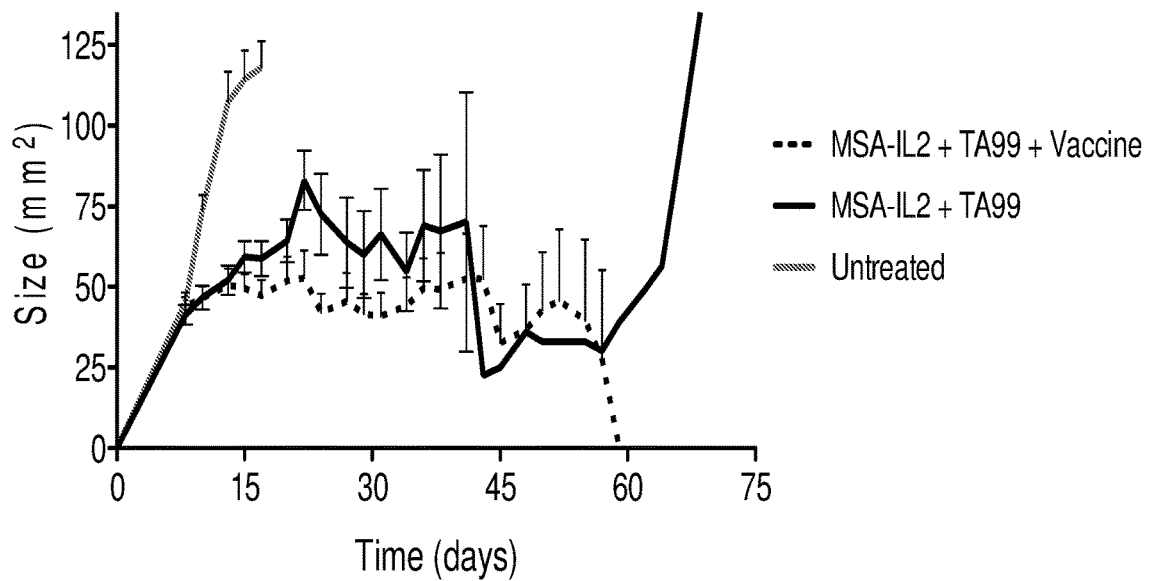
FIGS. 2A and 2B depict the effects of various combination therapies including vehicle, TA99 antibody, MSA-IL2, and/or amphiphile vaccine on tumor control.

Tumor area was measured throughout the course of the experiment and is summarized in FIG. 2A. Tumor area was measured using calipers. The longest dimension of the tumor in any direction was measured first, followed by the measurement of the longest perpendicular dimension. The two values were then multiplied to quantify tumor area in square millimeters. Synergistic reduction of tumor growth was observed when all 3 components (i.e., cancer vaccine, TA99, and MSA-IL-2) were administered, relative to the double combination (MSA-IL-2+TA99) and vehicle (PBS).

Figure 2B:
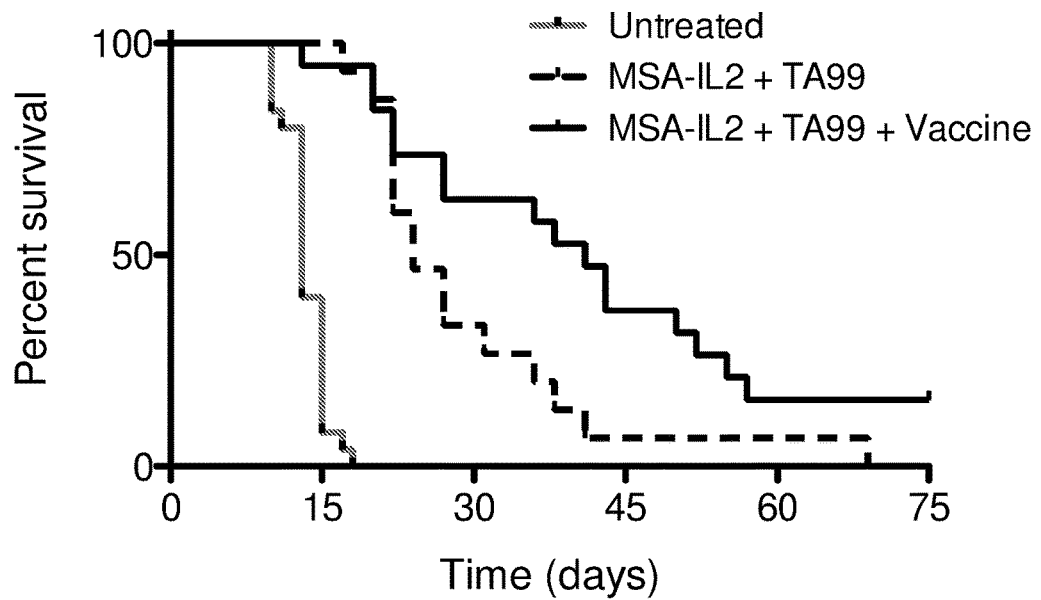

Survival was examined throughout the course of the experiment and plotted in FIG. 2B. Survival was substantially improved with the triple combination (i.e., MSA-IL-2+TA99+ vaccine) relative to the double combination.

Example 2

Vitiligo with Triple Combination Therapy

Figure 3:
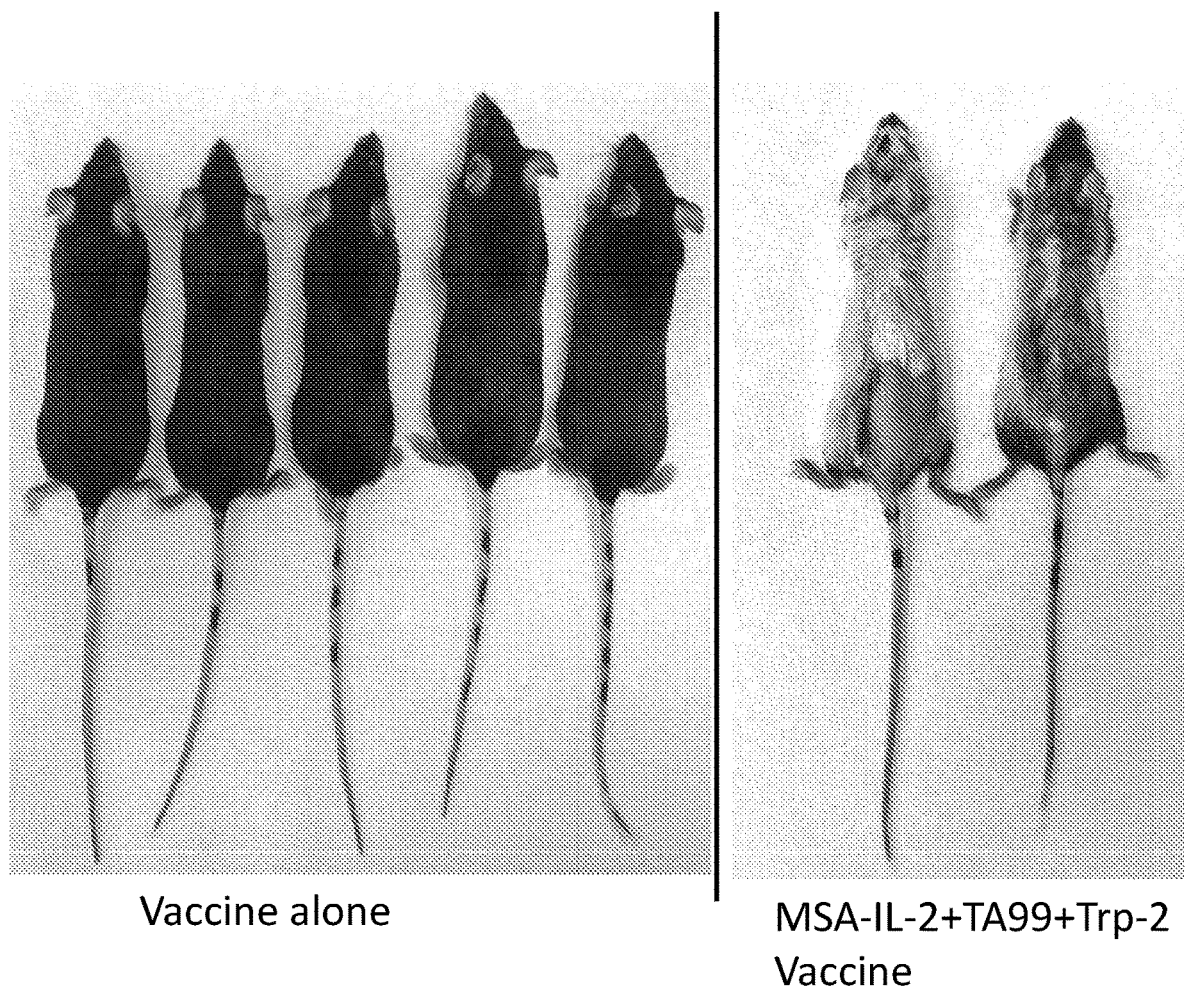
FIG. 3 is an image of mice treated with the Trp-2 vaccine alone (control) or MSA-IL-2+TA99+Trp-2 vaccine. Images were taken of surviving mice 55 days after tumor inoculation. Vitiligo is observed in mice treated with the combination therapy.

To assess the immune response to the various combination therapies, mice inoculated with B16F10 cells and subsequently treated as described in Example 1, were observed for vitiligo, a depigmentation of the skin, 55 days after tumor inoculation. Control mice were age matched and treated with vaccine alone with no inoculation of tumor cells. FIG. 3 shows that surviving mice treated with the triple combination (i.e., MSA-IL-2+TA99+Trp-2 vaccine) displayed vitiligo, whereas control mice did not. This indicates a potent and sustained immune response against the melanoma tumors. Vitiligo has long been an established positive prognostic factor in clinical outcomes of melanoma patients (Quaglino, 2010).

Example 3

Antigen-Reactive CD8+ T Cells in Mice Treated with Combination Therapy

Figure 4:
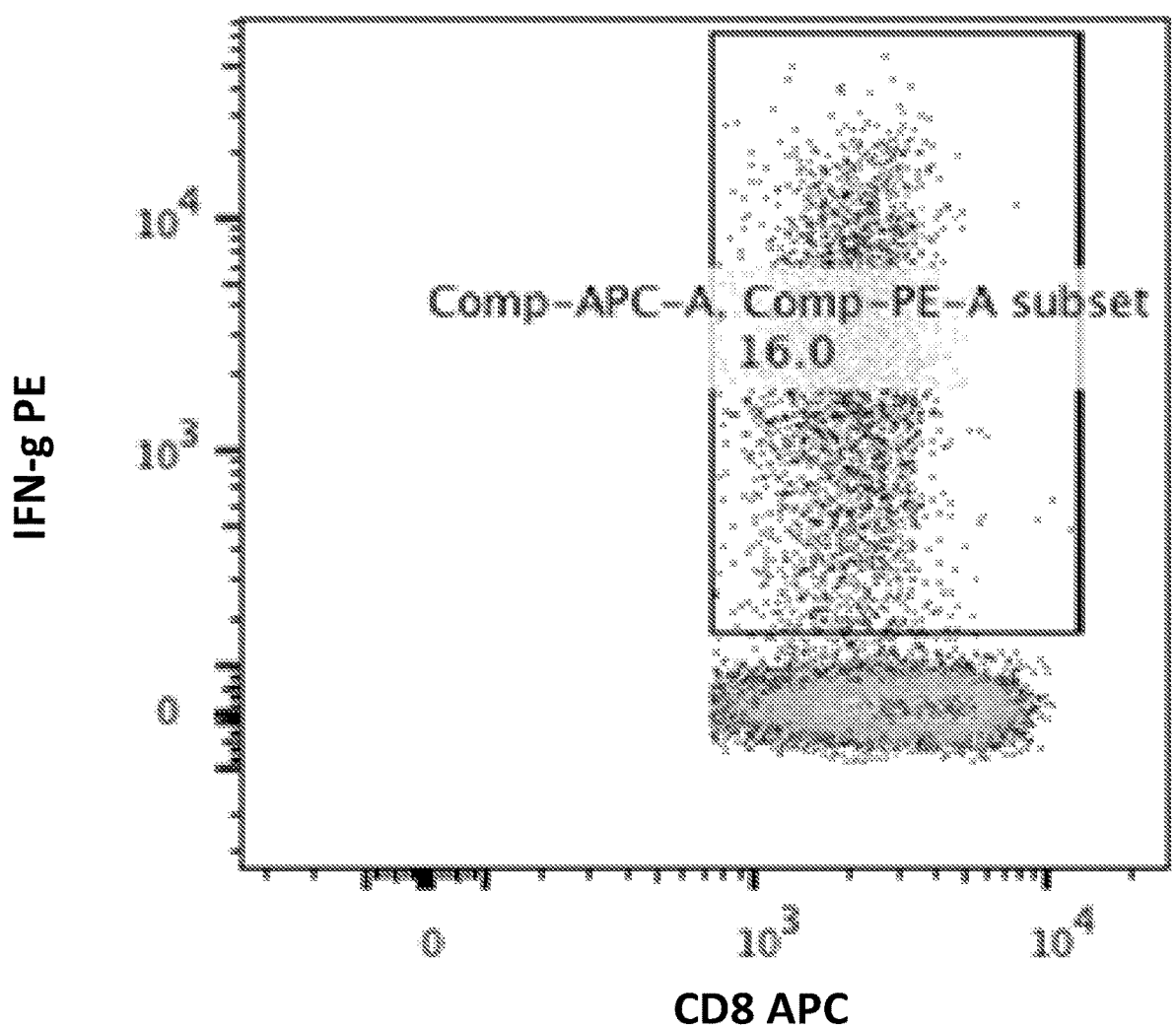
FIG. 4 is a plot representative of the Trp-2 assay, where the gating and subsequent percentage of Trp-2 reactive CD8+ T cells is shown. Peripheral blood mononuclear cells were removed from the mice and stimulated with Trp-2 antigen. The response to Trp-2 was measured by counting the number of IFNγ producing cells via FACS in CD8+ T cells.

In this experiment, the reactivity of CD8+ T cells to the Trp-2 antigen administered by way of vaccine was assessed. To measure antigen-reactive T cells, peripheral blood mononuclear cells (PBMCs) were isolated from mice inoculated with B16F10 cells the day before each treatment and then once a week for the duration of the study. PBMCs were incubated in media containing 0.1 mg/mL Trp-2 peptide for 2 hours at 37° C. Brefeldin A was then added to the cells and incubated at 37° C. for another 4 hours. After peptide incubation, cells were washed and stained for CD8 for 30 minutes at 4° C. The cells were then washed, fixed, and permeabilized before being stained for IFNγ for 30 minutes at 4° C. Cells were then washed and analyzed on a flow cytometer. FIG. 4 depicts a representative readout for the Trp-2 assay and how the positive cells were determined.

Figure 5:
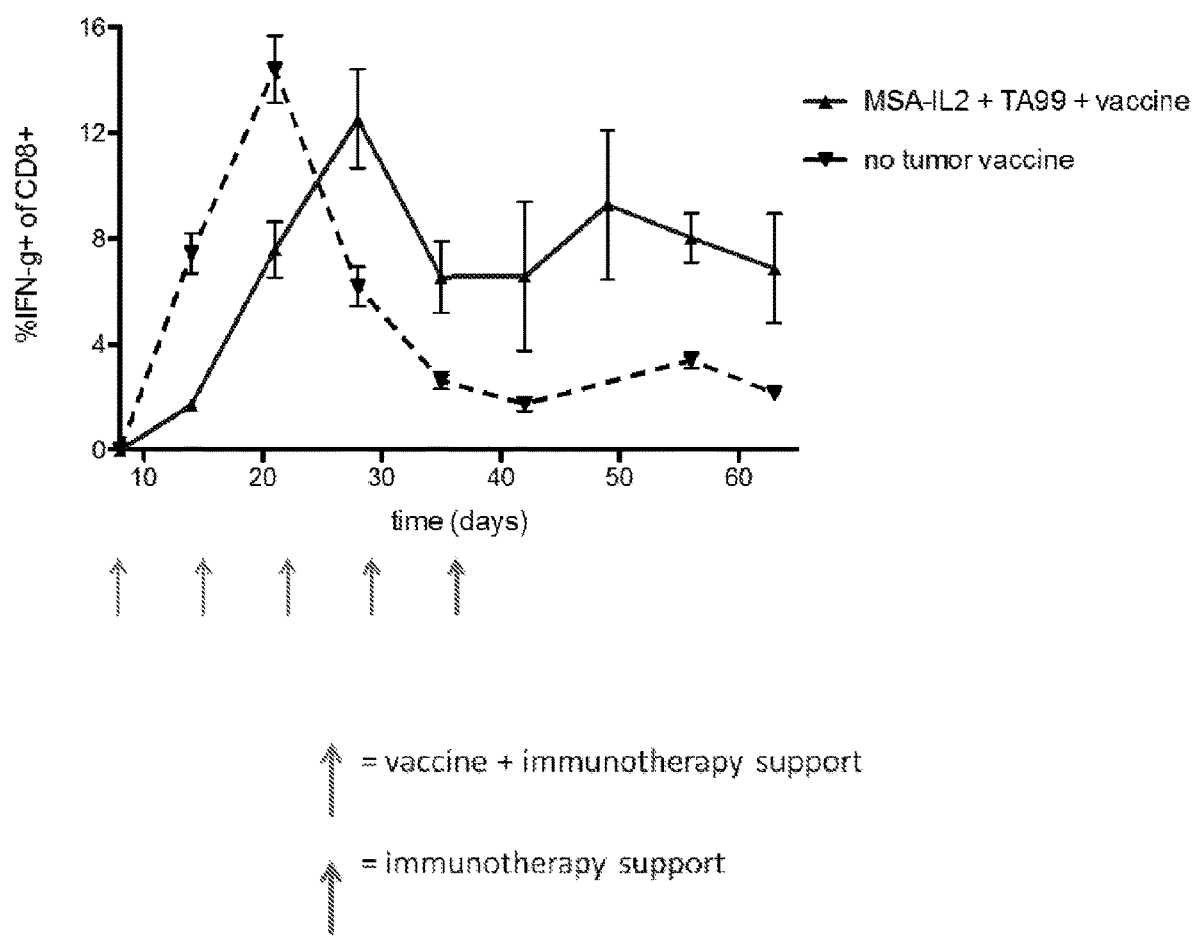
FIG. 5 is a line graph showing the temporal change in percentage of IFNγ producing CD8+ T cells after tumor inoculation. Peripheral blood mononuclear cells were isolated from mice throughout the duration of treatment. Trp-2 was used to stimulate the cells to determine the strength of the IFNγ response, a reflection of memory T cells.

The percentage of IFNγ producing CD8+ T cells was compared between the control (no tumor vaccine) and combination treatment groups. As shown in FIG. 5, the percentage of IFNγ producing CD8+ T cells reactive to Trp-2 was maintained over time, where MSA-IL-2, TA99, and cancer vaccine treatment resulted in increased reactive T cells compared to cells not treated with the cancer vaccine (for up to 70 days after inoculation of B16F10 cells).

Example 4

Enhanced Tumor Control and Survival by Addition of Immune Checkpoint Blocker (Quadruple Combination)

Figure 8A:
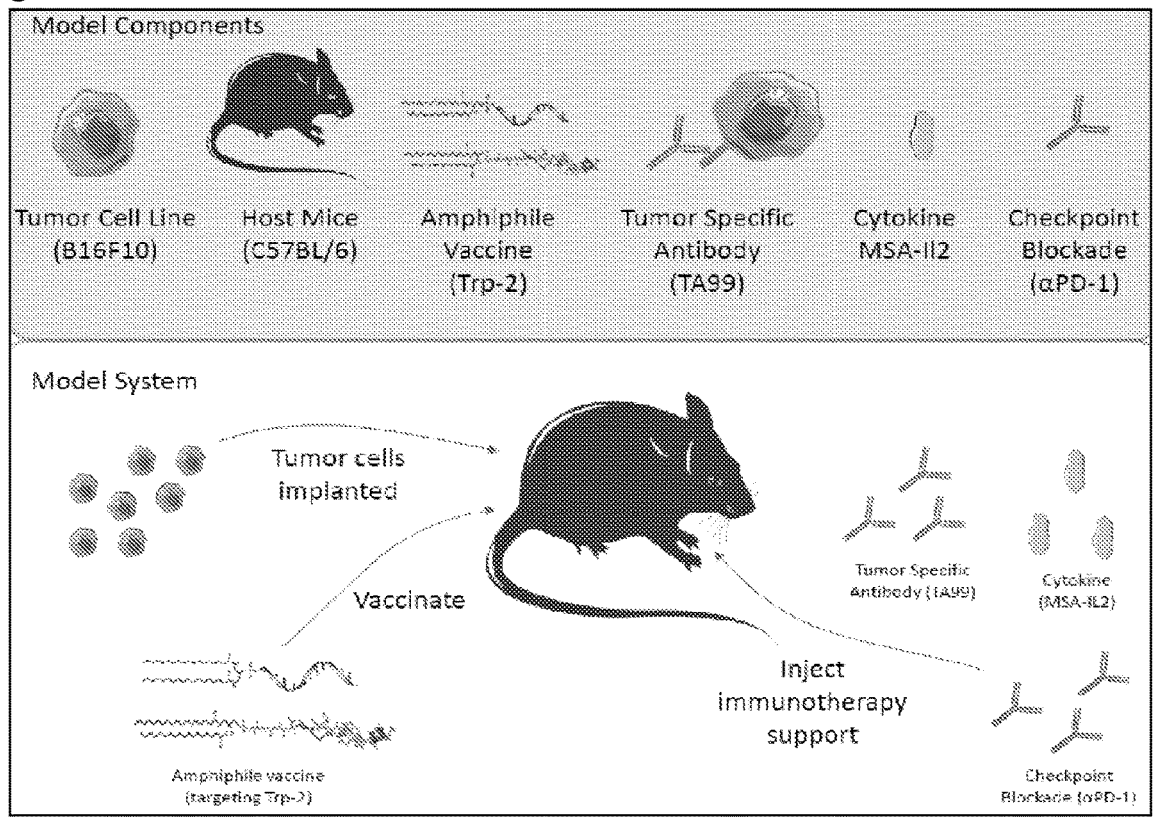
FIG. 8A is a schematic of the melanoma in vivo model depicting components for tumor establishment and treatment, as described in the Examples. B16F10 melanoma cells were injected into C57BL/6 mice. After tumor establishment, the indicated treatments (e.g., amphiphile vaccine against Trp-2, a tumor-specific antibody against Trp-1 (TA99), MSA-IL-2, or an immune checkpoint blocker antibody targeting PD-1, or combinations thereof) were administered.
Figure 8B:
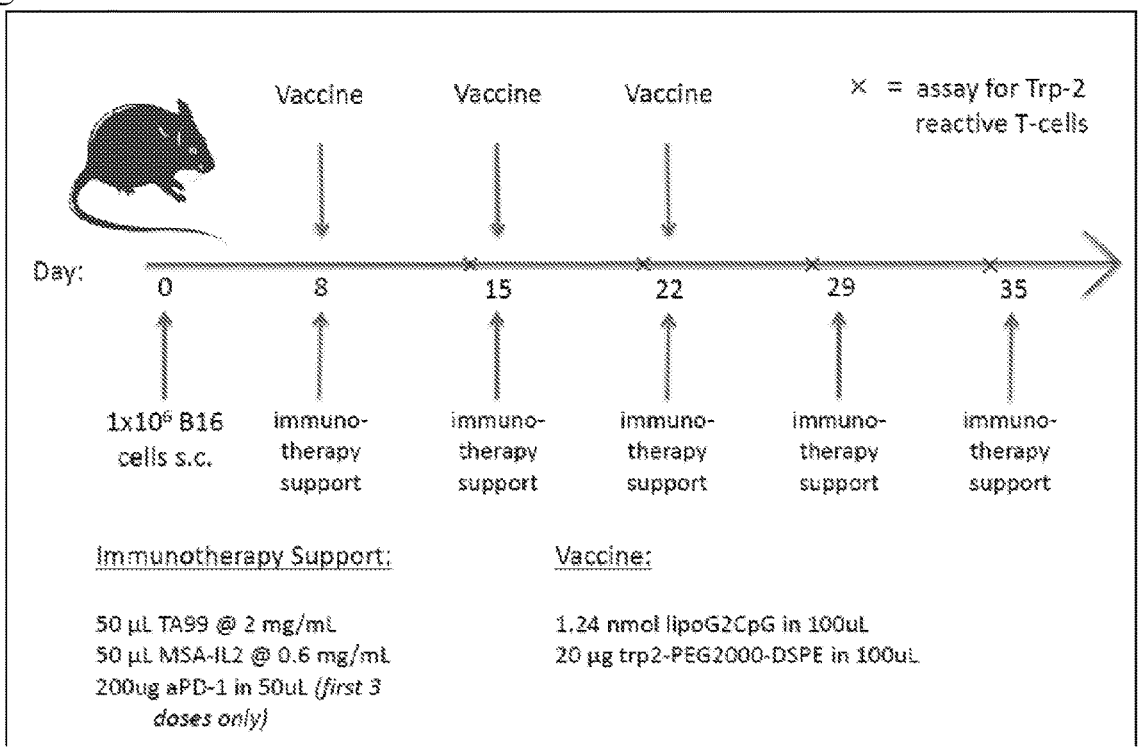
FIG. 8B is a schematic depicting the treatment regimen administered after tumor establishment, as described in the Examples. 1×10⁶ B16F10 melanoma cells were injected subcutaneously into C57BL/6 mice; 8, 15, and 22 days after tumor injection, immunotherapy support and/or a vaccine was administered to the mice. Additional immunotherapy support was administered at days 29 and 35 after tumor injection. Blood was collected prior to immunotherapy support and an assay to measure Trp-2 reactive T-cells was performed (marked as "x" on the time line).

To assess the effectiveness of combination treatment which additionally includes an immune checkpoint blocker, the B16F10 melanoma was utilized as described in Example 1. In addition to the administration of MSA-IL-2, TA99 and cancer vaccine, 200 μg anti-PD-1 antibody (clone RMP1-14 from BioXcell) was administered on days 8, 15, 22, 29 and 35 after inoculation of B16F10 cells. A schematic of the treatment regimen is found in FIG. 8B.

Figures 9A, 9B:
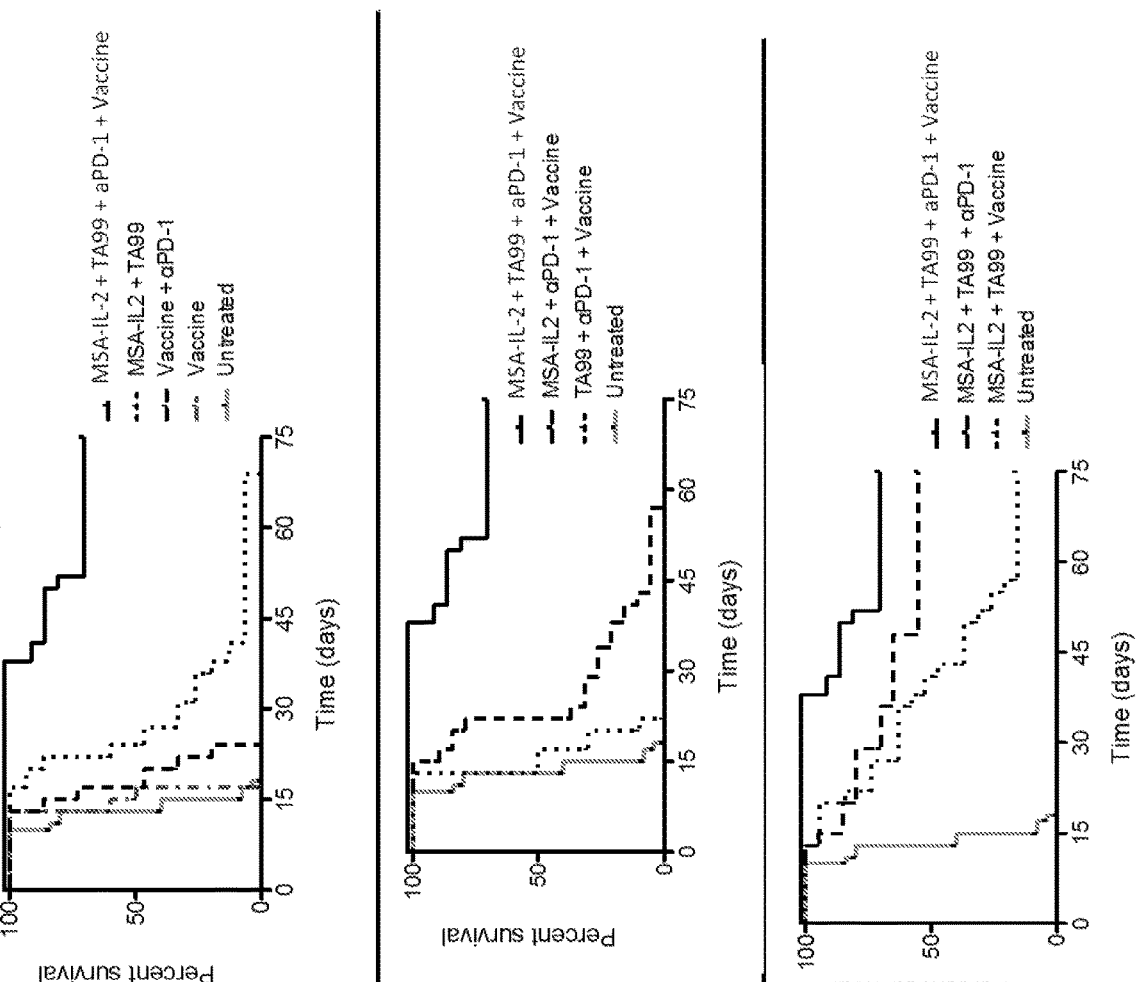
FIGS. 9A and 9B depict the effects of various combination therapies including vehicle, anti-PD-1 antibody, TA99 antibody, MSA-IL2, and amphiphile vaccine, and combinations thereof, on tumor control. Tumor size trajectories are shown in FIG. 9A. Kaplan-Meier survival plots are shown in FIG. 9B.

Tumor area was measured throughout the course of the experiment and is summarized in FIG. 9A. Synergistic reduction of tumor growth was observed when all 4 components (i.e., cancer vaccine, anti-PD1 antibody, TA99, and MSA-IL-2) were administered. Tumor growth was also controlled with the triple combinations (i.e., MSA-IL-2+TA99+vaccine and MSA-IL-2+TA99+anti-PD-1 antibody), relative to the double combinations (anti-PD-1 antibody+TA99, anti-PD-1 antibody+vaccine, anti-PD-1 antibody+MSA-IL-2, and MSA-IL-2+TA99) and vehicle (PBS).

Survival was also examined and plotted in FIG. 9B. Survival was substantially improved with the quadruple combination (i.e., MSA-IL-2+anti-PD1 antibody+TA99+ vaccine). The triple combinations (MSA-IL-2+TA99+vaccine and MSA-IL-2+TA99+anti-PD-1 antibody) also substantially improved survival relative to the double and single combinations. The quadruple combination was not overtly toxic as animals were otherwise healthy and steadily gained weight comparable to control animals (data not shown).

Example 5

Quadruple Combination Treated Mice Survive Secondary Challenge

Figure 10:
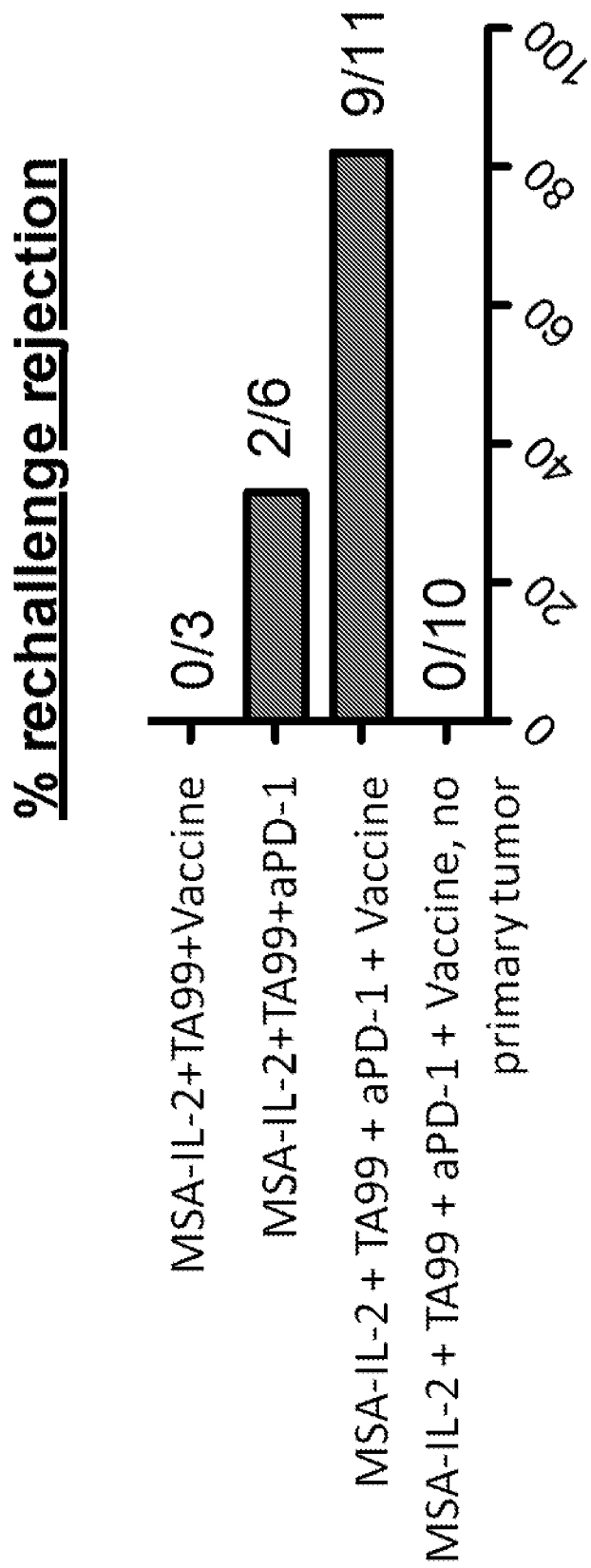
FIG. 10 is a graph depicting the percentage of rejection of secondary tumor challenge. 75 days after initial tumor injection, B16F10 cells were injected into the same mice to "rechallenge" them with tumor cells.

To determine the effect of adding an immune checkpoint blocker to the triple combination (i.e., MSA-IL-2, TA99, and cancer vaccine) on the memory of immune cells against tumor cells, surviving mice that underwent the regimen described in Example 4 were re-challenged 75 days after initial tumor inoculation. These mice were injected with 100,000 B16F10 cells and survival was monitored. Mice originally treated with MSA-IL-2+anti-PD1 antibody+TA99+vaccine survived the re-challenge (FIG. 10). At 35 days post-secondary challenge, none of the remaining mice had visible tumors and were deemed to have rejected the secondary tumors.

Example 6

Vitiligo with Quadruple Combination Therapy

Figure 11:
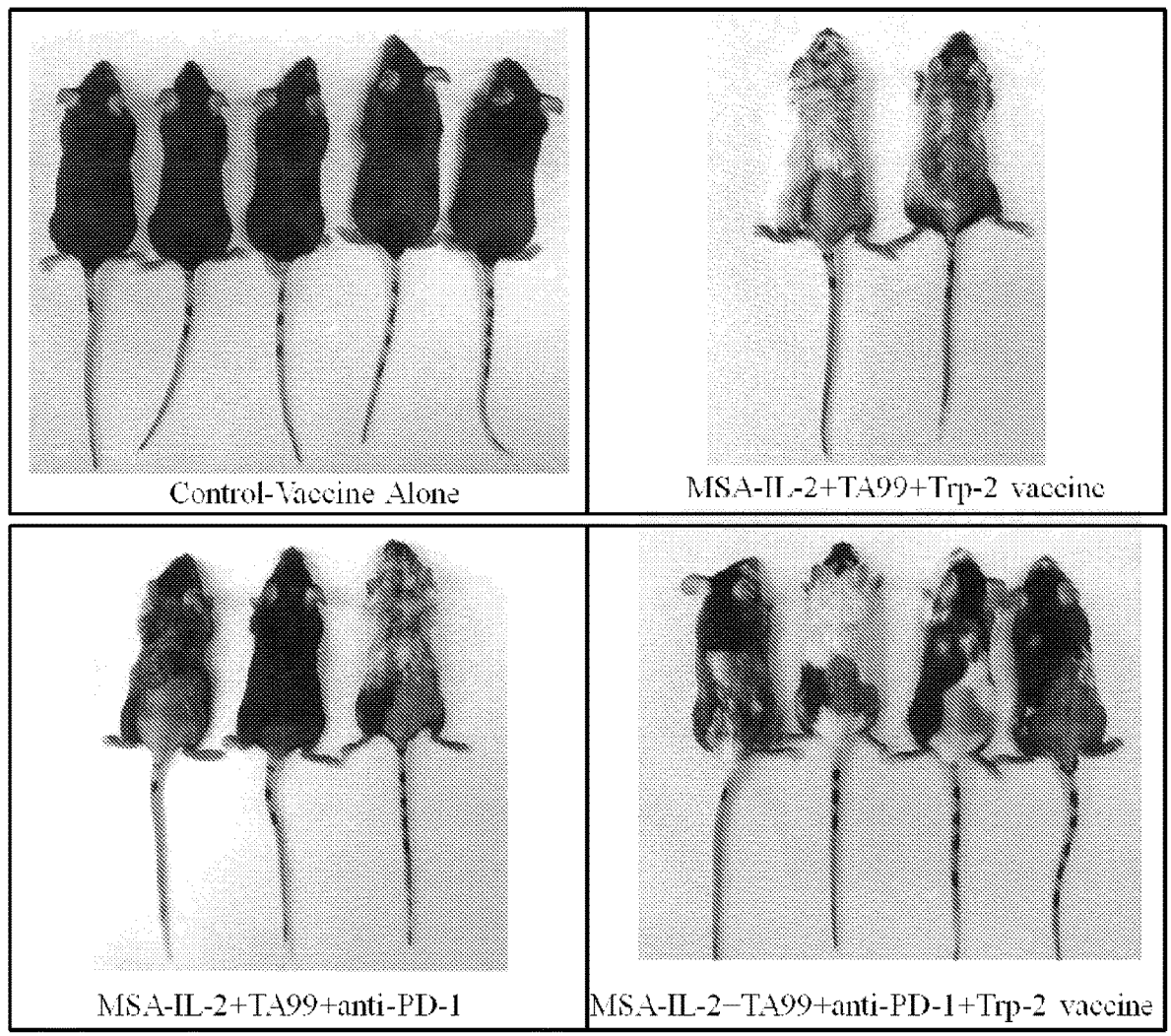
FIG. 11 is an image of control mice and mice treated with a combination of MSA-IL-2, TA99 antibody, anti-PD-1 antibody, and/or vaccine. Images were taken of surviving mice 55 days after tumor inoculation. Vitiligo is observed in mice treated with the combination therapies.

To assess the immune response when tumor-bearing mice are treated with the quadruple combination therapy, mice inoculated with B16F10 cells and subsequently treated as described in Example 4 were observed for vitiligo, 55 days after tumor inoculation. Control mice were age matched and treated with vaccine alone with no inoculation of tumor cells. FIG. 11 shows that surviving mice treated with the quadruple combination (i.e., MSA-IL-2+TA99+anti-PD-1 antibody+Trp-2 vaccine) and triple combinations (i.e., MSA-IL-2+TA99+Trp-2 vaccine and MSA-IL-2+TA99+anti-PD1 antibody) all displayed vitiligo, whereas control mice did not. This indicates a potent and sustained immune response against Trp-2, a melanocyte antigen, wherein targeting this antigen results in depigmentation.

Example 7

Antigen-Reactive CD8+ T Cells in Mice Treated with Quadruple Combination Therapy To assess the role of an immune checkpoint blocker on the reactivity of CD8+ T cells to the Trp-2 antigen administered by way of vaccine, CD8+ T cells were measured as described in Example 3.

Figure 12:
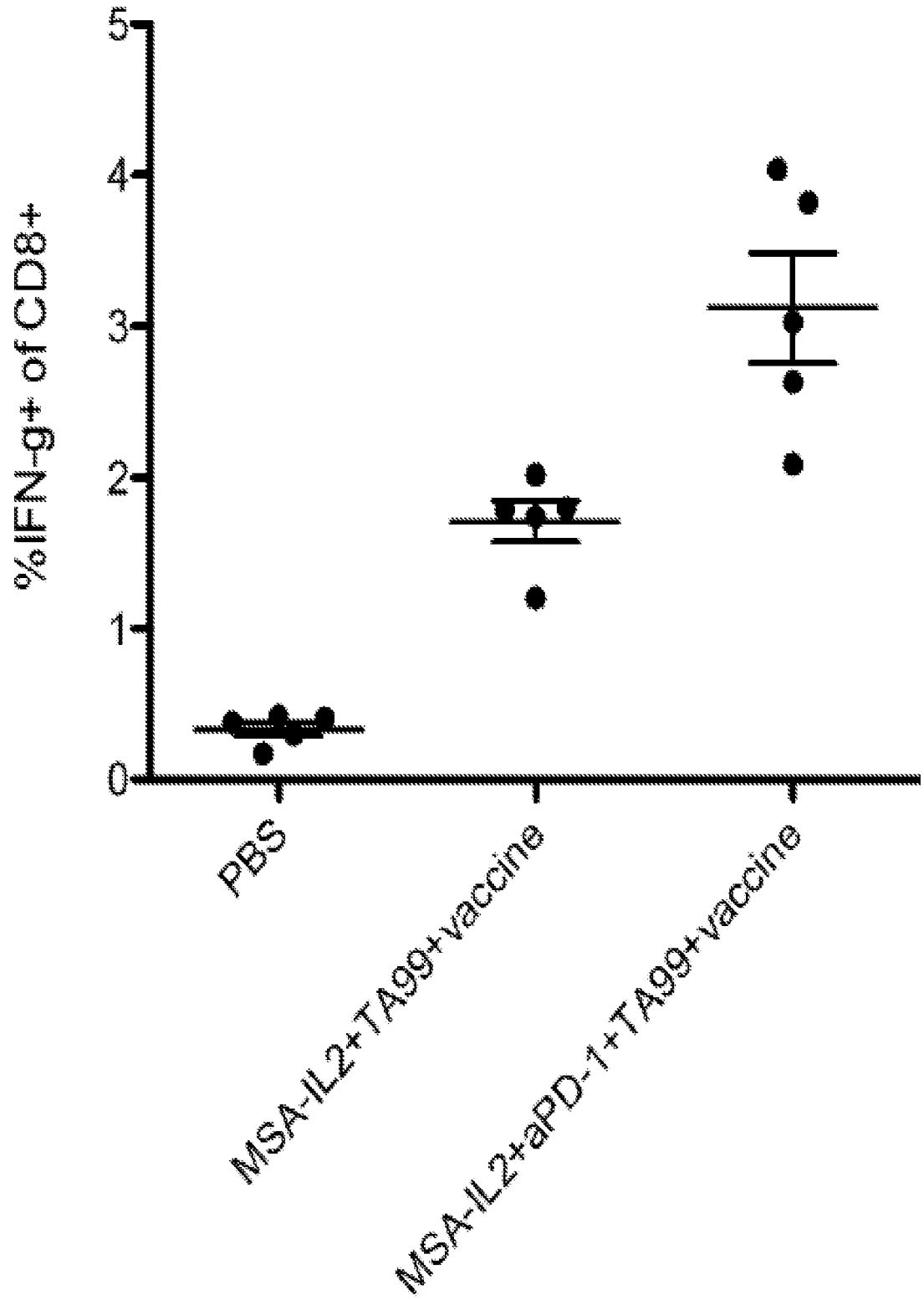
FIG. 12 is a graph depicting the percentage of CD8+ T cells that produce IFNγ after the 1st treatment (i.e., 14 days after tumor inoculation, 6 days after the 1$^{st}$ treatment).
Figure 13:
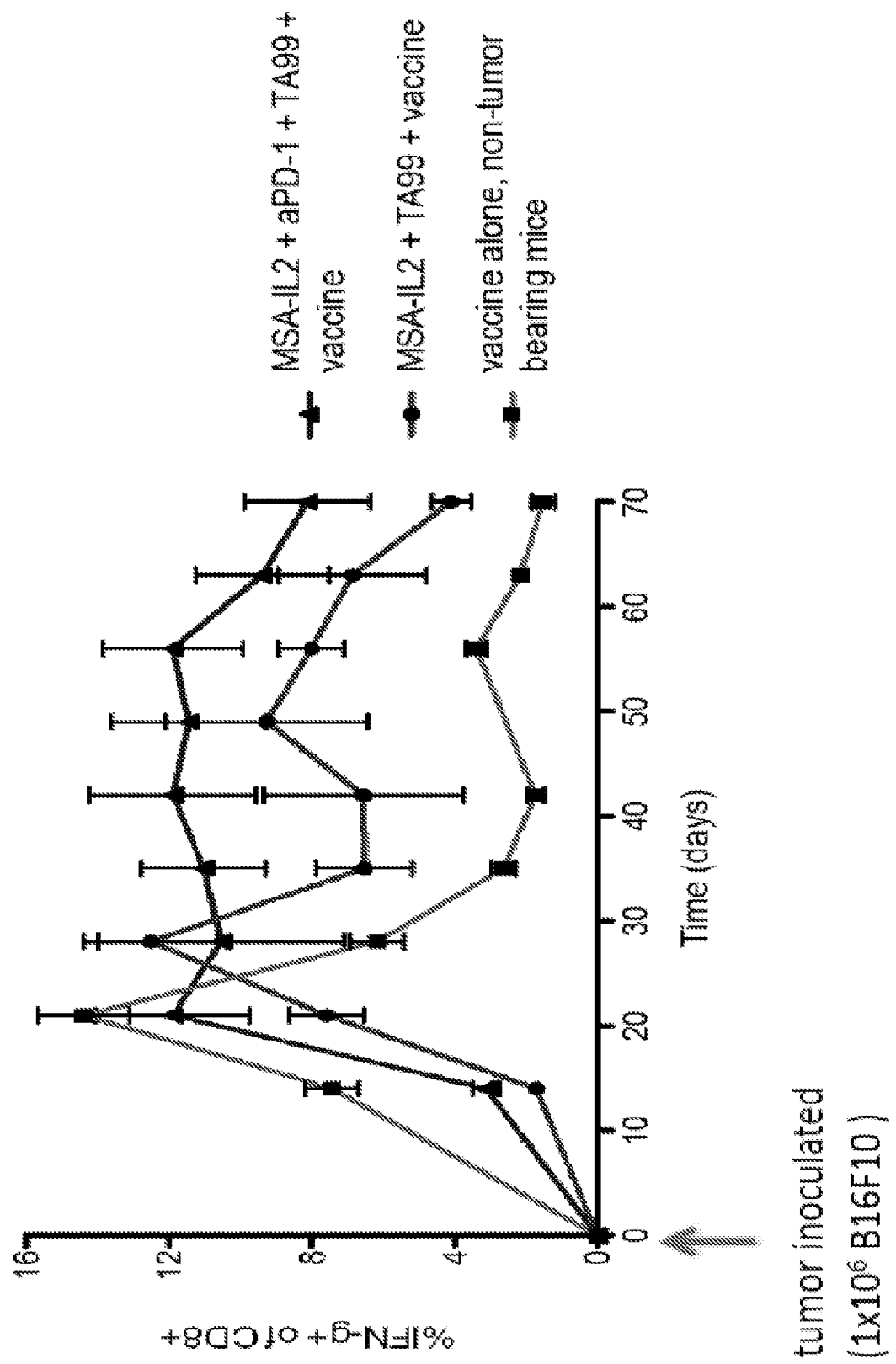
FIG. 13 is a line graph showing the temporal change in percentage of IFNγ-producing CD8+ T cells after tumor inoculation. Peripheral blood mononuclear cells were isolated from mice throughout the duration of treatment. Trp-2 was used to stimulate cells in order to determine the strength of the IFNγ response, a reflection of the T cell response induced by the vaccine.

The percentage of IFNγ producing CD8+ T cells was compared between treatment combinations. As shown in FIG. 12, the triple combination of MSA-IL-2+TA99+vaccine resulted in about 2% reactive T cells, whereas the quadruple combination of MSA-IL-2+anti-PD-1 antibody+TA99+vaccine resulted in about 3% reactive T cells after one treatment. This result indicates that inclusion of the anti-PD-1 antibody increased the number of reactive T cells 14 days after tumor inoculation (i.e., 6 days after the first treatment). This was also observed over the course of 70 days after inoculation of B16F10 cells. FIG. 13 shows that the percentage of IFNγ producing CD8+ T cells reactive to Trp-2 is maintained over time, where MSA-IL-2+anti-PD-1 antibody+TA99+cancer vaccine treatment resulted in increased reactive T cells compared to vaccine alone or MSA-IL-2+TA99+cancer vaccine treatment.

Example 8

Response to Rechallenge in Mice without Primary Tumors

To further assess the immune response with the quadruple combination therapy (i.e., MSA-IL-2+TA99+anti-PD-1 antibody+vaccine) in mice after tumor challenge, mice inoculated with or without B16F10 cells, subsequently treated as described in Example 4, and then rechallenged as described in Example 5, were observed for Trp-2 reactive T cells and vitiligo.

Figure 14:
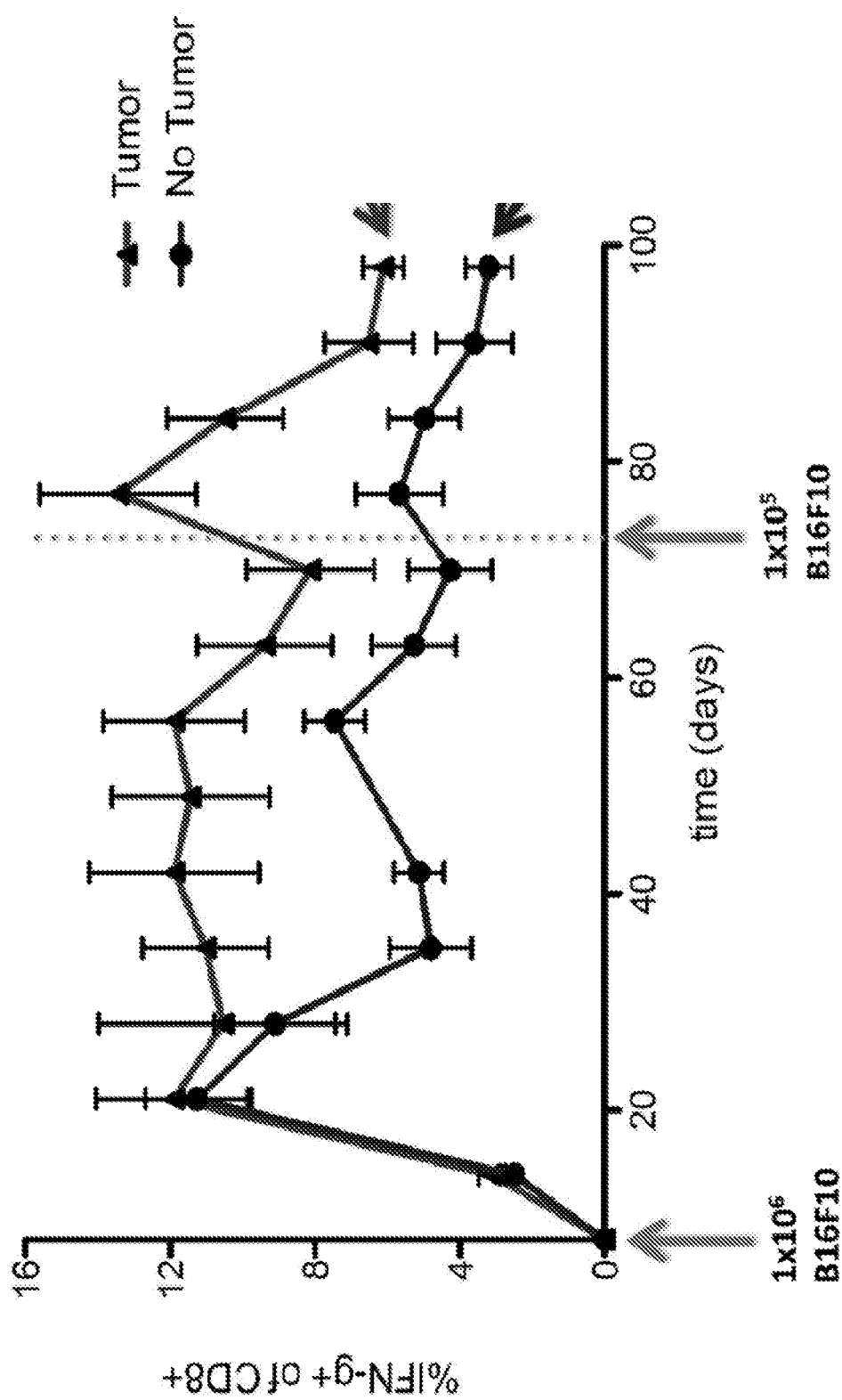
FIG. 14 is a line graph showing the temporal change in percentage of IFNγ-producing CD8+ T cells after rechallenge with B16F10 cells in mice with or without a primary tumor. Peripheral blood mononuclear cells were isolated from mice throughout the duration of treatment. Trp-2 was used to stimulate the cells to determine the strength of the IFNγ response, a reflection of the T cell response induced by the vaccine.

Unlike equivalently treated mice that were inoculated with primary tumors, mice treated with the quadruple combination, but with no primary tumors, were unable to reject subsequent tumor challenge. 9 out of 11 mice rejected subsequent tumor challenges if they had a primary tumor, whereas 0 out of 5 mice rejected subsequent tumor challenges if they did not have a primary tumor. FIG. 14 shows that the T cell response was tumor antigen dependent and boosted after the subsequent rechallenge. Mice without primary tumors and treated with the quadruple combination did not sustain high levels of Trp2 reactive T cells after rechallenge. Mice treated with the quadruple combination showed a stronger rechallenge response than equivalently treated mice without primary tumors. This may explain why mice without primary tumors were unable to reject subsequent tumor challenges.

Figure 15:
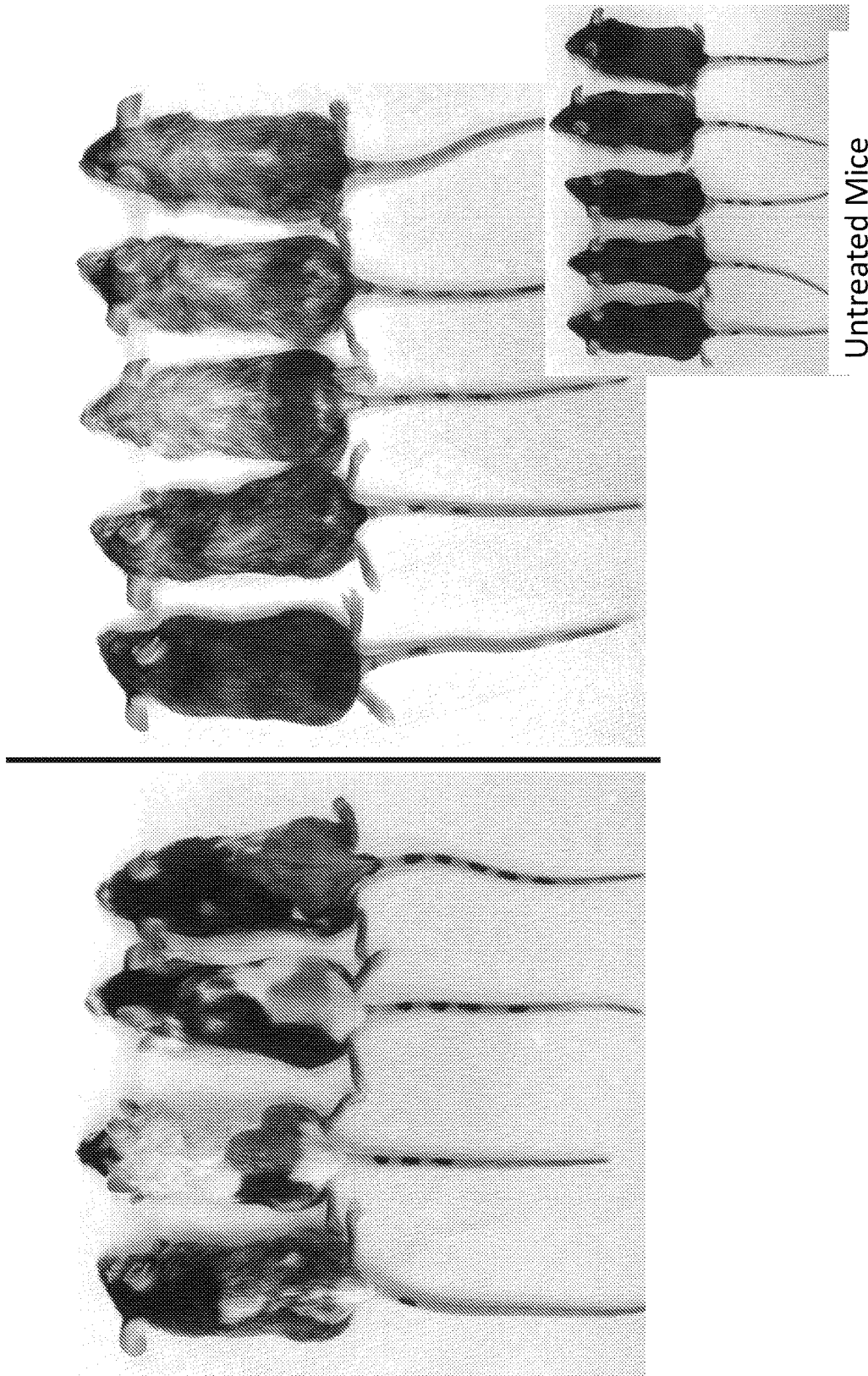
FIG. 15 is an image of mice with or without primary tumors treated with a combination of MSA-IL-2, TA99 antibody, anti-PD-1 antibody, and vaccine, along with untreated mice. Images were taken of surviving mice 55 days after tumor inoculation. Vitiligo is observed in mice treated with the quadruple combination therapy, with or without primary tumors.

Despite this lack of protection from rechallenge, mice without primary tumors underwent strong vitiligo responses, normally associated with successful immunotherapies (FIG. 15). The dissociation between vitiligo and successful immunotherapies has been observed previously (Byrne et al., J. Immunol. (2014), Vol 192: 1433-1439). These results highlight the importance of the tumor-derived antigen and suggest that cross-presentation of that antigen may have led to antigen spreading. It also suggests that vitiligo may indicate a strong immunological response to targeted melanoma differentiation markers, but a complex, suppressive tumor microenvironment may overcome this response.

Example 9

Immune Cell Populations Important for Survival in Mice Treated with Quadruple Combination To assess the role of various immune cell populations in the observed improved survival of mice with B16F10 tumors treated with the quadruple combination (i.e., MSA-IL-2+TA99+anti-PD-1 antibody+vaccine), depletion antibodies were administered twice a week starting one day prior to the first treatment. Cytotoxic lymphocytes were depleted with an anti-CD8a antibody (clone 2.43). Natural killer cells were depleted with an anti-NK1.1 antibody (clone PK136), and neutrophils were depleted with an anti-Ly-6G antibody (clone 1A8). These antibodies were administered at 400 μg per dose. All antibodies were purchased from BioXcell. Cross-presenting dendritic cells were depleted by using Batf3−/− mice. Batf3−/− mice lack the function of the basic leucine zipper transcription factor, ATF-like 3. Deletion of Batf3 has been shown to prevent the development of CD8+ dendritic cells, which are important for the cross-presentation of exogenous antigen on MHC Class I.

Figure 16:
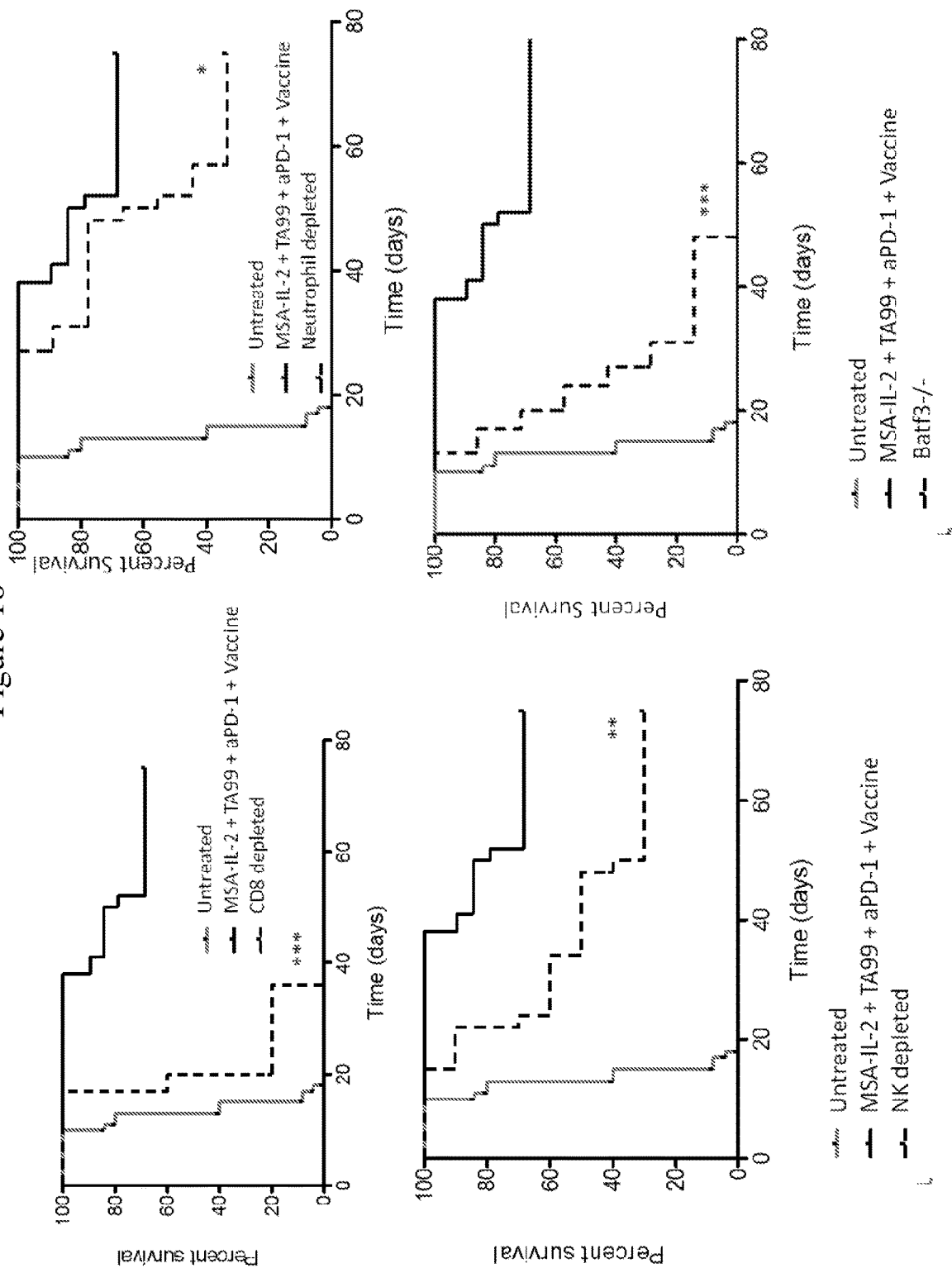
FIG. 16 shows Kaplan-Meier survival plots depicting the effects of various immune cell depletions performed in mice after tumor inoculation with B16F10 cells and one day prior to treatment with a combination of MSA-IL-2, TA99 antibody, anti-PD-1 antibody, and vaccine. Neutrophils, natural killer cells (NK) and CD8+ T cells (CD8) were depleted with antibodies against Ly-6G, NK1.1, and CD8, respectively, at a dose of 400 µg administered twice a week starting one day prior to the first treatment. The role of dendritic cells was determined using Batf3−/− mice. * $p<0.05$  $p<0.01$ *$p<0.001$

FIG. 16 shows the survival of mice treated with the quadruple combination without the various immune cells. CD8+ T cells and cross-presenting dendritic cells were identified as two critical cell types contributing to the potency of the quadruple combination therapy. Natural killer cells and neutrophils were not essential, but their depletion led to significant reductions in overall survival rates. A notable result of these depletion experiments is that the vaccine and checkpoint blockade therapies are marginalized since they primarily act through T cell mediated pathways. More generally, these results suggest that the adaptive immune system is a critical part of the quadruple combination immunotherapy.

Example 10

Immune Cell Infiltration in Tumors

Figures 17A, 17B, 17C:
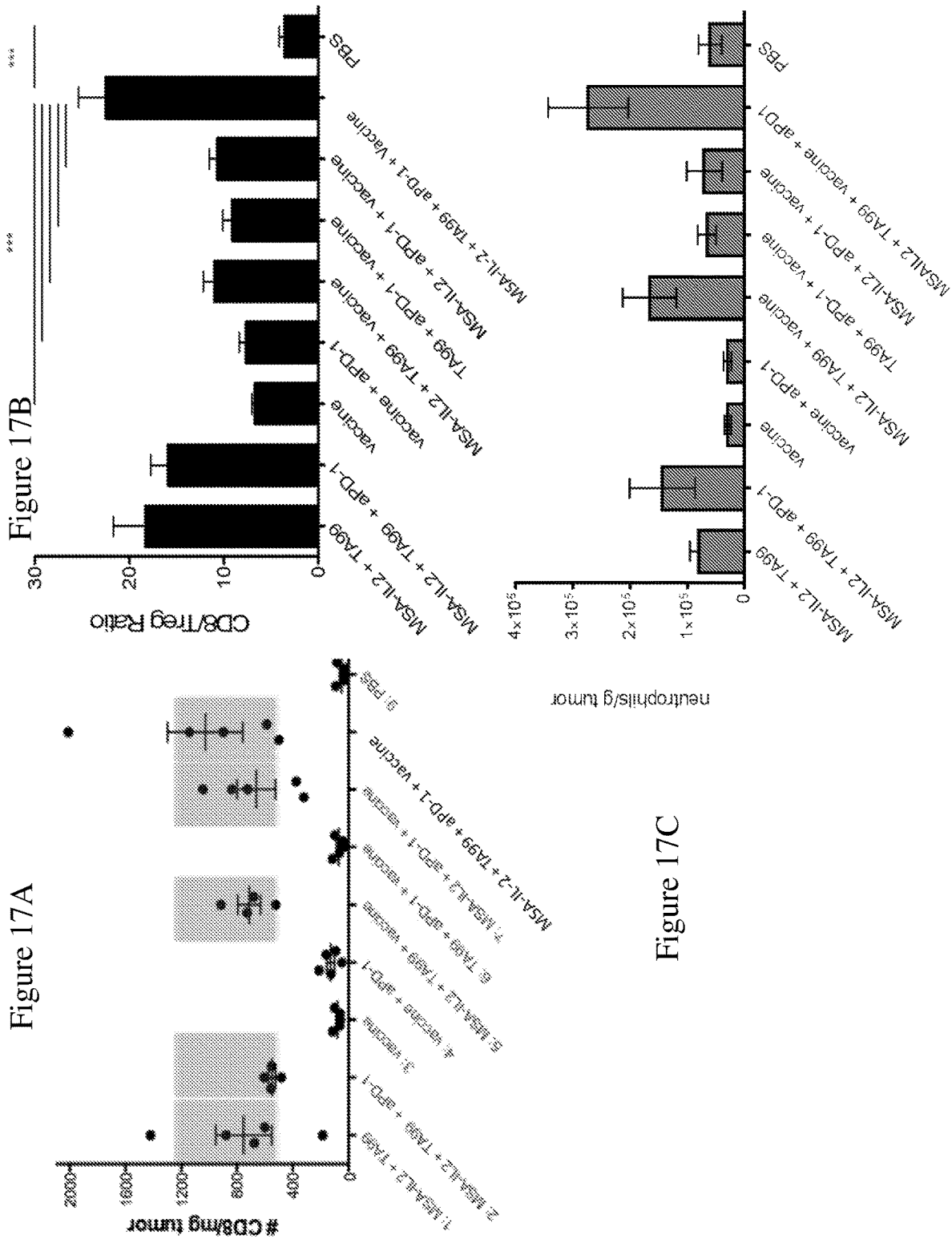
FIG. 17A is a graph depicting the number of CD8+ T cells per mg of tumor in B16F10 tumors 4 days after a single dose of the indicated combinations of MSA-IL-2, TA99 antibody, anti-PD-1 antibody, and/or vaccine, or PBS, as measured by intracellular cytokine staining.
FIG. 17B is a graph depicting the ratio of CD8+ T cells:regulatory T cells (Tregs). Along with the measurement of CD8+ T cells in FIG. 17A, Tregs in tumors were measured via flow cytometry 4 days after a single dose of the indicated combinations. *** $p<0.001$
FIG. 17C is a graph showing the number of neutrophils per gram of tumor in B16F10 tumors, measured the same as CD8+ T cells and Tregs.

To assess the role of immune cell populations in the control of tumor growth in mice treated with the various combination therapies, mice inoculated with B16F10 cells were sacrificed and tumors harvested 1-3 days after a single dose of the different combination therapies. The number of CD8+ T cells, CD4+ T cells (regulatory or non-regulatory), neutrophils, natural killer cells and dendritic cells in the tumors were measured via flow cytometry as previously described (Zhu et al., *Cancer Cell* (2015) Vol 27: 489-501). CD8+ T cells were critical to the efficacy of the treatments as shown in Example 9. Their role in tumor control was confirmed by the observation of high levels of infiltrates in effective combinations (FIG. 17A). FIG. 17B shows the ratio of CD8 to Treg cells, which is considered an accurate indicator of an effective immune response. An increased ratio correlated with successful therapies. In addition, the total number of dendritic cells was enhanced by administration of MSA-IL-2 (data not shown). Infiltrating neutrophils were significantly increased in the most effective treatments (i.e., MSA-IL-2+TA99+anti-PD-1 antibody+vaccine, MSA-IL-2+TA99+vaccine, and MSA-IL-1+TA99+anti-PD-1 antibody) (FIG. 17C). This further demonstrated the need to engage both the adaptive and innate immune systems in effective immunotherapy combinations.

Example 11

Cross-Presentation of Antigens and Antigen Spreading

Figure 18:
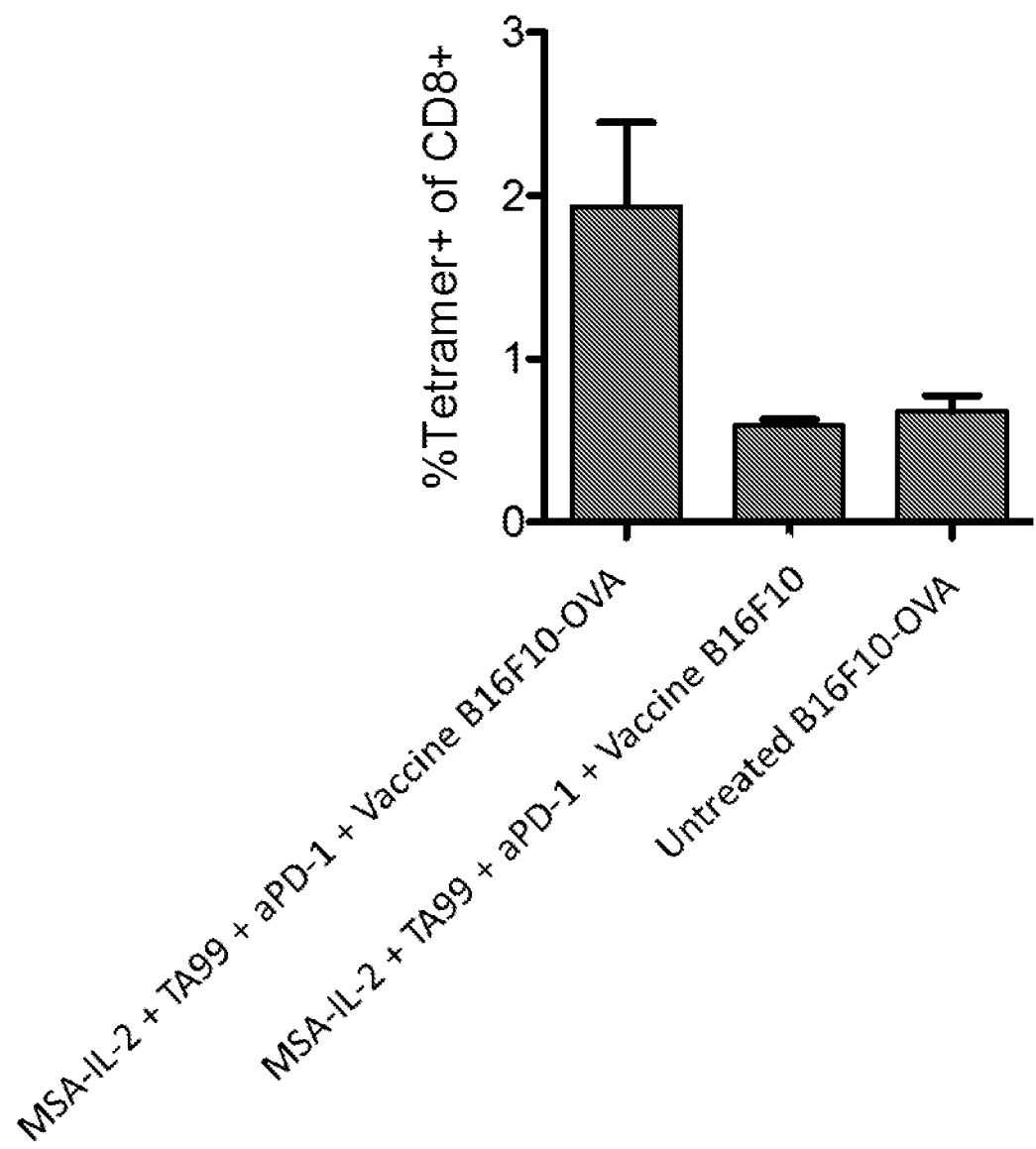
FIG. 18 is a graph depicting the response to OVA peptide when using B16F10-OVA cells. Shown is the proportion of tetramer+CD8+ T cells, as determined by intracellular cytokine staining at day 21.

To assess the ability of the quadruple combination to induce antigen spreading facilitated by cross-presentation of tumor-derived antigen, OVA was used as a surrogate. B16F10-OVA cells were used to inoculate tumors in B6 mice, which were then treated with the quadruple combination (i.e., MSA-IL-2+TA99+anti-PD-1 antibody+vaccine) as described in Example 4. Tetramers complexed with OVA peptides were purchased from MBL. Tetramer staining was performed in buffer containing 50 nM dasatinib. 21 days after tumor inoculation, T cells were analyzed for OVA-specific T cell receptor expression by tetramer staining and flow cytometry. A significant response to OVA peptide was observed by flow cytometry, despite specifically not targeting the OVA antigen (FIG. 18). Because none of the therapies targeted OVA or were specifically engineered to elicit an OVA-specific response, the immune system itself developed this response. This indicated that cross-presentation of tumor derived antigens was occurring as a consequence of the combination immunotherapy.

Figure 19:
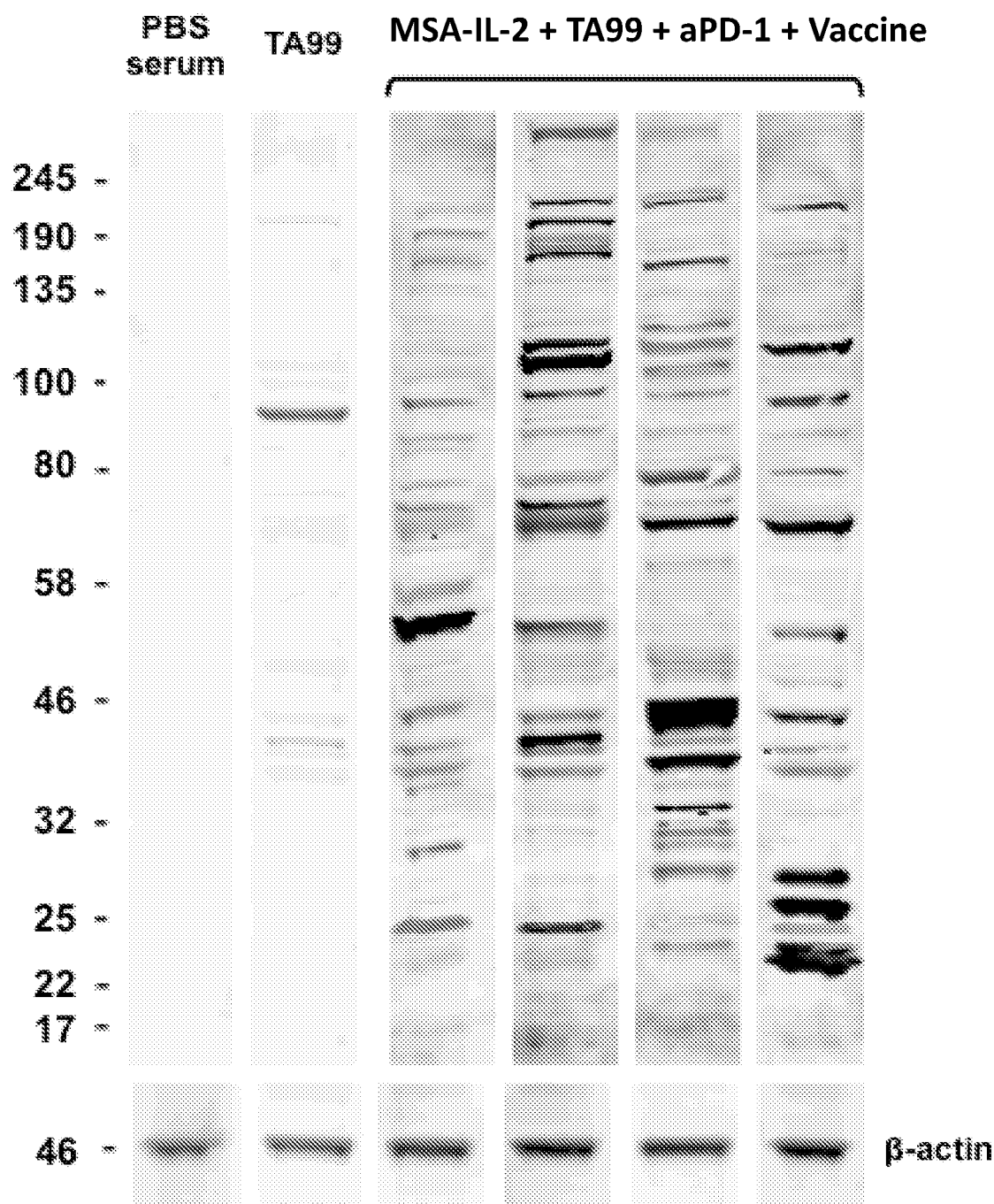
FIG. 19 is an image of B16F10 lysate run on an SDS-PAGE gel. Serum from mice was used to probe the cell lysate for binding. Serum from untreated mice, mice treated with TA99 antibody, and mice treated with the quadruple combination of MSA-IL-2, TA99 antibody, anti-PD-1 antibody, and vaccine after secondary challenge (i.e., 100 days post initial tumor inoculation) was used.

Antigen spreading occurs when the immune system identifies novel epitopes against the targeted tumor and raises an adaptive response against them. It is highly effective in curing established tumors and preventing recurrence (Corbiere et al., *Cancer Res.* (2011) Vol 71: 1253-1262). To test for antigen spreading following the quadruple treatment, B16F10 cell lysate was run on an SDS-PAGE gel (FIG. 19). Serum from quadruple combination-treated mice was used to probe the cell lysate for binding. Untreated serum from naïve mice was used as a control. After secondary binding and imaging, a robust humoral response was observed in treated mice compared to untreated mice. Serum was also collected post-secondary challenge (i.e., 100 days after tumor inoculation). A clear increase in response was observed after rechallenge, consistent with the CD8+ T cell response boost. These findings demonstrate the engagement of the humoral immune system against tumor antigens via antigen spreading.

Example 12

Inducible Tumor Model for Quadruple Combination Therapy

Figure 20:
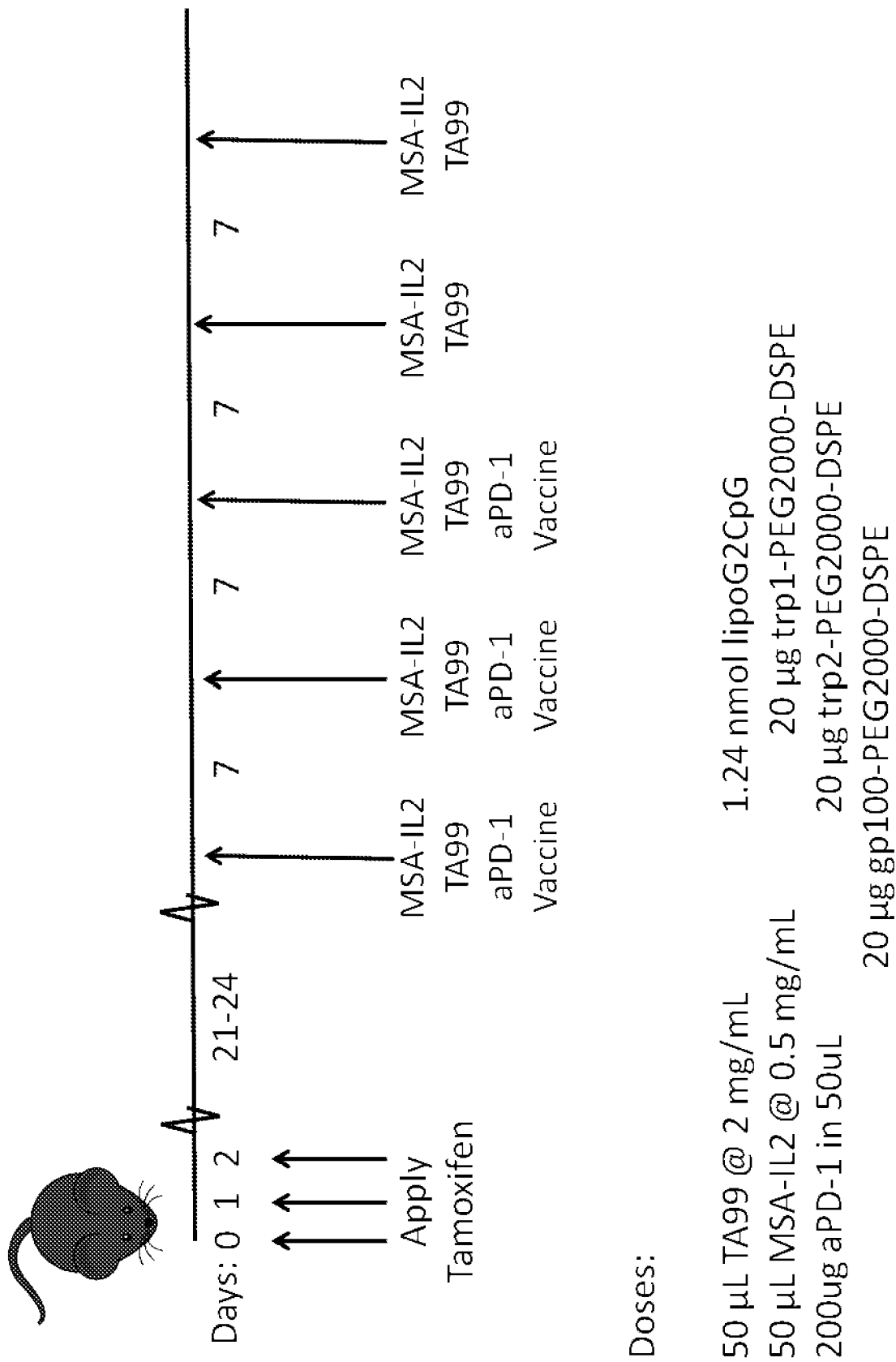
FIG. 20 is a schematic depicting the treatment regimen administered after tumor establishment using the BRAF/PTEN mouse model, as described in the Examples. Tamoxifen was administered to the left ear of BRAF/PTEN-TG mice on three consecutive days. Treatment started 24-26 days later, when visible tumor lesions were present. A combination of MSA-IL-2, TA99 antibody, anti-PD-1 antibody, and a vaccine was administered to the mice every 7 days for 3 treatments total. Following this, MSA-IL-2 and TA99 antibody were administered another two times with 7 days in between each treatment.

To further assess the efficacy of the quadruple combination treatment, the BRaf/Pten inducible tumor system was used. BRaf/Pten mice (Dankort et al., *Nat. Genet.* (2009) Vol 41: 544-552) were crossed with mT/mG (Muzumdar et al., *Genes* (2007) Vol 45: 593-605) to generate BRaf/Pten-TG mice. To induce tumors, 2 µL of 5 mg/mL tamoxifen was administered to the left ear on three consecutive days. 24-26 days later, when visible tumor lesions were present, treatment was begun and executed as described for the subcutaneous tumor model (FIG. 20). The vaccine used was a combination of three amph-peptides (15 µg amph-gp100, 15 µg amph-Trp-1, and 15 µg amph-Trp2) and 1.24 nmol amph-CpG, administered as a single dose. Mice were euthanized when pigmented lesions covered the induced ear (about 90% coverage) or when apigmented tumors reached 10 mm in diameter.

Figure 21:
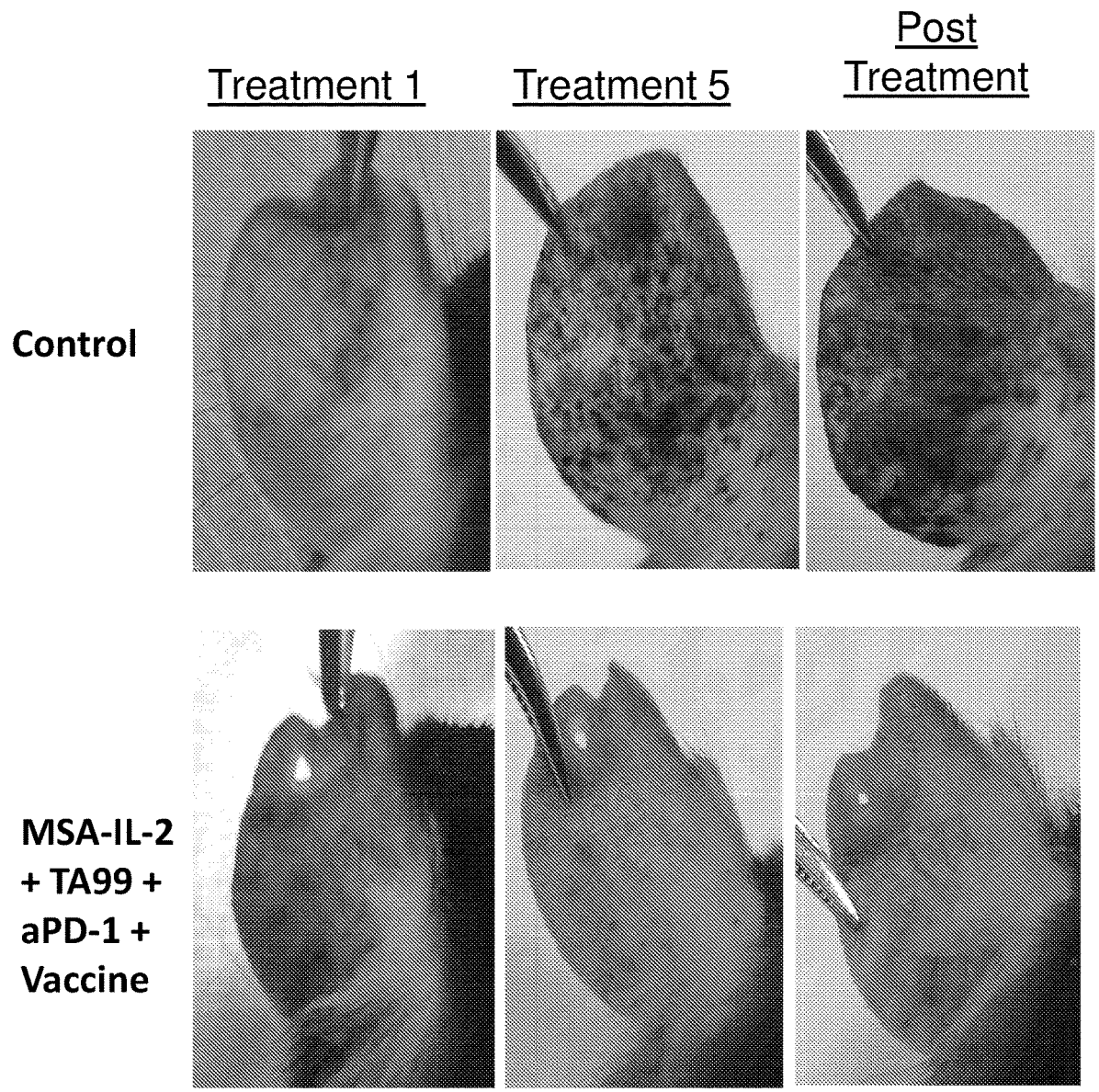
FIG. 21 shows images of ears from BRAF/PTEN-TG mice that received no treatment or a combination of MSA-IL-2, TA99 antibody, PD-1 antibody, and a vaccine, during the first 60 days of tumor establishment and treatment. Images were taken on the day of the first treatment (i.e., approximately 24-26 days after tumor induction), the fifth treatment (i.e., approximately 50 days after tumor induction), and post treatment (i.e., approximately 60 days after tumor induction).
Figure 22:
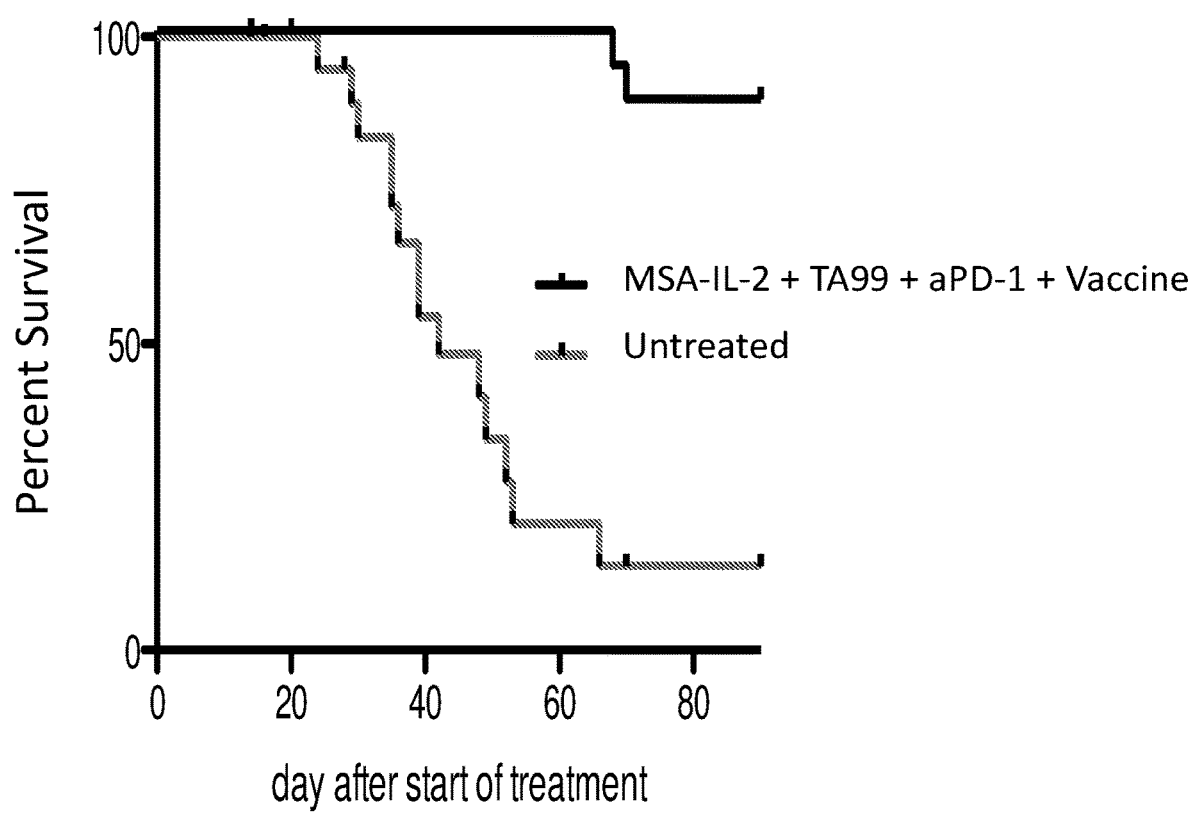
FIG. 22 is a Kaplan-Meier plot depicting the survival of BRAF/PTEN-TG mice that received no treatment or a combination of MSA-IL-2, TA99 antibody, anti-PD-1 antibody, and a vaccine, up to 90 days post-treatment.

The quadruple combination therapy was effective at controlling the initial pigmented lesions, as shown in FIG. 21. These images are representative of the level of response achieved during the first 60 days of tumor establishment and treatment. By day 60, almost all of the untreated mice had complete coverage of their ears by the pigmented tumor cells. In contrast, lesions in quadruple combination-treated mice became smaller and in many cases disappeared. Overall survival of BRaf/Pten-TG mice also significantly improved with the quadruple combination treatment (FIG. 22). Eventually, however, apigmented tumors appeared in approximately half of the treated mice and grew progressively until euthanasia criteria were met. This may indicate that in more complex tumor pathologies, escape variants can emerge which the immune system is unable to contain.

Example 13

Knottin-Fc Treatment is as Effective as TA99 Treatment in B16F10 Tumors

The use of therapeutic antibodies in the combination therapy described in the foregoing Examples is limited to cancers that have known antigens. To address the lack of general tumor-associated antigens, a knottin-Fc protein was engineered to be used in place of a therapeutic antibody. The knottin-Fc protein comprises two parts: 1) an engineered cystine knot (knottin) peptide that binds with high affinity to tumor-associated αvβ3, αvβ5, and α5β1 integrin receptors (specifically 2.5F, SEQ ID NO: 94 or 96), and 2) an antibody Fc domain that mediates immune effector functions in vivo. The knottin-Fc used is 2.5F with a K155 substitution, fused to a mouse IgG2a Fc domain, SEQ ID NO: 45.

To determine the effects of the knottin-Fc on tumor growth, $2.5 \times 10^5$ B16F10 murine melanoma cells were injected into the flanks of C57BL/6 mice subcutaneously. Prophylactic treatment was done with 80 µg knottin-Fc, 80 µg knottin-D265A (The D265A mutation in the murine IgG2a Fc domain eliminates binding to FcγR and complement), or 200 µg TA99, administered intraperitoneally every two days, starting on the day of tumor inoculation, for a total of ten treatments. TA99 is an antibody which binds to TYRP-1, (an antigen found on melanoma cells) and inhibits melanoma tumor growth.

Figure 23:
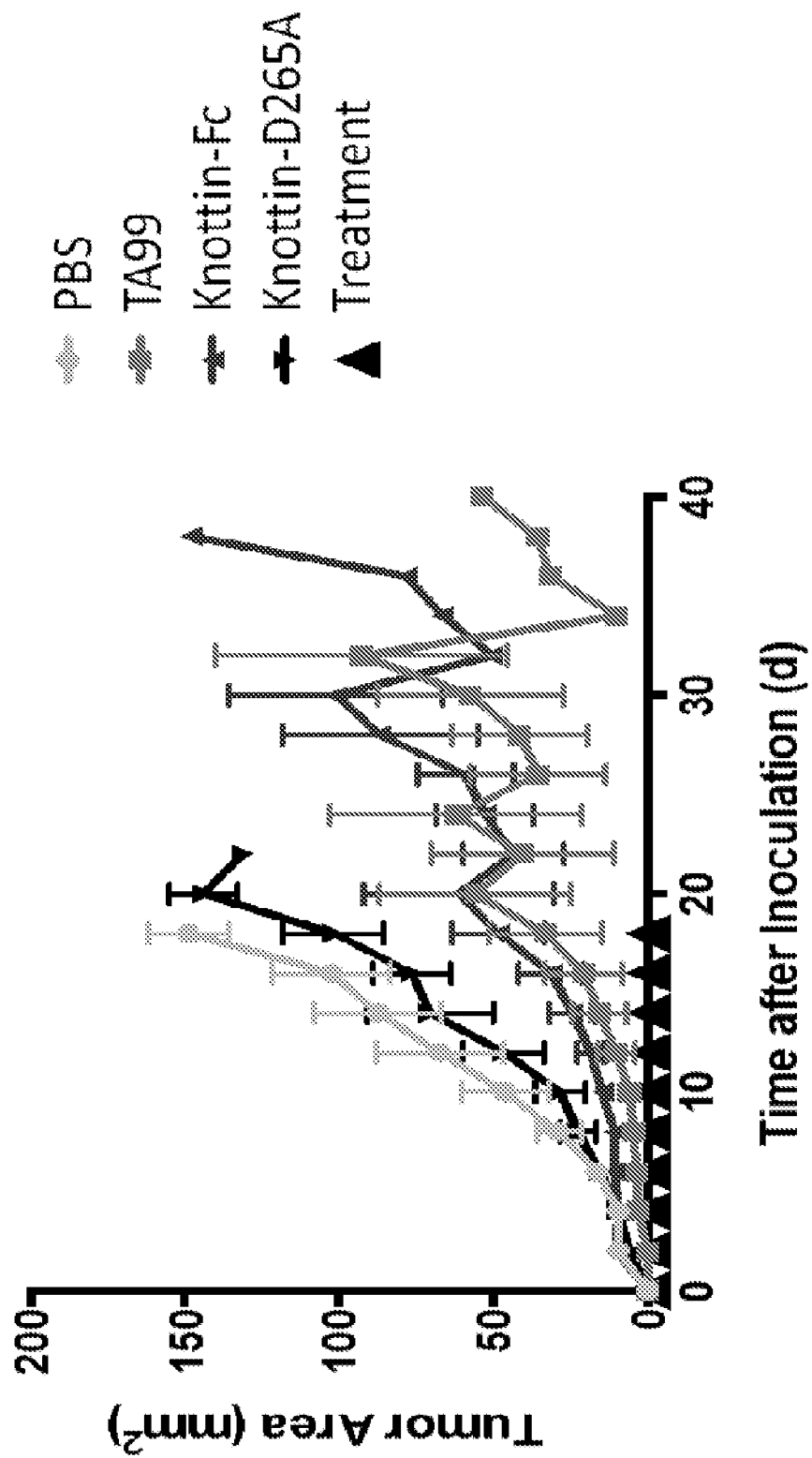
FIG. 23 is a graph comparing tumor control with TA99 and integrin binding knottin-Fc (SEQ ID NO: 45) in subcutaneous B16F10 melanoma tumors. Tumors were established by injecting $2.5\times10^5$ B16F10 cells into the flanks of C57BL/6 mice. Starting on the day of tumor inoculation and every 2 days after, 80 µg knottin-Fc, 80 µg knottin-Fc D265A, or 200 µg TA99 was administered. Error bars represent standard error of the mean (SEM).

Tumor area was measured and plotted (FIG. 23). Both the TA99 treatment and the knottin-Fc treatment controlled tumor growth to a similar extent. The failure of knottin-D265A to prevent tumor growth indicates that tumor control by knottin-Fc is mediated by the effector function of Fc. These data indicated knottin-Fc could be a suitable replacement for therapeutic antibodies in combination therapy for cancers with unknown antigens.

Example 14

Knottin-Fc and Extended-PK IL-2 Synergistically Control Tumor Growth of B16F10 Tumors A therapeutic study was conducted to examine the effect of adding MSA/IL-2 to knottin-Fc treatment. Tumors were established by injecting C57BL/6 mice subcutaneously with $1 \times 10^6$ B16F10 murine melanoma cells. 30 µg MSA/IL-2 and/or 500 µg knottin-Fc was administered intraperitoneally on day 6 after tumor inoculation and every 6 days after that for 4 treatments total.

Figure 24A:
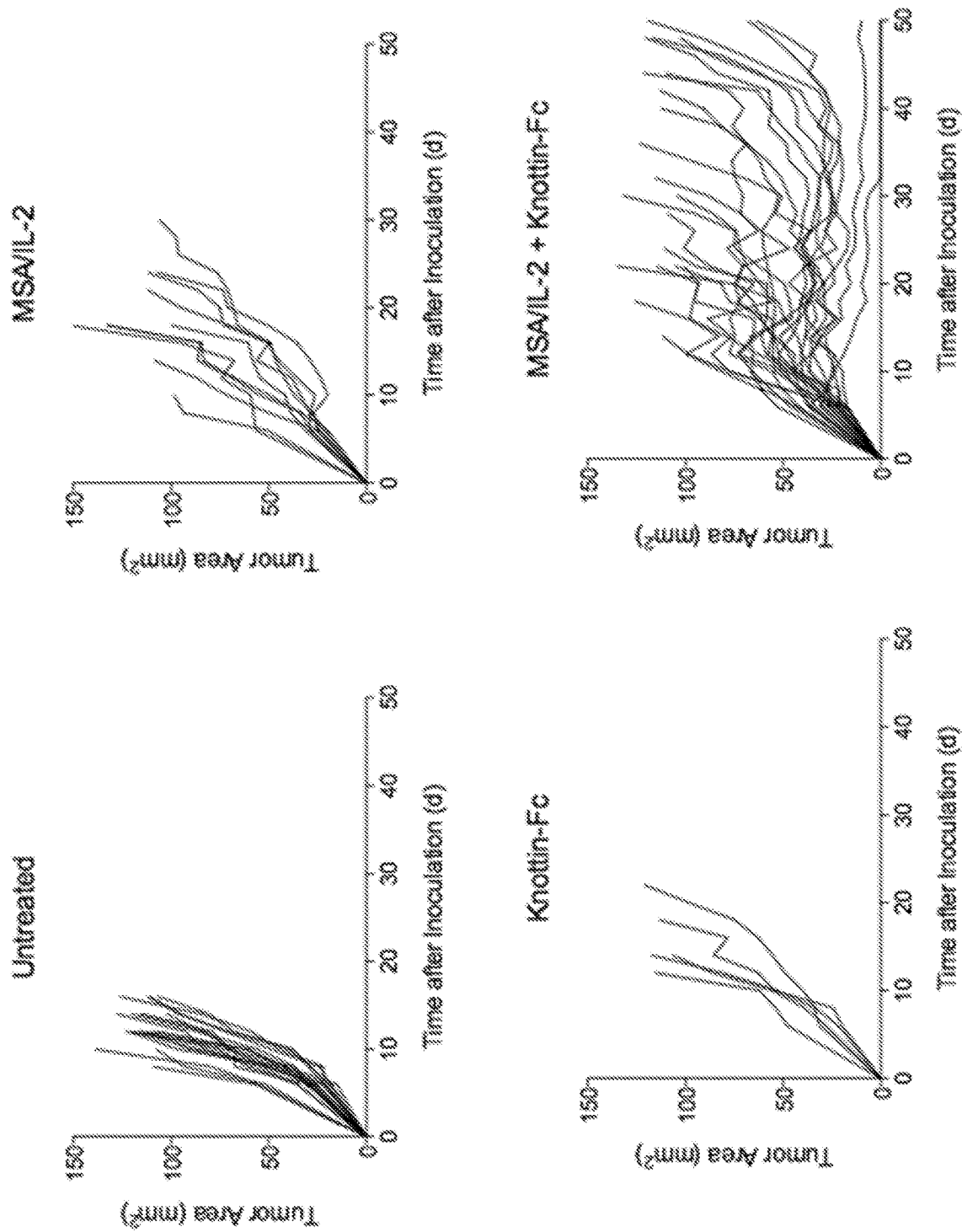
FIGS. 24A and 24B depict synergistic tumor control in established B16F10 melanoma tumors. $1\times10^6$ B16F10 cells were injected into the flanks of C57BL/6 mice. 30 µg MSA/IL-2 and/or 500 µg knottin-Fc was administered on day 6 after tumor inoculation, and every 6 days after for a total of four treatments.
Figure 24B:
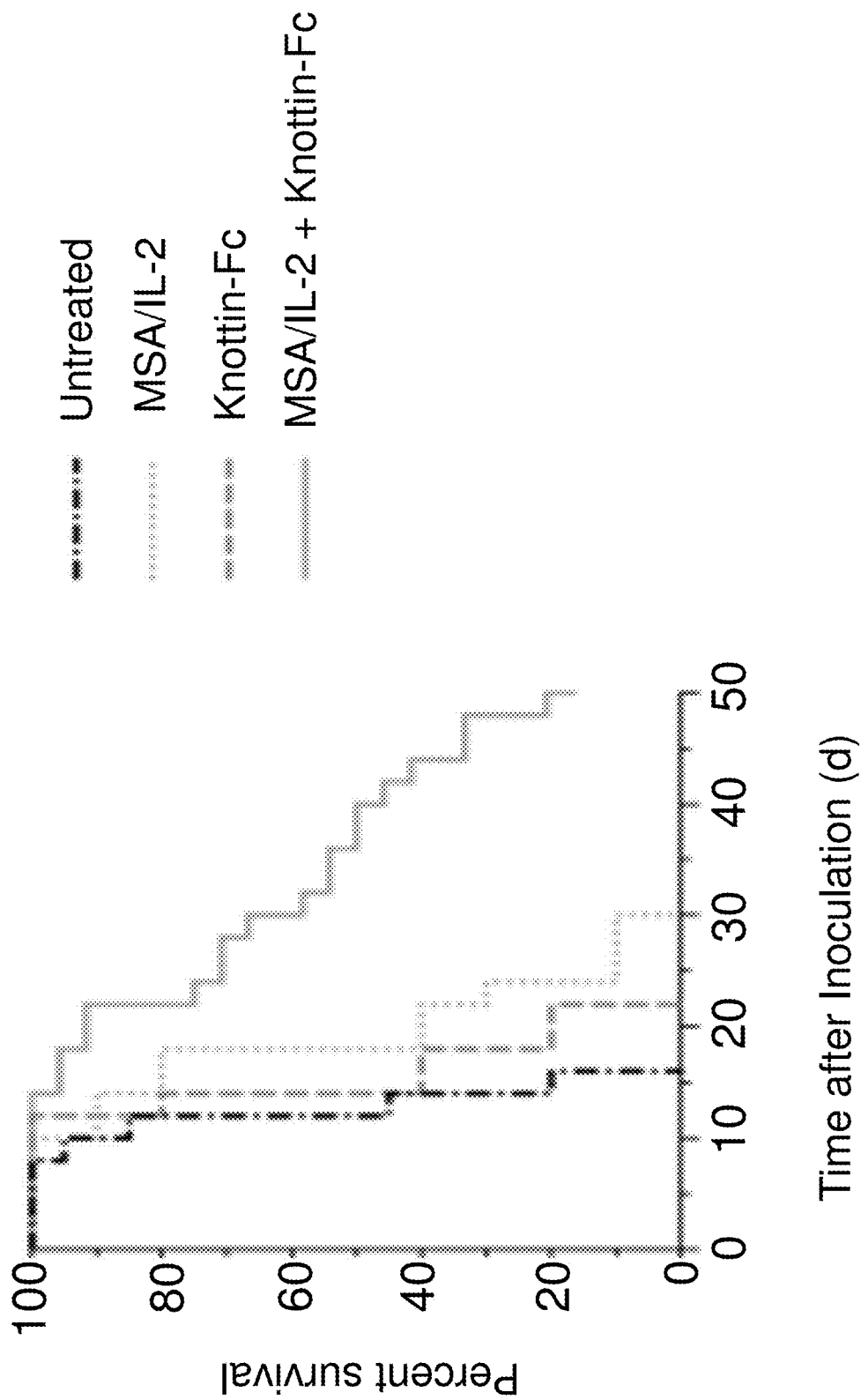

Tumor area was measured and plotted (FIG. 24A). While MSA/IL-2 and knottin-Fc alone had no effect on tumor growth, the combination of MSA/IL-2 and knottin-Fc effectively controlled tumor growth. A Kaplan-Meier survival plot revealed that the combination of MSA/IL-2 and knottin-Fc extended the survival of these mice, whereas monotherapies had no significant effect (FIG. 24B).

Example 15

Knottin-Fc and Extended-PK IL-2 Synergistically Control Tumor Growth of MC38 Tumors A separate therapeutic study was conducted to examine the effect of MSA/IL-2 on knottin-Fc efficacy in a tumor type that has no reported targetable antigens. $1 \times 10^6$ MC38 murine colon carcinoma cells were injected into the flanks of C57BL/6 mice. 6 days after tumor inoculation and every 6 days after for a total of 4 treatments, 30 µg MSA-IL-2 and/or 500 µg knottin-Fc was administered intraperitoneally.

Figure 25A:
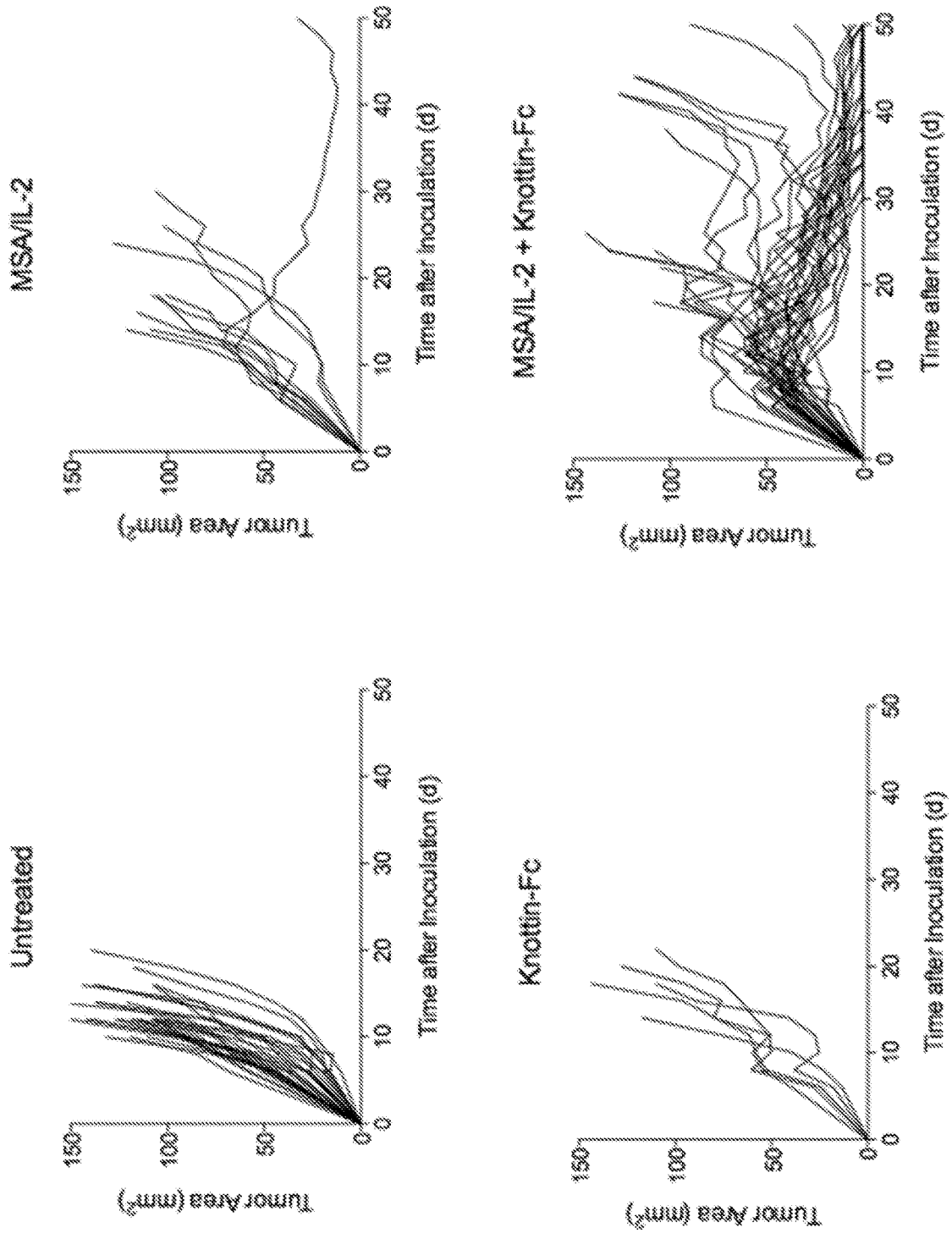
FIGS. 25A and 25B depict synergistic tumor control in established MC38 colon tumors. $1\times10^6$ MC38 cells were injected into the flanks of C57BL/6 mice and 30 µg MSA/IL-2 and/or 500 µg knottin-Fc was administered on day 6 after tumor inoculation, and every 6 days after for a total of four treatments.
Figure 25B:
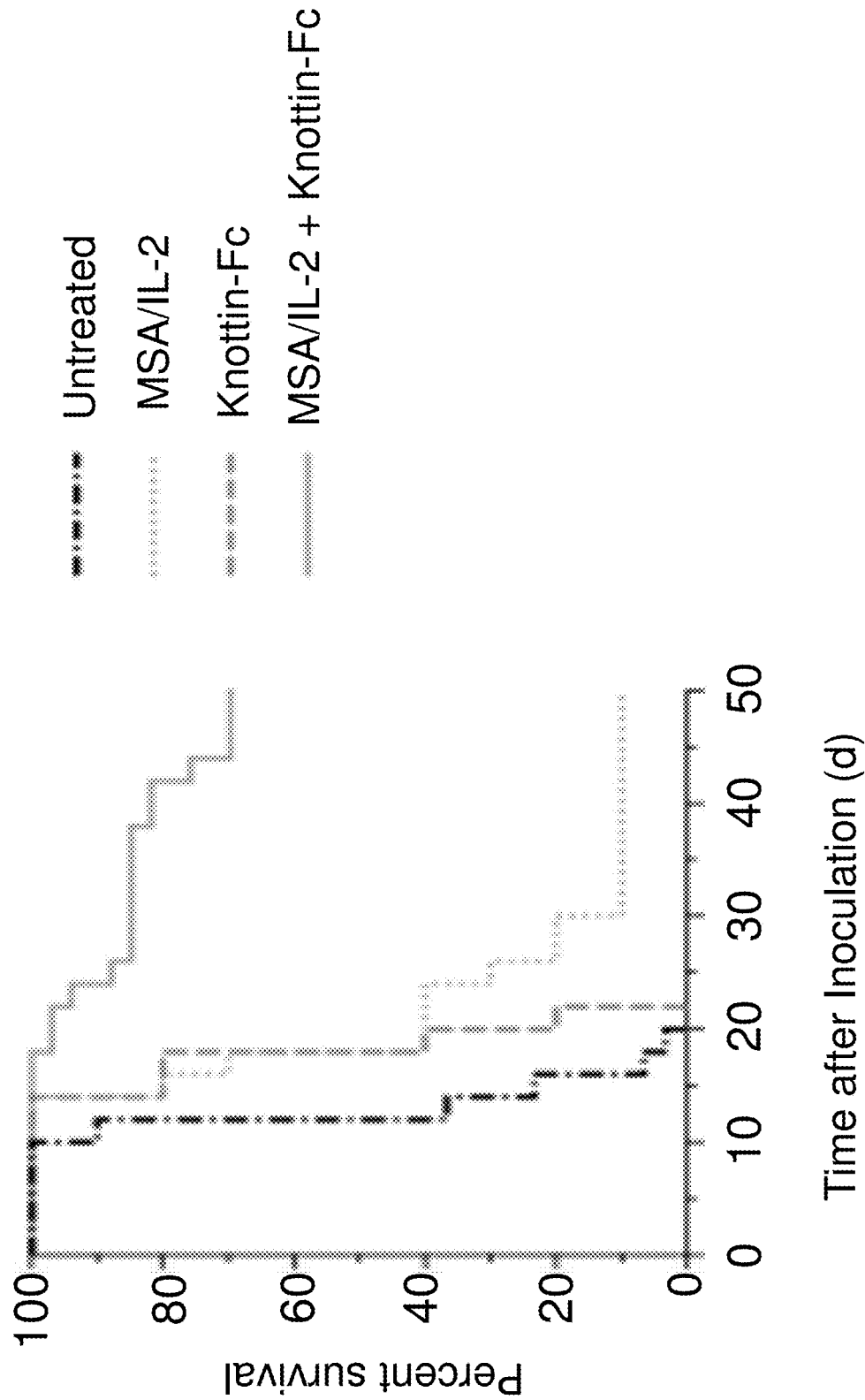

Tumor growth was controlled with the combination of MSA/IL-2 and knottin-Fc, but not when each component was administered as a monotherapy (FIG. 25A). A Kaplan-Meier survival plot shows an increase in survival in the mice treated with the combination of MSA/IL-2 and knottin-Fc compared to when each component was administered as a monotherapy (FIG. 25B).

Example 16

Knottin-Fc and Extended-PK IL-2 Synergistically Control Tumor Growth of Ag104A Tumors An additional study was conducted to examine the effects of MSA/IL-2 on knottin-Fc efficacy in a different tumor type. Ag104A fibrosarcoma tumors were established by injecting $1.0 \times 10^6$ Ag104A cells into the flanks of C3H/HeN mice. Starting six days after tumor inoculation and every 6 days after, 30 µg MSA/IL-2 and/or 500 µg knottin-Fc was administered intraperitoneally.

Figure 26A:
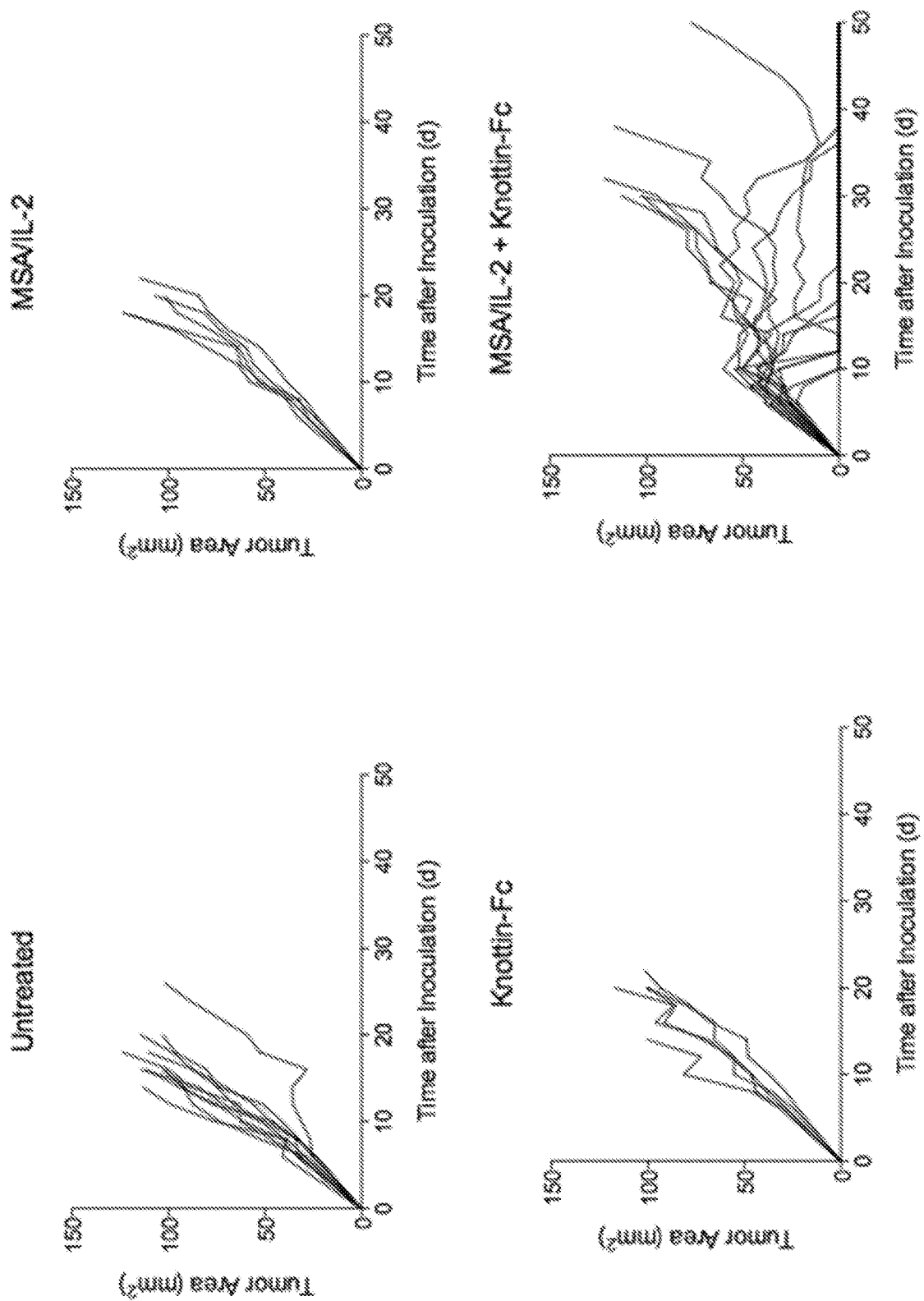
FIGS. 26A and 26B depict synergistic tumor control in established Ag104A fibrosarcoma tumors. $1\times10^6$ Ag104A cells were injected into the flanks of C3H/HeN mice. 12.5 µg MSA/IL-2 and/or 500 µg knottin-Fc was administered on day 6 after tumor inoculation, and every 6 days after for a total of four treatments.
Figure 26B:
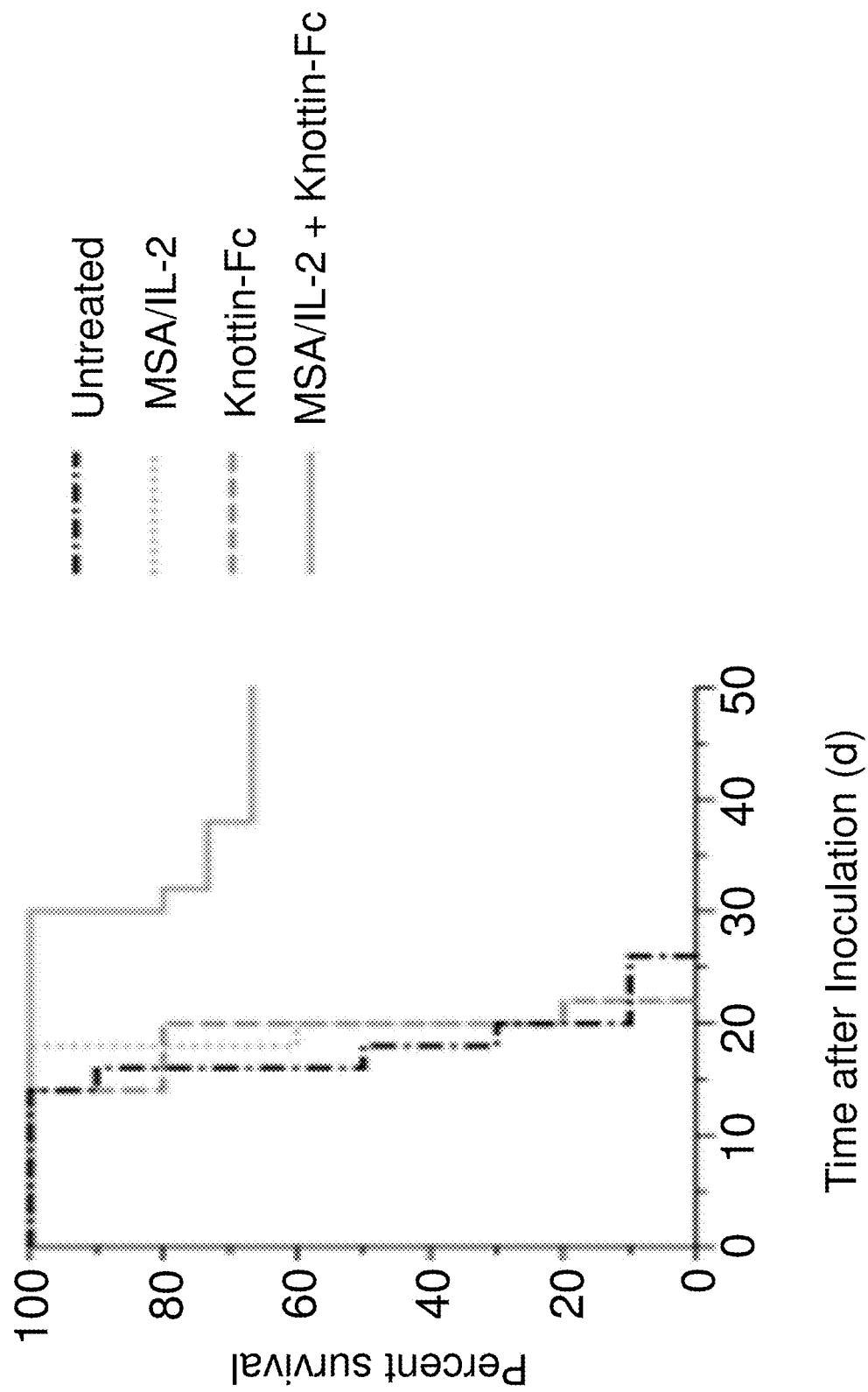

Tumor growth was controlled with the combination of MSA/IL-2 and knottin-Fc, but not when each component was administered as a monotherapy (FIG. 26A). A Kaplan-Meier survival plot shows an increase in survival in mice treated with the combination of MSA/IL-2 and knottin-Fc compared to when each component was administered alone (FIG. 26B).

Example 17

Therapeutic Antibody and Immune Checkpoint Blocker Enhance the Efficacy of Knottin-Fc and Extended-PK IL-2 in B16F10 Tumors To determine the effect of antibodies on knottin-Fc and extended-PK IL-2 synergistic tumor control, an additional study was carried out using B16F10 cells. $1 \times 10^6$ B16F10 cells were injected into the flanks of C57BL/6 mice. 30 µg MSA/IL-2 was administered every 6 days beginning on day 6 after tumor inoculation for a total of 5 treatments and 200 µg knottin-Fc was administered daily from days 6-30 after tumor inoculation. Antibodies against TYRP-1 (TA99) were administered at 100 µg per mouse every 6 days starting on day 6 after B16F10 tumor inoculation. Antibodies against PD-1 were administered at 200 µg per mouse every 6 days starting on day 6 after tumor inoculation.

Figure 27A:
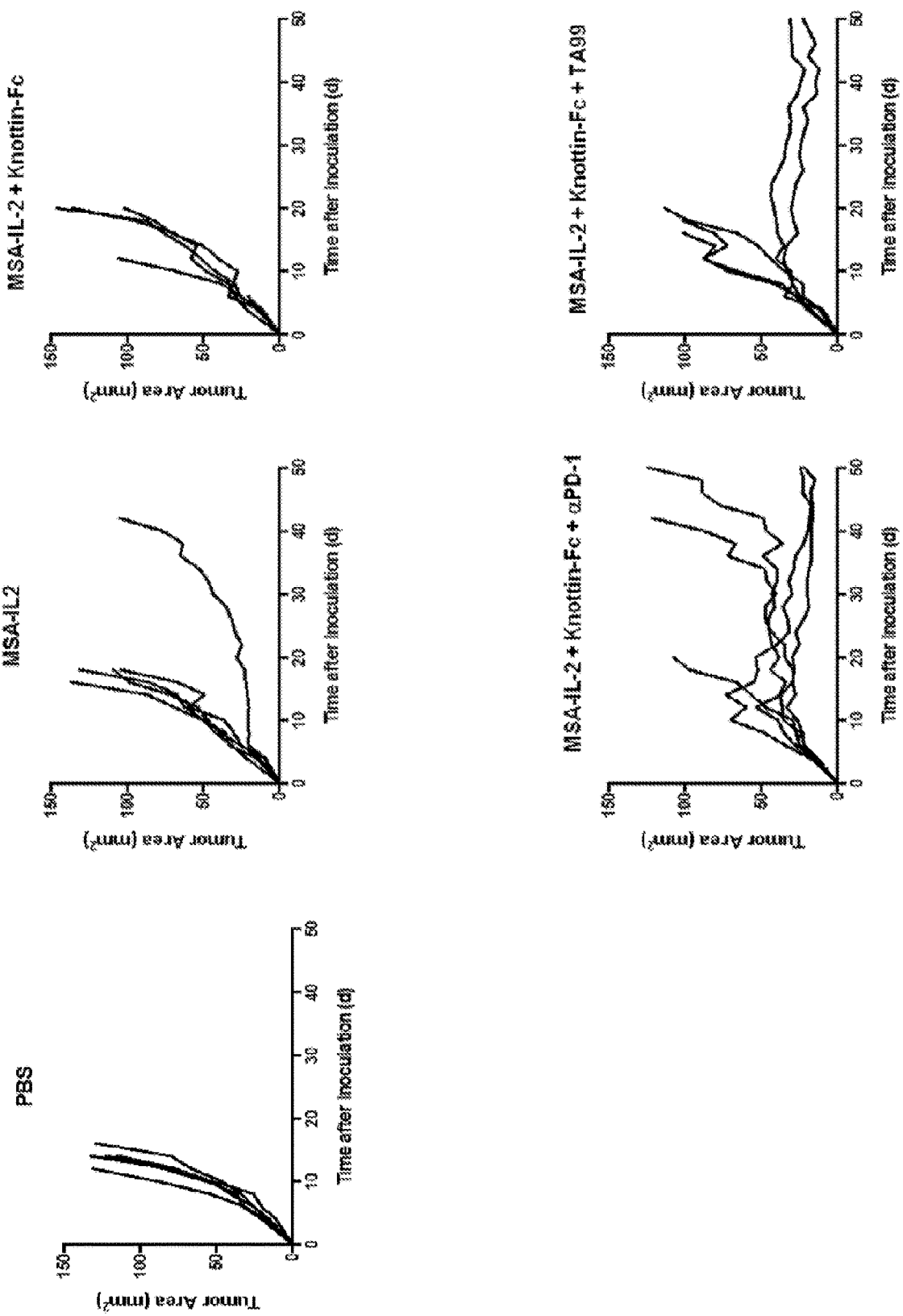
FIGS. 27A and 27B depict synergistic tumor control with an antibody in established B16F10 tumors. $1\times10^6$ B16F10 cells were injected into the flanks of C57BL/6 mice. 30 µg MSA/IL-2 was administered every 6 days beginning on day 6 after tumor inoculation for a total of 5 treatments. 200 µg knottin-Fc was administered daily from days 6-30 after tumor inoculation. Antibodies against TRP-1 (TA99) were administered at 100 µg per mouse every 6 days starting on day 6 after tumor inoculation. Antibodies against PD-1 (for immune checkpoint blockade) were administered at 200 µg per mouse every 6 days starting on day 6 after tumor inoculation.
Figure 27B:
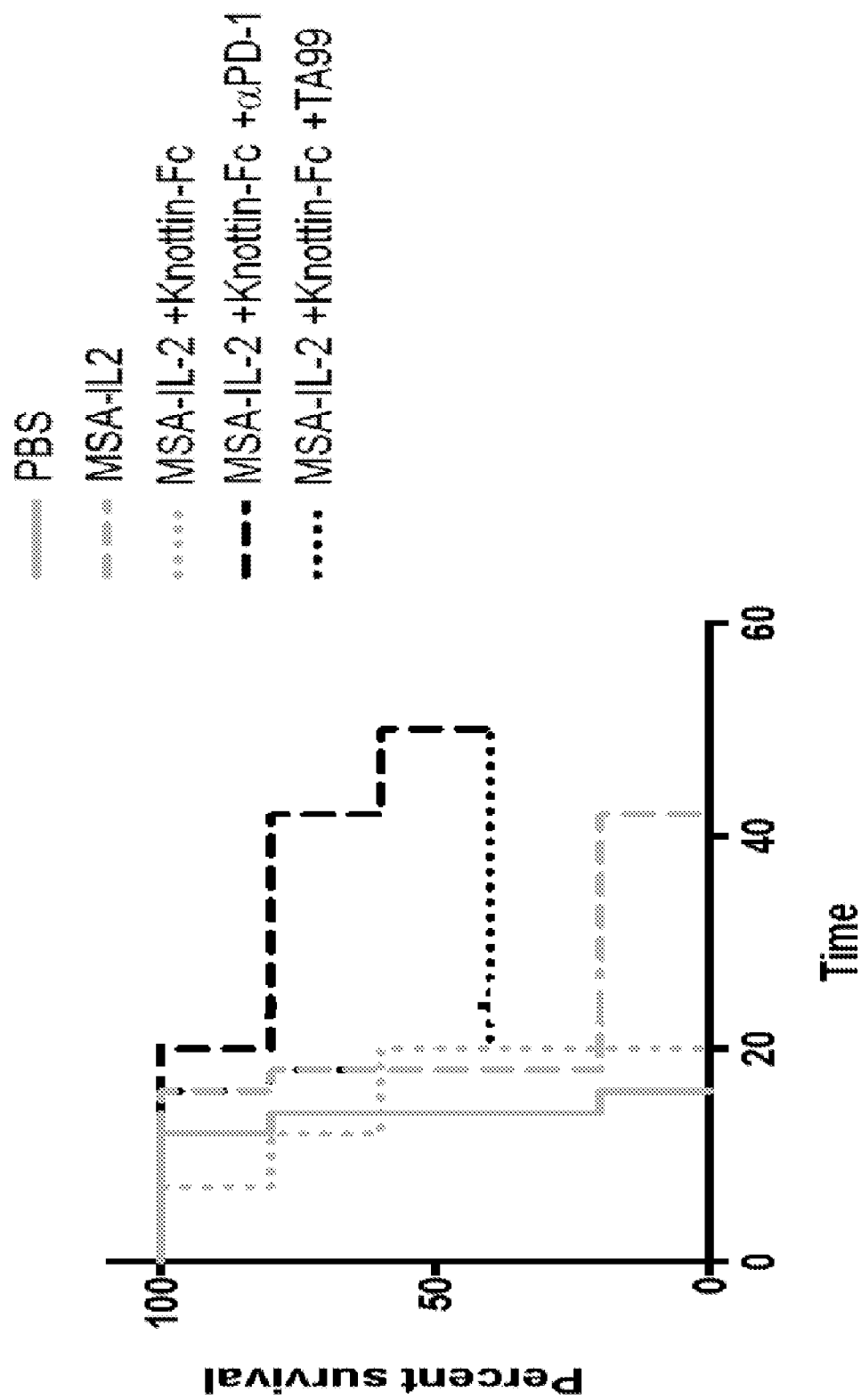

Individual tumor size measurements (FIG. 27A) and a survival plot (FIG. 27B) indicate that antibodies enhanced tumor control via knottin-Fc and MSA/IL-2. However, this is only effective if the antibody targets an antigen present on the tumor cells. Combining knottin-Fc and MSA/IL-2 with a therapeutic antibody or immune checkpoint blocker increased the efficacy of tumor control and survival improvement.

Example 18

Immune Checkpoint Blocker Enhances the Efficacy of Knottin-Fc and Extended-PK IL-2 in MC38 Tumors To determine the effect of antibodies on knottin-Fc and extended-PK IL-2 synergistic tumor control, an additional study was carried out using MC38 cells. $1 \times 10^6$ MC38 cells were injected into the flanks of C57BL/6 mice. 30 µg MSA/IL-2 and 500 µg knottin-Fc were administered every 6 days beginning on day 6 after tumor inoculation for a total of 4 treatments. Antibodies against PD-1 were administered at 200 µg per mouse every 6 days starting on day 6 after tumor inoculation.

Figure 28A:
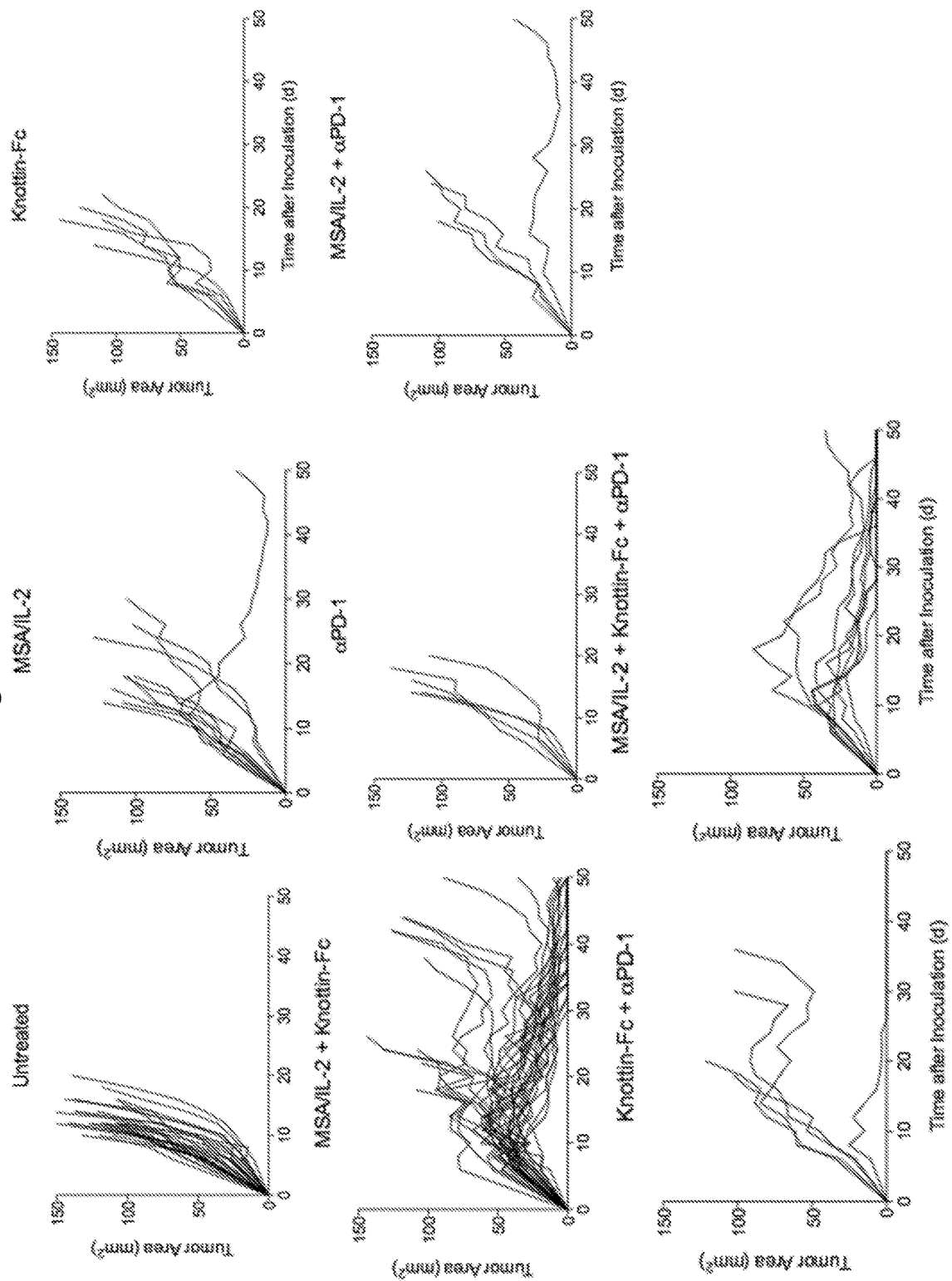
FIGS. 28A and 28B depict synergistic tumor control with an antibody in established MC38 tumors. $1\times10^6$ MC38 cells were injected into the flanks of C57BL/6 mice. 30 µg MSA/IL-2, 500 µg knottin-Fc, and/or 200 µg anti-PD-1 antibody was administered on day 6 after tumor inoculation and every 6 days after for a total of four treatments. FIG.
Figure 28B:
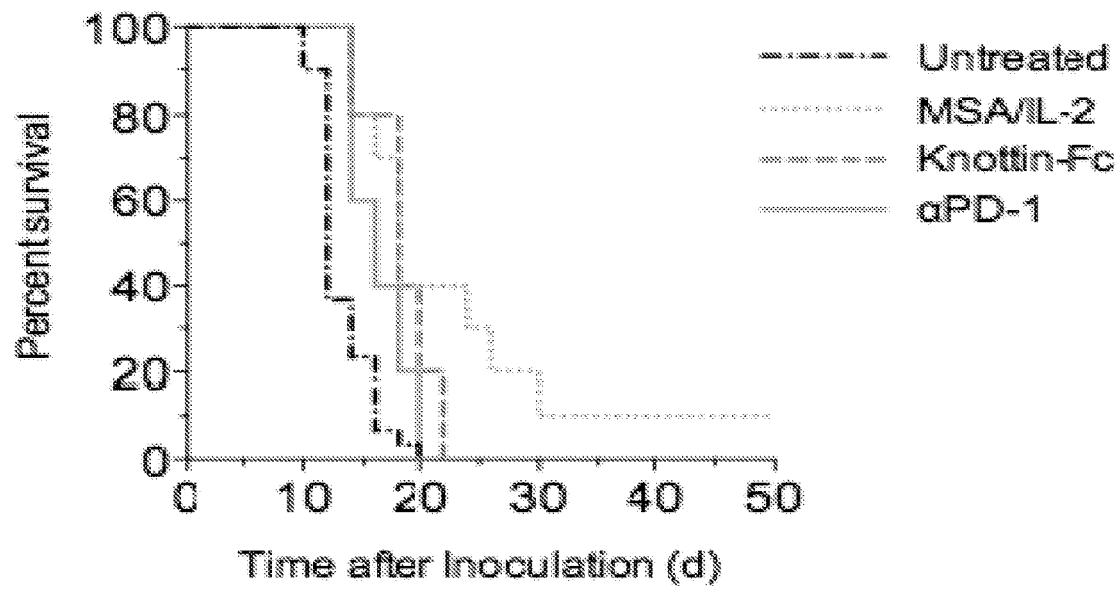
Figure 28B:
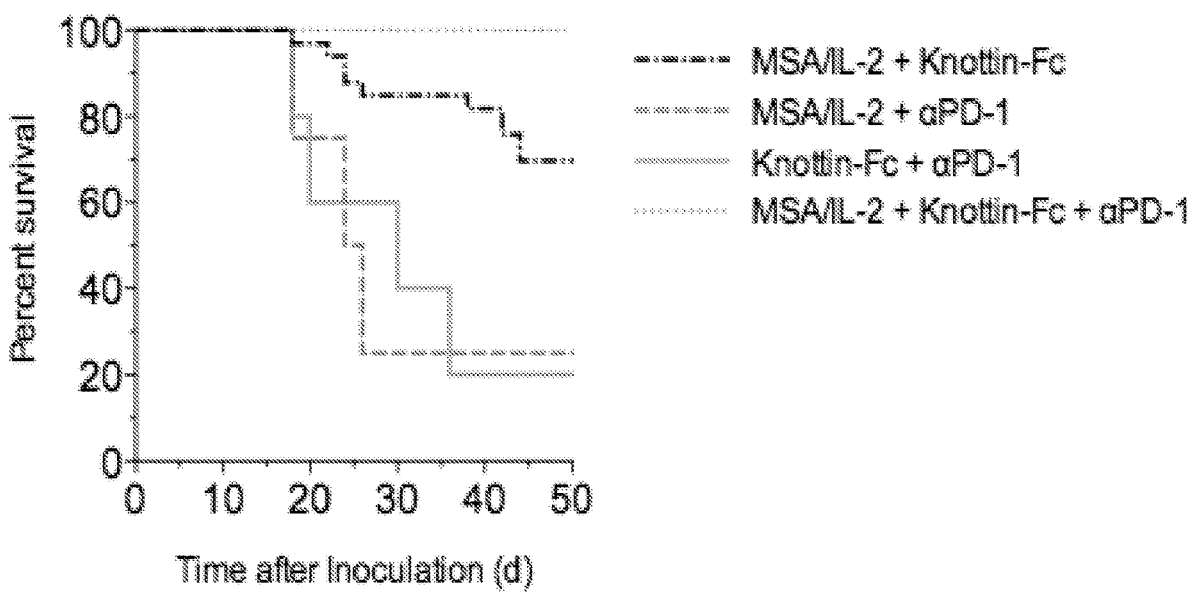

Individual tumor size measurements (FIG. 28A) and survival plots (FIG. 28B) indicate that antibodies enhanced tumor control via knottin-Fc and MSA/IL-2. However, this is only effective if the antibody targets an antigen present on the tumor cells. The most effective treatment was to combine knottin-Fc and MSA/IL-2 with an immune checkpoint blockade (anti-PD-1) antibody.

Example 19

Knottin-Fc and IL-2 Combination Protects Against Secondary Tumor Challenge

To determine if the combination of knottin-Fc and MSA/IL-2 could protect treated mice from a secondary challenge, the MC38 tumor model was used. 1×10$^6$ MC38 cells were injected into the flanks of C57BL/6 mice and both 30 µg MSA/IL-2 and 500 µg knottin-Fc were administered every 6 days beginning on day 6 after tumor inoculation for a total of 4 treatments. 16-20 weeks after the initial tumor inoculation, previously cured mice or age-matched naïve mice were inoculated with 1×10$^6$ MC38 cells in the opposite flank. No further treatment was administered.

Figure 29A:
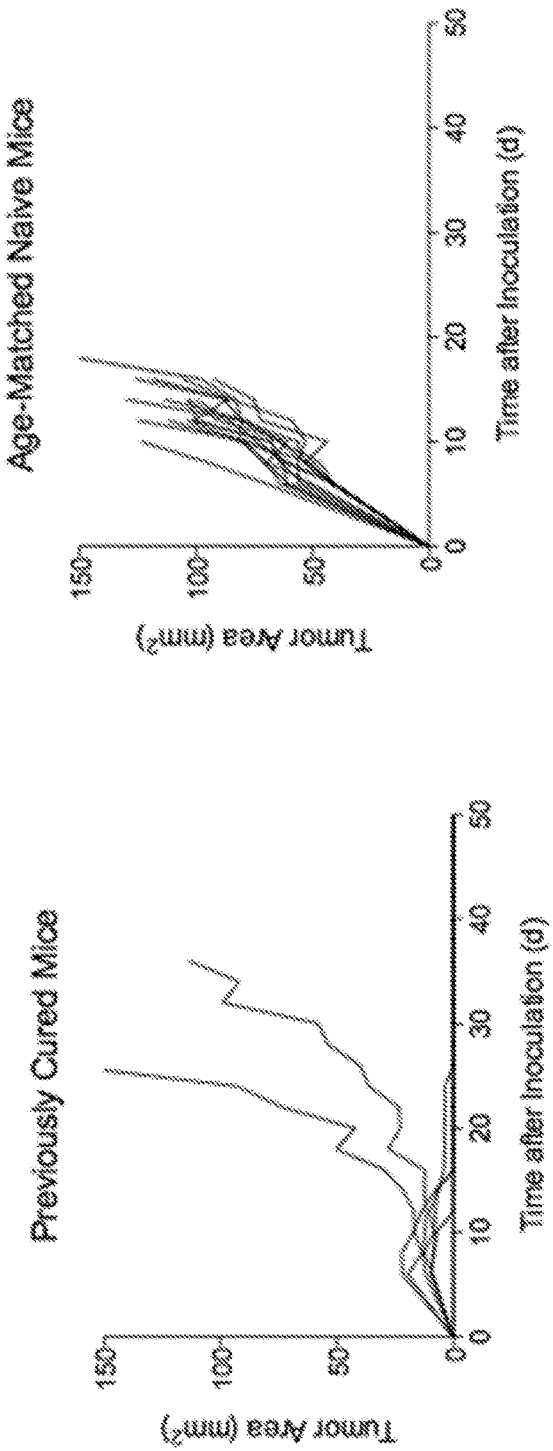
FIGS. 29A and 29B depict tumor control after secondary tumor challenge with MC38 tumors cells. Previously cured mice (treated with MSA/IL-2 and knottin-Fc) and age-matched naïve mice were inoculated with 1×10⁶ MC38 tumor cells in the opposite flank 16-20 weeks after the initial tumor inoculation. No further treatment was administered.
Figure 29B:
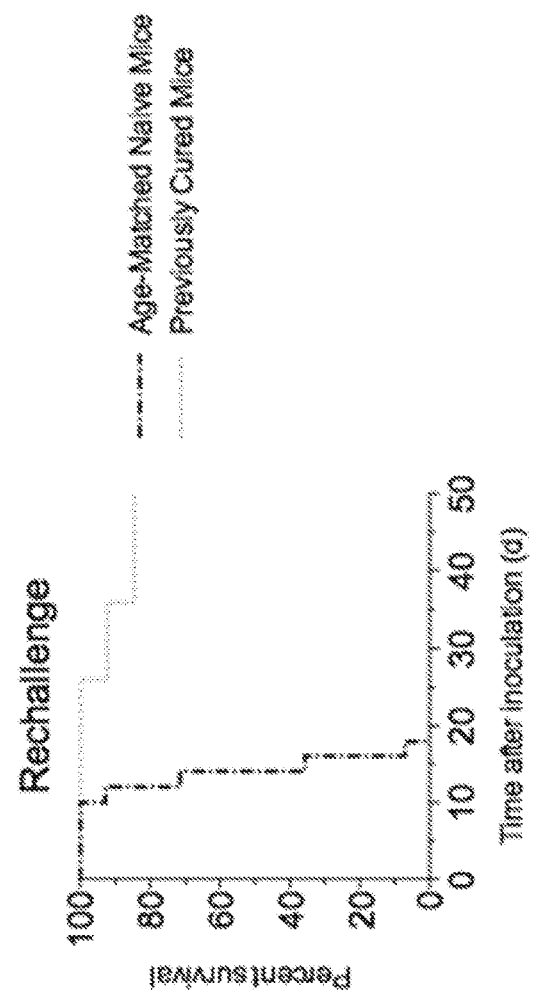

Individual tumor size measurements (FIG. 29A) and survival plot (FIG. 29B) indicate that knottin-Fc and MSA/IL-2 protect previously treated mice against secondary tumor challenge, demonstrating a potent and sustained immune response against the tumors.

Example 20

Antagonizing Immune Suppression Improves Survival of Tumor-Bearing Mice

Figure 30A:
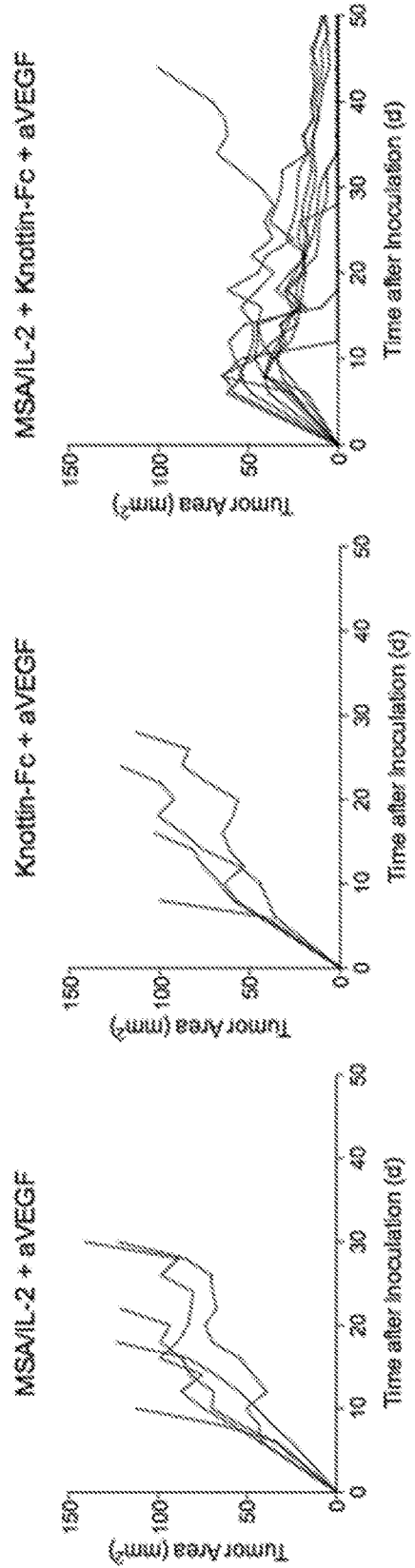
FIGS. 30A and 30B depict synergistic tumor control in established MC38 tumors. 1×10⁶ MC38 cells were injected into the flanks of C57BL/6 mice. 30 μg MSA/IL-2, 500 μg knottin-Fc, and/or 200 μg anti-VEGF antibody was administered on day 6 after tumor inoculation, and every 6 days after for a total for 4 treatments.
Figure 31:
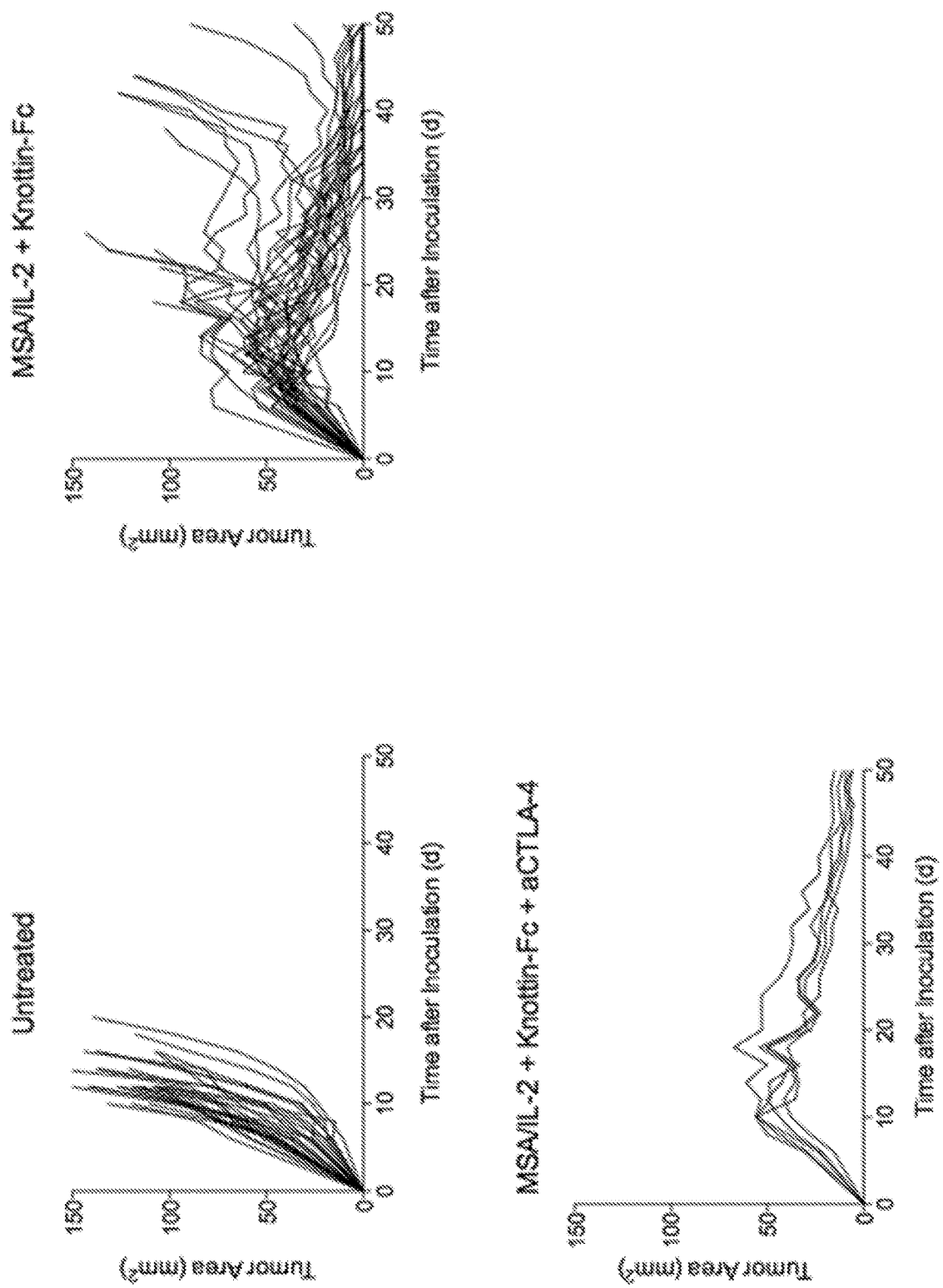
FIG. 31 shows tumor area graphs depicting synergistic tumor control in established MC38 tumors. 1×10⁶ MC38 cells were injected into the flanks of C57BL/6 mice. 30 μg MSA/IL-2, 500 μg knottin-Fc, and/or 200 μg anti-CTLA-4 antibody was administered on day 6 after tumor inoculation, and every 6 days after for a total for 4 treatments.
Figure 32A:
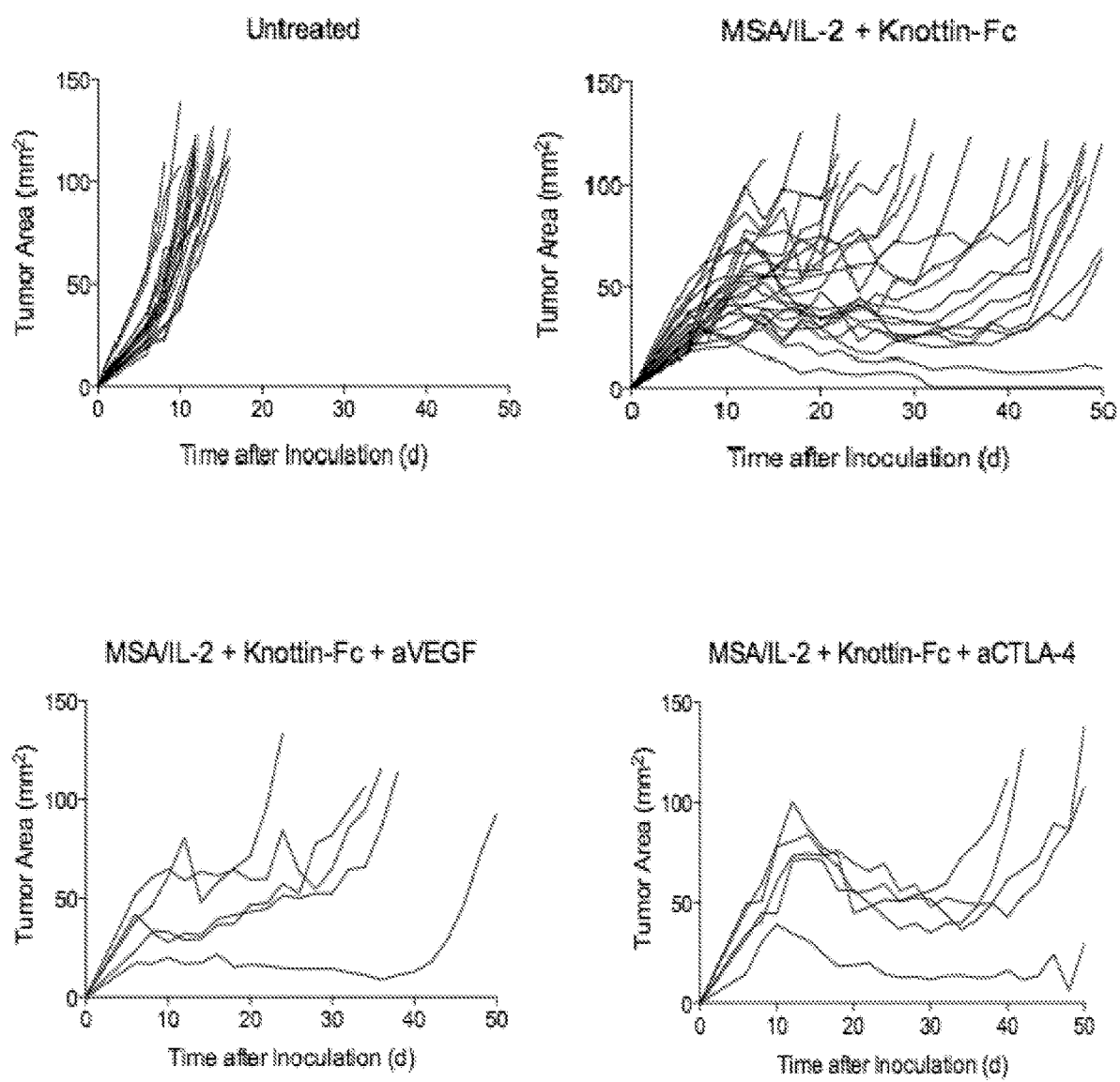
FIGS. 32A and 32B depict the synergistic tumor control in established B16F10 tumors. 1×10⁶ B16F10 cells were injected into the flanks of C57BL/6 mice. 30 μg MSA/IL-2, 500 μg knottin-Fc, 200 μg anti-VEGF antibody and/or 200 μg anti-CTLA-4 antibody was administered on day 6 after tumor inoculation, and every 6 days after for a total for 4 treatments.

To determine whether the efficacy of tumor control could be enhanced by inhibiting suppressors of the immune system, an antagonist of vascular endothelial growth factor (VEGF) or cytotoxic T-lymphocyte-associated protein 4 (CTLA-4) was administered in mice with MC38 or B16F10 tumors. 1×10$^6$ MC38 cells (FIGS. 30A, 30B and 31) or B16F10 (FIGS. 32A and 32B) were injected into the flanks of C57BL/6 mice. 30 µg MSA/IL-2, 500 µg knottin-Fc, and 200 µg anti-VEGF antibody or anti-CTLA-4 antibody were administered every 6 days beginning on day 6 after tumor inoculation for a total of 4 treatments.

Synthetic genes, encoding the heavy (VH) and light (VL) chain variable regions of anti-VEGF (clone B20-4.1.1) (Bagri et al., Clin. Cancer Res. (2010) Vol 16: 3887-900) and anti-CTLA-4 (9D9) (Selby et al., Cancer Immunol. Res. (2013) Vol 1:32-42) antibodies, were codon-optimized for expression in mammalian cells (GeneArt, Life Technologies). B20-4.1.1 antibody constructs were generated by PCR-amplification of DNA inserts encoding for VH and VL regions and cloned via Gibson assembly into separate gWiz expression vectors (Genlantis) containing a CMV promoter, a kanamycin antibiotic resistance gene and the DNA sequence encoding for either murine IgG2a heavy-chain (CH1, CH2 and CH3) or light-chain (CL) constant regions (see below Sequence 1 and 2 for B20-4.1.1). The 9D9 antibody construct was generated by PCR-amplification of DNA inserts encoding the VH and VL regions and subcloned into a double cassette p2MPT expression vector (EPFL Protein expression core facility, http://pecf.epfl.ch), containing a CMV promoter, an ampicillin antibiotic resistance gene and both murine IgG2a heavy-chain (CH1, CH2 and CH3) or light-chain (CL) constant regions, via the restriction sites NotI/BamHI and EcoRI/XbaI, respectively. All constructs were verified by DNA sequencing (Macrogen).

Anti-VEGF antibody B20-4.1.1 was expressed in transiently transfected human embryonic kidney (HEK293-F) cells using the Free-Style 293 Expression System (Life Technologies) as described previously (Zhu et al., Cancer Cell (2015) Vol 27: 489-501). Antibody 9D9 was expressed in transiently transfected Chinese hamster ovary (CHO) cells and provided by EPFL Protein expression core facility (http://pecf.epfl.ch). After 7 days of expression, cells were removed by centrifugation (15,000×g for 30 min at 4° C.) and filtration (0.22 µm PES membranes filter) and the proteins in the supernatant purified by protein A chromatography according to the manufacturer's instructions (GE Healthcare). Eluted antibodies were further desalted and purified on a HiLoad Superdex 200 10/600 size exclusion column (GE Healthcare) connected to an AKTApurifier system and equilibrated with buffer PBS 1×pH 7.4. The purified antibodies were concentrated using a 30000 NMWL Amicon Ultra centrifugal filter device (Millipore) at 4000 g and 4° C. and quantified by measuring absorbance at 280 nm using a NanoDrop 2000 spectrophotometer (Thermo Scientific). Molecular weights were confirmed by reducing and non-reducing SDS/PAGE. Purity was evaluated by FPLC. Protein samples were analyzed by SDS-PAGE under denaturating and reducing conditions using NuPAGE 4-12% Bis-Tris Gels (Life Technologies) in MOPS buffer followed by Coomassie staining. Native size and oligomerization state of antibodies after concentration were also analyzed by size-exclusion chromatography with a Superdex 200 10/300 GL column (GE Healthcare) connected to an AKTApurifier system and equilibrated with buffer PBS 1×pH 7.4.

Figure 30B:
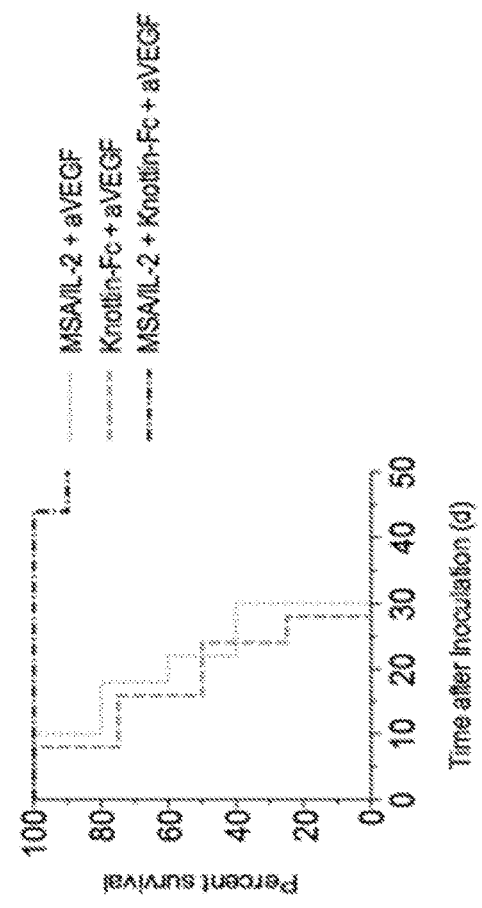
Figure 32B:
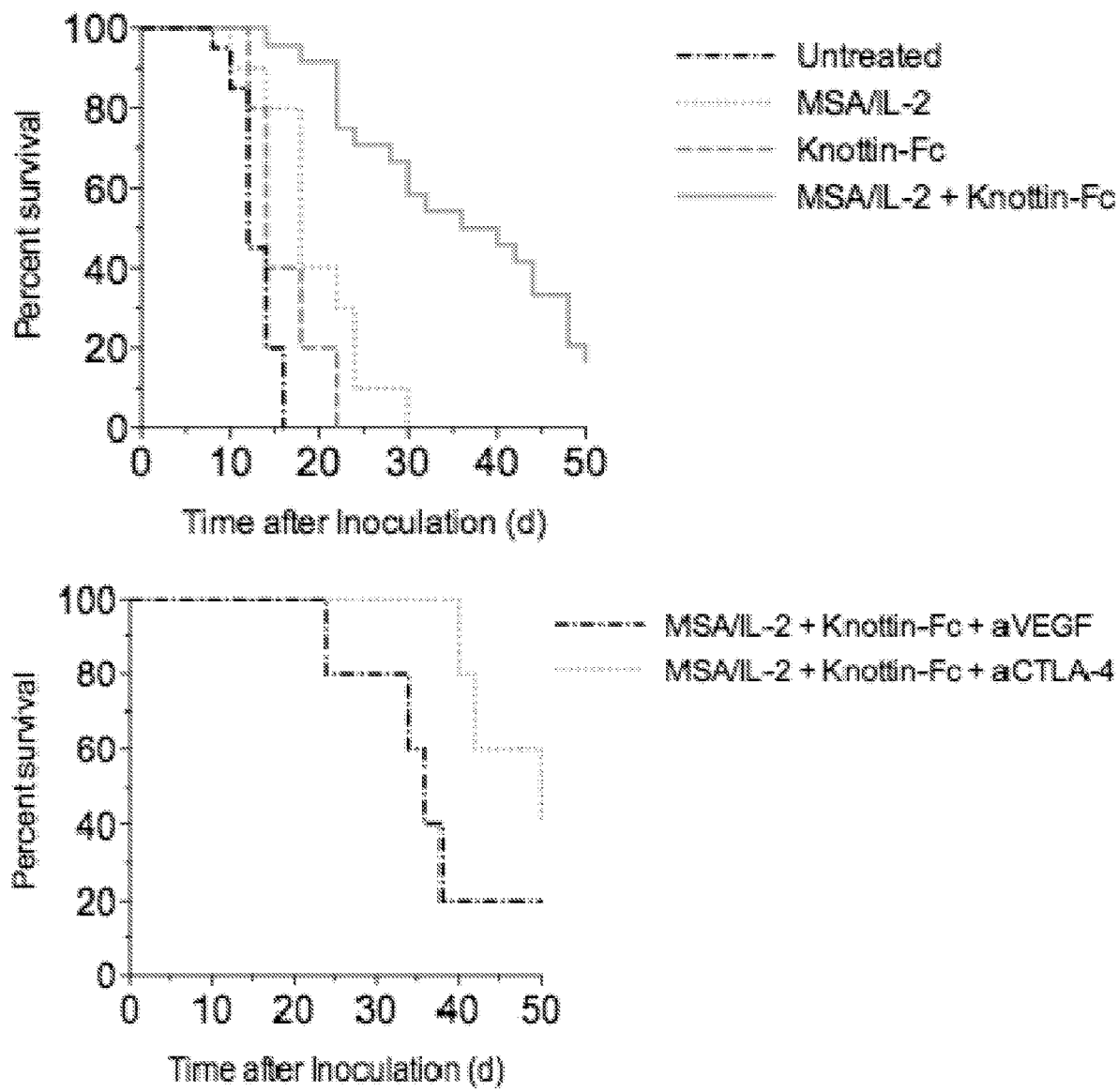

Tumor area was measured and plotted (FIGS. 30A, 31 and 32A) and survival plots were generated (FIGS. 30B and 32B). The triple combinations (i.e., MSA/IL-2+knottin-Fc+anti-VEGF and MSA/IL-2+knottin-Fc+anti-CTLA-4) significantly controlled tumor growth and improved survival compared to the double combinations (i.e., MSA/IL-2+anti-VEGF and knottin-Fc+anti-VEGF or MSA/IL-2+anti-CTLA-4 and knottin-Fc+anti-CTLA-4). This is similar to the results observed when adding an anti-PD-1 antibody to the combination of MSA/IL-2 and knottin-Fc, which indicated that other suppressors of the immune system could be inhibited to improve the efficacy of the combination of MSA/IL-2+knottin-Fc. The improved therapeutic efficacy by addition of an anti-VEGF antibody was also observed in RENCA (renal adenocarcinoma) and LLC (Lewis lung carcinoma) tumor models (data not shown).

Example 21

Knottin-Fc is Effective in Quadruple Combination Therapy in TC-1 Tumors

Figure 33:
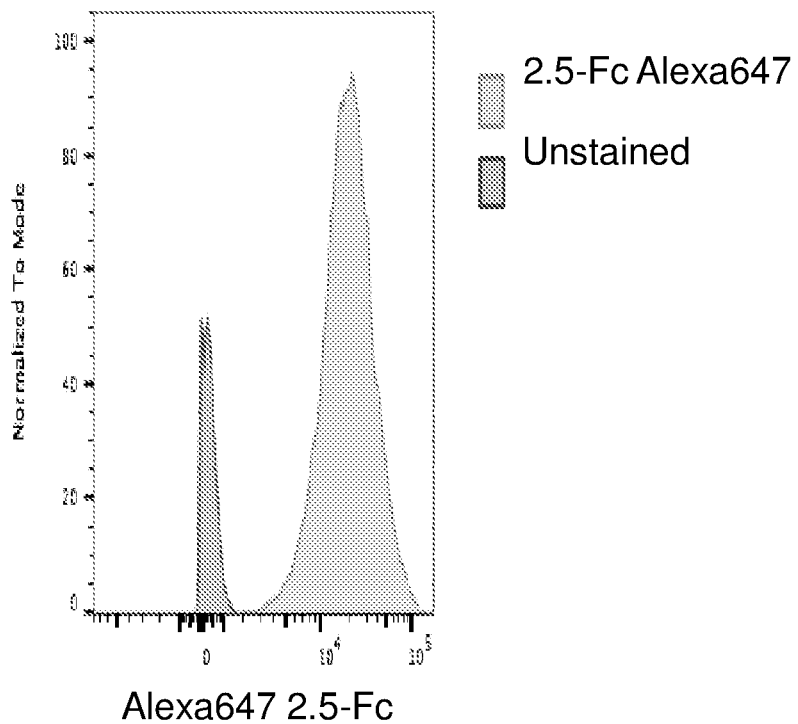
FIG. 33 depicts the binding of knottin-Fc (i.e., 2.5F-Fc) to TC-1 tumors as measured by flow cytometry.

To determine the effect of knottin-Fc in the quadruple combination therapy, TC-1 tumors were used. TC-1 tumors express cervical/head and neck cancer oncoantigens E6 and E7 from human papillomavirus (HPV). To determine whether knottin-Fc could bind TC-1 tumors, labeled 2.5F-Fc was incubated with TC-1 tumor cells at 4° C. for 20 minutes in PBS, 1% BSA, 5 mM EDTA, washed, and then analyzed by flow cytometry. FIG. 33 shows that 2.5F-Fc was capable of binding to TC-1 tumors and therefore had the potential to be effective in treating TC-1 tumors.

To assess the effectiveness of the combination treatment, 1×10$^6$ TC-1 tumors were injected into the flanks of C57BL/6 mice subcutaneously. Immunotherapy was administered 8, 15, 22, 29, and 36 days after tumor inoculation. This consisted of 500 µg knottin-Fc and 30 µg mouse serum albumin (MSA)-IL-2 (produced by researcher). In addition, 200 µg anti-PD-1 antibody (clone RMP1-14 from BioXcell) was administered on days 8, 15, and 22 after inoculation of TC-1 cells.

Figure 34:
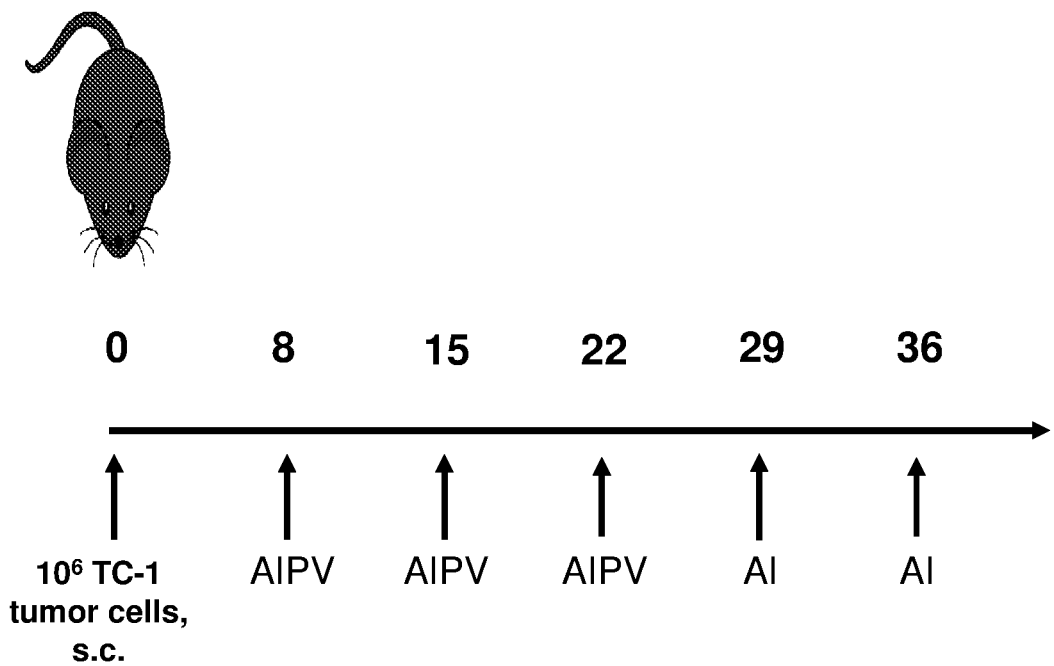
FIG. 34 is a schematic depicting the treatment regimen administered after tumor establishment, as described in the Examples. 1×10⁶ TC-1 tumors were injected subcutaneously into C57BL/6 mice; 8, 15, and 22 days after tumor injection, immunotherapy support and/or a vaccine was administered to the mice. Additional immunotherapy support was administered at days 29 and 36 after tumor injection. A=knottin-Fc; I=MSA-IL=2; P=anti-PD-1; V=HPV-E7 cancer vaccine.

An ampiphile cancer vaccine targeting HPV-E7 was administered on days 8, 15, and 22 after inoculation of TC-1 tumors. The tumor-associated antigen HPV E7$_{43-62}$ (GQAE-PDRAHYNIVTFCCKCD) (SEQ ID NO: 146) from cervical cancer was conjugated to 1,2-distearoyl-sn-glycero-3-phophoethanolamine-N-PEG (DSPE-PEG 2 kDa) to generate amph-peptides for vaccination studies. Antigen amphiphiles were synthesized by reacting internal cysteines in the HPV E7 peptide with maleimide-PEG$_{2000}$-DSPE in dimethyl formamide. A schematic of the treatment regimen is shown in FIG. 34.

Figure 35A:
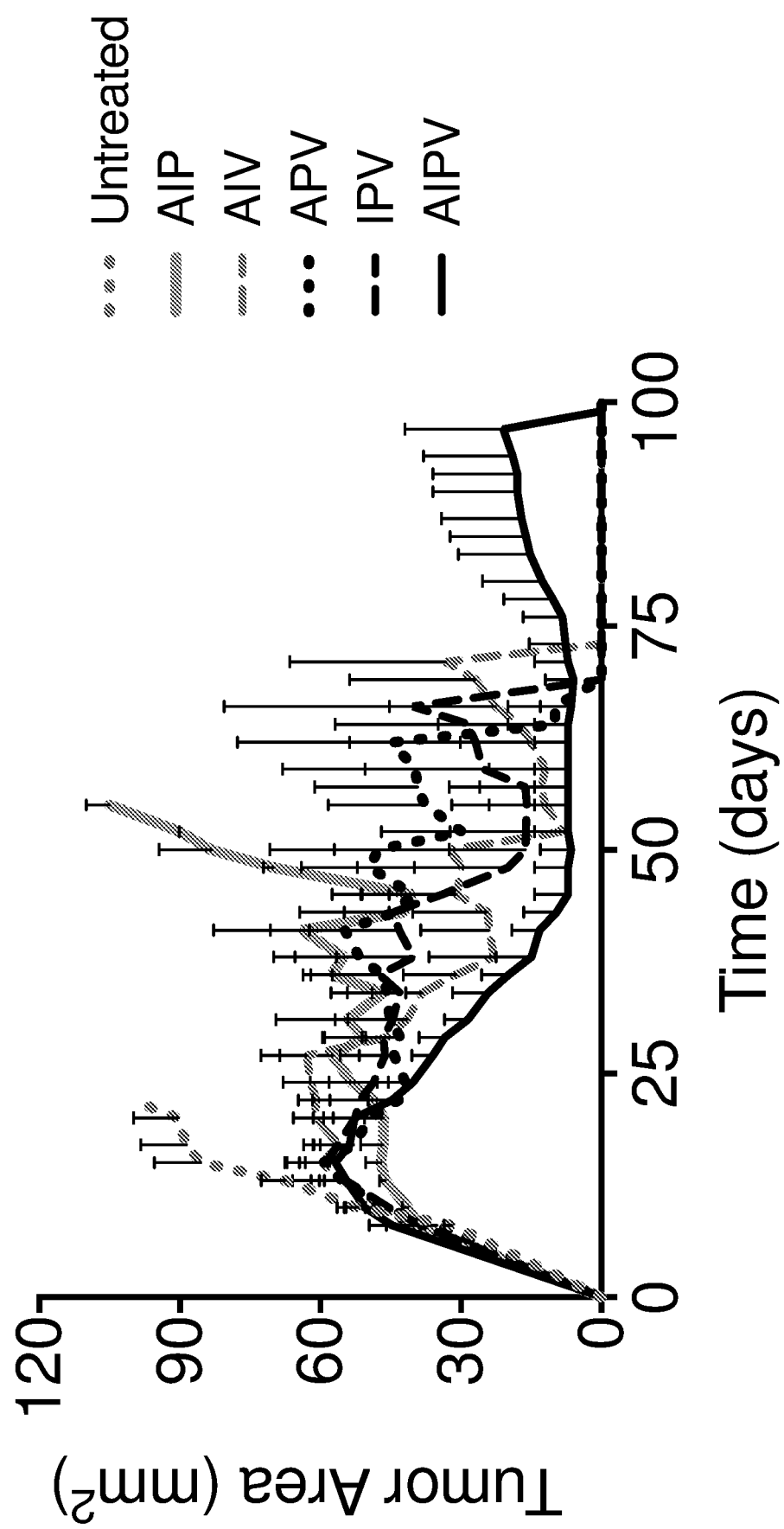
FIGS. 35A and 35B depict the effects of various combination therapies including vehicle, anti-PD-1 antibody, knottin-Fc, MSA-IL2, and amphiphile vaccine, and combinations thereof, on tumor control.

Tumor area was measured throughout the course of the experiment and is summarized in FIG. 35A. Synergistic reduction of tumor growth was observed when all 4 components (i.e., cancer vaccine, anti-PD1 antibody, knottin-Fc, and MSA-IL-2) were administered. Tumor growth was also controlled with the triple combinations (i.e., MSA-IL-2+knottin-Fc+vaccine; MSA-IL-2+knottin-Fc+anti-PD-1 antibody; MSA-IL-2+anti-PD-1 antibody+vaccine; anti-PD-1 antibody+knottin-Fc+vaccine), relative to vehicle (PBS).

Figure 35B:
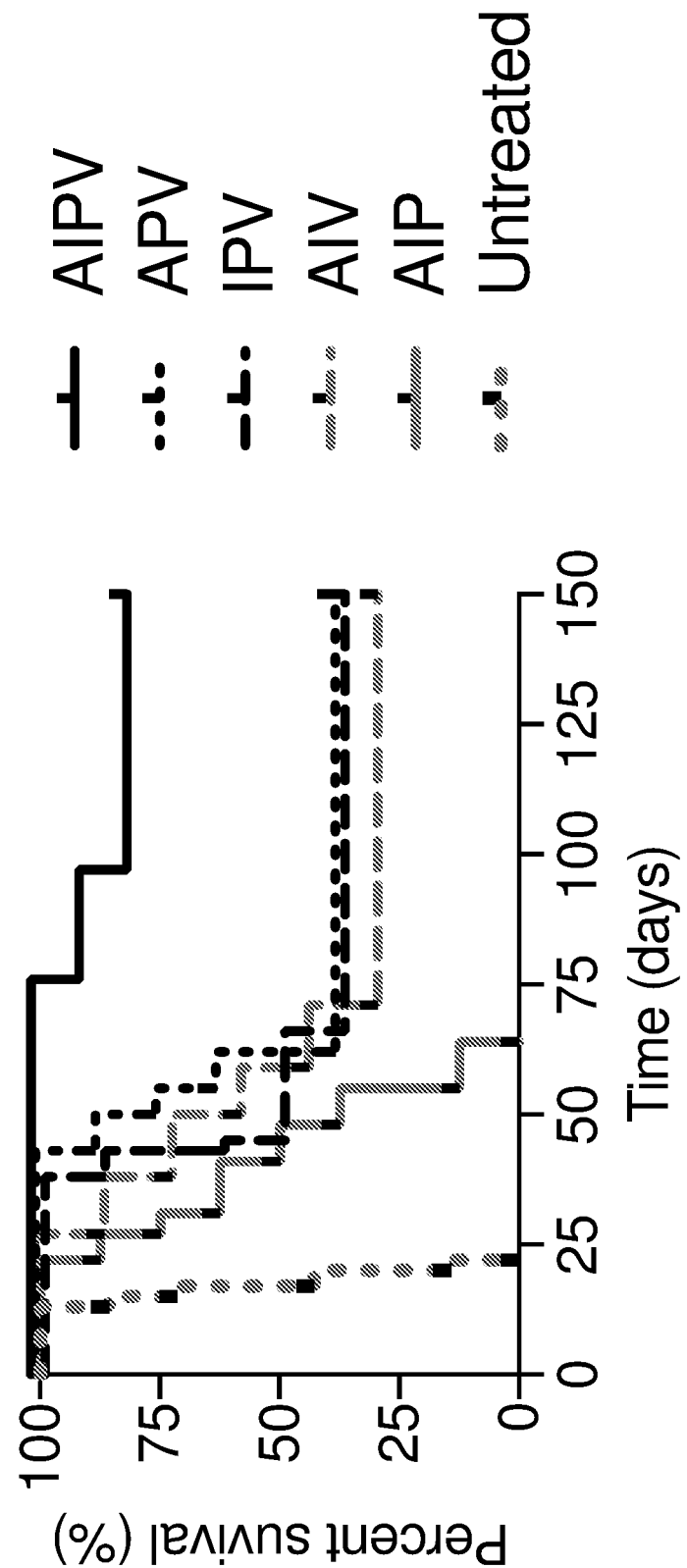

Survival was also examined and plotted in FIG. 35B. Survival was substantially improved with the quadruple combination (i.e., cancer vaccine, anti-PD1 antibody, knottin-Fc, and MSA-IL-2). The triple combinations (i.e., MSA-IL-2+knottin-Fc+vaccine; MSA-IL-2+knottin-Fc+anti-PD-1 antibody; MSA-IL-2+anti-PD-1 antibody+vaccine; anti-PD-1 antibody+knottin-Fc+vaccine) also substantially improved survival relative to vehicle (PBS). These results indicate a productive role for knottin-Fc when added to the triple combination of a cancer vaccine, MSA-IL-2, and anti-PD-1 antibody.

TABLE 2

Sequence Summary

| SEQ ID NO | Description | Sequence |
|---|---|---|
| 1 | Human IgG1 constant region (amino acid sequence) | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYNST YRVVSVLTVLHQDWLNGKEYKCKVSNKALPAPIEKTISKAKGQPR EPQVYTLPPSRDELTKNQVSLTCLVKGFYPSDIAVEWESNGQPEN NYKTTPPVLDSDGSFFLYSKLTVDKSRWQQGNVFSCSVMHEALH NHYTQKSLSLSPGK |
| 2 | Human IgG1 Fc domain (amino acid sequence) | EPKSCDKTHTCPPCPAPELLGGPSVFLFPPKPKDTLMISRTPEVTCV VVDVSHEDPEVKFNWYVDGVEVHNAKTKPREEQYNSTYRVVSV LTVLHQDWLNGKEYKCKVSNKALPAPIEKTISKAKGQPREPQVYT LPPSRDELTKNQVSLTCLVKGFYPSDIAVEWESNGQPENNYKTTPP VLDSDGSFFLYSKLTVDKSRWQQGNVFSCSVMHEALHNHYTQKS LSLSPGK |
| 3 | Human IgG1 Fc domain (amino acid sequence) Deletion (ΔEPKSC) Upper Hinge | DKTHTCPPCPAPELLGGPSVFLFPPKPKDTLMISRTPEVTCVVVDV SHEDPEVKFNWYVDGVEVHNAKTKPREEQYNSTYRVVSVLTVLH QDWLNGKEYKCKVSNKALPAPIEKTISKAKGQPREPQVYTLPPSR DELTKNQVSLTCLVKGFYPSDIAVEWESNGQPENNYKTTPPVLDS DGSFFLYSKLTVDKSRWQQGNVFSCSVMHEALHNHYTQKSLSLSP GK |
| 4 | Mouse IL-2 (nucleic acid sequence) | GCACCCACTTCAAGCTCCACTTCAAGCTCTACAGCGGAAGCAC AGCAGCAGCAGCAGCAGCAGCAGCAGCAGCAGCAGCACCTGG AGCAGCTGTTGATGGACCTACAGGAGCTCCTGAGCAGGATGGA GAATTACAGGAACCTGAAACTCCCCAGGATGCTCACCTTCAAA TTTTACTTGCCCAAGCAGGCCACAGAATTGAAAGATCTTCAGTG CCTAGAAGATGAACTTGGACCTCTGCGGCATGTTCTGGATTTGA CTCAAAGCAAAAGCTTTCAATTGGAAGATGCTGAGAATTTCAT CAGCAATATCAGAGTAACTGTTGTAAAACTAAAGGGCTCTGAC AACACATTTGAGTGCCAATTCGATGATGAGTCAGCAACTGTGG TGGACTTTCTGAGGAGATGGATAGCCTTCTGTCAAAGCATCATC TCAACAAGCCCTCAA |
| 5 | Mouse IL-2 (amino acid sequence) | APTSSSTSSSTAEAQQQQQQQQQQQHLEQLLMDLQELLSRMEN YRNLKLPRMLTFKFYLPKQATELKDLQCLEDELGPLRHVLDLTQS KSFQLEDAENFISNIRVTVVKLKGSDNTFECQFDDESATVVDFLRR WIAFCQSIISTSPQ |
| 6 | QQ6210 (nucleic acid sequence) | GCACCCACTTCAAGCTCCACTTCAAGCTCTACAGCGGAAGCAC AACAGCAGCAGCAGCAGCAGCAGCAGCAGCAGCAGCACCTGG AGCAGCTGTTGATGGACCTACAGGAACTCCTGAGTAGGATGGA GGATCACAGGAACCTGAGACTCCCCAGGATGCTCACCTTCAAA TTTTACTTGCCCGAGCAGGCCACAGAATTGGAAGATCTTCAGTG CCTAGAAGATGAACTTGAACCACTGCGGCAAGTTCTGGATTTG ACTCAAAGCAAAAGCTTTCAATTGGAAGATGCTGAGAATTTCA TCAGCAATATCAGAGTAACTGTTGTAAAACTAAAGGGCTCTGA CAACACATTTGAGTGCCAATTCGACGATGAGCCAGCAACTGTG |

TABLE 2 -continued

Sequence Summary

| SEQ ID NO | Description | Sequence |
|---|---|---|
| | | GTGGACTTTCTGAGGAGATGGATAGCCTTCTGTCAAAGCATCAT CTCAACAAGCCCTCAA |
| 7 | QQ6210 (amino acid sequence) | APTSSSTSSSTAEAQQQQQQQQQQQQHLEQLLMDLQELLSRMED HRNLRLPRMLTFKFYLPEQATELEDLQCLEDELEPLRQVLDLTQSK SFQLEDAENFISNIRVTVVKLKGSDNTFECQFDDEPATVVDFLRRW IAFCQSIISTSPQ |
| 8 | E76A (nucleic acid sequence) | GCACCCACTTCAAGCTCCACTTCAAGCTCTACAGCGGAAGCAC AGCAGCAGCAGCAGCAGCAGCAGCAGCAGCAGCAGCACCTGG AGCAGCTGTTGATGGACCTACAGGAGCTCCTGAGCAGGATGGA GAATTACAGGAACCTGAAACTCCCCAGGATGCTCACCTTCAAA TTTTACTTGCCCAAGCAGGCCACAGAATTGAAAGATCTTCAGTG CCTAGAAGATGCTCTTGGACCTCTGCGGCATGTTCTGGATTTGA CTCAAAGCAAAAGCTTTCAATTGGAAGATGCTGAGAATTTCAT CAGCAATATCAGAGTAACTGTTGTAAAACTAAAGGGCTCTGAC AACACATTTGAGTGCCAATTCGATGATGAGTCAGCAACTGTGG TGGACTTTCTGAGGAGATGGATAGCCTTCTGTCAAAGCATCATC TCAACAAGCCCTCAA |
| 9 | E76A (amino acid sequence) | APTSSSTSSSTAEAQQQQQQQQQQQQHLEQLLMDLQELLSRMEN YRNLKLPRMLTFKFYLPKQATELKDLQCLEDALGPLRHVLDLTQS KSFQLEDAENFISNIRVTVVKLKGSDNTFECQFDDESATVVDFLRR WIAFCQSIISTSPQ |
| 10 | E76G (nucleic acid sequence) | GCACCCACTTCAAGCTCCACTTCAAGCTCTACAGCGGAAGCAC AGCAGCAGCAGCAGCAGCAGCAGCAGCAGCAGCAGCACCTGG AGCAGCTGTTGATGGACCTACAGGAGCTCCTGAGCAGGATGGA GAATTACAGGAACCTGAAACTCCCCAGGATGCTCACCTTCAAA TTTTACTTGCCCAAGCAGGCCACAGAATTGAAAGATCTTCAGTG CCTAGAAGATGGTCTTGGACCTCTGCGGCATGTTCTGGATTTGA CTCAAAGCAAAAGCTTTCAATTGGAAGATGCTGAGAATTTCAT CAGCAATATCAGAGTAACTGTTGTAAAACTAAAGGGCTCTGAC AACACATTTGAGTGCCAATTCGATGATGAGTCAGCAACTGTGG TGGACTTTCTGAGGAGATGGATAGCCTTCTGTCAAAGCATCATC TCAACAAGCCCTCAA |
| 11 | E76G (amino acid sequence) | APTSSSTSSSTAEAQQQQQQQQQQQQHLEQLLMDLQELLSRMEN YRNLKLPRMLTFKFYLPKQATELKDLQCLEDGLGPLRHVLDLTQS KSFQLEDAENFISNIRVTVVKLKGSDNTFECQFDDESATVVDFLRR WIAFCQSIISTSPQ |
| 12 | D265A Fc/Flag (nucleic acid sequence) (C-terminal flag tag is underlined) | ATGAGGGTCCCCGCTCAGCTCCTGGGGCTCCTGCTGCTCTGGCT CCCAGGTGCACGATGTGAGCCCAGAGTGCCCATAACACAGAAC CCCTGTCCTCCACTCAAAGAGTGTCCCCCATGCGCAGCTCCAGA CCTCTTGGGTGGACCATCCGTCTTCATCTTCCCTCCAAAGATCA AGGATGTACTCATGATCTCCCTGAGCCCCATGGTCACATGTGTG GTGGTGGCCGTGAGCGAGGATGACCCAGATGTCCAGATCAGCT GGTTTGTGAACAACGTGGAAGTACACACAGCTCAGACACAAAC CCATAGAGAGGATTACAACAGTACTCTCCGGGTGGTCAGTGCC CTCCCCATCCAGCACCAGGACTGGATGAGTGGCAAGGAGTTCA AATGCAAGGTCAACAACAGAGCCCTCCCATCCCCCATCGAGAA AACCATCTCAAAACCCAGAGGGCCAGTAAGAGCTCCACAGGTA TATGTCTTGCCTCCACCAGCAGAAGAGATGACTAAGAAAGAGT TCAGTCTGACCTGCATGATCACAGGCTTCTTACCTGCCGAAATT GCTGTGGACTGGACCAGCAATGGGCGTACAGAGCAAAACTACA AGAACACCGCAACAGTCCTGGACTCTGATGGTTCTTACTTCATG TACAGCAAGCTCAGAGTACAAAAGAGCACTTGGGAAAGAGGA AGTCTTTTCGCCTGCTCAGTGGTCCACGAGGGTCTGCACAATCA CCTTACGACTAAGACCATCTCCCGGTCTCTGGGTAAAGGTGGC GGATCT<u>GACTACAAGGACGACGATGACAAGTGATAA</u> |
| 13 | D265A Fc/Flag (amino acid sequence) (C-terminal flag tag is underlined) | MRVPAQLLGLLLLWLPGARCEPRVPITQNPCPPLKECPPCAAPDLL GGPSVFIFPPKIKDVLMISLSPMVTCVVVAVSEDDPDVQISWFVNN VEVHTAQTQTHREDYNSTLRVVSALPIQHQDWMSGKEFKCKVNN RALPSPIEKTISKPRGPVRAPQVYVLPPPAEEMTKKEFSLTCMITGF LPAEIAVDWTSNGRTEQNYKNTATVLDSDGSYFMYSKLRVQKST WERGSLFACSVVHEGLHNHLTTKTISRSLGKGGGS<u>DYKDDDDK</u> |
| 14 | D265A Fc/wt mIL-2 (nucleic | ATGAGGGTCCCCGCTCAGCTCCTGGGGCTCCTGCTGCTCTGGCT CCCAGGTGCACGATGTGAGCCCAGAGTGCCCATAACACAGAAC CCCTGTCCTCCACTCAAAGAGTGTCCCCCATGCGCAGCTCCAGA |

TABLE 2 -continued

Sequence Summary

| SEQ ID NO | Description | Sequence |
|---|---|---|
|  | acid sequence) (C-terminal 6x his tag is underlined) | CCTCTTGGGTGGACCATCCGTCTTCATCTTCCCTCCAAAGATCA AGGATGTACTCATGATCTCCCTGAGCCCCATGGTCACATGTGTG GTGGTGGCCGTGAGCGAGGATGACCCAGACGTCCAGATCAGCT GGTTTGTGAACAACGTGGAAGTACACACAGCTCAGACACAAAC CCATAGAGAGGATTACAACAGTACTCTCCGGGTGGTCAGTGCC CTCCCCATCCAGCACCAGGACTGGATGAGTGGCAAGGAGTTCA AATGCAAGGTCAACAACAGAGCCCTCCCATCCCCCATCGAGAA AACCATCTCAAAACCCAGAGGGCCAGTAAGAGCTCCACAGGTA TATGTCTTGCCTCCACCAGCAGAAGAGATGACTAAGAAAGAGT TCAGTCTGACCTGCATGATCACAGGCTTCTTACCTGCCGAAATT GCTGTGGACTGGACCAGCAATGGGCGTACAGAGCAAAACTACA AGAACACCGCAACAGTCCTGGACTCTGATGGTTCTTACTTCATG TACAGCAAGCTCAGAGTACAAAAGAGCACTTGGGAAAGAGGA AGTCTTTTCGCCTGCTCAGTGGTCCACGAGGGTCTGCACAATCA CCTTACGACTAAGACCATCTCCCGGTCTCTGGGTAAAGGAGGG GGCTCCGCACCCACTTCAAGCTCCACTTCAAGCTCTACAGCGGA AGCACAGCAGCAGCAGCAGCAGCAGCAGCAGCAGCAGCAGCA CCTGGAGCAGCTGTTGATGGACCTACAGGAGCTCCTGAGCAGG ATGGAGAATTACAGGAACCTGAAACTCCCCAGGATGCTCACCT TCAAATTTTACTTGCCCAAGCAGGCCACAGAATTGAAAGATCTT CAGTGCCTAGAAGATGAACTTGGACCTCTGCGGCATGTTCTGG ATTTGACTCAAAGCAAAAGCTTTCAATTGGAAGATGCTGAGAA TTTCATCAGCAATATCAGAGTAACTGTTGTAAAACTAAAGGGC TCTGACAACACATTTGAGTGCCAATTCGATGATGAGTCAGCAA CTGTGGTGGACTTTCTGAGGAGATGGATAGCCTTCTGTCAAAGC ATCATCTCAACAAGCCCTCAA<u>ACCATCACCACCATCACT</u>GATA A |
| 15 | D265A Fc/wt mIL-2 (amino acid sequence) (C-terminal 6x his tag is underlined) | MRVPAQLLGLLLLWLPGARCEPRVPITQNPCPPLKECPPCAAPDLL GGPSVFIFPPKIKDVLMISLSPMVTCVVVAVSEDDPDVQISWFVNN VEVHTAQTQTHREDYNSTLRVVSALPIQHQDWMSGKEFKCKVNN RALPSPIEKTISKPRGPVRAPQVYVLPPPAEEMTKKEFSLTCMITGF LPAEIAVDWTSNGRTEQNYKNTATVLDSDGSYFMYSKLRVQKST WERGSLFACSVVHEGLHNHLTTKTISRSLGKGGGSAPTSSSTSSST AEAQQQQQQQQQQQHLEQLLMDLQELLSRMENYRNLKLPRML TFKFYLPKQATELKDLQCLEDELGPLRHVLDLTQSKSFQLEDAENF ISNIRVTVVKLKGSDNTFECQFDDESATVVDFLRRWIAFCQSIISTS PQ<u>HHHHHH</u>** |
| 16 | D265A Fc/ QQ6210 (nucleic acid sequence) (C-terminal 6x his tag is underlined) | ATGAGGGTCCCCGCTCAGCTCCTGGGGCTCCTGCTGCTCTGGCT CCCAGGTGCACGATGTGAGCCCAGAGTGCCCATAACACAGAAC CCCTGTCCTCCACTCAAAGAGTGTCCCCCATGCGCAGCTCCAGA CCTCTTGGGTGGACCATCCGTCTTCATCTTCCCTCCAAAGATCA AGGATGTACTCATGATCTCCCTGAGCCCCATGGTCACATGTGTG GTGGTGGCCGTGAGCGAGGATGACCCAGACGTCCAGATCAGCT GGTTTGTGAACAACGTGGAAGTACACACAGCTCAGACACAAAC CCATAGAGAGGATTACAACAGTACTCTCCGGGTGGTCAGTGCC CTCCCCATCCAGCACCAGGACTGGATGAGTGGCAAGGAGTTCA AATGCAAGGTCAACAACAGAGCCCTCCCATCCCCCATCGAGAA AACCATCTCAAAACCCAGAGGGCCAGTAAGAGCTCCACAGGTA TATGTCTTGCCTCCACCAGCAGAAGAGATGACTAAGAAAGAGT TCAGTCTGACCTGCATGATCACAGGCTTCTTACCTGCCGAAATT GCTGTGGACTGGACCAGCAATGGGCGTACAGAGCAAAACTACA AGAACACCGCAACAGTCCTGGACTCTGATGGTTCTTACTTCATG TACAGCAAGCTCAGAGTACAAAAGAGCACTTGGGAAAGAGGA AGTCTTTTCGCCTGCTCAGTGGTCCACGAGGGTCTGCACAATCA CCTTACGACTAAGACCATCTCCCGGTCTCTGGGTAAAGGAGGG GGCTCCGCACCCACTTCAAGCTCCACTTCAAGCTCTACAGCGGA AGCACAACAGCAGCAGCAGCAGCAGCAGCAGCAGCAGCAGCA CCTGGAGCAGCTGTTGATGGACCTACAGGAACTCCTGAGTAGG ATGGAGGATCACAGGAACCTGAGACTCCCCAGGATGCTCACCT TCAAATTTTACTTGCCCGAGCAGGCCACAGAATTGGAAGATCTT CAGTGCCTAGAAGATGAACTTGAACCACTGCGGCAAGTTCTGG ATTTGACTCAAAGCAAAAGCTTTCAATTGGAAGATGCTGAGAA TTTCATCAGCAATATCAGAGTAACTGTTGTAAAACTAAAGGGC TCTGACAACACATTTGAGTGCCAATTCGACGATGAGCCAGCAA CTGTGGTGGACTTTCTGAGGAGATGGATAGCCTTCTGTCAAAGC ATCATCTCAACAAGCCCTCAA<u>ACCATCACCACCATCACT</u>GATA A |
| 17 | D265A Fc/ QQ6210 (amino acid sequence) | MRVPAQLLGLLLLWLPGARCEPRVPITQNPCPPLKECPPCAAPDLL GGPSVFIFPPKIKDVLMISLSPMVTCVVVAVSEDDPDVQISWFVNN VEVHTAQTQTHREDYNSTLRVVSALPIQHQDWMSGKEFKCKVNN RALPSPIEKTISKPRGPVRAPQVYVLPPPAEEMTKKEFSLTCMITGF |

TABLE 2 -continued

Sequence Summary

| SEQ ID NO | Description | Sequence |
|---|---|---|
|  | (C-terminal 6x his tag is underlined) | LPAEIAVDWTSNGRTEQNYKNTATVLDSDGSYFMYSKLRVQKST WERGSLFACSVVHEGLHNHLTTKTISRSLGKGGGSAPTSSSTSSST AEAQQQQQQQQQQQQHLEQLLMDLQELLSRMEDHRNLRLPRML TFKFYLPEQATELEDLQCLEDELEPLRQVLDLTQSKSFQLEDAENFI SNIRVTVVKLKGSDNTFECQFDDEPATVVDFLRRWIAFCQSIISTSP QH<u>HHHHH</u> |
| 18 | D265A Fc/ E76A (nucleic acid sequence) (C-terminal 6x his tag is underlined) | ATGAGGGTCCCCGCTCAGCTCCTGGGGCTCCTGCTGCTCTGGCT CCCAGGTGCACGATGTGAGCCCAGAGTGCCCATAACACAGAAC CCCTGTCCTCCACTCAAAGAGTGTCCCCCATGCGCAGCTCCAGA CCTCTTGGGTGGACCATCCGTCTTCATCTTCCCTCCAAAGATCA AGGATGTACTCATGATCTCCCTGAGCCCCATGGTCACATGTGTG GTGGTGGCCGTGAGCGAGGATGACCCAGACGTCCAGATCAGCT GGTTTGTGAACAACGTGGAAGTACACAGCTCAGACACAAAC CCATAGAGAGGATTACAACAGTACTCTCCGGGTGGTCAGTGCC CTCCCCATCCAGCACCAGGACTGGATGAGTGGCAAGGAGTTCA AATGCAAGGTCAACAACAGAGCCCTCCCATCCCCCATCGAGAA AACCATCTCAAAACCCAGAGGGCCAGTAAGAGCTCCACAGGTA TATGTCTTGCCTCCACCAGCAGAAGAGATGACTAAGAAAGAGT TCAGTCTGACCTGCATGATCACAGGCTTCTTACCTGCCGAAATT GCTGTGGACTGGACCAGCAATGGGCGTACAGAGCAAAACTACA AGAACACCGCAACAGTCCTGGACTCTGATGGTTCTTACTTCATG AGTCTTTTCGCCTGCTCAGTGGTCCACGAGGGTCTGCACAATCA CCTTACGACTAAGACCATCTCCCGGTCTCTGGGTAAAGGAGGG GGCTCCGCACCCACTTCAAGCTCCACTTCAAGCTCTACAGCGGA AGCACAGCAGCAGCAGCAGCAGCAGCAGCAGCAGCAGCAGCA CCTGGAGCAGCTGTTGATGGACCTACAGGAGCTCCTGAGCAGG ATGGAGAATTACAGGAACCTGAAACTCCCCAGGATGCTCACCT TCAAAATTTTACTTGCCCAAGCAGGCCACAGAATTGAAAGATCTT CAGTGCCTAGAAGATGCTCTTGGACCTCTGCGGCATGTTCTGGA TTTGACTCAAAGCAAAAGCTTTCAATTGGAAGATGCTGAGAAT TTCATCAGCAATATCAGAGTAACTGTTGTAAAACTAAAGGGCT CTGACAACACATTTGAGTGCCAATTCGATGATGAGTCAGCAAC TGTGGTGGACTTTCTGAGGAGATGGATAGCCTTCTGTCAAAGC ATCATCTCAACAAGCCCTCAA<u>CACCATCACCACCATCACTGATA A</u> |
| 19 | D265A Fc/ E76A (amino acid sequence) (C-terminal 6x his tag is underlined) | MRVPAQLLGLLLLWLPGARCEPRVPITQNPCPPLKECPPCAAPDLL GGPSVFIFPPKIKDVLMISLSPMVTCVVVAVSEDDPDVQISWFVNN VEVHTAQTQTHREDYNSTLRVVSALPIQHQDWMSGKEFKCKVNN RALPSPIEKTISKPRGPVRAPQVYVLPPPAEEMTKKEFSLTCMITGF LPAEIAVDWTSNGRTEQNYKNTATVLDSDGSYFMYSKLRVQKST WERGSLFACSVVHEGLHNHLTTKTISRSLGKGGGSAPTSSSTSSST AEAQQQQQQQQQQQQHLEQLLMDLQELLSRMENYRNLKLPRML TFKFYLPKQATELKDLQCLEDALGPLRHVLDLTQSKSFQLEDAEN FISNIRVTVVKLKGSDNTFECQFDDESATVVDFLRRWIAFCQSIIST SPQ<u>HHHHHH</u> |
| 20 | D265A Fc/ E76G (nucleic acid sequence) (C-terminal 6x his tag is underlined) | ATGAGGGTCCCCGCTCAGCTCCTGGGGCTCCTGCTGCTCTGGCT CCCAGGTGCACGATGTGAGCCCAGAGTGCCCATAACACAGAAC CCCTGTCCTCCACTCAAAGAGTGTCCCCCATGCGCAGCTCCAGA CCTCTTGGGTGGACCATCCGTCTTCATCTTCCCTCCAAAGATCA AGGATGTACTCATGATCTCCCTGAGCCCCATGGTCACATGTGTG GTGGTGGCCGTGAGCGAGGATGACCCAGACGTCCAGATCAGCT GGTTTGTGAACAACGTGGAAGTACACAGCTCAGACACAAAC CCATAGAGAGGATTACAACAGTACTCTCCGGGTGGTCAGTGCC CTCCCCATCCAGCACCAGGACTGGATGAGTGGCAAGGAGTTCA AATGCAAGGTCAACAACAGAGCCCTCCCATCCCCCATCGAGAA AACCATCTCAAAACCCAGAGGGCCAGTAAGAGCTCCACAGGTA TATGTCTTGCCTCCACCAGCAGAAGAGATGACTAAGAAAGAGT TCAGTCTGACCTGCATGATCACAGGCTTCTTACCTGCCGAAATT GCTGTGGACTGGACCAGCAATGGGCGTACAGAGCAAAACTACA AGAACACCGCAACAGTCCTGGACTCTGATGGTTCTTACTTCATG TACAGCAAGCTCAGAGTACAAAGAGCACTTGGGAAAGAGGA AGTCTTTTCGCCTGCTCAGTGGTCCACGAGGGTCTGCACAATCA CCTTACGACTAAGACCATCTCCCGGTCTCTGGGTAAAGGAGGG GGCTCCGCACCCACTTCAAGCTCCACTTCAAGCTCTACAGCGGA AGCACAGCAGCAGCAGCAGCAGCAGCAGCAGCAGCAGCAGCA CCTGGAGCAGCTGTTGATGGACCTACAGGAGCTCCTGAGCAGG ATGGAGAATTACAGGAACCTGAAACTCCCCAGGATGCTCACCT TCAAAATTTTACTTGCCCAAGCAGGCCACAGAATTGAAAGATCTT CAGTGCCTAGAAGATGGTCTTGGACCTCTGCGGCATGTTCTGGA TTTGACTCAAAGCAAAAGCTTTCAATTGGAAGATGCTGAGAAT TTCATCAGCAATATCAGAGTAACTGTTGTAAAACTAAAGGGCT |

TABLE 2 -continued

Sequence Summary

| SEQ ID NO | Description | Sequence |
|---|---|---|
|  |  | CTGACAACACATTTGAGTGCCAATTCGATGATGAGTCAGCAAC TGTGGTGGACTTTCTGAGGAGATGGATAGCCTTCTGTCAAAGC ATCATCTCAACAAGCCCTCAA<u>CACCATCACCACCATCAC</u>TGATA A |
| 21 | D265A Fc/ E76G (amino acid sequence) (C-terminal 6x his tag is underlined) | MRVPAQLLGLLLLWLPGARCEPRVPITQNPCPPLKECPPCAAPDLL GGPSVFIFPPKIKDVLMISLSPMVTCVVVAVSEDDPDVQISWFVNN VEVHTAQTQTHREDYNSTLRVVSALPIQHQDWMSGKEFKCKVNN RALPSPIEKTISKPRGPVRAPQVYVLPPPAEEMTKKEFSLTCMITGF LPAEIAVDWTSNGRTEQNYKNTATVLDSDGSYFMYSKLRVQKST WERGSLFACSVVHEGLHNHLTTKTISRSLGKGGGSAPTSSSTSSST AEAQQQQQQQQQQQHLEQLLMDLQELLSRMENYRNLKLPRML TFKFYLPKQATELKDLQCLEDGLGPLRHVLDLTQSKSFQLEDAEN FISNIRVTVVKLKGSDNTFECQFDDESATVVDFLRRWIAFCQSIIST SPQ<u>HHHHHH</u> |
| 22 | mIL-2 QQ 6.2-4 (nucleic acid sequence) | GCACCCACCTCAAGCTCCACTTCAAGCTCTACAGCGGAAGCAC AACAGCAGCAGCAGCAGCAGCAGCAGCAGCAGCACCTGG AGCAGCTGTTGATGGACCTACAGGAGCTCCTGAGCAGGATGGA GGATTCCAGGAACCTGAGACTCCCCAGGATGCTCACCTTCAAA TTTTACTTGCCCAAGCAGGCCACAGAATTGGAAGATCTTCAGTG CCTAGAAGATGAACTTGAACCTCTGCGGCAAGTTCTGGATTTG ACTCAAAGCAAAAGCTTTCAATTGGAAGATGCTGAGAATTTCA TCAGCAATATCAGAGTAACTGTTGTAAAACTAAAGGGCTCTGA CAACACATTTGAGTGCCAATTCGATGATGAGCCAGCAACTGTG GTGGGCTTTCTGAGGAGATGGATAGCCTTCTGTCAAAGCATCAT CTCAACGAGCCCTCAA |
| 23 | mIL-2 QQ 6.2-4 (amino acid sequence) | APTSSSTSSSTAEAQQQQQQQQQQQHLEQLLMDLQELLSRMEDS RNLRLPRMLTFKFYLPKQATELEDLQCLEDELEPLRQVLDLTQSKS FQLEDAENFISNIRVTVVKLKGSDNTFECQFDDEPATVVGFLRRWI AFCQSIISTSPQ |
| 24 | mIL-2 QQ 6.2-8 (nucleic acid sequence) | GCACCCACCTCAAGCTCCACTTCAAGCTCTACAGCGGAAGCAC AACAGCAGCAGCAGCAGCAGCAGCACCTGGAGCAGCTGTTGAT GGACCTACAGGAGCTCCTGAGTAGGATGGAGGATCACAGGAAC CTGAGACTCCCCAGGATGCTCACCTTCAAATTTTACTTGCCCAA GCAGGCCACAGAATTGGAAGATCTTCAGTGCCTAGAAGATGAA CTTGAACCTCTGCGGCAAGTTCTGGATTTGACTCAAAGCAAAA GCTTTCAATTGGAAGATGCTGAGAATTTCATCAGCAATATCAG AGTAACTGTTGTAAAACTAAAGGGCTCTGACAACACATTTGAG TGCCAATTCGATGATGAGCCAGCAACTGTGGTGGACTTTCTGA GGAGATGGATAGCCTTCTGTCAAAGCATCATCTCAACAAGCCC TCGA |
| 25 | mIL-2 QQ 6.2-8 (amino acid sequence) | APTSSSTSSSTAEAQQQQQQQQQQHLEQLLMDLQELLSRMEDHRNLR LPRMLTFKFYLPKQATELEDLQCLEDELEPLRQVLDLTQSKSFQLE DAENFISNIRVTVVKLKGSDNTFECQFDDEPATVVDFLRRWIAFCQ SIISTSPR |
| 26 | mIL-2 QQ 6.2-10 (nucleic acid sequence) | GCACCCACCTCAAGCTCCACTTCAAGCTCTACAGCGGAAGCAC AACAGCAGCAGCAGCAGCAGCAGCAGCAGCAGCACCTGG AGCAGCTGTTGATGGACCTACAGGAACTCCTGAGTAGGATGGA GGATCACAGGAACCTGAGACTCCCCAGGATGCTCACCTTCAAA TTTTACTTGCCCGAGCAGGCCACAGAATTGGAAGATCTTCAGTG CCTAGAAGATGAACTTGAACCACTGCGGCAAGTTCTGGATTTG ACTCAAAGCAAAAGCTTTCAATTGGAAGATGCTGAGAATTTCA TCAGCAATATCAGAGTAACTGTTGTAAAACTAAAGGGCTCTGA CAACACATTTGAGTGCCAATTCGACGATGAGCCAGCAACTGTG GTGGACTTTCTGAGGAGATGGATAGCCTTCTGTCAAAGCATCAT CTCAACAAGCCCTCAG |
| 27 | mIL-2 QQ 6.2-10 (amino acid sequence) | APTSSSTSSSTAEAQQQQQQQQQQQHLEQLLMDLQELLSRMED HRNLRLPRMLTFKFYLPEQATELEDLQCLEDELEPLRQVLDLTQSK SFQLEDAENFISNIRVTVVKLKGSDNTFECQFDDEPATVVDFLRRW IAFCQSIISTSPQ |
| 28 | mIL-2 QQ 6.2-11 (nucleic acid sequence) | GCACCCACCTCAAGCTCCACTTCAAGCTCTACAGCGGAAGCAC AACAGCAGCAGCAGCAGCAGCAGCACCTGGAGCAGCAGCTGTT GATGGACCTACAGGAGCTCCTGAGCAGGATGGAGGATTCCAGG AACCTGAGACTCCCCAGAATGCTCACCTTCAAATTTTACTTGCC CGAGCAGGCCACAGAATTGAAAGATCTCCAGTGCCTAGAAGAT GAACTTGAACCTCTGCGGCAAGTTCTGGATTTGACTCAAAGCA AAAGCTTTCAATTGGAAGATGCTGAGAATTTCATCAGCAATAT |

TABLE 2 -continued

Sequence Summary

| SEQ ID NO | Description | Sequence |
|---|---|---|
| | | CAGAGTAACTGTTGTAAAACTAAAGGGCTCTGACAACACATTT GAGTGCCAATTCGACGATGAGCCAGCAACTGTGGTGGACTTTC TGAGGAGATGGATAGCCTTCTGTCAAAGCATCATCTCAACAAG CCCTCAG |
| 29 | mIL-2 QQ 6.2-11 (amino acid sequence) | APTSSSTSSSTAEAQQQQQQQQQHLEQLLMDLQELLSRMEDSRNL RLPRMLTFKFYLPEQATELKDLQCLEDELEPLRQVLDLTQSKSFQL EDAENFISNIRVTVVKLKGSDNTFECQFDDEPATVVDFLRRWIAFC QSIISTSPQ |
| 30 | mIL-2 QQ 6.2-13 (nucleic acid sequence) | GCACCCACCTCAAGCTCCACTTCAAGCTCTACAGCGGAAGCAC AACAGCAGCAGCAGCAGCAGCAGCAGCAGCAGCAGCACCTGG AGCAGCTGTTGATGGACCTACAGGAGCTCCTGAGTAGGATGGA GGATCACAGGAACCTGAGACTCCCCAGGATGCTCACCTTCAAA TTTTACTTGCCCGAGCAGGCCACAGAATTGAAAGATCTCCAGT GCCTAGAAGATGAACTTGAACCTCTGCGGCAGGTTCTGGATTT GACTCAAAGCAAAAGCTTTCAATTGGAAGATGCTGAGAATTTC ATCAGCAATATCAGAGTAACTGTTGTAAAACTAAAGGGCTCTG ACAACACATTTGAGTGCCAATTCGATGATGAGCCAGCAACTGT GGTGGACTTTCTGAGGAGATGGATAGCCTTCTGTCAAAGCATC ATCTCAACAAGCCCTCAG |
| 31 | mIL-2 QQ 6.2-13 (amino acid sequence) | APTSSSTSSSTAEAQQQQQQQQQQHLEQLLMDLQELLSRMED HRNLRLPRMLTFKFYLPEQATELKDLQCLEDELEPLRQVLDLTQS KSFQLEDAENFISNIRVTVVKLKGSDNTFECQFDDEPATVVDFLRR WIAFCQSIISTSPQ |
| 32 | Full length human IL-2 (nucleic acid sequence) | ATGTACAGGATGCAACTCCTGTCTTGCATTGCACTAAGTCTTGC ACTTGTCACAAACAGTGCACCTACTTCAAGTTCTACAAAGAAA ACACAGCTACAACTGGAGCATTTACTGCTGGATTTACAGATGA TTTTGAATGGAATTAATAATTACAAGAATCCCAAACTCACCAG GATGCTCACATTTAAGTTTTACATGCCCAAGAAGGCCACAGAA CTGAAACATCTTCAGTGTCTAGAAGAAGAACTCAAACCTCTGG AGGAAGTGCTAAATTTAGCTCAAAGCAAAAACTTTCACTTAAG ACCCAGGGACTTAATCAGCAATATCAACGTAATAGTTCTGGAA CTAAAGGGATCTGAAACAACATTCATGTGTAATATGCTGATGA GACAGCAACCATTGTAGAATTTCTGAACAGATGGATTACCTTTT GTCAAAGCATCATCTCAACACTGACTTGA |
| 33 | Full length human IL-2 (amino acid sequence) | MYRMQLLSCIALSLALVTNSAPTSSSTKKTQLQLEHLLLDLQMILN GINNYKNPKLTRMLTFKFYMPKKATELKHLQCLEEELKPLEEVLN LAQSKNFHLRPRDLISNINVIVLELKGSETTFMCEYADETATIVEFL NRWITFCQSIISTLT |
| 34 | Human IL-2 without signal peptide (nucleic acid sequence) | GCACCTACTTCAAGTTCTACAAAGAAAACACAGCTACAACTGG AGCATTTACTGCTGGATTTACAGATGATTTTGAATGGAATTAAT AATTACAAGAATCCCAAACTCACCAGGATGCTCACATTTAAGT TTTACATGCCCAAGAAGGCCACAGAACTGAAACATCTTCAGTG TCTAGAAGAAGAACTCAAACCTCTGGAGGAAGTGCTAAATTTA GCTCAAAGCAAAAACTTTCACTTAAGACCCAGGGACTTAATCA GCAATATCAACGTAATAGTTCTGGAACTAAAGGGATCTGAAAC AACATTCATGTGTAATATGCTGATGAGACAGCAACCATTGTAG AATTTCTGAACAGATGGATTACCTTTTGTCAAAGCATCATCTCA ACACTGACTTGA |
| 35 | Human IL-2 without signal peptide (amino acid sequence) | APTSSSTKKTQLQLEHLLLDLQMILNGINNYKNPKLTRMLTFKFY MPKKATELKHLQCLEEELKPLEEVLNLAQSKNFHLRPRDLISNINV IVLELKGSETTFMCEYADETATIVEFLNRWITFCQSITSTLT |
| 36 | Human serum albumin (amino acid sequence) | MDMRVPAQLLGLLLLWLPGARCADAHKSEVAHRFKDLGEENFK ALVLIAFAQYLQQCPFEDHVKLVNEVTEFAKTCVADESAENCDKS LHTLFGDKLCTVATLRETYGEMADCCAKQEPERNECFLQHKDDN PNLPRLVRPEVDVMCTAFHDNEETFLKKYLYEIARRHPYFYAPEL LFFAKRYKAAFTECCQAADKAACLLPKLDELRDEGKASSAKQRL KCASLQKFGERAFKAWAVARLSQRFPKAEFAEVSKLVTDLTKVH TECCHGDLLECADDRADLAKYICENQDSISSKLKECCEKPLLEKSH CIAEVENDEMPADLPSLAADFVESKDVCKNYAEAKDVFLGMFLY EYARRHPDYSVVLLLRLAKTYETTLEKCCAAADPHECYAKVFDEF KPLVEEPQNLIKQNCELFEQLGEYKFQNALLVRYTKKVPQVSTPTL VEVSRNLGKVGSKCCKHPEAKRMPCAEDYLSVVLNQLCVLHEKT PVSDRVTKCCTESLVNRRPCFSALEVDETYVPKEFNAETFTFHADI |

TABLE 2 -continued

Sequence Summary

| SEQ ID NO | Description | Sequence |
|---|---|---|
| | | CTLSEKERQIKKQTALVELVKHKPKATKEQLKAVMDDFAAFVEK CCKADDKETCFAEEGKKLVAASQAALGLGGGSAPTSSSTKKTQL QLEHLLLDLQMILNGINNYKNPKLTRMLTFKFYMPKKATELKHLQ CLEEELKPLEEVLNLAQSKNFHLRPRDLISNINVIVLELKGSETTFM CEYADETATIVEFLNRWITFCQSIISTLTGGGS |
| 37 | Mature HSA (amino acid sequence) | DAHKSEVAHRFKDLGEENFKALVLIAFAQYLQQCPFEDHVKLVNE VTEFAKTCVADESAENCDKSLHTLFGDKLCTVATLRETYGEMAD CCAKQEPERNECFLQHKDDNPNLPRLVRPEVDVMCTAFHDNEETF LKKYLYEIARRHPYFYAPELLFFAKRYKAAFTECCQAADKAACLL PKLDELRDEGKASSAKQRLKCASLQKFGERAFKAWAVARLSQRF PKAEFAEVSKLVTDLTKVHTECCHGDLLECADDRADLAKYICENQ DSISSKLKECCEKPLLEKSHCIAEVENDEMPADLPSLAADFVESKD VCKNYAEAKDVFLGMFLYEYARRHPDYSVVLLLRLAKTY-ETTLE KCCAAADPHECYAKVFDEFKPLVEEPQNLIKQNCELFEQLGEYKF QNALLVRYTKKVPQVSTPTLVEVSRNLGKVGSKCCKHPEAKRMP CAEDYLSVVLNQLCVLHEKTPVSDRVTKCCTESLVNRRPCFSALE VDETYVPKEFNAETFTFHADICTLSEKERQIKKQTALVELVKHKPK ATKEQLKAVMDDFAAFVEKCCKADDKETCFAEEGKKLVAASQA ALGLGGGSAPTSSSTKKTQLQLEHLLLDLQMILNGINNYKNPKLTR MLTFKFYMPKKATELKHLQCLEEELKPLEEVLNLAQSKNFHLRPR DLISNINVIVLELKGSETTFMCEYADETATIVEFLNRWITFCQSIIST LTGGGS |
| 38 | Human serum albumin (nucleic acid sequence) | ATGGATATGCGGGTGCCTGCTCAGCTGCTGGGACTGCTGCTGCT GTGGCTGCCTGGGGCTAGATGCGGATGCTCACAAAAGCGAA GTCGCACACAGGTTCAAAGATCTGGGGGAGGAAAACTTTAAGG CTCTGGTGCTGATTGCATTCGCCCAGTACCTGCAGCAGTGCCCC TTTGAGGACCACGTGAAACTGGTCAACGAAGTGACTGAGTTCG CCAAGACCTGCGTGGCCGACGAATCTGCTGAGAATTGTGATAA AAGTCTGCATACTCTGTTTGGGGATAAGCTGTGTACAGTGGCCA CTCTGCGAGAAACCTATGGAGAGATGGCAGACTGCTGTGCCAA ACAGGAACCCGAGCGGAACGAATGCTTCCTGCAGCATAAGGAC GATAACCCCAATCTGCCTCGCCTGGTGCGACCTGAGGTGGACG TCATGTGTACAGCCTTCCACGATAATGAGGAAACTTTTCTGAAG AAATACCTGTACGAAATCGCTCGGAGACATCCTTACTTTTATGC ACCAGAGCTGCTGTTCTTTGCCAAACGCTACAAGGCCGCTTTCA CCGAGTGCTGTCAGGCAGCCGATAAAGCTGCATGCCTGCTGCC TAAGCTGGACGAACTGAGGGATGAGGGCAAGGCCAGCTCCGCT AAACAGCGCCTGAAGTGTGCTAGCCTGCAGAAATTCGGGGAGC GAGCCTTCAAGGCTTGGGCAGTGGCACGGCTGAGTCAGAGATT CCCAAAGGCAGAATTTGCCGAGGTCTCAAAACTGGTGACCGAC CTGACAAAGGTGCACACCGAATGCTGTCATGGCGACCTGCTGG AGTGCGCCGACGATCGAGCTGATCGGCAAAGTATATTTGTGA GAACCAGGACTCCATCTCTAGTAAGCTGAAAGAATGCTGTGAG AAACCACTGCTGGAAAAGTCTCACTGCATTGCCGAAGTGGAGA ACGACGAGATGCCAGCTGATCTGCCCCTCACTGGCCGCTGACTTC GTCGAAAGCAAAGATGTGTGTAAGAATTACGCTGAGGCAAAGG ATGTGTTCCTGGGAATGTTTCTGTACGAGTATGCCAGGCGCCAC CCAGACTACTCCGTGGTCCTGCTGCTGAGGCTGGCTAAAACAT ATGAAACCACACTGGAGAAGTGCTGTGCAGCCGCTGATCCCCA TGAATGCTATGCCAAAGTCTTCGACGAGTTTAAGCCCCTGGTGG AGGAACCTCAGAACCTGATCAAACAGAATTGTGAACTGTTTGA GCAGCTGGGCGAGTACAAGTTCCAGAACGCCCTGCTGGTGCGC TATACCAAGAAAGTCCCACAGGTGTCCACACCCACTCTGGTGG AGGTGAGCCGGAATCTGGGCAAAGTGGGGAGTAAATGCTGTAA GCACCCTGAAGCAAGAGGATGCCATGCGCTGAGGATTACCTG AGTGTGGTCCTGAATCAGCTGTGTGTCCTGCATGAAAAAACAC CTGTCAGCGACCGGGTGACAAAGTGCTGTACTGAGTCACTGGT GAACCGACGCCCTGCTTTAGCGCCCTGGAAGTCGATGAGACT TATGTGCCTAAAGAGTTCAACGCTGAGACCTTCACATTTCACGC AGACATTTGTACCCTGAGCGAAAAGGAGAGACAGATCAAGAA ACAGACAGCCCTGGTCGAACTGGTGAAGCATAAACCCAAGGCC ACAAAAGAGCAGCTGAAGGCTGTCATGGACGATTTCGCAGCCT TTGTGGAAAAATGCTGTAAGGCAGACGATAAGGAGACTTGCTT TGCCGAGGAAGGAAAGAAACTGGTGGCTGCATCCCAGGCAGCT CTGGGACTGGGAGGAGGATCTGCCCCTACCTCAAGCTCCACTA AGAAAACCCAGCTGCAGCTGGAGCACCTGCTGCTGGACCTGCA GATGATTCTGAACGGGATCAACAATTACAAAAATCCAAAGCTG ACCCGGATGCTGACATTCAAGTTTTATATGCCCAAGAAAGCCA CAGAGCTGAAACACCTGCAGTGCCTGGAGGAAGAGCTGAAGCC TCTGGAAGAGGTGCTGAACCTGGCCCAGAGCAAGAATTTCCAT CTGAGACCAAGGGATCTGATCTCCAACATTAATGTGATCGTCCT |

TABLE 2 -continued

Sequence Summary

| SEQ ID NO | Description | Sequence |
|---|---|---|
| | | GGAACTGAAGGGATCTGAGACTACCTTTATGTGCGAATACGCT GACGAGACTGCAACCATTGTGGAGTTCCTGAACAGATGGATCA CCTTCTGCCAGTCCATCATTTCTACTCTGACAGGCGGGGGGAGC |
| 39 | EETI-II from Knottin Database | GC PRILMR CKQDSDCLAGCVCGPNGFCG |
| 40 | AgRP from Knottin Database "-" indicates where mini protein can be formed | GCVRLHESCLGQQVPCCDPCATCYCRFFNAFCYCR-KLGTAMNPCSRT |
| 41 | Omega agatoxin from Knottin Database "-" indicates where mini protein can be formed | EDN--CIAEDYGKCTWGGTKCCRGRPCRC SMIGTN CECTPRLIMEGLSFA |
| 42 | EETI-II Library | GCX$_1$X$_2$X$_3$RGDX$_7$X$_8$X$_9$X$_{10}$X$_{11}$CKQDSDCLAGCVCGPNGFCG |
| 43 | EETI-II K15S Mutation Library | GCX$_1$X$_2$X$_3$RGDX$_7$X$_8$X$_9$X$_{10}$X$_{11}$CSQDSDCLAGCVCGPNGFCG |
| 44 | 2.5F-(K15S) mIgG2aFc Nucleic Acid Sequence | GGTTGTCCAAGACCAAGAGGTGATAATCCACCATTGACTTGTTC TCAAGATTCTGATTGTTTGGCTGGTTGTGTTTGTGGTCCAAATG GTTTTTGTGGTGGTCGACTAGAGCCCAGAGTGCCCATAACACA GAACCCCTGTCCTCCACTCAAAGAGTGTCCCCCATGCGCAGCTC CAGACCTCTTGGGTGGACCATCCGTCTTCATCTTCCCTCCAAAG ATCAAGGATGTACTCATGATCTCCCTGAGCCCCATGGTCACATG TGTGGTGGTGGATGTGAGCGAGGATGACCCAGACGTCCAGATC AGCTGGTTTGTGAACAACGTGGAAGTACACACAGCTCAGACAC AAACCCATAGAGAGGATTACAACAGTACTCTCCGGGTGGTCAG TGCCCTCCCCATCCAGCACCAGGACTGGATGAGTGGCAAGGAG TTCAAATGCAAGGTCAACAACGAGCCCTCCCATCCCCCATCG AGAAAACCATCTCAAAACCCAGAGGGCCAGTAAGAGCTCCACA GGTATATGTCTTGCCTCCACCAGCAGAAGAGATGACTAAGAAA GAGTTCAGTCTGACCTGCATGATCACAGGCTTCTTACCTGCCGA AATTGCTGTGGACTGGACCAGCAATGGGCGTACAGAGCAAAC TACAAGAACACCGCAACAGTCCTGGACTCTGATGGTTCTTACTT CATGTACAGCAAGCTCAGAGTACAAAAGAGCACTTGGGAAAG AGGAAGTCTTTTCGCCTGCTCAGTGGTCCACGAGGGTCTGCACA ATCACCTTACGACTAAGACCATCTCCCGGTCTCTGGGTAAA |
| 45 | 2.5F-(K15S) mIgG2aFc Amino Acid Sequence | GCPRPRGDNPPLTCSQDSDCLAGCVCGPNGFCGEPRVPITQNPCPP LKECPPCAAPDLLGGPSVFIFPPKIKDVLMISLSPMVTCVVVDVSED DPDVQISWFVNNVEVHTAQTQTHREDYNSTLRVVSALPIQHQDW MSGKEFKCKVNNRALPSPIEKTISKPRGPVRAPQVYVLPPPAEEMT KKEFSLTCMITGFLPAEIAVDWTSNGRTEQNYKNTATVLDSDGSY FMYSKLRVQKSTWERGSLFACSVVHEGLHNHLTTKTISRSLGK |
| 46 | 2.5D-(K15S) mIgG2aFc Nucleic Acid Sequence | GGTTGTCCACAAGGCAGAGGTGATTGGGCTCCAACTTCTTGTTC TCAAGATTCTGATTGTTTGGCTGGTTGTGTTTGTGGTCCAAATG GTTTTTGTGGTGGTCGACTAGAGCCCAGAGTGCCCATAACACA GAACCCCTGTCCTCCACTCAAAGAGTGTCCCCCATGCGCAGCTC CAGACCTCTTGGGTGGACCATCCGTCTTCATCTTCCCTCCAAAG ATCAAGGATGTACTCATGATCTCCCTGAGCCCCATGGTCACATG TGTGGTGGTGGATGTGAGCGAGGATGACCCAGACGTCCAGATC AGCTGGTTTGTGAACAACGTGGAAGTACACACAGCTCAGACAC AAACCCATAGAGAGGATTACAACAGTACTCTCCGGGTGGTCAG TGCCCTCCCCATCCAGCACCAGGACTGGATGAGTGGCAAGGAG TTCAAATGCAAGGTCAACAACGAGCCCTCCCATCCCCCATCG AGAAAACCATCTCAAAACCCAGAGGGCCAGTAAGAGCTCCACA |

TABLE 2 -continued

Sequence Summary

| SEQ ID NO | Description | Sequence |
|---|---|---|
| | | GGTATATGTCTTGCCTCCACCAGCAGAAGAGATGACTAAGAAA GAGTTCAGTCTGACCTGCATGATCACAGGCTTCTTACCTGCCGA AATTGCTGTGGACTGGACCAGCAATGGGCGTACAGAGCAAAAC TACAAGAACACCGCAACAGTCCTGGACTCTGATGGTTCTTACTT CATGTACAGCAAGCTCGAGTACAAAAGAGCACTTGGGAAAG AGGAAGTCTTTTCGCCTGCTCAGTGGTCCACGAGGGTCTGCACA ATCACCTTACGACTAAGACCATCTCCCGGTCTCTGGGTAAA |
| 47 | 2.5D-(K15S) mIgG2aFc Amino Acid Sequence | GCPQGRGDWAPTSCSQDSDCLAGCVCGPNGFCGEPRVPITQNPCP PLKECPPCAAPDLLGGPSVFIFPPKIKDVLMISLSPMVTCVVVDVSE DDPDVQISWFVNNVEVHTAQTQTHREDYNSTLRVVSALPIQHQD WMSGKEFKCKVNNRALPSPIEKTISKPRGPVRAPQVYVLPPPAEE MTKKEFSLTCMITGFLPAEIAVDWTSNGRTEQNYKNTATVLDSDG SYFMYSKLRVQKSTWERGSLFACSVVHEGLHNHLTTKTISRSLGK |
| 48 | 2.5F-(K15S) hIgG1Fc Amino Acid Sequence | GCPRPRGDNPPLTCSQDSDCLAGCVCGPNGFCGEPKSCDKTHTCP PCPAPELLGGPSVFLFPPKPKDTLMISRTPEVTCVVVDVSHEDPEV KFNWYVDGVEVHNAKTKPREEQYNSTYRVVSVLTVLHQDWLNG KEYKCKVSNKALPAPIEKTISKAKGQPREPQVYTLPPSREEMTKNQ VSLTCLVKGFYPSDIAVEWESNGQPENNYKTTPPVLDSDGSFFLYS KLTVDKSRWQQGNVFSCSVMHEALHNHYTQKSLSLSPGK |
| 49 | 2.5F-(K15S) hIgG1Fc Fc Upper Hinge Deletion (ΔEPKSC) Amino Acid Sequence | GCPRPRGDNPPLTCSQDSDCLAGCVCGDKTHTCPPCPAP ELLGGPSVFLFPPKPKDTLMISRTPEVTCVVVDVSHEDPEVKFNWY VDGVEVHNAKTKPREEQYNSTYRVVSVLTVLHQDWLNGKEYKC KVSNKALPAPIEKTISKAKGQPREPQVYTLPPSREEMTKNQVSLTC LVKGFYPSDIAVEWESNGQPENNYKTTPPVLDSDGSFFLYSKLTV DKSRWQQGNVFSCSVMHEALHNHYTQKSLSLSPGK |
| 50 | 2.5D-(K15S) hIgG1Fc Amino Acid Sequence | GCPQGRGDWAPTSCSQDSDCLAGCVCGPNGFCGEPKSCDKTHTC PPCPAPELLGGPSVFLFPPKPKDTLMISRTPEVTCVVVDVSHEDPEV KFNWYVDGVEVHNAKTKPREEQYNSTYRVVSVLTVLHQDWLNG KEYKCKVSNKALPAPIEKTISKAKGQPREPQVYTLPPSREEMTKNQ VSLTCLVKGFYPSDIAVEWESNGQPENNYKTTPPVLDSDGSFFLYS KLTVDKSRWQQGNVFSCSVMHEALHNHYTQKSLSLSPGK |
| 51 | 2.5D-(K15S) hIgG1Fc Fc Upper Hinge Deletion (ΔEPKSC) Amino Acid Sequence | GCPQGRGDWAPTSCSQDSDCLAGCVCGDKTHTCPPCPA PELLGGPSVFLFPPKPKDTLMISRTPEVTCVVVDVSHEDPEVKFNW YVDGVEVHNAKTKPREEQYNSTYRVVSVLTVLHQDWLNGKEYK CKVSNKALPAPIEKTISKAKGQPREPQVYTLPPSREEMTKNQVSLT CLVKGFYPSDIAVEWESNGQPENNYKTTPPVLDSDGSFFLYSKLTV DKSRWQQGNVFSCSVMHEALHNHYTQKSLSLSPGK |
| 52 | hPD-1 amino acid sequence | MQIPQAPWPVVWAVLQLGWRPGWFLDSPDPWNPPTFFPALLVVT EGDNATFTCSFSNTSESFVLNWYRMSPSNQTDKLAAFPEDRSQPG QDCRFRVTQLPNGRDFHMSVVRARRNDSGTYLCGAISLAPKAQIK ESLRAELRVTERRAEVPTAHPSPSPRPAGQFQTLVVGVVGGLLGSL VLLVWVLAVICSRAARGTIGARRTGQPLKEDPSAVPVFSVDYGEL DFQWREKTPEPPVPCVPEQTEYATIVFPSGMGTSSPARRGSADGPR SAQPLRPEDGHCSWPL |
| 53 | hPD-L-1 amino acid sequence | MRIFAVFIFMTYWHLLNAFTVTVPKDLYVVEYGSNMTIECKFPVE KQLDLAALIVYWEMEDKNIIQFVHGEEDLKVQHSSYRQRARLLK DQLSLGNAALQITDVKLQDAGVYRCMISYGGADYKRITVKVNAP YNKINQRILVVDPVTSEHELTCQAEGYPKAEVIWTSSDHQVLSGK TTTTNSKREEKLFNVTSTLRINTTTNEIFYCTFRRLDPEENHTAELVI PELPLAHPPNERTHLVILGAILLC LGVALTFIFR LRKGRMMDVKKCGIQDTNSK KQSDTHLEET |
| 54 | hCTLA-4 amino acid sequence | MACLGFQRHKAQLNLATRTWPCTLLFFLLFIPVFCKAMHVAQPA VVLASS RGIASFVCEYASPGKATEVRVTVLRQADSQVTEVCAATYM MGNELTFLDDSICTGTSSGNQVNLTIQGLRAMDTGLYICKVELMY PPPYY LGIGNGTQIY VIDPEPCPDS DFLLWILAAVSSGLFFYSFL LTAVSLSKML KKRSPLTTGVYVKMPPTEPE CEKQFQPYFI PIN |

TABLE 2 -continued

Sequence Summary

| SEQ ID NO | Description | Sequence |
|---|---|---|
| 55 | hLAG3 amino acid sequence | MWEAQFLGLLFLQPLWVAPVKPLQPGAEVPVVWAQEGAPAQLP CSPTIPLQDLSLLRRAGVTWQHQPDSGPPAAAPGHPLAPGPHPAAP SSWGPRPRRYTVLSVGPGGLRSGRLPLQPRVQLDERGRQRGDFSL WLRPAR RADAGEYRAAVHLRDRALSCRLRLRLGQASMTASPPGSLR ASDWVILNCSFSRPDRPASVHWFRNRGQGRVPVRESPHHHLAESF LFLPQVSPMDSGPWGCILTYRDGFNVSIMYNLTVLGLEPPTPLTVY AGAGSRVGLPCRLPAGVGTRSFLTAKWTPPGGGPDLLVTGDNGD FTLRLEDVSQAQAGT YTCHIHLQEQ QLNATVTLAI ITVTPKSFGS PGSLGKLLCEVTPVSGQERFVWSSLDTPSQRSFSGPWLEAQEAQLL SQPWQCQLYQGERLLGAAVYFTEL SSPGAQRSGR APGALPAGHL LLFLILGVLS LLLLVTGAFG PHLWRRQWRPRRFSALEQGI HPPQAQSKIE ELEQEPEPEP EPEPEPEPEP EPEQL |
| 56 | hTIM3 amino acid sequence | MFSHLPFDCVLLLLLLLLTRSSEVEYRAEVGQNAYLPCFYTPAAPG NLVPVCWGKGACPVFECGNVVLRTDERDVNYWTSRYWLNGDFR KGDVSLTIENVTLADSGIYCCRIQIPGIMNDEKFNLKLVIKPAKVTP APTR QRDFTAAFPR MLTTRGHGPA ETQTLGSLPD INLTQISTLA NELRDSRLANDLRDSGATIRGIYIGAGICAGLALALIFGALIFKWYS HSKEKIQNLSLISLANLPPSGLANAVAEGIRSEENIYTIEENVYEVEE PNEYYCYVSSRQQPSQPLGCRFAMP |
| 57 | hB7-H3 amino acid sequence | MLRRRGSPGMGVHVGAALGALWFCLTGALEVQVPEDPVVALVG TDATLCC SFSPEPGFSLQLNLIWQLT DTKQLVHSFA EGQDQGSAYA NRTALFPDLLAQGNASLRLQRVRVADEGSFCFVSIRDFGSAAVSL QVAA PYSKPSMTLE PNKDLRPGDT VTITCSSYQG YPEAEVFWQD GQGVPLTGNVTTSQMANEQGLFDVHSILRVVLGANGTYSCLVRN PVLQQD AHSSVTITPQRSPTGAVEVQVPEDVVALVGTDATLRCSF SPEPGFSLAQLNLIWQLTDTKQLVHSFTEGRDQGSAYANRTALFP DLLAQ GNASLRLQRV RVADEGSFTC FVSIRDFGSA AVSLQVAAPY SKPSMTLEPNKDLRPGDTVTITCSSYRGYPEAEVFWQDGQGVPLT GNVTT SQMANEQGLFDVHSVLRVVLGANGTYSCLVRNPVLQQDAH GSVTITGQPMTFPPEALWVTGLSVCLIALLVALAFVCWRKIKQSC EEEN AGAEDQDGEGEGSKTALQPLKHSDSKEDDGQEIA |
| 58 | hB7-H4 amino acid sequence | MASLGQILFWSIISIIIILAGAIALIIGFGISAFSMPEVNVDYNASSETL RCEAPRWFPQPTVVWASQVDQGANFSEVSNTSFELNSENVTMKV VSVLYN VTINNTYSCM IENDIAKATGDIKVTESEIKRRSHLQLLNS KASLCVSSFFAISWALLPLSPYLMLK |
| 59 | Anti-VEGF clone B20-4.1.1 Heavy Chain nucleic acid sequence | *ATGGGCTGGTCCCTGATCCTGCTGTTCCTGGTGGCTGTGGCCACTG GCGTGCACTCT*GAAGTGCAGCTGGTGGAATCTGGCGGCGGA CTGGTGCAGCCTGGCGGATCTCTGAGACTGAGCTGTGCCG CCAGCGGCTTCAGCATCAGCGGCAGCTGGATCTTCTGGGTG CGCCAGGCCCCTGGAAAGGGCCTGGAATGGGTGGGAGCCA TCTGGCCTTTTGGCGGCTACACCCACTACGCCGACAGCGTG AAGGGCCGGTTTACCATCAGCGCCGACACCAGCAAGAACA CCGCCTACCTCCAGATGAACAGCCTGCGGGCCGAGGACAC CGCCGTGTACTATTGTGCCAGATGGGGCCACAGCACCTCCC CCTGGGCCATGGATTATTGGGGCCAGGGAACCCTCGTGAC CGTGTCCTCTGCCAAAACAACAGCCCCATCGGTCTATCCACTG GCCCCTGTGTGTGGAGGTACAACTGGCTCCTCGGTGACTCTAGG ATGCCTGGTCAAGGGTTATTTCCCTGAGCCAGTGACCTTGACCT GGAACTCTGGCTCACTGTCCAGTGGTGTGCACACCTTCCCAGCT CTCCTCCAATCTGGCCTCTACACCCTCAGCAGCTCAGTGACTGT AACCTCGAACACCTGGCCCAGCCAGACCATCACCTGCAATGTG GCCCACCCGGCAAGCAGCACCAAAGTGGACAAGAAAATTGAG CCCAGAGTGCCCATAACACAGAACCCCTGTCCTCCACTCAAAG AGTGTCCCCCATGCGCAGCTCCAGACCTCTTGGGTGGACCATCC GTCTTCATCTTCCCTCCAAAGATCAAGGATGTACTCATGATCTC CCTGAGCCCCATGGTCACATGTGTGGTGGTGGATGTGAGCGAG GATGACCCAGACGTCCAGATCAGCTGGTTTGTGAACAACGTGG AAGTACACACAGCTCAGACACAAACCCATAGAGAGGATTACAA CAGTACTCTCCGGGTGGTCAGTGCCCTCCCCATCCAGCACCAGG ACTGGATGAGTGGCAAGGAGTTCAAATGCAAGGTCAACAACAG AGCCCTCCCATCCCCCATCGAGAAAACCATCTCAAAACCCAGA GGGCCAGTAAGAGCTCCACAGGTATATGTCTTGCCTCCACCAG CAGAAGAGATGACTAAGAAAGAGTTCAGTCTGACCTGCATGAT |

TABLE 2 -continued

Sequence Summary

| SEQ ID NO | Description | Sequence |
|---|---|---|
| | | CACAGGCTTCTTACCTGCCGAAATTGCTGTGGACTGGACCAGC AATGGGCGTACAGAGCAAAACTACAAGAACACCGCAACAGTC CTGGACTCTGATGGTTCTTACTTCATGTACAGCAAGCTCAGAGT ACAAAAGAGCACTTGGGAAAGAGGAAGTCTTTTCGCCTGCTCA GTGGTCCACGAGGGTCTGCACAATCACCTTACGACTAAGACCA TCTCCCGGTCTCTGGGTAAA |
| 60 | Anti-VEGF clone B20-4.1.1 Heavy Chain amino acid sequence | *MGWSLILLFLVAVATGVHS*EVQLVESGGGLVQPGGSLRLSCAASG FSISGSWIFWVRQAPGKGLEWVGAIWPFGGYTHYADSVKGRF TISADTSKNTAYLQMNSLRAEDTAVYYCARWGHSTSPWAMDY WGQGTLVTVSSAKTTAPSVYPLAPVCGTTGSSVTLGCLVKGYF PEPVTLTWNSGSLSSGVHTFPALLQSGLYTLSSSVTVTSNTWPSQTI TCNVAHPASSTKVDKKIEPRVPITQNPCPPLKECPPCAAPDLLGGPS VFIFPPKIKDVLMISLSPMVTCVVVDVSEDDPDVQISWFVNNVEVH TAQTQTHREDYNSTLRVVSALPIQHQDWMSGKEFKCKVNNRALP SPIEKTISKPRGPVRAPQVYVLPPPAEEMTKKEFSLTCMITGFLPAEI AVDWTSNGRTEQNYKNTATVLDSDGSYFMYSKLRVQKSTWERG SLFACSVVHEGLHNHLTTKTISRSLGK |
| 61 | Anti-VEGF clone B20-4.1.1 Light Chain nucleic acid sequence | *ATGGACATGAGAGTGCCCGCCCAGCTGCTGGGACTTCTGCTGCTGT GGCTGCCAGGCGCCAGATGC*GACATCCAGATGACCCAGAGCC CCAGCAGCCTGTCTGCCAGCGTGGGCGACAGAGTGACCAT CACCTGTAGAGCCTCTCAGGGCGTGCGGACAAGCCTGGCC TGGTATCAGCAGAAGCCTGGCAAGGCCCCCAAGCTGCTGAT CTACGATGCCAGCTCTCTGGCCAGCGGCGTGCCCAGCAGAT TTTCTGGCAGCGGCTCCGGCACCGACTTCACCCTGACAATC AGCTCCCTCCAGCCCGAGGACTTCGCCACCTACTACTGCCA GCAGAGCTACAAGAGCCCCCTGACCTTTGGCCAGGGCACC AAGGTGGAAATCAAGCGGGCTGATGCTGCACCAACTGTATCC ATCTTCCCACCATCCAGTGAGCAGTTAACATCTGGAGGTGCCTC AGTCGTGTGCTTCTTGAACAACTTCTACCCCAAAGACATCAATG TCAAGTGGAAGATTGATGGCAGTGAACGACAAAATGGCGTCCT GAACAGTTGGACTGATCAGGACAGCAAAGACAGCACCTACAGC ATGAGCAGCACCCTCACGTTGACCAAGGACGAGTATGAACGAC ATAACAGCTATACCTGTGAGGCCACTCACAAGACATCAACTTC ACCCATTGTCAAGAGCTTCAACAGGAATGAGTGT |
| 62 | Anti-VEGF clone B20-4.1.1 Light Chain amino acid sequence | *MDMRVPAQLLGLLLLWLPGARC*DIQMTQSPSSLSASVGDRVTITC RASQGVRTSLAWYQQKPGKAPKLLIYDASSLASGVPSRFSGSG SGTDFTLTISSLQPEDFATYYCQQSYKSPLTFGQGTKVEIKRAD AAPTVSIFPPSSEQLTSGGASVVCFLNNFYPKDINVKWKIDGSERQ NGVLNSWTDQDSKDSTYSMSSTLTLTKDEYERHNSYTCEATHKTS TSPIVKSFNRNEC |
| 63 | Anti-CTLA-4 clone 9D9 Heavy Chain nucleic acid sequence | *ATGGGCTGGTCCCTGATCCTGCTGTTCCTGGTGGCTGTGGCCACC GGCGTGCACTCT*GAAGCCAAGCTCCAGGAATCCGGCCCTGTG CTCGTGAAGCCTGGCGCCTCTGTGAAGATGAGCTGCAAGG CCAGCGGCTACACCTTTACCGACTACTACATGAACTGGGTC AAGCAGAGCCACGGCAAGTCTCTGGAATGGATCGGCGTGA TCAACCCCTACAACGGCGACACCAGCTACAACCAGAAGTTC AAGGGCAAGGCCACCCTGACCGTGGACAAGAGCAGCAGCA CCGCCTACATGGAACTGAACAGCCTGACCAGCGAGGACAG CGCCGTGTACTATTGCGCCCGGTACTACGGCAGTTGGTTCG CCTATTGGGGCCAGGGCACCCTGATCACCGTGTCCACAGCC AAAACAACAGCCCCATCGGTCTATCCACTGGCCCCTGTGTGTG GAGGTACAACTGGCTCCTCGGTGACTCTAGGATGCCTGGTCAA GGGTTATTTCCCTGAGCCAGTGACCTTGACCTGGAACTCTGGCT CACTGTCCAGTGGTGTGCACACCTTCCCAGCTCTCCTCCAATCT GGCCTCTACACCCTCAGCAGCTCAGTGACTGTAACCTCGAACA CCTGGCCCAGCCAGACCATCACCTGCAATGTGGCCCACCCGGC AAGCAGCACCAAAGTGGACAAGAAAATTGAGCCCAGAGTGCC CATAACACAGAACCCCTGTCCTCCACTCAAAGAGTGTCCCCCAT GCGCAGCTCCAGACCTCTTGGGTGGACCATCCGTCTTCATCTTC CCTCCAAAGATCAAGGATGTACTCATGATCTCCCTGAGCCCCAT GGTCACATGTGTGGTGGTGGATGTGAGCGAGGATGACCCAGAC GTCCAGATCAGCTGGTTTGTGAACAACGTGGAAGTACACACAG CTCAGACACAAACCCATAGAGAGGATTACAACAGTACTCTCCG GGTGGTCAGTGCCCTCCCCATCCAGCACCAGGACTGGATGAGT GGCAAGGAGTTCAAATGCAAGGTCAACAACAAAGCCCTCCCAT CCCCCATCGAGAAAACCATCTCAAAACCCAGAGGGCCAGTAAG AGCTCCACAGGTATATGTCTTGCCTCCACCAGCAGAAGAGATG ACTAAGAAAGAGTTCAGTCTGACCTGCATGATCACAGGCTTCTT ACCTGCCGAAATTGCTGTGGACTGGACCAGCAATGGGCGTACA GAGCAAAACTACAAGAACACCGCAACAGTCCTGGACTCTGATG |

TABLE 2 -continued

Sequence Summary

| SEQ ID NO | Description | Sequence |
|---|---|---|
| | | GTTCTTACTTCATGTACAGCAAGCTCAGAGTACAAAAGAGCAC<br>TTGGGAAAGAGGAAGTCTTTTCGCCTGCTCAGTGGTCCACGAG<br>GGTCTGCACAATCACCTTACGACTAAGACCATCTCCCGGTCTCT<br>GGGTAAA |
| 64 | Anti-CTLA-4 clone 9D9 Heavy Chain amino acid sequence | *MGWSLILLFLVAVATGVHS*EAKLQESGPVLVKPGASVKMSCKAS<br>GYTFTDYYMNWVKQSHGKSLEWIGVINPYNGDTSYNQKFKG<br>KATLTVDKSSSTAYMELNSLTSEDSAVYYCARYYGSWFAYWG<br>QGTLITVSTAKTTAPSVYPLAPVCGGTTGSSVTLGCLVKGYFPEP<br>VTLTWNSGSLSSGVHTFPALLQSGLYTLSSSVTVTSNTWPSQTITC<br>NVAHPASSTKVDKKIEPRVPITQNPCPPLKECPPCAAPDLLGGPSVF<br>IFPPKIKDVLMISLSPMVTCVVVDVSEDDPDVQISWFVNNVEVHTA<br>QTQTHREDYNSTLRVVSALPIQHQDWMSGKEFKCKVNNRALPSPI<br>EKTISKPRGPVRAPQVYVLPPPAEEMTKKEFSLTCMITGFLPAEIAV<br>DWTSNGRTEQNYKNTATVLDSDGSYFMYSKLRVQKSTWERGSLF<br>ACSVVHEGLHNHLTTKTISRSLGK |
| 65 | Anti-CTLA-4 clone 9D9 Light Chain nucleic acid sequence | *ATGGACATGAGAGTGCCCGCCCAGCTGCTGGGACTTCTGCTGCTGT<br>GGCTGCCAGGCGCCAGATGC*GACATCGTGATGACCCAGACCA<br>CCCTGAGCCTGCCTGTGTCCCTGGGAGATCAGGCCAGCATC<br>AGCTGTCGGAGCAGCCAGAGCATCGTGCACAGCAACGGCA<br>ACACCTACCTGGAATGGTATCTCCAGAAGCCCGGCCAGAGC<br>CCCAAGCTGCTGATCTACAAGGTGTCCAACCGGTTCAGCGG<br>CGTGCCCGACAGATTTTCTGGCAGCGGCTCCGGCACCGACT<br>TCACCCTGAAGATCTCCCGGGTGGAAGCCGAGGACCTGGG<br>CGTGTACTACTGTTTTCAAGGCAGCCACGTGCCCTACACCT<br>TCGGCGGAGGCACCAAGCTGGAAATCAAGCGGGCTGATGCT<br>GCACCAACTGTATCCATCTTCCCACCATCCAGTGAGCAGTTAAC<br>ATCTGGAGGTGCCTCAGTCGTGTGCTTCTTGAACAACTTCTACC<br>CCAAAGACATCAATGTCAAGTGGAAGATTGATGGCAGTGAACG<br>ACAAAATGGCGTCCTGAACAGTTGGACTGATCAGGACAGCAAA<br>GACAGCACCTACAGCATGAGCAGCACCCTCACGTTGACCAAGG<br>ACGAGTATGAACGACATAACAGCTATACCTGTGAGGCCACTCA<br>CAAGACATCAACTTCACCCATTGTCAAGAGCTTCAACAGGAAT<br>GAGTGT |
| 66 | Anti-CTLA-4 clone 9D9 Light Chain amino acid sequence | *MDMRVPAQLLGLLLLWLPGARC*DIVMTQTTLSLPVSLGDQASISC<br>RSSQSIVHSNGNTYLEWYLQKPGQSPKLLIYKVSNRFSGVPDRF<br>SGSGSGTDFTLKISRVEAEDLGVYYCFQGSHVPYTFGGGTKLE<br>IKRADAAPTVSIFPPSSEQLTSGGASVVCFLNNFYPKDINVKWKID<br>GSERQNGVLNSWTDQDSKDSTYSMSSTLTLTKDEYERHNSYTCE<br>ATHKTSTSPIVKSFNRNEC |
| 67 | EETI-II 1.4A | GCAEPRGDMPWTWCKQDSDCLAGCVCGPNGFCG |
| 68 | EETI-II 1.4B | GCVGGRGDWSPKWCKQDSDCPAGCVCGPNGFCG |
| 69 | EETI-II 1.4C | GC AELRGDRSYPE CKQDSDCLAGCVCGPNGFCG |
| 70 | EETI-II 1.4E | GC RLPRGDVPRPH CKQDSDCQAGCVCGPNGFCG |
| 71 | EETI-II 1.4H | GC YPLRGDNPYAA CKQDSDCRAGCVCGPNGFCG |
| 72 | EETI-II 1.5B | GC TIGRGDWAPSE CKQDSDCLAGCVCGPNGFCG |
| 73 | EETI-II 1.5F | GC HPPRGDNPPVT CKQDSDCLAGCVCGPNGFCG |
| 74 | EETI-II 2.3A | GC PEPRGDNPPPS CKQDSDCRAGCVCGPNGFCG |
| 75 | EETI-II 2.3B | GC LPPRGDNPPPS CKQDSDCQAGCVCGPNGFCG |
| 76 | EETI-II 2.3C | GCHLGRGDWAPVGCKQDSDCPAGCVCGPNGFCG |

TABLE 2 -continued

Sequence Summary

| SEQ ID NO | Description | Sequence |
|---|---|---|
| 77 | EETI-II 2.3D | GCNVGRGDWAPSECKQDSDCPAGCVCGPNGFCG |
| 78 | EETI-II 2.3E | GCFPGRGDWAPSSCKQDSDCRAGCVCGPNGFCG |
| 79 | EETI-II 2.3F | GCPLPRGDNPPTECKQDSDCQAGCVCGPNGFCG |
| 80 | EETI-II 2.3G | GCSEARGDNPRLSCKQDSDCRAGCVCGPNGFCG |
| 81 | EETI-II 2.3H | GCLLGRGDWAPEACKQDSDCRAGCVCPNGFCG |
| 82 | EETI-II 2.3I | GCHVGRGDWAPLKCKQDSDCQAGCVCGPNGFCG |
| 83 | EETI-II 2.3J | GCVRGRGDWAPPSCKQDSDCPAGCVCGPNGFCG |
| 84 | EETI-II 2.4A | GCLGGRGDWAPPACKQDSDCRAGCVCGPNGFCG |
| 85 | EETI-II 2.4C | GCFVGRGDWAPLTCKQDSDCQAGCVCGPNGFCG |
| 86 | EETI-II 2.4D | GCPVGRGDWSPASCKQDSDCRAGCVCGPNGFCG |
| 87 | EETI-II 2.4E | GCPRPRGDNPPLTCKQDSDCLAGCVCGPNGFCG |
| 88 | EETI-II 2.4F | GCYQGRGDWSPSSCKQDSDCPAGCVCGPNGFCG |
| 89 | EETI-II 2.4G | GCAPGRGDWAPSECKQDSDCQAGCVCGPNGFCG |
| 90 | EETI-II 2.4J | GCVQGRGDWSPPSCKQDSDCPAGCVCGPNGFCG |
| 91 | EETI-II 2.5A | GCHVGRGDWAPEECKQDS DC QAGCVCGPNGFCG |
| 92 | EETI-II 2.5C | GCDGGRGDWAPPACKQDSDCRAGCVCGPNGFCG |
| 93 | EETI-II 2.5D | GCPQGRGDWAPTSCKQDSDCRAGCVCGPNGFCG |
| 94 | EETI-II 2.5F | GCPRPRGDNPPLTCKQDSDCLAGCVCGPNGFCG |
| 95 | EETI-II 2.5D K15S Mutant | GCPQGRGDWAPTSCSQDSDCLAGCVCGPNGFCG |
| 96 | EETI-II 2.5F K15S Mutant | GCPRPRGDNPPLTCSQDSDCLAGCVCGPNGFCG |
| 97 | EETI-II 2.5H | GCPQGRGDWAPEWCKQDSDCPAGCVCGPNGFCG |
| 98 | EETI-II 2.5J | GCPRGRGDWSPPACKQDSDCQAGCVCGPNGFCG |
| 99 | AgRp 3A | GCVRLHESCLGQQVPCCDPAATCYCVVRGDWRKRCYCR |

TABLE 2 -continued

Sequence Summary

| SEQ ID NO | Description | Sequence |
|---|---|---|
| 100 | AgRp 3B | GCVRLHESCLGQQVPCCDPAATCYCEERGDMLEKCYCR |
| 101 | AgRp 3C | GCVRLHESCLGQQVPCCDPAATCYCETRGDGKEKCYCR |
| 102 | AgRp 3D | GCVRLHESCLGQQVPCCDPAATCYCQWRGDGDVKCYCR |
| 103 | AgRp 3E | GCVRLHESCLGQQVPCCDPAATCYCSRRGDMRERCYCR |
| 104 | AgRp 3F | GCVRLHESCLGQQVPCCDPAATCYCQYRGDGMKHCYCR |
| 105 | AgRp 3G | GCVRLHESCLGQQVPCCDPAATCYCTGRGDTKVLCYCR |
| 106 | AgRp 3H | GCVRLHESCLGQQVPCCDPAATCYCVERGDMKRRCYCR |
| 107 | AgRp 3I | GCVRLHESCLGQQVPCCDPAATCYCTGRGDVRMNCYCR |
| 108 | AgRp 3J | GCVRLHESCLGQQVPCCDPAATCYCVERGDMSKCYCR |
| 109 | AgRp 4A | GCVRLHESCLGQQVPCCDPAATCYCRGRGDMRRECYCR |
| 110 | AgRp 4B | GCVRLHESCLGQQVPCCDPAATCYCEGRGDVKVNCYCR |
| 111 | AgRp 4C | GCVRLHESCLGQQVPCCDPAATCYCVGRGDEKMSCYCR |
| 112 | AgRp 4D | GCVRLHESCLGQQVPCCDPAATCYCVSRGDMRKRCYCR |
| 113 | AgRp 4E | GCVRLHESCLGQQVPCCDPAATCYCERRGDSVKKCYCR |
| 114 | AgRp 4F | GCVRLHESCLGQQVPCCDPAATCYCEGRGDTRRRCYCR |
| 115 | AgRp 4G | GCVRLHESCLGQQVPCCDPAATCYCEGRGDVVRRCYCR |
| 116 | AgRp 4H | GCVRLHESCLGQQVPCCDPAATCYCKGRGDNKRKCYCR |
| 117 | AgRp 4I | GCVRLHESCLGQQVPCCDPAXTCYCKGRGDVRRVCYCR |
| 118 | AgRp 4J | GCVRLHESCLGQQVPCCDPAATCYCVGRGDNKVKCYCR |
| 119 | AgRp 5A | GCVRLHESCLGQQVPCCDPAATCYCVGRGDNRLKCYCR |
| 120 | AgRp 5B | GCVRLHESCLGQQVPCCDPAATCYCVERGDMKKKCYCR |
| 121 | AgRp 5C | GCVRLHESCLGQQVPCCDPAATCYCEGRGDMRRRCYCR |
| 122 | AgRp 5D | GCVRLHESCLGQQVPCCDPAATCYCQGRGDGDVKCYCR |
| 123 | AgRp 5E | GCVRLHESCLGQQVPCCDPAATCYCSGRGDNDLVCYCR |
| 124 | AgRp 5F | GCVRLHESCLGQQVPCCDPAATCYCVERGDGMIRCYCR |
| 125 | AgRp 5G | GCVRLHESCLGQQVPCCDPAATCYCSGRGDNDLVCYCR |
| 126 | AgRp 5H | GCVRLHESCLGQQVPCCDPAATCYCEGRGDMKMKCYCR |
| 127 | AgRp 5I | GCVRLHESCLGQQVPCCDPAATCYCIGRGDVRRRCYCR |
| 128 | AgRp 5J | GCVRLHESCLGQQVPCCDPAATCYCEERGDGRKKCYCR |
| 129 | AgRp 6B | GCVRLHESCLGQQVPCCDPAATCYCEGRGDRDMKCYCR |
| 130 | AgRp 6C | GCVRLHESCLGQQVPCCDPAATCYCTGRGDEKLRCYCR |
| 131 | AgRp 6E | GCVRLHESCLGQQVPCCDPAATCYCVERGDGNRRCYCR |
| 132 | AgRp 6F | GCVRLHESCLGQQVPCCDPAATCYCESRGDVVRKCYCR |
| 133 | AgRp 7C | GCVRLHESCLGQQVPCCDPAATCYCYGRGDNDLRCYCR |

EQUIVALENTS

Those skilled in the art will recognize or be able to ascertain, using no more than routine experimentation, many equivalents of the specific embodiments described herein described herein. Such equivalents are intended to be encompassed by the following claims.

---

The invention claimed is:

1. A method for treating a cancer comprising tumor cells expressing a tumor-associated integrin in a subject, comprising administering to the subject a therapeutically effective amount of:
   (a) interleukin (IL)-2;
   (b) an integrin-binding-Fc fusion protein which binds to the tumor cells expressing the tumor-associated integrin; and
   (c) a cancer vaccine,
      wherein the integrin-binding-Fc fusion protein comprises (i) an integrin-binding polypeptide comprising an integrin-binding loop and a knottin polypeptide scaffold, and (ii) an immunoglobulin Fc domain, wherein the integrin-binding polypeptide is operably linked to the Fc domain.

2. The method of claim 1, wherein the IL-2 is an extended pharmacokinetic (PK) IL-2.

3. The method of claim 2, wherein the extended-PK IL-2 comprises a fusion protein.

4. The method of claim 3, wherein the fusion protein comprises an IL-2 moiety and a moiety selected from the group consisting of an immunoglobulin fragment, serum albumin, transferrin, and Fn3, or variants thereof.

5. The method of claim 1, wherein the IL-2 comprises an IL-2 moiety conjugated to a non-protein polymer.

6. The method of claim 5, wherein the non-protein polymer is polyethylene glycol.

7. The method of claim 4, wherein the fusion protein comprises an IL-2 moiety operably linked to an immunoglobulin Fc domain or human serum albumin.

8. The method of claim 1, wherein the tumor-associated integrin is selected from the group consisting of αvβ3, αvβ5, and α5β1, or combination thereof.

9. The method of claim 1, wherein the knottin polypeptide scaffold comprises at least three cysteine disulfide linkages or crosslinked cysteine residues, and wherein the integrin-binding loop is adjacent to cysteine residues of the knottin polypeptide scaffold.

10. The method of claim 9, wherein the integrin-binding loop comprises an RGD peptide sequence.

11. The method of claim 9, wherein the knottin polypeptide scaffold is derived from a knottin protein selected from the group consisting of EETI-II, AgRP, and agatoxin.

12. The method of claim 1, wherein the knottin polypeptide scaffold is derived from EETI-II and the integrin-binding loop comprises the sequence $X_1X_2X_3RGDX_7X_8X_9X_{10}X_{11}$, wherein each X represents any amino acid, wherein the loop is inserted between 2 cysteine residues in the EETI-II sequence and replaces the native EETI-II sequence.

13. The method of claim 1, wherein the integrin-binding polypeptide comprises the amino acid sequence set forth SEQ ID NO: 42 or 43, wherein $X_1$ is selected from the group consisting of A, V, L, P, F, Y, S, H, D, and N; $X_2$ is selected from the group consisting of G, V, L, P, R, E, and Q; $X_3$ is selected from the group consisting of G, A, and P; $X_7$ is selected from the group consisting of W and N; $X_8$ is selected from the group consisting of A, P, and S; $X_9$ is selected from the group consisting of P and R; $X_{10}$ is selected from the group consisting of A, V, L, P, S, T, and E; and $X_{11}$ is selected from the group consisting of G, A, W, S, T, K, and E.

14. The method of claim 1, wherein the integrin-binding polypeptide comprises an amino acid sequence selected from the group consisting of SEQ ID NOs: 67-133.

15. The method of claim 1, wherein the Fc domain is a human IgG1 Fc domain.

16. The method of claim 1, wherein the integrin-binding polypeptide is operably linked with or without a linker to the Fc domain.

17. The method of claim 1,
   wherein the integrin-binding polypeptide is operably linked to the N-terminus of the Fc domain; or
   wherein the integrin-binding polypeptide is operably linked to the C-terminus of the Fc domain.

18. The method of claim 1, wherein the integrin-binding-Fc fusion protein comprises the amino acid sequence of SEQ ID NO: 48, 49, 50, or 51.

19. The method of claim 1, wherein the cancer vaccine is a population of cells comprising antigen presenting cells immunized in vitro with a tumor antigen and administered to the subject.

20. The method of claim 1, wherein the cancer vaccine is an amphiphilic peptide conjugate comprising a tumor-associated antigen, and a lipid component, and optionally a linker, wherein the amphiphilic peptide conjugate binds albumin under physiological conditions.

21. The method of claim 20, wherein the tumor-associated antigen is conjugated to a lipid via a linker.

22. The method of claim 20, wherein the lipid is a diacyl lipid.

23. The method of claim 20, wherein the cancer vaccine further comprises an adjuvant.

24. The method of claim 23, wherein the adjuvant is an amphiphilic oligonucleotide conjugate comprising an immunostimulatory oligonucleotide conjugated to a lipid with or without a linker, and optionally a polar compound, wherein the conjugate binds albumin under physiological conditions.

25. The method of claim 24, wherein the molecular adjuvant is an immunostimulatory oligonucleotide that can bind a pattern recognition receptor.

26. The method of claim 24,
   wherein the immunostimulatory oligonucleotide comprises CpG; or
   wherein the immunostimulatory oligonucleotide is a ligand for a toll-like receptor.

27. The method of claim 24, wherein the linker is an oligonucleotide linker.

28. The method of claim 24, wherein the oligonucleotide linker comprises "N" consecutive guanines, wherein N is between 0-2.

29. The method of claim 24, wherein the lipid is a diacyl lipid.

30. The method of claim 1, wherein IL-2 or extended-PK IL-2, integrin-binding-Fc fusion protein, and cancer vaccine are administered simultaneously or sequentially.

31. The method of claim 1, wherein the subject has a tumor.

32. The method of claim 31, wherein the treatment increases the number of interferon gamma expressing CD8+ T cells in the tumor.

33. The method of claim 31, wherein the treatment increases the ratio of CD8+ T cells to T regulatory cells in the tumor.

34. The method of claim 1, wherein the cancer is selected from the group consisting of melanoma, leukemia, lymphoma, lung cancer, breast cancer, prostate cancer, ovarian cancer, colon cancer, mesothelioma, renal cell carcinoma, and brain cancer.

35. A method for inhibiting growth and/or proliferation of tumor cells expressing a tumor-associated integrin in a subject comprising administering to the subject an effective amount of (a) an integrin-binding-Fc fusion protein which binds to the tumor cells expressing the tumor-associated integrin, wherein the integrin-binding-Fc fusion protein comprises (i) an integrin-binding polypeptide comprising an integrin-binding loop and a knottin polypeptide scaffold, and (ii) an immunoglobulin Fc domain, wherein the integrin-binding polypeptide is operably linked to the Fc domain; and (b) a cancer vaccine.

* * * * *

SEQUENCE LISTING

<160> NUMBER OF SEQ ID NOS: 147

<210> SEQ ID NO 1
<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: Human IgG1 constant region (amino acid sequence)

<400> SEQUENCE: 1

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
```

```
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 232
<212> TYPE: PRT
<213> ORGANISM: Homo sapiens
<220> FEATURE:
<221> NAME/KEY: misc_feature
<222> LOCATION: (1)..(232)
<223> OTHER INFORMATION: Human IgG1 Fc domain (amino acid sequence)

<400> SEQUENCE: 2

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 3
<211> LENGTH: 227
<212> TYPE: PRT
<213> ORGANISM: Homo sapiens
<220> FEATURE:
<221> NAME/KEY: misc_feature
<222> LOCATION: (1)..(227)
<223> OTHER INFORMATION: Human IgG1 Fc domain (amino acid sequence)
      Deletion (DEPKSC) Upper Hinge

<400> SEQUENCE: 3

Asp Lys Thr His Thr Cys Pro Pro Cys Pro Ala Pro Glu Leu Leu Gly
```

```
 1               5                   10                  15
Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225

<210> SEQ ID NO 4
<211> LENGTH: 447
<212> TYPE: DNA
<213> ORGANISM: Mus musculus
<220> FEATURE:
<221> NAME/KEY: misc_feature
<222> LOCATION: (1)..(447)
<223> OTHER INFORMATION: Mouse IL-2 (nucleic acid sequence)

<400> SEQUENCE: 4
gcacccactt caagctccac ttcaagctct acagcggaag cacagcagca gcagcagcag     60
cagcagcagc agcagcagca cctggagcag ctgttgatgg acctacagga gctcctgagc    120
aggatggaga attacaggaa cctgaaactc cccaggatgc tcaccttcaa attttacttg    180
cccaagcagg ccacagaatt gaaagatctt cagtgcctag aagatgaact tggacctctg    240
cggcatgttc tggatttgac tcaaagcaaa gctttcaat tggaagatgc tgagaatttc    300
atcagcaata tcagagtaac tgttgtaaaa ctaaagggct ctgacaacac atttgagtgc    360
caattcgatg atgagtcagc aactgtggtg gactttctga ggagatggat agccttctgt    420
caaagcatca tctcaacaag ccctcaa                                        447

<210> SEQ ID NO 5
<211> LENGTH: 149
<212> TYPE: PRT
<213> ORGANISM: Mus musculus
<220> FEATURE:
<221> NAME/KEY: misc_feature
```

<222> LOCATION: (1)..(149)
<223> OTHER INFORMATION: Mouse IL-2 (amino acid sequence)

<400> SEQUENCE: 5

Ala Pro Thr Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145

<210> SEQ ID NO 6
<211> LENGTH: 447
<212> TYPE: DNA
<213> ORGANISM: Artificial Sequence
<220> FEATURE:
<223> OTHER INFORMATION: Synthetic: QQ6210 (nucleic acid sequence)

<400> SEQUENCE: 6
gcacccactt caagctccac ttcaagctct acagcggaag cacaacagca gcagcagcag      60
cagcagcagc agcagcagca cctggagcag ctgttgatgg acctacagga actcctgagt     120
aggatggagg atcacaggaa cctgagactc cccaggatgc tcaccttcaa attttacttg     180
cccgagcagg ccacagaatt ggaagatctt cagtgcctag aagatgaact tgaaccactg     240
cggcaagttc tggatttgac tcaaagcaaa agctttcaat ggaagatgc tgagaatttc     300 atcagcaata tcagagtaac tgttgtaaaa ctaaagggct ctgacaacac atttgagtgc     360
caattcgacg atgagccagc aactgtggtg gactttctga ggagatggat agccttctgt     420
caaagcatca tctcaacaag ccctcaa                                        447

<210> SEQ ID NO 7
<211> LENGTH: 149
<212> TYPE: PRT
<213> ORGANISM: Artificial Sequence
<220> FEATURE:
<223> OTHER INFORMATION: Synthetic: QQ6210 (amino acid sequence)

<400> SEQUENCE: 7

Ala Pro Thr Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asp His Arg Asn Leu
        35                  40                  45

Arg Leu Pro Arg Met Leu Thr Phe Lys Phe Tyr Leu Pro Glu Gln Ala
    50                  55                  60

Thr Glu Leu Glu Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Glu Pro Ala Thr
            115                 120                 125

Val Val Asp Phe Leu Arg Arg Trp Ile Ala Phe Cys Gln Ser Ile Ile
            130                 135                 140

Ser Thr Ser Pro Gln
145

<210> SEQ ID NO 8
<211> LENGTH: 447
<212> TYPE: DNA
<213> ORGANISM: Artificial Sequence
<220> FEATURE:
<223> OTHER INFORMATION: Synthetic: E76A (nucleic acid sequence)

<400> SEQUENCE: 8
gcacccactt caagctccac ttcaagctct acagcggaag cacagcagca gcagcagcag     60
cagcagcagc agcagcagca cctggagcag ctgttgatgg acctacagga gctcctgagc    120
aggatggaga attacaggaa cctgaaactc cccaggatgc tcaccttcaa attttacttg    180
cccaagcagg ccacagaatt gaaagatctt cagtgcctag aagatgctct ggacctctg    240 cggcatgttc tggatttgac tcaaagcaaa agctttcaat ggaagatgc tgagaatttc    300 atcagcaata tcagagtaac tgttgtaaaa ctaaagggct ctgacaacac atttgagtgc    360
caattcgatg atgagtcagc aactgtggtg gactttctga ggagatggat agccttctgt    420
caaagcatca tctcaacaag ccctcaa                                        447

<210> SEQ ID NO 9
<211> LENGTH: 149
<212> TYPE: PRT
<213> ORGANISM: Artificial Sequence
<220> FEATURE:
<223> OTHER INFORMATION: Synthetic: E76A (amino acid sequence)

<400> SEQUENCE: 9

Ala Pro Thr Ser Ser Thr Ser Ser Thr Ala Glu Ala Gln Gln
1               5                   10                  15

Gln Gln Gln Gln Gln Gln Gln Gln Gln His Leu Glu Gln Leu Leu
                20                  25                  30

Met Asp Leu Gln Glu Leu Leu Ser Arg Met Glu Asn Tyr Arg Asn Leu
            35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Ala Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

```
Gly Ser Asp Asn Thr Phe Glu Cys Gln Phe Asp Glu Ser Ala Thr
            115                 120                 125

Val Val Asp Phe Leu Arg Arg Trp Ile Ala Phe Cys Gln Ser Ile Ile
        130                 135                 140

Ser Thr Ser Pro Gln
145

<210> SEQ ID NO 10
<211> LENGTH: 447
<212> TYPE: DNA
<213> ORGANISM: Artificial Sequence
<220> FEATURE:
<223> OTHER INFORMATION: Synthetic: E76G (nucleic acid sequence)

<400> SEQUENCE: 10
gcacccactt caagctccac ttcaagctct acagcggaag cacagcagca gcagcagcag      60
cagcagcagc agcagcagca cctggagcag ctgttgatgg acctacagga gctcctgagc     120
aggatggaga attacaggaa cctgaaactc cccaggatgc tcaccttcaa attttacttg     180
cccaagcagg ccacagaatt gaaagatctt cagtgcctag aagatggtct tggacctctg     240
cggcatgttc tggatttgac tcaaagcaaa agctttcaat ggaagatgc tgagaatttc      300 atcagcaata tcagagtaac tgttgtaaaa ctaaagggct ctgacaacac atttgagtgc     360
caattcgatg atgagtcagc aactgtggtg gactttctga ggagatggat agccttctgt     420
caaagcatca tctcaacaag ccctcaa                                         447

<210> SEQ ID NO 11
<211> LENGTH: 149
<212> TYPE: PRT
<213> ORGANISM: Artificial Sequence
<220> FEATURE:
<223> OTHER INFORMATION: Synthetic: E76G (amino acid sequence)

<400> SEQUENCE: 11

Ala Pro Thr Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Gly Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145

<210> SEQ ID NO 12
<211> LENGTH: 816
<212> TYPE: DNA
```

<213> ORGANISM: Artificial Sequence
<220> FEATURE:
<223> OTHER INFORMATION: Synthetic: D265A Fc/Flag (nucleic acid sequence)

<400> SEQUENCE: 12

```
atgagggtcc ccgctcagct cctggggctc ctgctgctct ggctcccagg tgcacgatgt    60
gagcccagag tgcccataac acagaacccc tgtcctccac tcaaagagtg tccccccatgc  120
gcagctccag acctcttggg tggaccatcc gtcttcatct ccctccaaa gatcaaggat    180
gtactcatga tctccctgag ccccatggtc acatgtgtgg tggtggccgt gagcgaggat   240
gacccagacg tccagatcag ctggtttgtg aacaacgtgg aagtacacac agctcagaca   300
caaacccata gagaggatta acagtact ctccgggtgg tcagtgccct ccccatccag    360
caccaggact ggatgagtgg caaggagttc aaatgcaagg tcaacaacag agccctccca   420
tcccccatcg agaaaaccat ctcaaaaccc agagggccag taagagctcc acaggtatat   480
gtcttgcctc caccagcaga agagatgact aagaaagagt tcagtctgac ctgcatgatc   540
acaggcttct acctgccga aattgctgtg actggacca gcaatgggcg tacagagcaa    600
aactacaaga caccgcaac agtcctggac tctgatggtt cttacttcat gtacagcaag   660
ctcagagtac aaaagagcac ttgggaaga ggaagtcttt tcgcctgctc agtggtccac    720
gagggtctgc acaatcacct tacgactaag accatctccc ggtctctggg taaaggtggc   780
ggatctgact acaaggacga cgatgacaag tgataa                             816
```

<210> SEQ ID NO 13
<211> LENGTH: 270
<212> TYPE: PRT
<213> ORGANISM: Artificial Sequence
<220> FEATURE:
<223> OTHER INFORMATION: Synthetic: D265A Fc/Flag (amino acid sequence)

<400> SEQUENCE: 13

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
```

```
                180             185             190
Thr Ser Asn Gly Arg Thr Glu Gln Asn Tyr Lys Asn Thr Ala Thr Val
            195             200             205

Leu Asp Ser Asp Gly Ser Tyr Phe Met Tyr Ser Lys Leu Arg Val Gln
        210             215             220

Lys Ser Thr Trp Glu Arg Gly Ser Leu Phe Ala Cys Ser Val Val His
225             230             235             240

Glu Gly Leu His Asn His Leu Thr Thr Lys Thr Ile Ser Arg Ser Leu
            245             250             255

Gly Lys Gly Gly Gly Ser Asp Tyr Lys Asp Asp Asp Lys
        260             265             270
```

<210> SEQ ID NO 14
<211> LENGTH: 1257
<212> TYPE: DNA
<213> ORGANISM: Artificial Sequence
<220> FEATURE:
<223> OTHER INFORMATION: Synthetic: D265A Fc/wt mIL-2 (nucleic acid sequence)

<400> SEQUENCE: 14

```
atgagggtcc ccgctcagct cctggggctc ctgctgctct ggctcccagg tgcacgatgt      60
gagcccagag tgcccataac acagaacccc tgtcctccac tcaaagagtg tcccccatgc    120
gcagctccag acctcttggg tggaccatcc gtcttcatct tccctccaaa gatcaaggat    180
gtactcatga tctccctgag ccccatggtc acatgtgtgg tggtggccgt gagcgaggat    240
gacccagacg tccagatcag ctggtttgtg aacaacgtgg aagtacacac agctcagaca    300
caaacccata gagaggatta caacagtact ctccgggtgg tcagtgccct ccccatccag    360
caccaggact ggatgagtgg caaggagttc aaatgcaagg tcaacaacag agccctccca    420
tcccccatcg agaaaaccat ctcaaaaccc agagggccag taagagctcc acaggtatat    480
gtcttgcctc caccagcaga gagatgactaagaaagagt tcagtctgac ctgcatgatc     540
acaggcttct acctgccga aattgctgtg actggaccagcaatgggcg tacagagcaa      600
aactacaaga caccgcaaca gtcctggac tctgatggtt cttacttcat gtacagcaag    660
ctcagagtac aaaagagcac ttgggaaaga ggaagtcttt tcgcctgctc agtggtccac    720
gagggtctgc acaatcacct tacgactaag accatctccc cggtctctgg gtaaaggaggg   780
ggctccgcac ccacttcaag ctccacttca agctctacag cggaagcaca gcagcagcag   840
cagcagcagc agcagcagca gcagcacctg gagcagctgt tgatggacct acaggagctc   900
ctgagcagga tggagaatta caggaacctg aaactcccca ggatgctcac cttcaaattt   960
tacttgccca gcaggccac agaattgaaa gatcttcagt gcctagaaga tgaacttgga  1020
cctctgcggc atgttctgga tttgactcaa agcaaaagct ttcaattgga agatgctgag  1080
aatttcatca gcaatatcag agtaactgtt gtaaaactaa agggctctga caacacattt  1140
gagtgccaat cgatgatga gtcagcaact gtggtggact tctgaggag atggatagcc   1200
ttctgtcaaa gcatcatctc aacaagccct caacaccatc accaccatca ctgataa    1257
```

<210> SEQ ID NO 15
<211> LENGTH: 417
<212> TYPE: PRT
<213> ORGANISM: Artificial Sequence
<220> FEATURE:
<223> OTHER INFORMATION: Synthetic: D265A Fc/wt mIL-2 (amino acid sequence)

<400> SEQUENCE: 15

```
Met Arg Val Pro Ala Gln Leu Leu Gly Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
            35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln
        275                 280                 285

His Leu Glu Gln Leu Leu Met Asp Leu Gln Glu Leu Leu Ser Arg Met
    290                 295                 300

Glu Asn Tyr Arg Asn Leu Lys Leu Pro Arg Met Leu Thr Phe Lys Phe
305                 310                 315                 320

Tyr Leu Pro Lys Gln Ala Thr Glu Leu Lys Asp Leu Gln Cys Leu Glu
                325                 330                 335

Asp Glu Leu Gly Pro Leu Arg His Val Leu Asp Leu Thr Gln Ser Lys
            340                 345                 350

Ser Phe Gln Leu Glu Asp Ala Glu Asn Phe Ile Ser Asn Ile Arg Val
        355                 360                 365

Thr Val Val Lys Leu Lys Gly Ser Asp Asn Thr Phe Glu Cys Gln Phe
    370                 375                 380

Asp Asp Glu Ser Ala Thr Val Val Asp Phe Leu Arg Arg Trp Ile Ala
385                 390                 395                 400

Phe Cys Gln Ser Ile Ile Ser Thr Ser Pro Gln His His His His
                405                 410                 415
```

His

<210> SEQ ID NO 16
<211> LENGTH: 1257
<212> TYPE: DNA
<213> ORGANISM: Artificial Sequence
<220> FEATURE:
<223> OTHER INFORMATION: Synthetic: D265A Fc /QQ6210 (nucleic acid sequence)

<400> SEQUENCE: 16

```
atgagggtcc ccgctcagct cctggggctc ctgctgctct ggctcccagg tgcacgatgt      60
gagcccagag tgcccataac acagaacccc tgtcctccac tcaaagagtg tccccatgc      120
gcagctccag acctcttggg tggaccatcc gtcttcatct ccctccaaa gatcaaggat       180
gtactcatga tctccctgag ccccatggtc acatgtgtgg tggtggccgt gagcgaggat      240
gacccagacg tccagatcag ctggtttgtg aacaacgtgg aagtacacac agctcagaca      300
caaacccata gagaggatta acacagtact ctccgggtgg tcagtgccct ccccatccag      360
caccaggact ggatgagtgg caaggagttc aaatgcaagg tcaacaacag agccctccca      420
tcccccatcg agaaaaccat ctcaaaaccc agagggccag taagagctcc acaggtatat      480
gtcttgcctc caccagcaga agagatgact aagaaagagt tcagtctgac ctgcatgatc      540
acaggcttct acctgccga aattgctgtg gactggacca gcaatgggcg tacagagcaa      600
aactacaaga acaccgcaac agtcctggac tctgatggtt cttacttcat gtacagcaag      660
ctcagagtac aaagagcac ttgggaaaga ggaagtcttt cgcctgctc agtggtccac       720
gagggtctgc acaatcacct tacgactaag accatctccc ggtctctggg taaaggaggg      780
ggctccgcac ccacttcaag ctccacttca agctctacag cggaagcaca acagcagcag      840
cagcagcagc agcagcagca gcagcacctg gagcagctgt tgatggacct acaggaactc      900
ctgagtagga tggaggatca caggaacctg agactcccca ggatgctcac cttcaaattt      960
tacttgcccg agcaggccac agaattggaa gatcttcagt gcctagaaga tgaacttgaa      1020
ccactgcgga agttctgga tttgactcaa agcaaaagct tcaattgga agatgctgag       1080
aatttcatca gcaatatcag agtaactgtt gtaaaactaa agggctctga caacacattt      1140
gagtgccaat tcgacgatga ccagcaact gtggtggact ttctgaggag atggatagcc       1200
ttctgtcaaa gcatcatctc aacaagccct caacaccatc accaccatca ctgataa        1257
```

<210> SEQ ID NO 17
<211> LENGTH: 417
<212> TYPE: PRT
<213> ORGANISM: Artificial Sequence
<220> FEATURE:
<223> OTHER INFORMATION: Synthetic: D265A Fc /QQ6210 (amino acid sequence)

<400> SEQUENCE: 17

Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

```
Ser Leu Ser Pro Met Val Thr Cys Val Val Val Ala Val Ser Glu Asp
 65                  70                  75                  80

Asp Pro Asp Val Gln Ile Ser Trp Phe Val Asn Asn Val Glu Val His
             85                  90                  95

Thr Ala Gln Thr Gln Thr His Arg Glu Asp Tyr Asn Ser Thr Leu Arg
        100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln Gln
        275                 280                 285

His Leu Glu Gln Leu Leu Met Asp Leu Gln Glu Leu Leu Ser Arg Met
    290                 295                 300

Glu Asp His Arg Asn Leu Arg Leu Pro Arg Met Leu Thr Phe Lys Phe
305                 310                 315                 320

Tyr Leu Pro Glu Gln Ala Thr Glu Leu Glu Asp Leu Gln Cys Leu Glu
                325                 330                 335

Asp Glu Leu Glu Pro Leu Arg Gln Val Leu Asp Leu Thr Gln Ser Lys
            340                 345                 350

Ser Phe Gln Leu Glu Asp Ala Glu Asn Phe Ile Ser Asn Ile Arg Val
        355                 360                 365

Thr Val Val Lys Leu Lys Gly Ser Asp Asn Thr Phe Glu Cys Gln Phe
370                 375                 380

Asp Asp Glu Pro Ala Thr Val Val Asp Phe Leu Arg Arg Trp Ile Ala
385                 390                 395                 400

Phe Cys Gln Ser Ile Ile Ser Thr Ser Pro Gln His His His His His
                405                 410                 415

His

<210> SEQ ID NO 18
<211> LENGTH: 1257
<212> TYPE: DNA
<213> ORGANISM: Artificial Sequence
<220> FEATURE:
<223> OTHER INFORMATION: Synthetic: D265A Fc / E76A (nucleic acid
      sequence)

<400> SEQUENCE: 18
```

```
atgagggtcc cgctcagct cctggggctc ctgctgctct ggctcccagg tgcacgatgt      60
gagcccagag tgcccataac acagaacccc tgtcctccac tcaaagagtg tccccatgc     120
gcagctccag acctcttggg tggaccatcc gtcttcatct cccctccaaa gatcaaggat    180
gtactcatga tctccctgag ccccatggtc acatgtgtgg tggtggccgt gagcgaggat    240
gacccagacg tccagatcag ctggtttgtg aacaacgtgg aagtacacac agctcagaca   300
caaacccata gagaggatta caacagtact ctccgggtgg tcagtgccct ccccatccag   360
caccaggact ggatgagtgg caaggagttc aaatgcaagg tcaacaacag agccctccca   420
tcccccatcg agaaaaccat ctcaaaaccc agagggccag taagagctcc acaggtatat   480
gtcttgcctc caccagcaga agagatgact aagaaagagt tcagtctgac ctgcatgatc   540
acaggcttct acctgccgaa aattgctgtg gactggacca gcaatgggcg tacagagcaa   600
aactacaaga acaccgcaac agtcctggac tctgatggtt cttacttcat gtacagcaag   660
ctcagagtac aaaagagcac ttgggaagaa ggaagtcttt tcgcctgctc agtggtccac   720
gagggtctgc acaatcacct tacgactaag accatctccc ggtctctggg taaaggaggg   780
ggctccgcac ccacttcaag ctccacttca agctctacag cggaagcaca gcagcagcag   840
cagcagcagc agcagcagca gcagcacctg gagcagctgt tgatggacct acaggagctc   900
ctgagcagga tggagaatta caggaacctg aaactcccca ggatgctcac cttcaaattt    960
tacttgccca gcaggccac agaattgaaa gatcttcagt gcctagaaga tgctcttgga   1020
cctctgcggc atgttctgga tttgactcaa agcaaaagct tcaattgga agatgctgag   1080
aatttcatca gcaatatcag agtaactgtt gtaaaactaa agggctctga caacacattt   1140
gagtgccaat tcgatgatga gtcagcaact gtggtggact ttctgaggag atggatagcc   1200
ttctgtcaaa gcatcatctc aacaagcct caacaccatc accaccatca ctgataa      1257
```

<210> SEQ ID NO 19
<211> LENGTH: 417
<212> TYPE: PRT
<213> ORGANISM: Artificial Sequence
<220> FEATURE:
<223> OTHER INFORMATION: Synthetic: D265A Fc / E76A (amino acid sequence)

<400> SEQUENCE: 19

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140
```

| | | | | | | | | | | | | | | |
|---|---|---|---|---|---|---|---|---|---|---|---|---|---|---|
|Lys|Thr|Ile|Ser|Lys|Pro|Arg|Gly|Pro|Val|Arg|Ala|Pro|Gln|Val|Tyr|
|145| | | | |150| | | | |155| | | | |160|

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln Gln
        275                 280                 285

His Leu Glu Gln Leu Leu Met Asp Leu Gln Glu Leu Leu Ser Arg Met
    290                 295                 300

Glu Asn Tyr Arg Asn Leu Lys Leu Pro Arg Met Leu Thr Phe Lys Phe
305                 310                 315                 320

Tyr Leu Pro Lys Gln Ala Thr Glu Leu Lys Asp Leu Gln Cys Leu Glu
                325                 330                 335

Asp Ala Leu Gly Pro Leu Arg His Val Leu Asp Leu Thr Gln Ser Lys
            340                 345                 350

Ser Phe Gln Leu Glu Asp Ala Glu Asn Phe Ile Ser Asn Ile Arg Val
        355                 360                 365

Thr Val Val Lys Leu Lys Gly Ser Asp Asn Thr Phe Glu Cys Gln Phe
    370                 375                 380

Asp Asp Glu Ser Ala Thr Val Val Asp Phe Leu Arg Arg Trp Ile Ala
385                 390                 395                 400

Phe Cys Gln Ser Ile Ile Ser Thr Ser Pro Gln His His His His His
                405                 410                 415

His

<210> SEQ ID NO 20
<211> LENGTH: 1257
<212> TYPE: DNA
<213> ORGANISM: Artificial Sequence
<220> FEATURE:
<223> OTHER INFORMATION: Synthetic: D265A Fc / E76G (nucleic acid
      sequence)

<400> SEQUENCE: 20
atgagggtcc cgctcagct cctggggctc ctgctgctct ggctcccagg tgcacgatgt    60
gagcccagag tgcccataac acagaacccc tgtcctccac tcaaagagtg tccccccatgc  120 gcagctccag acctcttggg tggaccatcc gtcttcatct ccctccaaa gatcaaggat    180 gtactcatga tctcccctgag ccccatggtc acatgtgtgg tggtggccgt gagcgaggat  240
gacccagacg tccagatcag ctggtttgtg aacaacgtgg aagtacacac agctcagaca  300
caaacccata gagaggatta caacagtact ctccgggtgg tcagtgccct ccccatccag  360
caccaggact ggatgagtgg caaggagttc aaatgcaagg tcaacaacag agccctccca  420

```
tcccccatcg agaaaaccat ctcaaaaccc agagggccag taagagctcc acaggtatat    480
gtcttgcctc caccagcaga agagatgact aagaaagagt tcagtctgac ctgcatgatc    540
acaggcttct tacctgccga aattgctgtg gactggacca gcaatgggcg tacagagcaa    600
aactacaaga acaccgcaac agtcctggac tctgatggtt cttacttcat gtacagcaag    660
ctcagagtac aaaagagcac ttgggaaaga ggaagtcttt tcgcctgctc agtggtccac    720
gagggtctgc acaatcacct tacgactaag accatctccc ggtctctggg taaaggaggg    780
ggctccgcac ccacttcaag ctccacttca agctctacag cggaagcaca gcagcagcag    840
cagcagcagc agcagcagca gcagcacctg gagcagctgt tgatggacct acaggagctc    900
ctgagcagga tggagaatta caggaacctg aaactcccca ggatgctcac cttcaaattt    960
tacttgccca gcaggccaca gaattgaaa gatcttcagt gcctagaaga tggtcttgga   1020
cctctgcggc atgttctgga tttgactcaa agcaaaagct ttcaattgga agatgctgag   1080
aatttcatca gcaatatcag agtaactgtt gtaaaactaa agggctctga caacacattt   1140
gagtgccaat tcgatgatga gtcagcaact gtggtggact tctgaggag atggatagcc   1200
ttctgtcaaa gcatcatctc aacaagccct caacaccatc accaccatca ctgataa     1257
```

<210> SEQ ID NO 21
<211> LENGTH: 417
<212> TYPE: PRT
<213> ORGANISM: Artificial Sequence
<220> FEATURE:
<223> OTHER INFORMATION: Synthetic: D265A Fc / E76G (amino acid sequence)

<400> SEQUENCE: 21

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
                20                  25                  30

Pro Leu Lys Glu Cys Pro Pro Cys Ala Ala Pro Asp Leu Leu Gly Gly
            35                  40                  45

Pro Ser Val Phe Ile Phe Pro Pro Lys Ile Lys Asp Val Leu Met Ile
        50                  55                  60

Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
```

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
            245                 250                 255

Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln Gln
        275                 280                 285

His Leu Glu Gln Leu Leu Met Asp Leu Gln Glu Leu Leu Ser Arg Met
    290                 295                 300

Glu Asn Tyr Arg Asn Leu Lys Leu Pro Arg Met Leu Thr Phe Lys Phe
305                 310                 315                 320

Tyr Leu Pro Lys Gln Ala Thr Glu Leu Lys Asp Leu Gln Cys Leu Glu
                325                 330                 335

Asp Gly Leu Gly Pro Leu Arg His Val Leu Asp Leu Thr Gln Ser Lys
            340                 345                 350

Ser Phe Gln Leu Glu Asp Ala Glu Asn Phe Ile Ser Asn Ile Arg Val
        355                 360                 365

Thr Val Val Lys Leu Lys Gly Ser Asp Asn Thr Phe Glu Cys Gln Phe
    370                 375                 380

Asp Asp Glu Ser Ala Thr Val Val Asp Phe Leu Arg Arg Trp Ile Ala
385                 390                 395                 400

Phe Cys Gln Ser Ile Ile Ser Thr Ser Pro Gln His His His His
                405                 410                 415

His

<210> SEQ ID NO 22
<211> LENGTH: 447
<212> TYPE: DNA
<213> ORGANISM: Artificial Sequence
<220> FEATURE:
<223> OTHER INFORMATION: Synthetic: mIL-2 QQ 6.2-4 (nucleic acid
      sequence)

<400> SEQUENCE: 22
gcacccacct caagctccac ttcaagctct acagcggaag cacaacagca gcagcagcag      60
cagcagcagc agcagcagca cctggagcag ctgttgatgg acctacagga gctcctgagc     120
aggatggagg attccaggaa cctgagactc cccaggatgc tcaccttcaa attttacttg     180
cccaagcagg ccacagaatt ggaagatctt cagtgcctag aagatgaact tgaacctctg     240
cggcaagttc tggatttgac tcaaagcaaa agctttcaat tggaagatgc tgagaatttc     300
atcagcaata tcagagtaac tgttgtaaaa ctaaagggct ctgacaacac atttgagtgc     360
caattcgatg atgagccagc aactgtggtg gctttctga ggagatggat agccttctgt      420
caaagcatca tctcaacgag ccctcaa                                          447

<210> SEQ ID NO 23
<211> LENGTH: 149
<212> TYPE: PRT
<213> ORGANISM: Artificial Sequence
<220> FEATURE:
<223> OTHER INFORMATION: Synthetic: mIL-2 QQ 6.2-4 (amino acid sequence)

<400> SEQUENCE: 23

Ala Pro Thr Ser Ser Ser Thr Ser Ser Ser Thr Ala Glu Ala Gln Gln
1               5                   10                  15

```
Gln Gln Gln Gln Gln Gln Gln Gln Gln His Leu Glu Gln Leu Leu
            20                  25                  30

Met Asp Leu Gln Glu Leu Leu Ser Arg Met Glu Asp Ser Arg Asn Leu
 35                  40                  45

Arg Leu Pro Arg Met Leu Thr Phe Lys Phe Tyr Leu Pro Lys Gln Ala
 50                  55                  60

Thr Glu Leu Glu Asp Leu Gln Cys Leu Glu Asp Glu Leu Gly Pro Leu
65                  70                  75                  80

Arg Gln Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Pro Ala Thr
        115                 120                 125

Val Val Gly Phe Leu Arg Arg Trp Ile Ala Phe Cys Gln Ser Ile Ile
    130                 135                 140

Ser Thr Ser Pro Gln
145

<210> SEQ ID NO 24
<211> LENGTH: 435
<212> TYPE: DNA
<213> ORGANISM: Artificial Sequence
<220> FEATURE:
<223> OTHER INFORMATION: Synthetic: mIL-2 QQ 6.2-8 (nucleic acid
      sequence)

<400> SEQUENCE: 24
gcacccacct caagctccac ttcaagctct acagcggaag cacaaacagca gcagcagcag    60 cagcagcacc tggagcagct gttgatggac ctacaggagc tcctgagtag gatggaggat   120
cacaggaacc tgagactccc caggatgctc accttcaaat tttacttgcc caagcaggcc   180
acagaattgg aagatcttca gtgcctagaa gatgaacttg aacctctgcg gcaagttctg   240
gatttgactc aaagcaaaag ctttcaattg gaagatgctg agaatttcat cagcaatatc   300
agagtaactg ttgtaaaact aaagggctct gacaacacat tgagtgcca attcgatgat   360 gagccagcaa ctgtggtgga ctttctgagg agatggatag ccttctgtca agcatcatc   420 tcaacaagcc ctcga                                                    435

<210> SEQ ID NO 25
<211> LENGTH: 145
<212> TYPE: PRT
<213> ORGANISM: Artificial Sequence
<220> FEATURE:
<223> OTHER INFORMATION: Synthetic: mIL-2 QQ 6.2-8 (amino acid sequence)

<400> SEQUENCE: 25

Ala Pro Thr Ser Ser Thr Ser Ser Ser Thr Ala Glu Ala Gln Gln Gln
 1               5                  10                  15

Gln Gln Gln Gln Gln Gln His Leu Glu Gln Leu Leu Met Asp Leu Gln
            20                  25                  30

Glu Leu Leu Ser Arg Met Glu Asp His Arg Asn Leu Arg Leu Pro Arg
 35                  40                  45

Met Leu Thr Phe Lys Phe Tyr Leu Pro Lys Gln Ala Thr Glu Leu Glu
 50                  55                  60

Asp Leu Gln Cys Leu Glu Asp Glu Leu Glu Pro Leu Arg Gln Val Leu
65                  70                  75                  80
```

```
Asp Leu Thr Gln Ser Lys Ser Phe Gln Leu Glu Asp Ala Glu Asn Phe
            85                  90                  95

Ile Ser Asn Ile Arg Val Thr Val Val Lys Leu Lys Gly Ser Asp Asn
            100                 105                 110

Thr Phe Glu Cys Gln Phe Asp Asp Glu Pro Ala Thr Val Val Asp Phe
            115                 120                 125

Leu Arg Arg Trp Ile Ala Phe Cys Gln Ser Ile Ile Ser Thr Ser Pro
            130                 135                 140

Arg
145

<210> SEQ ID NO 26
<211> LENGTH: 447
<212> TYPE: DNA
<213> ORGANISM: Artificial Sequence
<220> FEATURE:
<223> OTHER INFORMATION: Synthetic: mIL-2 QQ 6.2-10 (nucleic acid
      sequence)

<400> SEQUENCE: 26
gcacccacct caagctccac ttcaagctct acagcggaag cacaacagca gcagcagcag      60
cagcagcagc agcagcagca cctggagcag ctgttgatgg acctacagga actcctgagt     120
aggatggagg atcacaggaa cctgagactc cccaggatgc tcaccttcaa attttacttg     180
cccgagcagg ccacagaatt ggaagatctt cagtgcctag aagatgaact tgaaccactg     240
cggcaagttc tggatttgac tcaaagcaaa agctttcaat tggaagatgc tgagaatttc     300
atcagcaata tcagagtaac tgttgtaaaa ctaaagggct ctgacaacac atttgagtgc     360
caattcgacg atgagccagc aactgtggtg gactttctga ggagatggat agccttctgt     420
caaagcatca tctcaacaag ccctcag                                         447

<210> SEQ ID NO 27
<211> LENGTH: 149
<212> TYPE: PRT
<213> ORGANISM: Artificial Sequence
<220> FEATURE:
<223> OTHER INFORMATION: Synthetic: mIL-2 QQ 6.2-10 (amino acid
      sequence)

<400> SEQUENCE: 27

Ala Pro Thr Ser Ser Thr Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asp His Arg Asn Leu
            35                  40                  45

Arg Leu Pro Arg Met Leu Thr Phe Lys Phe Tyr Leu Pro Glu Gln Ala
    50                  55                  60

Thr Glu Leu Glu Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
            85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Pro Ala Thr
            115                 120                 125

Val Val Asp Phe Leu Arg Arg Trp Ile Ala Phe Cys Gln Ser Ile Ile
```

Ser Thr Ser Pro Gln
145

<210> SEQ ID NO 28
<211> LENGTH: 438
<212> TYPE: DNA
<213> ORGANISM: Artificial Sequence
<220> FEATURE:
<223> OTHER INFORMATION: Synthetic: mIL-2 QQ 6.2-11 (nucleic acid
      sequence)

<400> SEQUENCE: 28

| | | | | | |
|---|---|---|---|---|---|
| gcacccacct | caagctccac | ttcaagctct | acagcggaag | cacaacagca | gcagcagcag | 60 |
| cagcagcagc | acctggagca | gctgttgatg | gacctacagg | agctcctgag | caggatggag | 120 |
| gattccagga | acctgagact | ccccagaatg | ctcaccttca | aatttactt | gcccgagcag | 180 |
| gccacagaat | tgaaagatct | ccagtgccta | gaagatgaac | ttgaacctct | gcggcaagtt | 240 |
| ctggatttga | ctcaaagcaa | aagctttcaa | ttggaagatg | ctgagaattt | catcagcaat | 300 |
| atcagagtaa | ctgttgtaaa | actaaagggc | tctgacaaca | catttgagtg | ccaattcgac | 360 |
| gatgagccag | caactgtggt | ggactttctg | aggagatgga | tagccttctg | tcaaagcatc | 420 |
| atctcaacaa | gccctcag | | | | | 438 |

<210> SEQ ID NO 29
<211> LENGTH: 146
<212> TYPE: PRT
<213> ORGANISM: Artificial Sequence
<220> FEATURE:
<223> OTHER INFORMATION: Synthetic: mIL-2 QQ 6.2-11 (amino acid
      sequence)

<400> SEQUENCE: 29

Ala Pro Thr Ser Ser Ser Thr Ser Ser Ser Thr Ala Glu Ala Gln Gln
1               5                   10                  15

Gln Gln Gln Gln Gln Gln His Leu Glu Gln Leu Leu Met Asp Leu
            20                  25                  30

Gln Glu Leu Leu Ser Arg Met Glu Asp Ser Arg Asn Leu Arg Leu Pro
        35                  40                  45

Arg Met Leu Thr Phe Lys Phe Tyr Leu Pro Glu Gln Ala Thr Glu Leu
    50                  55                  60

Lys Asp Leu Gln Cys Leu Glu Asp Glu Leu Glu Pro Leu Arg Gln Val
65                  70                  75                  80

Leu Asp Leu Thr Gln Ser Lys Ser Phe Gln Leu Glu Asp Ala Glu Asn
                85                  90                  95

Phe Ile Ser Asn Ile Arg Val Thr Val Val Lys Leu Lys Gly Ser Asp
            100                 105                 110

Asn Thr Phe Glu Cys Gln Phe Asp Asp Glu Pro Ala Thr Val Val Asp
        115                 120                 125

Phe Leu Arg Arg Trp Ile Ala Phe Cys Gln Ser Ile Ile Ser Thr Ser
    130                 135                 140

Pro Gln
145

<210> SEQ ID NO 30
<211> LENGTH: 447
<212> TYPE: DNA
<213> ORGANISM: Artificial Sequence
<220> FEATURE:

<223> OTHER INFORMATION: Synthetic: mIL-2 QQ 6.2-13 (nucleic acid
       sequence)

<400> SEQUENCE: 30

```
gcacccacct caagctccac ttcaagctct acagcggaag cacaacagca gcagcagcag    60
cagcagcagc agcagcagca cctggagcag ctgttgatgg acctacagga gctcctgagt   120
aggatggagg atcacaggaa cctgagactc cccaggatgc tcaccttcaa atttacttg    180
cccgagcagg ccacagaatt gaaagatctc cagtgcctag aagatgaact gaacctctg    240
cggcaggttc tggatttgac tcaaagcaaa agctttcaat tggaagatgc tgagaatttc   300
atcagcaata tcagagtaac tgttgtaaaa ctaaagggct ctgacaacac atttgagtgc   360
caattcgatg atgagccagc aactgtggtg gactttctga ggagatggat agccttctgt   420
caaagcatca tctcaacaag ccctcag                                       447
```

<210> SEQ ID NO 31
<211> LENGTH: 149
<212> TYPE: PRT
<213> ORGANISM: Artificial Sequence
<220> FEATURE:
<223> OTHER INFORMATION: Synthetic: mIL-2 QQ 6.2-13 (amino acid
       sequence)

<400> SEQUENCE: 31

Ala Pro Thr Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
                20                  25                  30

Met Asp Leu Gln Glu Leu Leu Ser Arg Met Glu Asp His Arg Asn Leu
                35                  40                  45

Arg Leu Pro Arg Met Leu Thr Phe Lys Phe Tyr Leu Pro Glu Gln Ala
    50                  55                  60

Thr Glu Leu Lys Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
                100                 105                 110

Gly Ser Asp Asn Thr Phe Glu Cys Gln Phe Asp Asp Glu Pro Ala Thr
                115                 120                 125

Val Val Asp Phe Leu Arg Arg Trp Ile Ala Phe Cys Gln Ser Ile Ile
    130                 135                 140

Ser Thr Ser Pro Gln
145

<210> SEQ ID NO 32
<211> LENGTH: 461
<212> TYPE: DNA
<213> ORGANISM: Homo sapiens
<220> FEATURE:
<221> NAME/KEY: misc_feature
<222> LOCATION: (1)..(461)
<223> OTHER INFORMATION: Full length human IL-2 (nucleic acid sequence)

<400> SEQUENCE: 32

```
atgtacagga tgcaactcct gtcttgcatt gcactaagtc ttgcacttgt cacaaacagt    60
gcacctactt caagttctac aaagaaaaca cagctacaac tggagcattt actgctggat   120
ttacagatga ttttgaatgg aattaataat tacaagaatc ccaaactcac caggatgctc   180
```

```
acatttaagt tttacatgcc caagaaggcc acagaactga acatcttca gtgtctagaa      240 gaagaactca aacctctgga ggaagtgcta aatttagctc aaagcaaaaa ctttcactta      300
agacccaggg acttaatcag caatatcaac gtaatagttc tggaactaaa gggatctgaa      360
acaacattca tgtgtaatat gctgatgaga cagcaaccat tgtagaattt ctgaacagat      420
ggattacctt ttgtcaaagc atcatctcaa cactgacttg a                         461
```

```
<210> SEQ ID NO 33
<211> LENGTH: 153
<212> TYPE: PRT
<213> ORGANISM: Homo sapiens
<220> FEATURE:
<221> NAME/KEY: misc_feature
<222> LOCATION: (1)..(153)
<223> OTHER INFORMATION: Full length human IL-2 (amino acid sequence)

<400> SEQUENCE: 33

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

```
<210> SEQ ID NO 34
<211> LENGTH: 401
<212> TYPE: DNA
<213> ORGANISM: Homo sapiens
<220> FEATURE:
<221> NAME/KEY: misc_feature
<222> LOCATION: (1)..(401)
<223> OTHER INFORMATION: Human IL-2 without signal peptide (nucleic acid
      sequence)

<400> SEQUENCE: 34
gcacctactt caagttctac aaagaaaaca cagctacaac tggagcattt actgctggat      60
ttacagatga ttttgaatgg aattaataat acaagaatc ccaaactcac caggatgctc      120
acatttaagt tttacatgcc caagaaggcc acagaactga acatcttca gtgtctagaa      180 gaagaactca aacctctgga ggaagtgcta aatttagctc aaagcaaaaa ctttcactta      240
agacccaggg acttaatcag caatatcaac gtaatagttc tggaactaaa gggatctgaa      300
acaacattca tgtgtaatat gctgatgaga cagcaaccat tgtagaattt ctgaacagat      360
ggattacctt ttgtcaaagc atcatctcaa cactgacttg a                         401
```

<210> SEQ ID NO 35
<211> LENGTH: 133
<212> TYPE: PRT
<213> ORGANISM: Homo sapiens
<220> FEATURE:
<221> NAME/KEY: misc_feature
<222> LOCATION: (1)..(133)
<223> OTHER INFORMATION: Human IL-2 without signal peptide (amino acid
      sequence)

<400> SEQUENCE: 35

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 36
<211> LENGTH: 749
<212> TYPE: PRT
<213> ORGANISM: Homo sapiens
<220> FEATURE:
<221> NAME/KEY: misc_feature
<222> LOCATION: (1)..(749)
<223> OTHER INFORMATION: Human serum albumin (amino acid sequence)

<400> SEQUENCE: 36

Met Asp Met Arg Val Pro Ala Gln Leu Leu Gly Leu Leu Leu Leu Trp
1               5                   10                  15

Leu Pro Gly Ala Arg Cys Ala Asp Ala His Lys Ser Glu Val Ala His
            20                  25                  30

Arg Phe Lys Asp Leu Gly Glu Glu Asn Phe Lys Ala Leu Val Leu Ile
        35                  40                  45

Ala Phe Ala Gln Tyr Leu Gln Gln Cys Pro Phe Glu Asp His Val Lys
    50                  55                  60

Leu Val Asn Glu Val Thr Glu Phe Ala Lys Thr Cys Val Ala Asp Glu
65                  70                  75                  80

Ser Ala Glu Asn Cys Asp Lys Ser Leu His Thr Leu Phe Gly Asp Lys
                85                  90                  95

Leu Cys Thr Val Ala Thr Leu Arg Glu Thr Tyr Gly Glu Met Ala Asp
            100                 105                 110

Cys Cys Ala Lys Gln Glu Pro Glu Arg Asn Glu Cys Phe Leu Gln His
        115                 120                 125

Lys Asp Asp Asn Pro Asn Leu Pro Arg Leu Val Arg Pro Glu Val Asp
    130                 135                 140

```
Val Met Cys Thr Ala Phe His Asp Asn Glu Glu Thr Phe Leu Lys Lys
145                 150                 155                 160

Tyr Leu Tyr Glu Ile Ala Arg Arg His Pro Tyr Phe Tyr Ala Pro Glu
                165                 170                 175

Leu Leu Phe Phe Ala Lys Arg Tyr Lys Ala Ala Phe Thr Glu Cys Cys
            180                 185                 190

Gln Ala Ala Asp Lys Ala Ala Cys Leu Leu Pro Lys Leu Asp Glu Leu
        195                 200                 205

Arg Asp Glu Gly Lys Ala Ser Ser Ala Lys Gln Arg Leu Lys Cys Ala
    210                 215                 220

Ser Leu Gln Lys Phe Gly Glu Arg Ala Phe Lys Ala Trp Ala Val Ala
225                 230                 235                 240

Arg Leu Ser Gln Arg Phe Pro Lys Ala Glu Phe Ala Glu Val Ser Lys
                245                 250                 255

Leu Val Thr Asp Leu Thr Lys Val His Thr Glu Cys Cys His Gly Asp
            260                 265                 270

Leu Leu Glu Cys Ala Asp Asp Arg Ala Asp Leu Ala Lys Tyr Ile Cys
        275                 280                 285

Glu Asn Gln Asp Ser Ile Ser Ser Lys Leu Lys Glu Cys Cys Glu Lys
    290                 295                 300

Pro Leu Leu Glu Lys Ser His Cys Ile Ala Glu Val Glu Asn Asp Glu
305                 310                 315                 320

Met Pro Ala Asp Leu Pro Ser Leu Ala Ala Asp Phe Val Glu Ser Lys
                325                 330                 335

Asp Val Cys Lys Asn Tyr Ala Glu Ala Lys Asp Val Phe Leu Gly Met
            340                 345                 350

Phe Leu Tyr Glu Tyr Ala Arg Arg His Pro Asp Tyr Ser Val Val Leu
        355                 360                 365

Leu Leu Arg Leu Ala Lys Thr Tyr Glu Thr Thr Leu Glu Lys Cys Cys
    370                 375                 380

Ala Ala Ala Asp Pro His Glu Cys Tyr Ala Lys Val Phe Asp Glu Phe
385                 390                 395                 400

Lys Pro Leu Val Glu Glu Pro Gln Asn Leu Ile Lys Gln Asn Cys Glu
                405                 410                 415

Leu Phe Glu Gln Leu Gly Glu Tyr Lys Phe Gln Asn Ala Leu Leu Val
            420                 425                 430

Arg Tyr Thr Lys Lys Val Pro Gln Val Ser Thr Pro Thr Leu Val Glu
        435                 440                 445

Val Ser Arg Asn Leu Gly Lys Val Gly Ser Lys Cys Cys Lys His Pro
    450                 455                 460

Glu Ala Lys Arg Met Pro Cys Ala Glu Asp Tyr Leu Ser Val Val Leu
465                 470                 475                 480

Asn Gln Leu Cys Val Leu His Glu Lys Thr Pro Val Ser Asp Arg Val
                485                 490                 495

Thr Lys Cys Cys Thr Glu Ser Leu Val Asn Arg Arg Pro Cys Phe Ser
            500                 505                 510

Ala Leu Glu Val Asp Glu Thr Tyr Val Pro Lys Glu Phe Asn Ala Glu
        515                 520                 525

Thr Phe Thr Phe His Ala Asp Ile Cys Thr Leu Ser Glu Lys Glu Arg
    530                 535                 540

Gln Ile Lys Lys Gln Thr Ala Leu Val Glu Leu Val Lys His Lys Pro
545                 550                 555                 560
```

-continued

```
Lys Ala Thr Lys Glu Gln Leu Lys Ala Val Met Asp Asp Phe Ala Ala
                565                 570                 575

Phe Val Glu Lys Cys Cys Lys Ala Asp Asp Lys Glu Thr Cys Phe Ala
            580                 585                 590

Glu Glu Gly Lys Lys Leu Val Ala Ala Ser Gln Ala Ala Leu Gly Leu
                595                 600                 605

Gly Gly Gly Ser Ala Pro Thr Ser Ser Ser Thr Lys Lys Thr Gln Leu
            610                 615                 620

Gln Leu Glu His Leu Leu Leu Asp Leu Gln Met Ile Leu Asn Gly Ile
625                 630                 635                 640

Asn Asn Tyr Lys Asn Pro Lys Leu Thr Arg Met Leu Thr Phe Lys Phe
                645                 650                 655

Tyr Met Pro Lys Lys Ala Thr Glu Leu Lys His Leu Gln Cys Leu Glu
                660                 665                 670

Glu Glu Leu Lys Pro Leu Glu Glu Val Leu Asn Leu Ala Gln Ser Lys
                675                 680                 685

Asn Phe His Leu Arg Pro Arg Asp Leu Ile Ser Asn Ile Asn Val Ile
                690                 695                 700

Val Leu Glu Leu Lys Gly Ser Glu Thr Thr Phe Met Cys Glu Tyr Ala
705                 710                 715                 720

Asp Glu Thr Ala Thr Ile Val Glu Phe Leu Asn Arg Trp Ile Thr Phe
                725                 730                 735

Cys Gln Ser Ile Ile Ser Thr Leu Thr Gly Gly Gly Ser
                740                 745

<210> SEQ ID NO 37
<211> LENGTH: 726
<212> TYPE: PRT
<213> ORGANISM: Homo sapiens
<220> FEATURE:
<221> NAME/KEY: misc_feature
<222> LOCATION: (1)..(726)
<223> OTHER INFORMATION: Mature HSA (amino acid sequence)

<400> SEQUENCE: 37

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
```

-continued

```
                 165                 170                 175
Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Ser Ala Pro Thr
            580                 585                 590
```

```
Ser Ser Ser Thr Lys Lys Thr Gln Leu Gln Leu Glu His Leu Leu Leu
        595                 600                 605

Asp Leu Gln Met Ile Leu Asn Gly Ile Asn Asn Tyr Lys Asn Pro Lys
        610                 615                 620

Leu Thr Arg Met Leu Thr Phe Lys Phe Tyr Met Pro Lys Ala Thr
625                 630                 635                 640

Glu Leu Lys His Leu Gln Cys Leu Glu Glu Glu Leu Lys Pro Leu Glu
                645                 650                 655

Glu Val Leu Asn Leu Ala Gln Ser Lys Asn Phe His Leu Arg Pro Arg
                660                 665                 670

Asp Leu Ile Ser Asn Ile Asn Val Ile Val Leu Glu Leu Lys Gly Ser
        675                 680                 685

Glu Thr Thr Phe Met Cys Glu Tyr Ala Asp Glu Thr Ala Thr Ile Val
        690                 695                 700

Glu Phe Leu Asn Arg Trp Ile Thr Phe Cys Gln Ser Ile Ile Ser Thr
705                 710                 715                 720

Leu Thr Gly Gly Gly Ser
                725

<210> SEQ ID NO 38
<211> LENGTH: 2247
<212> TYPE: DNA
<213> ORGANISM: Homo sapiens
<220> FEATURE:
<221> NAME/KEY: misc_feature
<222> LOCATION: (1)..(2247)
<223> OTHER INFORMATION: Human serum albumin (nucleic acid sequence)

<400> SEQUENCE: 38
atggatatgc gggtgcctgc tcagctgctg ggactgctgc tgctgtggct gcctggggct      60
agatgcgccg atgctcacaa aagcgaagtc gcacacaggt tcaaagatct gggggaggaa     120
aactttaagg ctctggtgct gattgcattc gcccagtacc tgcagcagtg cccctttgag     180
gaccacgtga aactggtcaa cgaagtgact gagttcgcca agaccctgcgt ggccgacgaa     240 tctgctgaga attgtgataa aagtctgcat actctgtttg gggataagct gtgtacagtg     300
gccactctgc gagaaaccta tggagagatg gcagactgct gtgccaaaca ggaacccgag     360
cggaacgaat gcttcctgca gcataaggac gataaccccca atctgcctcg cctggtgcga     420
cctgaggtgg acgtcatgtg tacagccttc cacgataatg aggaaacttt tctgaagaaa     480
tacctgtacg aaatcgctcg gagacatcct tactttatg caccagagct gctgttcttt     540
gccaaacgct acaaggccgc tttcaccgag tgctgtcagg cagccgataa agctgcatgc     600
ctgctgccta gctggacgga actgagggat gagggcaagg ccagctccgc taaacagcgc     660
ctgaagtgtg ctagcctgca gaaattcggg gagcgagcct tcaaggcttg gcagtggca     720 cggctgagtc agagattccc aaaggcagaa tttgccgagg tctcaaaact ggtgaccgac     780
ctgacaaagg tgcacaccga tgctgtcat ggcgacctgc tggagtgcgc cgacgatcga     840
gctgatctgg caaagtatat ttgtgagaac caggactcca tctctagtaa gctgaaagaa     900
tgctgtgaga aaccactgct ggaaaagtct cactgcattg ccgaagtgga gaacgacgag     960
atgccagctg atctgccctc actggccgct gacttcgtcg aaagcaaaga tgtgtgtaag    1020
aattacgctg aggcaaagga tgtgttcctg ggaatgtttc tgtacgagta tgccaggcgc    1080
cacccagact actccgtggt cctgctgctg aggctggcta aaacatatga aaccacactg    1140
gagaagtgct gtgcagccgc tgatcccccat gaatgctatg ccaaagtctt cgacgagttt    1200
```

```
aagcccctgg tggaggaacc tcagaacctg atcaaacaga attgtgaact gtttgagcag    1260
ctgggcgagt acaagttcca gaacgccctg ctggtgcgct ataccaagaa agtcccacag    1320
gtgtccacac ccactctggt ggaggtgagc cggaatctgg gcaaagtggg gagtaaatgc    1380
tgtaagcacc ctgaagccaa gaggatgcca tgcgctgagg attacctgag tgtggtcctg    1440
aatcagctgt gtgtcctgca tgaaaaaaca cctgtcagcg accgggtgac aaagtgctgt    1500
actgagtcac tggtgaaccg acggccctgc tttagcgccc tggaagtcga tgagacttat    1560
gtgcctaaag agttcaacgc tgagaccttc acatttcacg cagacatttg taccctgagc    1620
gaaaaggaga gacagatcaa gaaacagaca gccctggtcg aactggtgaa gcataaaccc    1680
aaggccacaa agagcagct gaaggctgtc atggacgatt tcgcagcctt tgtggaaaaa    1740
tgctgtaagg cagacgataa ggagacttgc tttgccgagg aaggaaagaa actggtggct    1800
gcatcccagg cagctctggg actgggagga ggatctgccc ctacctcaag ctccactaag    1860
aaaacccagc tgcagctgga gcacctgctg ctggacctgc agatgattct gaacgggatc    1920
aacaattaca aaaatccaaa gctgacccgg atgctgacat tcaagtttta tatgcccaag    1980
aaagccacag agctgaaaca cctgcagtgc ctggaggaag agctgaagcc tctggaagag    2040
gtgctgaacc tggcccagag caagaatttc catctgagac aagggatct gatctccaac    2100
attaatgtga tcgtcctgga actgaaggga tctgagacta cctttatgtg cgaatacgct    2160
gacgagactg caaccattgt ggagttcctg aacagatgga tcaccttctg ccagtccatc    2220
atttctactc tgacaggcgg ggggagc                                        2247
```

<210> SEQ ID NO 39
<211> LENGTH: 28
<212> TYPE: PRT
<213> ORGANISM: Artificial Sequence
<220> FEATURE:
<223> OTHER INFORMATION: Synthetic: EETI-II from Knottin Database

<400> SEQUENCE: 39

Gly Cys Pro Arg Ile Leu Met Arg Cys Lys Gln Asp Ser Asp Cys Leu
1               5                   10                  15

Ala Gly Cys Val Cys Gly Pro Asn Gly Phe Cys Gly
            20                  25

<210> SEQ ID NO 40
<211> LENGTH: 47
<212> TYPE: PRT
<213> ORGANISM: Artificial Sequence
<220> FEATURE:
<223> OTHER INFORMATION: Synthetic: AgRP from Knottin Database

<400> SEQUENCE: 40

Gly Cys Val Arg Leu His Glu Ser Cys Leu Gly Gln Gln Val Pro Cys
1               5                   10                  15

Cys Asp Pro Cys Ala Thr Cys Tyr Cys Arg Phe Phe Asn Ala Phe Cys
            20                  25                  30

Tyr Cys Arg Lys Leu Gly Thr Ala Met Asn Pro Cys Ser Arg Thr
        35                  40                  45

<210> SEQ ID NO 41
<211> LENGTH: 48
<212> TYPE: PRT
<213> ORGANISM: Artificial Sequence
<220> FEATURE:
<223> OTHER INFORMATION: Synthetic: Omega agatoxin from Knottin Database

<400> SEQUENCE: 41

Glu Asp Asn Cys Ile Ala Glu Asp Tyr Gly Lys Cys Thr Trp Gly Gly
1               5                   10                  15

Thr Lys Cys Cys Arg Gly Arg Pro Cys Arg Cys Ser Met Ile Gly Thr
                20                  25                  30

Asn Cys Glu Cys Thr Pro Arg Leu Ile Met Glu Gly Leu Ser Phe Ala
            35                  40                  45

<210> SEQ ID NO 42
<211> LENGTH: 33
<212> TYPE: PRT
<213> ORGANISM: Artificial Sequence
<220> FEATURE:
<223> OTHER INFORMATION: Synthetic: EETI-II Library
<220> FEATURE:
<221> NAME/KEY: misc_feature
<222> LOCATION: (3)..(3)
<223> OTHER INFORMATION: X is selected from the group consisting of A,
      V, L, P, F, Y, S, H, D, and N
<220> FEATURE:
<221> NAME/KEY: misc_feature
<222> LOCATION: (4)..(4)
<223> OTHER INFORMATION: X is selected from the group consisting of G,
      V, L, P, R, E, and Q
<220> FEATURE:
<221> NAME/KEY: misc_feature
<222> LOCATION: (5)..(5)
<223> OTHER INFORMATION: X is selected from the group consisting of G,
      A, and P
<220> FEATURE:
<221> NAME/KEY: misc_feature
<222> LOCATION: (9)..(9)
<223> OTHER INFORMATION: X is selected from the group consisting of W
      and N
<220> FEATURE:
<221> NAME/KEY: misc_feature
<222> LOCATION: (10)..(10)
<223> OTHER INFORMATION: X is selected from the group consisting of A,
      P, and S
<220> FEATURE:
<221> NAME/KEY: misc_feature
<222> LOCATION: (11)..(11)
<223> OTHER INFORMATION: X is selected from the group consisting of P
      and R
<220> FEATURE:
<221> NAME/KEY: misc_feature
<222> LOCATION: (12)..(12)
<223> OTHER INFORMATION: X is selected from the group consisting of A,
      V, L, P, S, T, and E
<220> FEATURE:
<221> NAME/KEY: misc_feature
<222> LOCATION: (13)..(13)
<223> OTHER INFORMATION: X is selected from the group consisting of G,
      A, W, S, T, K, and E

<400> SEQUENCE: 42

Gly Cys Xaa Xaa Xaa Arg Gly Asp Xaa Xaa Xaa Xaa Cys Lys Gln
1               5                   10                  15

Asp Ser Asp Cys Leu Ala Gly Cys Val Cys Gly Pro Asn Gly Phe Cys
                20                  25                  30

Gly

<210> SEQ ID NO 43
<211> LENGTH: 33
<212> TYPE: PRT
<213> ORGANISM: Artificial Sequence
<220> FEATURE:
<223> OTHER INFORMATION: Synthetic: EETI-II K15S Mutation Library
<220> FEATURE:
<221> NAME/KEY: misc_feature

```
<222> LOCATION: (3)..(3)
<223> OTHER INFORMATION: X is selected from the group consisting of A,
      V, L, P, F, Y, S, H, D, and N
<220> FEATURE:
<221> NAME/KEY: misc_feature
<222> LOCATION: (4)..(4)
<223> OTHER INFORMATION: X is selected from the group consisting of G,
      V, L, P, R, E, and Q
<220> FEATURE:
<221> NAME/KEY: misc_feature
<222> LOCATION: (5)..(5)
<223> OTHER INFORMATION: X is selected from the group consisting of G,
      A, and P
<220> FEATURE:
<221> NAME/KEY: misc_feature
<222> LOCATION: (9)..(9)
<223> OTHER INFORMATION: X is selected from the group consisting of W
      and N
<220> FEATURE:
<221> NAME/KEY: misc_feature
<222> LOCATION: (10)..(10)
<223> OTHER INFORMATION: X is selected from the group consisting of A,
      P, and S
<220> FEATURE:
<221> NAME/KEY: misc_feature
<222> LOCATION: (11)..(11)
<223> OTHER INFORMATION: X is selected from the group consisting of P
      and R
<220> FEATURE:
<221> NAME/KEY: misc_feature
<222> LOCATION: (12)..(12)
<223> OTHER INFORMATION: X is selected from the group consisting of A,
      V, L, P, S, T, and E
<220> FEATURE:
<221> NAME/KEY: misc_feature
<222> LOCATION: (13)..(13)
<223> OTHER INFORMATION: X is selected from the group consisting of G,
      A, W, S, T, K, and E

<400> SEQUENCE: 43

Gly Cys Xaa Xaa Xaa Arg Gly Asp Xaa Xaa Xaa Xaa Xaa Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 44
<211> LENGTH: 822
<212> TYPE: DNA
<213> ORGANISM: Artificial Sequence
<220> FEATURE:
<223> OTHER INFORMATION: Synthetic: 2.5F- (K15S) mIgG2aFc  Nucleic Acid
      Sequence

<400> SEQUENCE: 44
ggttgtccaa gaccaagagg tgataatcca ccattgactt gttctcaaga ttctgattgt     60
ttggctggtt gtgtttgtgg tccaaatggt ttttgtggtg gtcgactaga gcccagagtg    120
cccataacac agaaccctg tcctccactc aaagagtgtc cccatgcgc agctccagac      180 ctcttgggtg gaccatccgt cttcatcttc cctccaaaga tcaaggatgt actcatgatc    240
tccctgagcc ccatggtcac atgtgtggtg gtggatgtga gcgaggatga cccagacgtc    300
cagatcagct ggtttgtgaa caacgtggaa gtacacacag ctcagacaca aacccataga    360
gaggattaca acagtactct ccgggtggtc agtgccctcc ccatccagca ccaggactgg    420
atgagtggca aggagttcaa atgcaaggtc aacaacagag ccctcccatc ccccatcgag    480
aaaccatctc aaacccagag ggccagtaa gagctccac aggtatatgt cttgcctcca     540
ccagcagaag agatgactaa gaaagagttc agtctgacct gcatgatcac aggcttctta    600
```

```
cctgccgaaa ttgctgtgga ctggaccagc aatgggcgta cagagcaaaa ctacaagaac    660
accgcaacag tcctggactc tgatggttct tacttcatgt acagcaagct cagagtacaa    720
aagagcactt gggaaagagg aagtctttc gcctgctcag tggtccacga gggtctgcac    780
aatcacctta cgactaagac catctcccgg tctctgggta aa                       822
```

<210> SEQ ID NO 45
<211> LENGTH: 271
<212> TYPE: PRT
<213> ORGANISM: Artificial Sequence
<220> FEATURE:
<223> OTHER INFORMATION: Synthetic: 2.5F- (K15S) mIgG2aFc Amino Acid
      Sequence

<400> SEQUENCE: 45

```
Gly Cys Pro Arg Pro Arg Gly Asp Asn Pro Leu Thr Cys Ser Gln
1               5                   10                  15

Asp Ser Asp Cys Leu Ala Gly Cys Val Cys Gly Pro Asn Gly Phe Cys
            20                  25                  30

Gly Glu Pro Arg Val Pro Ile Thr Gln Asn Pro Cys Pro Pro Leu Lys
        35                  40                  45

Glu Cys Pro Pro Cys Ala Ala Pro Asp Leu Leu Gly Gly Pro Ser Val
    50                  55                  60

Phe Ile Phe Pro Pro Lys Ile Lys Asp Val Leu Met Ile Ser Leu Ser
65                  70                  75                  80

Pro Met Val Thr Cys Val Val Val Asp Val Ser Glu Asp Asp Pro Asp
                85                  90                  95

Val Gln Ile Ser Trp Phe Val Asn Asn Val Glu Val His Thr Ala Gln
            100                 105                 110

Thr Gln Thr His Arg Glu Asp Tyr Asn Ser Thr Leu Arg Val Val Ser
        115                 120                 125

Ala Leu Pro Ile Gln His Gln Asp Trp Met Ser Gly Lys Glu Phe Lys
    130                 135                 140

Cys Lys Val Asn Asn Arg Ala Leu Pro Ser Pro Ile Glu Lys Thr Ile
145                 150                 155                 160

Ser Lys Pro Arg Gly Pro Val Arg Ala Pro Gln Val Tyr Val Leu Pro
                165                 170                 175

Pro Pro Ala Glu Glu Met Thr Lys Lys Glu Phe Ser Leu Thr Cys Met
            180                 185                 190

Ile Thr Gly Phe Leu Pro Ala Glu Ile Ala Val Asp Trp Thr Ser Asn
        195                 200                 205

Gly Arg Thr Glu Gln Asn Tyr Lys Asn Thr Ala Thr Val Leu Asp Ser
    210                 215                 220

Asp Gly Ser Tyr Phe Met Tyr Ser Lys Leu Arg Val Gln Lys Ser Thr
225                 230                 235                 240

Trp Glu Arg Gly Ser Leu Phe Ala Cys Ser Val Val His Glu Gly Leu
                245                 250                 255

His Asn His Leu Thr Thr Lys Thr Ile Ser Arg Ser Leu Gly Lys
            260                 265                 270
```

<210> SEQ ID NO 46
<211> LENGTH: 822
<212> TYPE: DNA
<213> ORGANISM: Artificial Sequence
<220> FEATURE:
<223> OTHER INFORMATION: Synthetic: 2.5D- (K15S) mIgG2aFc Nucleic Acid
      Sequence

<400> SEQUENCE: 46

```
ggttgtccac aaggcagagg tgattgggct ccaacttctt gttctcaaga ttctgattgt    60
ttggctggtt gtgtttgtgg tccaaatggt ttttgtggtg gtcgactaga gcccagagtg   120
cccataacac agaacccctg tcctccactc aaagagtgtc ccccatgcgc agctccagac   180
ctcttgggtg gaccatccgt cttcatcttc cctccaaaga tcaaggatgt actcatgatc   240
tccctgagcc ccatggtcac atgtgtggtg gtggatgtga gcgaggatga cccagacgtc   300
cagatcagct ggtttgtgaa caacgtggaa gtacacacag ctcagacaca aacccataga   360
gaggattaca acagtactct ccgggtggtc agtgccctcc ccatccagca ccaggactgg   420
atgagtggca aggagttcaa atgcaaggtc aacaacagag ccctcccatc ccccatcgag   480
aaaaccatct caaacccag agggccagta agagctccac aggtatatgt cttgcctcca   540
ccagcagaag agatgactaa gaaagagttc agtctgacct gcatgatcac aggcttctta   600
cctgccgaaa ttgctgtgga ctggaccagc aatgggcgta cagagcaaaa ctacaagaac   660
accgcaacag tcctggactc tgatggttct tacttcatgt acagcaagct cagagtacaa   720
aagagcactt gggaaagagg aagtcttttc gcctgctcag tggtccacga gggtctgcac   780
aatcaccta cgactaagac catctcccgg tctctgggta aa                       822
```

<210> SEQ ID NO 47
<211> LENGTH: 271
<212> TYPE: PRT
<213> ORGANISM: Artificial Sequence
<220> FEATURE:
<223> OTHER INFORMATION: Synthetic: 2.5D- (K15S) mIgG2aFc Amino Acid Sequence

<400> SEQUENCE: 47

```
Gly Cys Pro Gln Gly Arg Gly Asp Trp Ala Pro Thr Ser Cys Ser Gln
1               5                   10                  15
Asp Ser Asp Cys Leu Ala Gly Cys Val Cys Gly Pro Asn Gly Phe Cys
            20                  25                  30
Gly Glu Pro Arg Val Pro Ile Thr Gln Asn Pro Cys Pro Pro Leu Lys
        35                  40                  45
Glu Cys Pro Pro Cys Ala Ala Pro Asp Leu Leu Gly Gly Pro Ser Val
    50                  55                  60
Phe Ile Phe Pro Pro Lys Ile Lys Asp Val Leu Met Ile Ser Leu Ser
65                  70                  75                  80
Pro Met Val Thr Cys Val Val Val Asp Val Ser Glu Asp Asp Pro Asp
                85                  90                  95
Val Gln Ile Ser Trp Phe Val Asn Asn Val Glu Val His Thr Ala Gln
            100                 105                 110
Thr Gln Thr His Arg Glu Asp Tyr Asn Ser Thr Leu Arg Val Val Ser
        115                 120                 125
Ala Leu Pro Ile Gln His Gln Asp Trp Met Ser Gly Lys Glu Phe Lys
    130                 135                 140
Cys Lys Val Asn Asn Arg Ala Leu Pro Ser Pro Ile Glu Lys Thr Ile
145                 150                 155                 160
Ser Lys Pro Arg Gly Pro Val Arg Ala Pro Gln Val Tyr Val Leu Pro
                165                 170                 175
Pro Pro Ala Glu Glu Met Thr Lys Lys Glu Phe Ser Leu Thr Cys Met
            180                 185                 190
Ile Thr Gly Phe Leu Pro Ala Glu Ile Ala Val Asp Trp Thr Ser Asn
```

```
                195                 200                 205
Gly Arg Thr Glu Gln Asn Tyr Lys Asn Thr Ala Thr Val Leu Asp Ser
    210                 215                 220

Asp Gly Ser Tyr Phe Met Tyr Ser Lys Leu Arg Val Gln Lys Ser Thr
225                 230                 235                 240

Trp Glu Arg Gly Ser Leu Phe Ala Cys Ser Val Val His Glu Gly Leu
                245                 250                 255

His Asn His Leu Thr Thr Lys Thr Ile Ser Arg Ser Leu Gly Lys
                260                 265                 270

<210> SEQ ID NO 48
<211> LENGTH: 265
<212> TYPE: PRT
<213> ORGANISM: Artificial Sequence
<220> FEATURE:
<223> OTHER INFORMATION: Synthetic: 2.5F- (K15S) hIgG1Fc  Amino Acid
      Sequence

<400> SEQUENCE: 48

Gly Cys Pro Arg Pro Arg Gly Asp Asn Pro Pro Leu Thr Cys Ser Gln
1               5                   10                  15

Asp Ser Asp Cys Leu Ala Gly Cys Val Cys Gly Pro Asn Gly Phe Cys
            20                  25                  30

Gly Glu Pro Lys Ser Cys Asp Lys Thr His Thr Cys Pro Pro Cys Pro
        35                  40                  45

Ala Pro Glu Leu Leu Gly Gly Pro Ser Val Phe Leu Phe Pro Pro Lys
    50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
    130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Glu Glu Met
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
    210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly Lys
            260                 265

<210> SEQ ID NO 49
<211> LENGTH: 260
```

<212> TYPE: PRT
<213> ORGANISM: Artificial Sequence
<220> FEATURE:
<223> OTHER INFORMATION: Synthetic: 2.5F- (K15S) hIgG1Fc Fc Upper Hinge
      Deletion (DEPKSC) Amino Acid Sequence

<400> SEQUENCE: 49

Gly Cys Pro Arg Pro Arg Gly Asp Asn Pro Leu Thr Cys Ser Gln
1               5                   10                  15

Asp Ser Asp Cys Leu Ala Gly Cys Val Cys Gly Pro Asn Gly Phe Cys
            20                  25                  30

Gly Asp Lys Thr His Thr Cys Pro Cys Pro Ala Pro Glu Leu Leu
        35                  40                  45

Gly Gly Pro Ser Val Phe Leu Phe Pro Pro Lys Pro Lys Asp Thr Leu
    50                  55                  60

Met Ile Ser Arg Thr Pro Glu Val Thr Cys Val Val Val Asp Val Ser
65                  70                  75                  80

His Glu Asp Pro Glu Val Lys Phe Asn Trp Tyr Val Asp Gly Val Glu
                85                  90                  95

Val His Asn Ala Lys Thr Lys Pro Arg Glu Glu Gln Tyr Asn Ser Thr
            100                 105                 110

Tyr Arg Val Val Ser Val Leu Thr Val Leu His Gln Asp Trp Leu Asn
        115                 120                 125

Gly Lys Glu Tyr Lys Cys Lys Val Ser Asn Lys Ala Leu Pro Ala Pro
130                 135                 140

Ile Glu Lys Thr Ile Ser Lys Ala Lys Gly Gln Pro Arg Glu Pro Gln
145                 150                 155                 160

Val Tyr Thr Leu Pro Pro Ser Arg Glu Glu Met Thr Lys Asn Gln Val
                165                 170                 175

Ser Leu Thr Cys Leu Val Lys Gly Phe Tyr Pro Ser Asp Ile Ala Val
            180                 185                 190

Glu Trp Glu Ser Asn Gly Gln Pro Glu Asn Asn Tyr Lys Thr Thr Pro
        195                 200                 205

Pro Val Leu Asp Ser Asp Gly Ser Phe Phe Leu Tyr Ser Lys Leu Thr
    210                 215                 220

Val Asp Lys Ser Arg Trp Gln Gln Gly Asn Val Phe Ser Cys Ser Val
225                 230                 235                 240

Met His Glu Ala Leu His Asn His Tyr Thr Gln Lys Ser Leu Ser Leu
                245                 250                 255

Ser Pro Gly Lys
            260

<210> SEQ ID NO 50
<211> LENGTH: 265
<212> TYPE: PRT
<213> ORGANISM: Artificial Sequence
<220> FEATURE:
<223> OTHER INFORMATION: Synthetic: 2.5D- (K15S) hIgG1Fc  Amino Acid
      Sequence

<400> SEQUENCE: 50

Gly Cys Pro Gln Gly Arg Gly Asp Trp Ala Pro Thr Ser Cys Ser Gln
1               5                   10                  15

Asp Ser Asp Cys Leu Ala Gly Cys Val Cys Gly Pro Asn Gly Phe Cys
            20                  25                  30

Gly Glu Pro Lys Ser Cys Asp Lys Thr His Thr Cys Pro Pro Cys Pro
        35                  40                  45

Ala Pro Glu Leu Leu Gly Gly Pro Ser Val Phe Leu Phe Pro Pro Lys
   50                  55                  60

Pro Lys Asp Thr Leu Met Ile Ser Arg Thr Pro Glu Val Thr Cys Val
 65                  70                  75                  80

Val Val Asp Val Ser His Glu Asp Pro Glu Val Lys Phe Asn Trp Tyr
                 85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
            115                 120                 125

Gln Asp Trp Leu Asn Gly Lys Glu Tyr Lys Cys Lys Val Ser Asn Lys
        130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Glu Glu Met
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
            195                 200                 205

Tyr Lys Thr Thr Pro Pro Val Leu Asp Ser Asp Gly Ser Phe Phe Leu
    210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly Lys
                260                 265

<210> SEQ ID NO 51
<211> LENGTH: 260
<212> TYPE: PRT
<213> ORGANISM: Artificial Sequence
<220> FEATURE:
<223> OTHER INFORMATION: Synthetic: 2.5D- (K15S) hIgG1Fc  Fc Upper Hinge
      Deletion (DEPKSC) Amino Acid Sequence

<400> SEQUENCE: 51

Gly Cys Pro Gln Gly Arg Gly Asp Trp Ala Pro Thr Ser Cys Ser Gln
 1               5                  10                  15

Asp Ser Asp Cys Leu Ala Gly Cys Val Cys Gly Pro Asn Gly Phe Cys
                20                  25                  30

Gly Asp Lys Thr His Thr Cys Pro Pro Cys Pro Ala Pro Glu Leu Leu
            35                  40                  45

Gly Gly Pro Ser Val Phe Leu Phe Pro Pro Lys Pro Lys Asp Thr Leu
    50                  55                  60

Met Ile Ser Arg Thr Pro Glu Val Thr Cys Val Val Val Asp Val Ser
 65                  70                  75                  80

His Glu Asp Pro Glu Val Lys Phe Asn Trp Tyr Val Asp Gly Val Glu
                 85                  90                  95

Val His Asn Ala Lys Thr Lys Pro Arg Glu Glu Gln Tyr Asn Ser Thr
            100                 105                 110

Tyr Arg Val Val Ser Val Leu Thr Val Leu His Gln Asp Trp Leu Asn
        115                 120                 125

Gly Lys Glu Tyr Lys Cys Lys Val Ser Asn Lys Ala Leu Pro Ala Pro
    130                 135                 140

Ile Glu Lys Thr Ile Ser Lys Ala Lys Gly Gln Pro Arg Glu Pro Gln
145                 150                 155                 160

Val Tyr Thr Leu Pro Pro Ser Arg Glu Glu Met Thr Lys Asn Gln Val
                165                 170                 175

Ser Leu Thr Cys Leu Val Lys Gly Phe Tyr Pro Ser Asp Ile Ala Val
            180                 185                 190

Glu Trp Glu Ser Asn Gly Gln Pro Glu Asn Asn Tyr Lys Thr Thr Pro
        195                 200                 205

Pro Val Leu Asp Ser Asp Gly Ser Phe Phe Leu Tyr Ser Lys Leu Thr
    210                 215                 220

Val Asp Lys Ser Arg Trp Gln Gln Gly Asn Val Phe Ser Cys Ser Val
225                 230                 235                 240

Met His Glu Ala Leu His Asn His Tyr Thr Gln Lys Ser Leu Ser Leu
                245                 250                 255

Ser Pro Gly Lys
            260

<210> SEQ ID NO 52
<211> LENGTH: 287
<212> TYPE: PRT
<213> ORGANISM: Artificial Sequence
<220> FEATURE:
<223> OTHER INFORMATION: Synthetic: hPD-1  amino acid sequence

<400> SEQUENCE: 52

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp Asn
                20                  25                  30

Pro Pro Thr Phe Phe Pro Ala Leu Leu Val Val Thr Glu Gly Asp Asn
            35                  40                  45

Ala Thr Phe Thr Cys Ser Phe Ser Asn Thr Ser Glu Ser Phe Val Leu
        50                  55                  60

Asn Trp Tyr Arg Met Ser Pro Ser Asn Gln Thr Asp Lys Leu Ala Ala
65                  70                  75                  80

Phe Pro Glu Asp Arg Ser Gln Pro Gly Gln Asp Cys Arg Phe Arg Val
                85                  90                  95

Thr Gln Leu Pro Asn Gly Arg Asp Phe His Met Ser Val Val Arg Ala
            100                 105                 110

Arg Arg Asn Asp Ser Gly Thr Tyr Leu Cys Gly Ala Ile Ser Leu Ala
        115                 120                 125

Pro Lys Ala Gln Ile Lys Glu Ser Leu Arg Ala Glu Leu Arg Val Thr
    130                 135                 140

Glu Arg Arg Ala Glu Val Pro Thr Ala His Pro Ser Pro Ser Pro Arg
145                 150                 155                 160

Pro Ala Gly Gln Phe Gln Thr Leu Val Val Gly Val Val Gly Gly Leu
                165                 170                 175

Leu Gly Ser Leu Val Leu Leu Val Trp Val Leu Ala Val Ile Cys Ser
            180                 185                 190

Arg Ala Ala Arg Gly Thr Ile Gly Ala Arg Arg Thr Gly Gln Pro Leu
        195                 200                 205

Lys Glu Asp Pro Ser Ala Val Pro Val Phe Ser Val Asp Tyr Gly Glu
    210                 215                 220

Leu Asp Phe Gln Trp Arg Glu Lys Thr Pro Glu Pro Pro Val Pro Cys
225                 230                 235                 240

Val Pro Glu Gln Thr Glu Tyr Ala Thr Ile Val Phe Pro Ser Gly Met
            245                 250                 255

Gly Thr Ser Ser Pro Ala Arg Arg Gly Ser Ala Asp Gly Pro Arg Ser
            260                 265                 270

Ala Gln Pro Leu Arg Pro Glu Asp Gly His Cys Ser Trp Pro Leu
            275                 280                 285

<210> SEQ ID NO 53
<211> LENGTH: 290
<212> TYPE: PRT
<213> ORGANISM: Artificial Sequence
<220> FEATURE:
<223> OTHER INFORMATION: Synthetic: hPD-L-1 amino acid sequence

<400> SEQUENCE: 53

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 54

```
<211> LENGTH: 180
<212> TYPE: PRT
<213> ORGANISM: Artificial Sequence
<220> FEATURE:
<223> OTHER INFORMATION: Synthetic: hCTLA-4 amino acid sequence

<400> SEQUENCE: 54

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu
            180

<210> SEQ ID NO 55
<211> LENGTH: 525
<212> TYPE: PRT
<213> ORGANISM: Artificial Sequence
<220> FEATURE:
<223> OTHER INFORMATION: Synthetic: hLAG3 amino acid sequence

<400> SEQUENCE: 55

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
```

```
            130                 135                 140
Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
        290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
        450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Gln Leu
        515                 520                 525

<210> SEQ ID NO 56
<211> LENGTH: 300
<212> TYPE: PRT
<213> ORGANISM: Artificial Sequence
```

-continued

<220> FEATURE:
<223> OTHER INFORMATION: Synthetic: hTIM3 amino acid sequence

<400> SEQUENCE: 56

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Gly Ile Tyr Ile Gly Ala Gly Ile
        195                 200                 205

Cys Ala Gly Leu Ala Leu Ala Leu Ile Phe Gly Ala Leu Ile Phe Lys
    210                 215                 220

Trp Tyr Ser His Ser Lys Glu Lys Ile Gln Asn Leu Ser Leu Ile Ser
225                 230                 235                 240

Leu Ala Asn Leu Pro Pro Ser Gly Leu Ala Asn Ala Val Ala Glu Gly
                245                 250                 255

Ile Arg Ser Glu Glu Asn Ile Tyr Thr Ile Glu Glu Asn Val Tyr Glu
            260                 265                 270

Val Glu Glu Pro Asn Glu Tyr Tyr Cys Tyr Val Ser Ser Arg Gln Gln
        275                 280                 285

Pro Ser Gln Pro Leu Gly Cys Arg Phe Ala Met Pro
    290                 295                 300

<210> SEQ ID NO 57
<211> LENGTH: 178
<212> TYPE: PRT
<213> ORGANISM: Artificial Sequence
<220> FEATURE:
<223> OTHER INFORMATION: Synthetic: hB7-H3 amino acid sequence

<400> SEQUENCE: 57

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu

```
                35                  40                  45
Cys Cys Ser Phe Ser Pro Glu Pro Gly Phe Ser Leu Gln Leu Asn Leu
 50                  55                  60

Ile Trp Gln Leu Thr Asp Thr Lys Gln Leu Val His Ser Phe Ala Glu
 65                  70                  75                  80

Gly Gln Asp Gln Gly Ser Ala Tyr Ala Asn Arg Thr Ala Leu Phe Pro
                 85                  90                  95

Asp Leu Leu Ala Gln Gly Asn Ala Ser Leu Arg Leu Arg Val Arg
                100                 105                 110

Val Ala Asp Glu Gly Ser Phe Cys Phe Val Ser Ile Arg Asp Phe Gly
            115                 120                 125

Ser Ala Ala Val Ser Leu Gln Val Ala Ala Pro Tyr Ser Lys Pro Ser
            130                 135                 140

Met Thr Leu Glu Pro Asn Lys Asp Leu Arg Pro Gly Asp Thr Val Thr
145                 150                 155                 160

Ile Thr Cys Ser Ser Tyr Gln Gly Tyr Pro Glu Ala Glu Val Phe Trp
                165                 170                 175

Gln Asp

<210> SEQ ID NO 58
<211> LENGTH: 166
<212> TYPE: PRT
<213> ORGANISM: Artificial Sequence
<220> FEATURE:
<223> OTHER INFORMATION: Synthetic: hB7-H4 amino acid sequence

<400> SEQUENCE: 58

Met Ala Ser Leu Gly Gln Ile Leu Phe Trp Ser Ile Ile Ser Ile Ile
 1               5                  10                  15

Ile Ile Leu Ala Gly Ala Ile Ala Leu Ile Ile Gly Phe Gly Ile Ser
                20                  25                  30

Ala Phe Ser Met Pro Glu Val Asn Val Asp Tyr Asn Ala Ser Ser Glu
            35                  40                  45

Thr Leu Arg Cys Glu Ala Pro Arg Trp Phe Pro Gln Pro Thr Val Val
 50                  55                  60

Trp Ala Ser Gln Val Asp Gln Gly Ala Asn Phe Ser Glu Val Ser Asn
 65                  70                  75                  80

Thr Ser Phe Glu Leu Asn Ser Glu Asn Val Thr Met Lys Val Val Ser
                 85                  90                  95

Val Leu Tyr Asn Val Thr Ile Asn Asn Thr Tyr Ser Cys Met Ile Glu
                100                 105                 110

Asn Asp Ile Ala Lys Ala Thr Gly Asp Ile Lys Val Thr Glu Ser Glu
            115                 120                 125

Ile Lys Arg Arg Ser His Leu Gln Leu Leu Asn Ser Lys Ala Ser Leu
            130                 135                 140

Cys Val Ser Ser Phe Phe Ala Ile Ser Trp Ala Leu Leu Pro Leu Ser
145                 150                 155                 160

Pro Tyr Leu Met Leu Lys
                165

<210> SEQ ID NO 59
<211> LENGTH: 1425
<212> TYPE: DNA
<213> ORGANISM: Artificial Sequence
<220> FEATURE:
<223> OTHER INFORMATION: Synthetic: Anti-VEGF clone B20-4.1.1 Heavy
      Chain nucleic acid sequence
```

<400> SEQUENCE: 59

```
atgggctggt ccctgatcct gctgttcctg gtggctgtgg ccactggcgt gcactctgaa      60
gtgcagctgg tggaatctgg cggcggactg gtgcagcctg gcggatctct gagactgagc     120
tgtgccgcca gcggcttcag catcagcggc agctggatct tctgggtgcg ccaggcccct     180
ggaaagggcc tggaatgggt gggagccatc tggcctttg gcggctacac ccactacgcc      240
gacagcgtga agggccggtt taccatcagc gccgacacca gcaagaacac cgcctacctc     300
cagatgaaca gcctgcgggc cgaggacacc gccgtgtact attgtgccag atggggccac     360
agcacctccc cctgggccat ggattattgg ggccagggaa ccctcgtgac cgtgtcctct     420
gccaaaacaa cagccccatc ggtctatcca ctggcccctg tgtgtggagg tacaactggc     480
tcctcggtga ctctaggatg cctggtcaag ggttatttcc ctgagccagt gaccttgacc     540
tggaactctg gctcactgtc cagtggtgtg cacaccttcc cagctctcct ccaatctggc     600
ctctacaccc tcagcagctc agtgactgta acctcgaaca cctggcccag ccagaccatc     660
acctgcaatg tggcccaccc ggcaagcagc accaaagtgg acaagaaaat tgagcccaga     720
gtgcccataa cacagaaccc ctgtcctcca ctcaaagagt gtcccccatg cgcagctcca     780
gacctcttgg gtggaccatc cgtcttcatc ttccctccaa agatcaagga tgtactcatg     840
atctccctga gccccatggt cacatgtgtg gtggtggatg tgagcgagga tgacccagac     900
gtccagatca gctggtttgt gaacaacgtg gaagtacaca cagctcagac acaaacccat     960
agagaggatt acaacagtac tctccgggtg gtcagtgccc tccccatcca gcaccaggac    1020
tggatgagtg gcaaggagtt caaatgcaag gtcaacaaca gagccctccc atcccccatc    1080
gagaaaacca tctcaaaacc cagagggcca gtaagagctc acaggtata tgtcttgcct    1140
ccaccagcag aagagatgac taagaaagag ttcagtctga cctgcatgat cacaggcttc    1200
ttacctgccg aaattgctgt ggactggacc agcaatgggc gtacagagca aaactacaag    1260
aacaccgcaa cagtcctgga ctctgatggt tcttacttca tgtacagcaa gctcagagta    1320
caaaagagca cttgggaaag aggaagtctt ttcgcctgct cagtggtcca cgagggtctg    1380
cacaatcacc ttacgactaa gaccatctcc cggtctctgg gtaaa                   1425
```

<210> SEQ ID NO 60
<211> LENGTH: 475
<212> TYPE: PRT
<213> ORGANISM: Artificial Sequence
<220> FEATURE:
<223> OTHER INFORMATION: Synthetic: Anti-VEGF clone B20-4.1.1 Heavy
      Chain amino acid sequence

<400> SEQUENCE: 60

```
Met Gly Trp Ser Leu Ile Leu Leu Phe Leu Val Ala Val Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Ile
        35                  40                  45

Ser Gly Ser Trp Ile Phe Trp Val Arg Gln Ala Pro Gly Lys Gly Leu
    50                  55                  60

Glu Trp Val Gly Ala Ile Trp Pro Phe Gly Gly Tyr Thr His Tyr Ala
65                  70                  75                  80

Asp Ser Val Lys Gly Arg Phe Thr Ile Ser Ala Asp Thr Ser Lys Asn
                85                  90                  95
```

Thr Ala Tyr Leu Gln Met Asn Ser Leu Arg Ala Glu Asp Thr Ala Val
            100                 105                 110

Tyr Tyr Cys Ala Arg Trp Gly His Ser Thr Ser Pro Trp Ala Met Asp
        115                 120                 125

Tyr Trp Gly Gln Gly Thr Leu Val Thr Val Ser Ala Lys Thr Thr
130                 135                 140

Ala Pro Ser Val Tyr Pro Leu Ala Pro Val Cys Gly Gly Thr Thr Gly
145                 150                 155                 160

Ser Ser Val Thr Leu Gly Cys Leu Val Lys Gly Tyr Phe Pro Glu Pro
                165                 170                 175

Val Thr Leu Thr Trp Asn Ser Gly Ser Leu Ser Ser Gly Val His Thr
            180                 185                 190

Phe Pro Ala Leu Leu Gln Ser Gly Leu Tyr Thr Leu Ser Ser Ser Val
        195                 200                 205

Thr Val Thr Ser Asn Thr Trp Pro Ser Gln Thr Ile Thr Cys Asn Val
210                 215                 220

Ala His Pro Ala Ser Ser Thr Lys Val Asp Lys Lys Ile Glu Pro Arg
225                 230                 235                 240

Val Pro Ile Thr Gln Asn Pro Cys Pro Pro Leu Lys Glu Cys Pro Pro
                245                 250                 255

Cys Ala Ala Pro Asp Leu Leu Gly Gly Pro Ser Val Phe Ile Phe Pro
            260                 265                 270

Pro Lys Ile Lys Asp Val Leu Met Ile Ser Leu Ser Pro Met Val Thr
        275                 280                 285

Cys Val Val Asp Val Ser Glu Asp Asp Pro Asp Val Gln Ile Ser
290                 295                 300

Trp Phe Val Asn Asn Val Glu Val His Thr Ala Gln Thr Gln Thr His
305                 310                 315                 320

Arg Glu Asp Tyr Asn Ser Thr Leu Arg Val Val Ser Ala Leu Pro Ile
                325                 330                 335

Gln His Gln Asp Trp Met Ser Gly Lys Glu Phe Lys Cys Lys Val Asn
            340                 345                 350

Asn Arg Ala Leu Pro Ser Pro Ile Glu Lys Thr Ile Ser Lys Pro Arg
        355                 360                 365

Gly Pro Val Arg Ala Pro Gln Val Tyr Val Leu Pro Pro Pro Ala Glu
370                 375                 380

Glu Met Thr Lys Lys Glu Phe Ser Leu Thr Cys Met Ile Thr Gly Phe
385                 390                 395                 400

Leu Pro Ala Glu Ile Ala Val Asp Trp Thr Ser Asn Gly Arg Thr Glu
                405                 410                 415

Gln Asn Tyr Lys Asn Thr Ala Thr Val Leu Asp Ser Asp Gly Ser Tyr
            420                 425                 430

Phe Met Tyr Ser Lys Leu Arg Val Gln Lys Ser Thr Trp Glu Arg Gly
        435                 440                 445

Ser Leu Phe Ala Cys Ser Val Val His Glu Gly Leu His Asn His Leu
450                 455                 460

Thr Thr Lys Thr Ile Ser Arg Ser Leu Gly Lys
465                 470                 475

<210> SEQ ID NO 61
<211> LENGTH: 708
<212> TYPE: DNA
<213> ORGANISM: Artificial Sequence
<220> FEATURE:

<223> OTHER INFORMATION: Synthetic: Anti-VEGF clone B20-4.1.1 Light
Chain nucleic acid sequence

<400> SEQUENCE: 61

```
atggacatga gagtgcccgc ccagctgctg ggacttctgc tgctgtggct gccaggcgcc      60
agatgcgaca tccagatgac ccagagcccc agcagcctgt ctgccagcgt gggcgacaga    120
gtgaccatca cctgtagagc ctctcagggc gtgcggacaa gcctggcctg gtatcagcag    180
aagcctggca aggccccaa gctgctgatc tacgatgcca gctctctggc cagcggcgtg     240
cccagcagat tttctggcag cggctccggc accgacttca ccctgacaat cagctccctc    300
cagcccgagg acttcgccac ctactactgc cagcagagct acaagagccc cctgaccttt    360
ggccagggca ccaaggtgga aatcaagcgg gctgatgctg caccaactgt atccatcttc    420
ccaccatcca gtgagcagtt aacatctgga ggtgcctcag tcgtgtgctt cttgaacaac    480
ttctacccca agacatcaa tgtcaagtgg aagattgatg gcagtgaacg acaaaatggc     540
gtcctgaaca gttggactga tcaggacagc aaagacagca cctacagcat gagcagcacc    600
ctcacgttga ccaaggacga gtatgaacga cataacagct atacctgtga ggccactcac    660
aagacatcaa cttcacccat tgtcaagagc ttcaacagga atgagtgt                708
```

<210> SEQ ID NO 62
<211> LENGTH: 236
<212> TYPE: PRT
<213> ORGANISM: Artificial Sequence
<220> FEATURE:
<223> OTHER INFORMATION: Synthetic: Anti-VEGF clone B20-4.1.1 Light
Chain amino acid sequence

<400> SEQUENCE: 62

```
Met Asp Met Arg Val Pro Ala Gln Leu Leu Gly Leu Leu Leu Leu Trp
1               5                   10                  15

Leu Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Val Arg Thr Ser Leu Ala Trp Tyr Gln Gln Lys Pro Gly Lys
    50                  55                  60

Ala Pro Lys Leu Leu Ile Tyr Asp Ala Ser Ser Leu Ala Ser Gly Val
65                  70                  75                  80

Pro Ser Arg Phe Ser Gly Ser Gly Ser Gly Thr Asp Phe Thr Leu Thr
            85                  90                  95

Ile Ser Ser Leu Gln Pro Glu Asp Phe Ala Thr Tyr Tyr Cys Gln Gln
        100                 105                 110

Ser Tyr Lys Ser Pro Leu Thr Phe Gly Gln Gly Thr Lys Val Glu Ile
    115                 120                 125

Lys Arg Ala Asp Ala Ala Pro Thr Val Ser Ile Phe Pro Pro Ser Ser
130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
            165                 170                 175

Arg Gln Asn Gly Val Leu Asn Ser Trp Thr Asp Gln Asp Ser Lys Asp
        180                 185                 190

Ser Thr Tyr Ser Met Ser Ser Thr Leu Thr Leu Thr Lys Asp Glu Tyr
    195                 200                 205
```

Glu Arg His Asn Ser Tyr Thr Cys Glu Ala Thr His Lys Thr Ser Thr
        210                 215                 220

Ser Pro Ile Val Lys Ser Phe Asn Arg Asn Glu Cys
225                 230                 235

<210> SEQ ID NO 63
<211> LENGTH: 1413
<212> TYPE: DNA
<213> ORGANISM: Artificial Sequence
<220> FEATURE:
<223> OTHER INFORMATION: Synthetic: Anti-CTLA-4 clone 9D9 Heavy Chain
      nucleic acid sequence

<400> SEQUENCE: 63
atgggctggt ccctgatcct gctgttcctg gtggctgtgg ccaccggcgt gcactctgaa     60
gccaagctcc aggaatccgg ccctgtgctc gtgaagcctg gcgcctctgt gaagatgagc    120
tgcaaggcca gcggctacac ctttaccgac tactacatga actgggtcaa gcagagccac    180
ggccagtctc tggaatggat cggcgtgatc aaccccctac acggcgacac cagctacaac    240
cagaagttca agggcaaggc cacctgacc gtggacaaga gcagcagcac cgcctacatg     300
gaactgaaca gcctgaccag cgaggacagc gccgtgtact attgcgcccg gtactacggc    360
agttggttcg cctattgggg ccagggcacc ctgatcaccg tgtccacagc caaaacaaca    420
gccccatcgg tctatccact ggcccctgtg tgtggaggta caactggctc ctcggtgact    480
ctaggatgcc tggtcaaggg ttatttccct gagccagtga ccttgacctg aactctggc     540 tcactgtcca gtggtgtgca ccttccca gctctcctcc aatctggcct ctacaccctc      600
agcagctcag tgactgtaac ctcgaacacc tggcccagcc agaccatcac ctgcaatgtg    660
gcccacccgg caagcagcac caaagtggac aagaaaattg agcccagagt gcccataaca    720
cagaacccct gtcctccact caaagagtgt cccccatgcg cagctccaga cctcttgggt    780
ggaccatccg tcttcatctt ccctccaaag atcaaggatg tactcatgat ctccctgagc    840
cccatggtca catgtgtggt ggtggatgtg agcgaggatg acccagacgt ccagatcagc    900
tggtttgtga acaacgtgga agtacacaca gctcagacac aaacccatag agaggattac    960
aacagtactc tccgggtggt cagtgccctc cccatccagc accaggactg gatgagtggc   1020
aaggagttca atgcaaggt caacaacaga gccctcccat cccccatcga gaaaccatc    1080 tcaaaaccca gagggccagt aagagctcca caggtatatg tcttgcctcc accagcagaa   1140
gagatgacta agaaagagtt cagtctgacc tgcatgatca caggcttctt acctgccgaa   1200
attgctgtgg actggaccag caatgggcgt acagagcaaa actacaagaa caccgcaaca   1260
gtcctggact ctgatggttc ttacttcatg tacagcaagc tcagagtaca aaagagcact   1320
tgggaaagag gaagtctttt cgcctgctca gtgtccacg agggtctgca caatcacctt   1380
acgactaaga ccatctcccg gtctctgggt aaa                               1413

<210> SEQ ID NO 64
<211> LENGTH: 471
<212> TYPE: PRT
<213> ORGANISM: Artificial Sequence
<220> FEATURE:
<223> OTHER INFORMATION: Synthetic: Anti-CTLA-4 clone 9D9 Heavy Chain
      amino acid sequence

<400> SEQUENCE: 64

Met Gly Trp Ser Leu Ile Leu Leu Phe Leu Val Ala Val Ala Thr Gly
1               5                   10                  15

-continued

```
Val His Ser Glu Ala Lys Leu Gln Glu Ser Gly Pro Val Leu Val Lys
                20                  25                  30
Pro Gly Ala Ser Val Lys Met Ser Cys Lys Ala Ser Gly Tyr Thr Phe
            35                  40                  45
Thr Asp Tyr Tyr Met Asn Trp Val Lys Gln Ser His Gly Lys Ser Leu
        50                  55                  60
Glu Trp Ile Gly Val Ile Asn Pro Tyr Asn Gly Asp Thr Ser Tyr Asn
65                  70                  75                  80
Gln Lys Phe Lys Gly Lys Ala Thr Leu Thr Val Asp Lys Ser Ser Ser
                85                  90                  95
Thr Ala Tyr Met Glu Leu Asn Ser Leu Thr Ser Glu Asp Ser Ala Val
            100                 105                 110
Tyr Tyr Cys Ala Arg Tyr Tyr Gly Ser Trp Phe Ala Tyr Trp Gly Gln
        115                 120                 125
Gly Thr Leu Ile Thr Val Ser Thr Ala Lys Thr Thr Ala Pro Ser Val
        130                 135                 140
Tyr Pro Leu Ala Pro Val Cys Gly Gly Thr Thr Gly Ser Ser Val Thr
145                 150                 155                 160
Leu Gly Cys Leu Val Lys Gly Tyr Phe Pro Glu Pro Val Thr Leu Thr
                165                 170                 175
Trp Asn Ser Gly Ser Leu Ser Ser Gly Val His Thr Phe Pro Ala Leu
            180                 185                 190
Leu Gln Ser Gly Leu Tyr Thr Leu Ser Ser Ser Val Thr Val Thr Ser
        195                 200                 205
Asn Thr Trp Pro Ser Gln Thr Ile Thr Cys Asn Val Ala His Pro Ala
210                 215                 220
Ser Ser Thr Lys Val Asp Lys Lys Ile Glu Pro Arg Val Pro Ile Thr
225                 230                 235                 240
Gln Asn Pro Cys Pro Pro Leu Lys Glu Cys Pro Pro Cys Ala Ala Pro
                245                 250                 255
Asp Leu Leu Gly Gly Pro Ser Val Phe Ile Phe Pro Pro Lys Ile Lys
            260                 265                 270
Asp Val Leu Met Ile Ser Leu Ser Pro Met Val Thr Cys Val Val Val
        275                 280                 285
Asp Val Ser Glu Asp Asp Pro Asp Val Gln Ile Ser Trp Phe Val Asn
290                 295                 300
Asn Val Glu Val His Thr Ala Gln Thr Gln Thr His Arg Glu Asp Tyr
305                 310                 315                 320
Asn Ser Thr Leu Arg Val Val Ser Ala Leu Pro Ile Gln His Gln Asp
                325                 330                 335
Trp Met Ser Gly Lys Glu Phe Lys Cys Lys Val Asn Asn Arg Ala Leu
            340                 345                 350
Pro Ser Pro Ile Glu Lys Thr Ile Ser Lys Pro Arg Gly Pro Val Arg
        355                 360                 365
Ala Pro Gln Val Tyr Val Leu Pro Pro Ala Glu Glu Met Thr Lys
        370                 375                 380
Lys Glu Phe Ser Leu Thr Cys Met Ile Thr Gly Phe Leu Pro Ala Glu
385                 390                 395                 400
Ile Ala Val Asp Trp Thr Ser Asn Gly Arg Thr Glu Gln Asn Tyr Lys
                405                 410                 415
Asn Thr Ala Thr Val Leu Asp Ser Asp Gly Ser Tyr Phe Met Tyr Ser
            420                 425                 430
Lys Leu Arg Val Gln Lys Ser Thr Trp Glu Arg Gly Ser Leu Phe Ala
```

```
                435                 440                 445
Cys Ser Val Val His Glu Gly Leu His Asn His Leu Thr Thr Lys Thr
    450                 455                 460

Ile Ser Arg Ser Leu Gly Lys
465                 470

<210> SEQ ID NO 65
<211> LENGTH: 723
<212> TYPE: DNA
<213> ORGANISM: Artificial Sequence
<220> FEATURE:
<223> OTHER INFORMATION: Synthetic: Anti-CTLA-4 clone 9D9 Light Chain
      nucleic acid sequence

<400> SEQUENCE: 65
atggacatga gagtgcccgc ccagctgctg ggacttctgc tgctgtggct gccaggcgcc       60
agatgcgaca tcgtgatgac ccagaccacc ctgagcctgc ctgtgtccct gggagatcag      120
gccagcatca gctgtcggag cagccagagc atcgtgcaca gcaacggcaa cacctacctg      180
gaatggtatc tccagaagcc cggccagagc cccaagctgc tgatctacaa ggtgtccaac      240
cggttcagcg gcgtgcccga cagatttttct ggcagcggct ccggcaccga cttcaccctg      300
aagatctccc gggtggaagc cgaggacctg ggcgtgtact actgttttca aggcagccac      360
gtgccctaca ccttcggcgg aggcaccaag ctggaaatca gcgggctga tgctgcacca      420 actgtatcca tcttcccacc atccagtgag cagttaacat ctggaggtgc ctcagtcgtg      480
tgcttcttga caacttcta cccccaaagac atcaatgtca gtggaagat tgatggcagt      540 gaacgacaaa atggcgtcct gaacagttgg actgatcagg acagcaaaga cagcacctac      600
agcatgagca gcaccctcac gttgaccaag gacgagtatg aacgacataa cagctatacc      660
tgtgaggcca ctcacaagac atcaacttca cccattgtca gagcttcaa caggaatgag      720 tgt                                                                    723

<210> SEQ ID NO 66
<211> LENGTH: 241
<212> TYPE: PRT
<213> ORGANISM: Artificial Sequence
<220> FEATURE:
<223> OTHER INFORMATION: Synthetic: Anti-CTLA-4 clone 9D9 Light Chain
      amino acid sequence

<400> SEQUENCE: 66

Met Asp Met Arg Val Pro Ala Gln Leu Leu Gly Leu Leu Leu Leu Trp
1               5                   10                  15

Leu Pro Gly Ala Arg Cys Asp Ile Val Met Thr Gln Thr Thr Leu Ser
            20                  25                  30

Leu Pro Val Ser Leu Gly Asp Gln Ala Ser Ile Ser Cys Arg Ser Ser
        35                  40                  45

Gln Ser Ile Val His Ser Asn Gly Asn Thr Tyr Leu Glu Trp Tyr Leu
    50                  55                  60

Gln Lys Pro Gly Gln Ser Pro Lys Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Leu Gly Val
            100                 105                 110

Tyr Tyr Cys Phe Gln Gly Ser His Val Pro Tyr Thr Phe Gly Gly Gly
        115                 120                 125
```

```
Thr Lys Leu Glu Ile Lys Arg Ala Asp Ala Ala Pro Thr Val Ser Ile
        130                 135                 140

Phe Pro Pro Ser Ser Glu Gln Leu Thr Ser Gly Gly Ala Ser Val Val
145                 150                 155                 160

Cys Phe Leu Asn Asn Phe Tyr Pro Lys Asp Ile Asn Val Lys Trp Lys
                165                 170                 175

Ile Asp Gly Ser Glu Arg Gln Asn Gly Val Leu Asn Ser Trp Thr Asp
                180                 185                 190

Gln Asp Ser Lys Asp Ser Thr Tyr Ser Met Ser Ser Thr Leu Thr Leu
                195                 200                 205

Thr Lys Asp Glu Tyr Glu Arg His Asn Ser Tyr Thr Cys Glu Ala Thr
        210                 215                 220

His Lys Thr Ser Thr Ser Pro Ile Val Lys Ser Phe Asn Arg Asn Glu
225                 230                 235                 240

Cys

<210> SEQ ID NO 67
<211> LENGTH: 33
<212> TYPE: PRT
<213> ORGANISM: Artificial Sequence
<220> FEATURE:
<223> OTHER INFORMATION: Synthetic: EETI-II 1.4A

<400> SEQUENCE: 67

Gly Cys Ala Glu Pro Arg Gly Asp Met Pro Trp Thr Trp Cys Lys Gln
1               5                   10                  15

Asp Ser Asp Cys Leu Ala Gly Cys Val Cys Gly Pro Asn Gly Phe Cys
                20                  25                  30

Gly

<210> SEQ ID NO 68
<211> LENGTH: 33
<212> TYPE: PRT
<213> ORGANISM: Artificial Sequence
<220> FEATURE:
<223> OTHER INFORMATION: Synthetic: EETI-II 1.4B

<400> SEQUENCE: 68

Gly Cys Val Gly Gly Arg Gly Asp Trp Ser Pro Lys Trp Cys Lys Gln
1               5                   10                  15

Asp Ser Asp Cys Pro Ala Gly Cys Val Cys Gly Pro Asn Gly Phe Cys
                20                  25                  30

Gly

<210> SEQ ID NO 69
<211> LENGTH: 33
<212> TYPE: PRT
<213> ORGANISM: Artificial Sequence
<220> FEATURE:
<223> OTHER INFORMATION: Synthetic: EETI-II 1.4C

<400> SEQUENCE: 69

Gly Cys Ala Glu Leu Arg Gly Asp Arg Ser Tyr Pro Glu Cys Lys Gln
1               5                   10                  15

Asp Ser Asp Cys Leu Ala Gly Cys Val Cys Gly Pro Asn Gly Phe Cys
                20                  25                  30

Gly
```

-continued

```
<210> SEQ ID NO 70
<211> LENGTH: 33
<212> TYPE: PRT
<213> ORGANISM: Artificial Sequence
<220> FEATURE:
<223> OTHER INFORMATION: Synthetic: EETI-II 1.4E

<400> SEQUENCE: 70

Gly Cys Arg Leu Pro Arg Gly Asp Val Pro Arg Pro His Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 71
<211> LENGTH: 33
<212> TYPE: PRT
<213> ORGANISM: Artificial Sequence
<220> FEATURE:
<223> OTHER INFORMATION: Synthetic: EETI-II 1.4H

<400> SEQUENCE: 71

Gly Cys Tyr Pro Leu Arg Gly Asp Asn Pro Tyr Ala Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 72
<211> LENGTH: 33
<212> TYPE: PRT
<213> ORGANISM: Artificial Sequence
<220> FEATURE:
<223> OTHER INFORMATION: Synthetic: EETI-II 1.5B

<400> SEQUENCE: 72

Gly Cys Thr Ile Gly Arg Gly Asp Trp Ala Pro Ser Glu Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 73
<211> LENGTH: 33
<212> TYPE: PRT
<213> ORGANISM: Artificial Sequence
<220> FEATURE:
<223> OTHER INFORMATION: Synthetic: EETI-II 1.5F

<400> SEQUENCE: 73

Gly Cys His Pro Pro Arg Gly Asp Asn Pro Pro Val Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 74
<211> LENGTH: 33
<212> TYPE: PRT
<213> ORGANISM: Artificial Sequence
<220> FEATURE:
<223> OTHER INFORMATION: Synthetic: EETI-II 2.3A
```

<400> SEQUENCE: 74

Gly Cys Pro Glu Pro Arg Gly Asp Asn Pro Pro Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 75
<211> LENGTH: 33
<212> TYPE: PRT
<213> ORGANISM: Artificial Sequence
<220> FEATURE:
<223> OTHER INFORMATION: Synthetic: EETI-II 2.3B

<400> SEQUENCE: 75

Gly Cys Leu Pro Pro Arg Gly Asp Asn Pro Pro Ser Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 76
<211> LENGTH: 33
<212> TYPE: PRT
<213> ORGANISM: Artificial Sequence
<220> FEATURE:
<223> OTHER INFORMATION: Synthetic: EETI-II 2.3C

<400> SEQUENCE: 76

Gly Cys His Leu Gly Arg Gly Asp Trp Ala Pro Val Gly Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 77
<211> LENGTH: 33
<212> TYPE: PRT
<213> ORGANISM: Artificial Sequence
<220> FEATURE:
<223> OTHER INFORMATION: Synthetic: EETI-II 2.3D

<400> SEQUENCE: 77

Gly Cys Asn Val Gly Arg Gly Asp Trp Ala Pro Ser Glu Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 78
<211> LENGTH: 33
<212> TYPE: PRT
<213> ORGANISM: Artificial Sequence
<220> FEATURE:
<223> OTHER INFORMATION: Synthetic: EETI-II 2..3E

<400> SEQUENCE: 78

Gly Cys Phe Pro Gly Arg Gly Asp Trp Ala Pro Ser Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 79
<211> LENGTH: 33
<212> TYPE: PRT
<213> ORGANISM: Artificial Sequence
<220> FEATURE:
<223> OTHER INFORMATION: Synthetic: EETI-II 2.3F

<400> SEQUENCE: 79

Gly Cys Pro Leu Pro Arg Gly Asp Asn Pro Thr Glu Cys Lys Gln
1               5                   10                  15

Asp Ser Asp Cys Gln Ala Gly Cys Val Cys Pro Asn Gly Phe Cys
            20                  25                  30

Gly

<210> SEQ ID NO 80
<211> LENGTH: 33
<212> TYPE: PRT
<213> ORGANISM: Artificial Sequence
<220> FEATURE:
<223> OTHER INFORMATION: Synthetic: EETI-II 2.3G

<400> SEQUENCE: 80

Gly Cys Ser Glu Ala Arg Gly Asp Asn Pro Arg Leu Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 81
<211> LENGTH: 32
<212> TYPE: PRT
<213> ORGANISM: Artificial Sequence
<220> FEATURE:
<223> OTHER INFORMATION: Synthetic: EETI-II 2.3H

<400> SEQUENCE: 81

Gly Cys Leu Leu Gly Arg Gly Asp Trp Ala Pro Glu Ala Cys Lys Gln
1               5                   10                  15

Asp Ser Asp Cys Arg Ala Gly Cys Val Cys Pro Asn Gly Phe Cys Gly
            20                  25                  30

<210> SEQ ID NO 82
<211> LENGTH: 33
<212> TYPE: PRT
<213> ORGANISM: Artificial Sequence
<220> FEATURE:
<223> OTHER INFORMATION: Synthetic: EETI-II 2.3I

<400> SEQUENCE: 82

Gly Cys His Val Gly Arg Gly Asp Trp Ala Pro Leu Lys Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 83
<211> LENGTH: 33
<212> TYPE: PRT
<213> ORGANISM: Artificial Sequence
<220> FEATURE:

<223> OTHER INFORMATION: Synthetic: EETI-II 2.3J

<400> SEQUENCE: 83

Gly Cys Val Arg Gly Arg Gly Asp Trp Ala Pro Pro Ser Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 84
<211> LENGTH: 33
<212> TYPE: PRT
<213> ORGANISM: Artificial Sequence
<220> FEATURE:
<223> OTHER INFORMATION: Synthetic: EETI-II 2.4A

<400> SEQUENCE: 84

Gly Cys Leu Gly Gly Arg Gly Asp Trp Ala Pro Pro Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 85
<211> LENGTH: 33
<212> TYPE: PRT
<213> ORGANISM: Artificial Sequence
<220> FEATURE:
<223> OTHER INFORMATION: Synthetic: EETI-II 2.4C

<400> SEQUENCE: 85

Gly Cys Phe Val Gly Arg Gly Asp Trp Ala Pro Leu Thr Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 86
<211> LENGTH: 33
<212> TYPE: PRT
<213> ORGANISM: Artificial Sequence
<220> FEATURE:
<223> OTHER INFORMATION: Synthetic: EETI-II 2.4D

<400> SEQUENCE: 86

Gly Cys Pro Val Gly Arg Gly Asp Trp Ser Pro Ala Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 87
<211> LENGTH: 33
<212> TYPE: PRT
<213> ORGANISM: Artificial Sequence
<220> FEATURE:
<223> OTHER INFORMATION: Synthetic: EETI-II 2.4E

<400> SEQUENCE: 87

Gly Cys Pro Arg Pro Arg Gly Asp Asn Pro Pro Leu Thr Cys Lys Gln
1               5                   10                  15

```
Asp Ser Asp Cys Leu Ala Gly Cys Val Cys Gly Pro Asn Gly Phe Cys
            20                  25                  30

Gly

<210> SEQ ID NO 88
<211> LENGTH: 33
<212> TYPE: PRT
<213> ORGANISM: Artificial Sequence
<220> FEATURE:
<223> OTHER INFORMATION: Synthetic: EETI-II 2.4F

<400> SEQUENCE: 88

Gly Cys Tyr Gln Gly Arg Gly Asp Trp Ser Pro Ser Ser Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 89
<211> LENGTH: 33
<212> TYPE: PRT
<213> ORGANISM: Artificial Sequence
<220> FEATURE:
<223> OTHER INFORMATION: Synthetic: EETI-II 2.4G

<400> SEQUENCE: 89

Gly Cys Ala Pro Gly Arg Gly Asp Trp Ala Pro Ser Glu Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 90
<211> LENGTH: 33
<212> TYPE: PRT
<213> ORGANISM: Artificial Sequence
<220> FEATURE:
<223> OTHER INFORMATION: Synthetic: EETI-II 2.4J

<400> SEQUENCE: 90

Gly Cys Val Gln Gly Arg Gly Asp Trp Ser Pro Pro Ser Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 91
<211> LENGTH: 33
<212> TYPE: PRT
<213> ORGANISM: Artificial Sequence
<220> FEATURE:
<223> OTHER INFORMATION: Synthetic: EETI-II 2.5A

<400> SEQUENCE: 91

Gly Cys His Val Gly Arg Gly Asp Trp Ala Pro Glu Glu Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 92
```

```
<211> LENGTH: 33
<212> TYPE: PRT
<213> ORGANISM: Artificial Sequence
<220> FEATURE:
<223> OTHER INFORMATION: Synthetic: EETI-II 2.5C

<400> SEQUENCE: 92

Gly Cys Asp Gly Gly Arg Gly Asp Trp Ala Pro Pro Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 93
<211> LENGTH: 33
<212> TYPE: PRT
<213> ORGANISM: Artificial Sequence
<220> FEATURE:
<223> OTHER INFORMATION: Synthetic: EETI-II 2.5D

<400> SEQUENCE: 93

Gly Cys Pro Gln Gly Arg Gly Asp Trp Ala Pro Thr Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 94
<211> LENGTH: 33
<212> TYPE: PRT
<213> ORGANISM: Artificial Sequence
<220> FEATURE:
<223> OTHER INFORMATION: Synthetic: EETI-II 2.5F

<400> SEQUENCE: 94

Gly Cys Pro Arg Pro Arg Gly Asp Asn Pro Pro Leu Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 95
<211> LENGTH: 33
<212> TYPE: PRT
<213> ORGANISM: Artificial Sequence
<220> FEATURE:
<223> OTHER INFORMATION: Synthetic: EETI-II 2.5D K15S Mutant

<400> SEQUENCE: 95

Gly Cys Pro Gln Gly Arg Gly Asp Trp Ala Pro Thr Ser Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 96
<211> LENGTH: 33
<212> TYPE: PRT
<213> ORGANISM: Artificial Sequence
<220> FEATURE:
<223> OTHER INFORMATION: Synthetic: EETI-II 2.5F K15S Mutant

<400> SEQUENCE: 96
```

```
Gly Cys Pro Arg Pro Arg Gly Asp Asn Pro Pro Leu Thr Cys Ser Gln
1               5                   10                  15

Asp Ser Asp Cys Leu Ala Gly Cys Val Cys Pro Asn Gly Phe Cys
            20                  25                  30

Gly

<210> SEQ ID NO 97
<211> LENGTH: 33
<212> TYPE: PRT
<213> ORGANISM: Artificial Sequence
<220> FEATURE:
<223> OTHER INFORMATION: Synthetic: EETI-II 2.5H

<400> SEQUENCE: 97

Gly Cys Pro Gln Gly Arg Gly Asp Trp Ala Pro Glu Trp Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 98
<211> LENGTH: 33
<212> TYPE: PRT
<213> ORGANISM: Artificial Sequence
<220> FEATURE:
<223> OTHER INFORMATION: Synthetic: EETI-II 2.5J

<400> SEQUENCE: 98

Gly Cys Pro Arg Gly Arg Gly Asp Trp Ser Pro Pro Ala Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 99
<211> LENGTH: 38
<212> TYPE: PRT
<213> ORGANISM: Artificial Sequence
<220> FEATURE:
<223> OTHER INFORMATION: Synthetic: AgRp 3A

<400> SEQUENCE: 99

Gly Cys Val Arg Leu His Glu Ser Cys Leu Gly Gln Gln Val Pro Cys
1               5                   10                  15

Cys Asp Pro Ala Ala Thr Cys Tyr Cys Val Val Arg Gly Asp Trp Arg
            20                  25                  30

Lys Arg Cys Tyr Cys Arg
        35

<210> SEQ ID NO 100
<211> LENGTH: 38
<212> TYPE: PRT
<213> ORGANISM: Artificial Sequence
<220> FEATURE:
<223> OTHER INFORMATION: Synthetic: AgRp 3B

<400> SEQUENCE: 100

Gly Cys Val Arg Leu His Glu Ser Cys Leu Gly Gln Gln Val Pro Cys
1               5                   10                  15

Cys Asp Pro Ala Ala Thr Cys Tyr Cys Glu Glu Arg Gly Asp Met Leu
            20                  25                  30
```

Glu Lys Cys Tyr Cys Arg
        35

<210> SEQ ID NO 101
<211> LENGTH: 38
<212> TYPE: PRT
<213> ORGANISM: Artificial Sequence
<220> FEATURE:
<223> OTHER INFORMATION: Synthetic: AgRp 3C

<400> SEQUENCE: 101

Gly Cys Val Arg Leu His Glu Ser Cys Leu Gly Gln Gln Val Pro Cys
1               5                   10                  15

Cys Asp Pro Ala Ala Thr Cys Tyr Cys Glu Thr Arg Gly Asp Gly Lys
            20                  25                  30

Glu Lys Cys Tyr Cys Arg
        35

<210> SEQ ID NO 102
<211> LENGTH: 38
<212> TYPE: PRT
<213> ORGANISM: Artificial Sequence
<220> FEATURE:
<223> OTHER INFORMATION: Synthetic: AgRp 3D

<400> SEQUENCE: 102

Gly Cys Val Arg Leu His Glu Ser Cys Leu Gly Gln Gln Val Pro Cys
1               5                   10                  15

Cys Asp Pro Ala Ala Thr Cys Tyr Cys Gln Trp Arg Gly Asp Gly Asp
            20                  25                  30

Val Lys Cys Tyr Cys Arg
        35

<210> SEQ ID NO 103
<211> LENGTH: 38
<212> TYPE: PRT
<213> ORGANISM: Artificial Sequence
<220> FEATURE:
<223> OTHER INFORMATION: Synthetic: AgRp 3E

<400> SEQUENCE: 103

Gly Cys Val Arg Leu His Glu Ser Cys Leu Gly Gln Gln Val Pro Cys
1               5                   10                  15

Cys Asp Pro Ala Ala Thr Cys Tyr Cys Ser Arg Arg Gly Asp Met Arg
            20                  25                  30

Glu Arg Cys Tyr Cys Arg
        35

<210> SEQ ID NO 104
<211> LENGTH: 38
<212> TYPE: PRT
<213> ORGANISM: Artificial Sequence
<220> FEATURE:
<223> OTHER INFORMATION: Synthetic: AgRp 3F

<400> SEQUENCE: 104

Gly Cys Val Arg Leu His Glu Ser Cys Leu Gly Gln Gln Val Pro Cys
1               5                   10                  15

Cys Asp Pro Ala Ala Thr Cys Tyr Cys Gln Tyr Arg Gly Asp Gly Met
            20                  25                  30

Lys His Cys Tyr Cys Arg
        35

```
<210> SEQ ID NO 105
<211> LENGTH: 38
<212> TYPE: PRT
<213> ORGANISM: Artificial Sequence
<220> FEATURE:
<223> OTHER INFORMATION: Synthetic: AgRp 3G

<400> SEQUENCE: 105

Gly Cys Val Arg Leu His Glu Ser Cys Leu Gly Gln Gln Val Pro Cys
1               5                   10                  15

Cys Asp Pro Ala Ala Thr Cys Tyr Cys Thr Gly Arg Gly Asp Thr Lys
                20                  25                  30

Val Leu Cys Tyr Cys Arg
        35

<210> SEQ ID NO 106
<211> LENGTH: 38
<212> TYPE: PRT
<213> ORGANISM: Artificial Sequence
<220> FEATURE:
<223> OTHER INFORMATION: Synthetic: AgRp 3H

<400> SEQUENCE: 106

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Met Lys
                20                  25                  30

Arg Arg Cys Tyr Cys Arg
        35

<210> SEQ ID NO 107
<211> LENGTH: 38
<212> TYPE: PRT
<213> ORGANISM: Artificial Sequence
<220> FEATURE:
<223> OTHER INFORMATION: Synthetic: AgRp 3I

<400> SEQUENCE: 107

Gly Cys Val Arg Leu His Glu Ser Cys Leu Gly Gln Gln Val Pro Cys
1               5                   10                  15

Cys Asp Pro Ala Ala Thr Cys Tyr Cys Thr Gly Arg Gly Asp Val Arg
                20                  25                  30

Met Asn Cys Tyr Cys Arg
        35

<210> SEQ ID NO 108
<211> LENGTH: 38
<212> TYPE: PRT
<213> ORGANISM: Artificial Sequence
<220> FEATURE:
<223> OTHER INFORMATION: Synthetic: AgRp 3J

<400> SEQUENCE: 108

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Met
                20                  25                  30

Ser Lys Cys Tyr Cys Arg
        35

<210> SEQ ID NO 109
```

<211> LENGTH: 38
<212> TYPE: PRT
<213> ORGANISM: Artificial Sequence
<220> FEATURE:
<223> OTHER INFORMATION: Synthetic: AgRp 4A

<400> SEQUENCE: 109

Gly Cys Val Arg Leu His Glu Ser Cys Leu Gly Gln Gln Val Pro Cys
1               5                   10                  15

Cys Asp Pro Ala Ala Thr Cys Tyr Cys Arg Gly Arg Gly Asp Met Arg
            20                  25                  30

Arg Glu Cys Tyr Cys Arg
        35

<210> SEQ ID NO 110
<211> LENGTH: 38
<212> TYPE: PRT
<213> ORGANISM: Artificial Sequence
<220> FEATURE:
<223> OTHER INFORMATION: Synthetic: AgRp 4B

<400> SEQUENCE: 110

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Val Lys
            20                  25                  30

Val Asn Cys Tyr Cys Arg
        35

<210> SEQ ID NO 111
<211> LENGTH: 38
<212> TYPE: PRT
<213> ORGANISM: Artificial Sequence
<220> FEATURE:
<223> OTHER INFORMATION: Synthetic: AgRp 4C

<400> SEQUENCE: 111

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Glu Lys
            20                  25                  30

Met Ser Cys Tyr Cys Arg
        35

<210> SEQ ID NO 112
<211> LENGTH: 38
<212> TYPE: PRT
<213> ORGANISM: Artificial Sequence
<220> FEATURE:
<223> OTHER INFORMATION: Synthetic: AgRp 4D

<400> SEQUENCE: 112

Gly Cys Val Arg Leu His Glu Ser Cys Leu Gly Gln Gln Val Pro Cys
1               5                   10                  15

Cys Asp Pro Ala Ala Thr Cys Tyr Cys Val Ser Arg Gly Asp Met Arg
            20                  25                  30

Lys Arg Cys Tyr Cys Arg
        35

<210> SEQ ID NO 113
<211> LENGTH: 38
<212> TYPE: PRT
<213> ORGANISM: Artificial Sequence
<220> FEATURE:
<223> OTHER INFORMATION: Synthetic: AgRp 4E

<400> SEQUENCE: 113

Gly Cys Val Arg Leu His Glu Ser Cys Leu Gly Gln Gln Val Pro Cys
1               5                   10                  15

Cys Asp Pro Ala Ala Thr Cys Tyr Cys Glu Arg Arg Gly Asp Ser Val
            20                  25                  30

Lys Lys Cys Tyr Cys Arg
        35

<210> SEQ ID NO 114
<211> LENGTH: 38
<212> TYPE: PRT
<213> ORGANISM: Artificial Sequence
<220> FEATURE:
<223> OTHER INFORMATION: Synthetic: AgRp 4F

<400> SEQUENCE: 114

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Thr Arg
            20                  25                  30

Arg Arg Cys Tyr Cys Arg
        35

<210> SEQ ID NO 115
<211> LENGTH: 38
<212> TYPE: PRT
<213> ORGANISM: Artificial Sequence
<220> FEATURE:
<223> OTHER INFORMATION: Synthetic: AgRp 4G

<400> SEQUENCE: 115

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Val Val
            20                  25                  30

Arg Arg Cys Tyr Cys Arg
        35

<210> SEQ ID NO 116
<211> LENGTH: 38
<212> TYPE: PRT
<213> ORGANISM: Artificial Sequence
<220> FEATURE:
<223> OTHER INFORMATION: Synthetic: AgRp 4H

<400> SEQUENCE: 116

Gly Cys Val Arg Leu His Glu Ser Cys Leu Gly Gln Gln Val Pro Cys
1               5                   10                  15

Cys Asp Pro Ala Ala Thr Cys Tyr Cys Lys Gly Arg Gly Asp Asn Lys
            20                  25                  30

Arg Lys Cys Tyr Cys Arg
        35

<210> SEQ ID NO 117
<211> LENGTH: 38
<212> TYPE: PRT
<213> ORGANISM: Artificial Sequence
<220> FEATURE:
<223> OTHER INFORMATION: Synthetic: AgRp 4I
<220> FEATURE:

```
<221> NAME/KEY: misc_feature
<222> LOCATION: (21)..(21)
<223> OTHER INFORMATION: Xaa can be any naturally occurring amino acid

<400> SEQUENCE: 117

Gly Cys Val Arg Leu His Glu Ser Cys Leu Gly Gln Gln Val Pro Cys
1               5                   10                  15

Cys Asp Pro Ala Xaa Thr Cys Tyr Cys Lys Gly Arg Gly Asp Val Arg
                20                  25                  30

Arg Val Cys Tyr Cys Arg
            35

<210> SEQ ID NO 118
<211> LENGTH: 38
<212> TYPE: PRT
<213> ORGANISM: Artificial Sequence
<220> FEATURE:
<223> OTHER INFORMATION: Synthetic: AgRp 4J

<400> SEQUENCE: 118

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Asn Lys
                20                  25                  30

Val Lys Cys Tyr Cys Arg
            35

<210> SEQ ID NO 119
<211> LENGTH: 38
<212> TYPE: PRT
<213> ORGANISM: Artificial Sequence
<220> FEATURE:
<223> OTHER INFORMATION: Synthetic: AgRp 5A

<400> SEQUENCE: 119

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Asn Arg
                20                  25                  30

Leu Lys Cys Tyr Cys Arg
            35

<210> SEQ ID NO 120
<211> LENGTH: 38
<212> TYPE: PRT
<213> ORGANISM: Artificial Sequence
<220> FEATURE:
<223> OTHER INFORMATION: Synthetic: AgRp 5B

<400> SEQUENCE: 120

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Met
                20                  25                  30

Lys Lys Cys Tyr Cys Arg
            35

<210> SEQ ID NO 121
<211> LENGTH: 38
<212> TYPE: PRT
<213> ORGANISM: Artificial Sequence
<220> FEATURE:
<223> OTHER INFORMATION: Synthetic: AgRp 5C
```

<400> SEQUENCE: 121

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Met Arg
                20                  25                  30

Arg Arg Cys Tyr Cys Arg
        35

<210> SEQ ID NO 122
<211> LENGTH: 38
<212> TYPE: PRT
<213> ORGANISM: Artificial Sequence
<220> FEATURE:
<223> OTHER INFORMATION: Synthetic: AgRp 5D

<400> SEQUENCE: 122

Gly Cys Val Arg Leu His Glu Ser Cys Leu Gly Gln Gln Val Pro Cys
1               5                   10                  15

Cys Asp Pro Ala Ala Thr Cys Tyr Cys Gln Gly Arg Gly Asp Gly Asp
                20                  25                  30

Val Lys Cys Tyr Cys Arg
        35

<210> SEQ ID NO 123
<211> LENGTH: 38
<212> TYPE: PRT
<213> ORGANISM: Artificial Sequence
<220> FEATURE:
<223> OTHER INFORMATION: Synthetic: AgRp 5E

<400> SEQUENCE: 123

Gly Cys Val Arg Leu His Glu Ser Cys Leu Gly Gln Gln Val Pro Cys
1               5                   10                  15

Cys Asp Pro Ala Ala Thr Cys Tyr Cys Ser Gly Arg Gly Asp Asn Asp
                20                  25                  30

Leu Val Cys Tyr Cys Arg
        35

<210> SEQ ID NO 124
<211> LENGTH: 38
<212> TYPE: PRT
<213> ORGANISM: Artificial Sequence
<220> FEATURE:
<223> OTHER INFORMATION: Synthetic: AgRp 5F

<400> SEQUENCE: 124

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Met
                20                  25                  30

Ile Arg Cys Tyr Cys Arg
        35

<210> SEQ ID NO 125
<211> LENGTH: 38
<212> TYPE: PRT
<213> ORGANISM: Artificial Sequence
<220> FEATURE:
<223> OTHER INFORMATION: Synthetic: AgRp 5G

<400> SEQUENCE: 125

Gly Cys Val Arg Leu His Glu Ser Cys Leu Gly Gln Gln Val Pro Cys
1               5                   10                  15

Cys Asp Pro Ala Ala Thr Cys Tyr Cys Ser Gly Arg Gly Asp Asn Asp
            20                  25                  30

Leu Val Cys Tyr Cys Arg
            35

<210> SEQ ID NO 126
<211> LENGTH: 38
<212> TYPE: PRT
<213> ORGANISM: Artificial Sequence
<220> FEATURE:
<223> OTHER INFORMATION: Synthetic: AgRp 5H

<400> SEQUENCE: 126

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Met Lys
            20                  25                  30

Met Lys Cys Tyr Cys Arg
            35

<210> SEQ ID NO 127
<211> LENGTH: 38
<212> TYPE: PRT
<213> ORGANISM: Artificial Sequence
<220> FEATURE:
<223> OTHER INFORMATION: Synthetic: AgRp 5I

<400> SEQUENCE: 127

Gly Cys Val Arg Leu His Glu Ser Cys Leu Gly Gln Gln Val Pro Cys
1               5                   10                  15

Cys Asp Pro Ala Ala Thr Cys Tyr Cys Ile Gly Arg Gly Asp Val Arg
            20                  25                  30

Arg Arg Cys Tyr Cys Arg
            35

<210> SEQ ID NO 128
<211> LENGTH: 38
<212> TYPE: PRT
<213> ORGANISM: Artificial Sequence
<220> FEATURE:
<223> OTHER INFORMATION: Synthetic: AgRp 5J

<400> SEQUENCE: 128

Gly Cys Val Arg Leu His Glu Ser Cys Leu Gly Gln Gln Val Pro Cys
1               5                   10                  15

Cys Asp Pro Ala Ala Thr Cys Tyr Cys Glu Glu Arg Gly Asp Gly Arg
            20                  25                  30

Lys Lys Cys Tyr Cys Arg
            35

<210> SEQ ID NO 129
<211> LENGTH: 38
<212> TYPE: PRT
<213> ORGANISM: Artificial Sequence
<220> FEATURE:
<223> OTHER INFORMATION: Synthetic: AgRp 6B

<400> SEQUENCE: 129

Gly Cys Val Arg Leu His Glu Ser Cys Leu Gly Gln Gln Val Pro Cys
1               5                   10                  15

```
Cys Asp Pro Ala Ala Thr Cys Tyr Cys Glu Gly Arg Gly Asp Arg Asp
            20                  25                  30

Met Lys Cys Tyr Cys Arg
        35

<210> SEQ ID NO 130
<211> LENGTH: 38
<212> TYPE: PRT
<213> ORGANISM: Artificial Sequence
<220> FEATURE:
<223> OTHER INFORMATION: Synthetic: AgRp 6C

<400> SEQUENCE: 130

Gly Cys Val Arg Leu His Glu Ser Cys Leu Gly Gln Gln Val Pro Cys
1               5                   10                  15

Cys Asp Pro Ala Ala Thr Cys Tyr Cys Thr Gly Arg Gly Asp Glu Lys
            20                  25                  30

Leu Arg Cys Tyr Cys Arg
        35

<210> SEQ ID NO 131
<211> LENGTH: 38
<212> TYPE: PRT
<213> ORGANISM: Artificial Sequence
<220> FEATURE:
<223> OTHER INFORMATION: Synthetic: AgRp 6E

<400> SEQUENCE: 131

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Asn
            20                  25                  30

Arg Arg Cys Tyr Cys Arg
        35

<210> SEQ ID NO 132
<211> LENGTH: 38
<212> TYPE: PRT
<213> ORGANISM: Artificial Sequence
<220> FEATURE:
<223> OTHER INFORMATION: Synthetic: AgRp 6F

<400> SEQUENCE: 132

Gly Cys Val Arg Leu His Glu Ser Cys Leu Gly Gln Gln Val Pro Cys
1               5                   10                  15

Cys Asp Pro Ala Ala Thr Cys Tyr Cys Glu Ser Arg Gly Asp Val Val
            20                  25                  30

Arg Lys Cys Tyr Cys Arg
        35

<210> SEQ ID NO 133
<211> LENGTH: 38
<212> TYPE: PRT
<213> ORGANISM: Artificial Sequence
<220> FEATURE:
<223> OTHER INFORMATION: Synthetic: AgRp 7C

<400> SEQUENCE: 133

Gly Cys Val Arg Leu His Glu Ser Cys Leu Gly Gln Gln Val Pro Cys
1               5                   10                  15

Cys Asp Pro Ala Ala Thr Cys Tyr Cys Tyr Gly Arg Gly Asp Asn Asp
            20                  25                  30
```

Leu Arg Cys Tyr Cys Arg
        35

<210> SEQ ID NO 134
<211> LENGTH: 51
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (2)..(51)
<223> OTHER INFORMATION: "Gly Gly Gly Gly Ser" is present at least one
      time, but may repeat up to ten times

<400> SEQUENCE: 134

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser Gly Gly
        35                  40                  45

Gly Gly Ser
    50

<210> SEQ ID NO 135
<211> LENGTH: 16
<212> TYPE: PRT
<213> ORGANISM: Artificial Sequence
<220> FEATURE:
<223> OTHER INFORMATION: Synthetic: linker

<400> SEQUENCE: 135

Ser Gly Gly Gly Gly Ser Gly Gly Gly Gly Ser Gly Gly Gly Gly Ser
1               5                   10                  15

<210> SEQ ID NO 136
<211> LENGTH: 21
<212> TYPE: PRT
<213> ORGANISM: Artificial Sequence
<220> FEATURE:
<223> OTHER INFORMATION: Synthetic: linker

<400> SEQUENCE: 136

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 137
<211> LENGTH: 30
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (1)..(30)
<223> OTHER INFORMATION: "Gly Gly Gly Gly Ser" is present at least one
      time, but may repeat up to six times

<400> SEQUENCE: 137

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

```
<210> SEQ ID NO 138
<211> LENGTH: 24
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (1)..(24)
<223> OTHER INFORMATION: "Gly Gly Gly Ser" is present at least one time,
      but may repeat up to six times

<400> SEQUENCE: 138

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 139
<211> LENGTH: 5
<212> TYPE: PRT
<213> ORGANISM: Artificial Sequence
<220> FEATURE:
<223> OTHER INFORMATION: Synthetic: peptide

<400> SEQUENCE: 139

Glu Pro Lys Ser Cys
1               5

<210> SEQ ID NO 140
<211> LENGTH: 12
<212> TYPE: PRT
<213> ORGANISM: Artificial Sequence
<220> FEATURE:
<223> OTHER INFORMATION: Synthetic: (lipo-G0T10-CG)

<400> SEQUENCE: 140

Thr Thr Thr Thr Thr Thr Thr Thr Thr Thr Cys Gly
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Synthetic: (lipo-G2T8-CG)

<400> SEQUENCE: 141

Gly Gly Thr Thr Thr Thr Thr Thr Thr Thr Cys Gly
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Synthetic: (lipo-G4T6-CG)

<400> SEQUENCE: 142

Gly Gly Gly Gly Thr Thr Thr Thr Thr Thr Cys Gly
1               5                   10

<210> SEQ ID NO 143
<211> LENGTH: 12
<212> TYPE: PRT
<213> ORGANISM: Artificial Sequence
```

```
<220> FEATURE:
<223> OTHER INFORMATION: Synthetic: (lipo-G6T4-CG)

<400> SEQUENCE: 143

Gly Gly Gly Gly Gly Gly Thr Thr Thr Thr Cys Gly
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Synthetic: (lipo-G8T2-CG)

<400> SEQUENCE: 144

Gly Gly Gly Gly Gly Gly Gly Gly Thr Thr Cys Gly
1               5                   10

<210> SEQ ID NO 145
<211> LENGTH: 12
<212> TYPE: PRT
<213> ORGANISM: Artificial Sequence
<220> FEATURE:
<223> OTHER INFORMATION: Synthetic: (lipo-G10T0-CG)

<400> SEQUENCE: 145

Gly Gly Gly Gly Gly Gly Gly Gly Gly Gly Cys Gly
1               5                   10

<210> SEQ ID NO 146
<211> LENGTH: 20
<212> TYPE: PRT
<213> ORGANISM: Artificial Sequence
<220> FEATURE:
<223> OTHER INFORMATION: Synthetic: tumor-associated antigen HPV E743-62

<400> SEQUENCE: 146

Gly Gln Ala Glu Pro Asp Arg Ala His Tyr Asn Ile Val Thr Phe Cys
1               5                   10                  15

Cys Lys Cys Asp
            20

<210> SEQ ID NO 147
<211> LENGTH: 25
<212> TYPE: DNA
<213> ORGANISM: Artificial Sequence
<220> FEATURE:
<223> OTHER INFORMATION: Synthetic: lipophilic-CpG oligonucleotide
<220> FEATURE:
<221> NAME/KEY: misc_feature
<223> OTHER INFORMATION: Lipophilic compound, such as diacyl lipid, on 5
      end
<220> FEATURE:
<221> NAME/KEY: misc_feature
<222> LOCATION: (1)..(5)
<223> OTHER INFORMATION: Guanine repeat linker: At least one "g" is
      present and up to four may be absent or present

<400> SEQUENCE: 147
gggggtccat gacgttcctg acgtt                                           25
```